(12) United States Patent
Wang et al.

(10) Patent No.: US 9,810,684 B2
(45) Date of Patent: Nov. 7, 2017

(54) METHOD FOR INCREASING NUMBER OF STEM CELLS IN HUMAN OR ANIMAL BODIES

(71) Applicant: StemBios Technologies, Inc., Monterey Park, CA (US)

(72) Inventors: James Wang, Monterey Park, CA (US); Steve K Chen, Pacific Palisades, CA (US); Mou-Shiung Lin, Hsin-Chu (TW); Yun Yen, Arcadin, CA (US)

(73) Assignee: StemBios Technologies, Inc., Monterey Park, CA (US)

( * ) Notice: Subject to any disclaimer, the term of this patent is extended or adjusted under 35 U.S.C. 154(b) by 0 days.

(21) Appl. No.: 14/135,553

(22) Filed: Dec. 19, 2013

(65) Prior Publication Data

US 2014/0178886 A1    Jun. 26, 2014

Related U.S. Application Data

(60) Provisional application No. 61/740,507, filed on Dec. 21, 2012, provisional application No. 61/819,529, filed on May 3, 2013.

(51) Int. Cl.
*G01N 33/53* (2006.01)
*G01N 33/50* (2006.01)

(52) U.S. Cl.
CPC ..... *G01N 33/5073* (2013.01); *G01N 33/5008* (2013.01); *G01N 2333/70596* (2013.01)

(58) Field of Classification Search
CPC ........ A61K 35/748; A61K 38/00; C12N 5/06; C12N 6/07
USPC ...................................... 424/195.17; 435/325
See application file for complete search history.

(56) References Cited

U.S. PATENT DOCUMENTS

| | | | |
|---|---|---|---|
| 6,004,807 A | 12/1999 | Banchereau et al. | |
| 6,440,735 B1 | 8/2002 | Gaeta | |
| 6,716,422 B1 | 4/2004 | Gajewski et al. | |
| 6,916,654 B1 | 7/2005 | Sims et al. | |
| 6,986,887 B2 | 1/2006 | Lawman et al. | |
| 7,316,932 B2 * | 1/2008 | Woodside | G01N 35/00 422/533 |
| 7,575,921 B2 | 8/2009 | Vacanti et al. | |
| 7,651,690 B2 * | 1/2010 | Jensen et al. | 424/195.17 |
| 7,972,847 B2 | 7/2011 | Kalinski | |
| 8,158,758 B2 | 4/2012 | Gurney | |
| 8,206,907 B2 * | 6/2012 | Milstein et al. | 435/6.1 |
| 8,337,858 B2 * | 12/2012 | Scoglio et al. | 424/195.17 |
| 8,394,630 B2 | 3/2013 | Wang et al. | |
| 8,673,296 B2 | 3/2014 | Karlsson-Parra et al. | |
| 2003/0161817 A1 | 8/2003 | Young et al. | |
| 2004/0136967 A1 | 7/2004 | Weiss et al. | |
| 2004/0175823 A1 | 9/2004 | Vacanti et al. | |
| 2005/0115059 A1 | 6/2005 | Fuseya et al. | |
| 2005/0255588 A1 | 11/2005 | Young et al. | |
| 2006/0035373 A1 | 2/2006 | Zhang et al. | |
| 2006/0040392 A1 | 2/2006 | Collins et al. | |
| 2006/0171931 A1 | 8/2006 | Rudnicki et al. | |
| 2006/0252150 A1 | 11/2006 | Cheng et al. | |
| 2007/0190023 A1 | 8/2007 | Battista et al. | |
| 2008/0152665 A1 | 6/2008 | Leclerc et al. | |
| 2008/0305079 A1 | 12/2008 | Chen et al. | |
| 2009/0004661 A1 | 1/2009 | Shetty | |
| 2009/0104158 A1 | 4/2009 | Young et al. | |
| 2009/0104160 A1 * | 4/2009 | Young et al. | 424/93.7 |
| 2009/0155225 A1 | 6/2009 | Ratajczak et al. | |
| 2009/0186334 A1 | 7/2009 | Young et al. | |
| 2010/0081199 A1 | 4/2010 | Slukvin et al. | |
| 2010/0183570 A1 | 7/2010 | Wang et al. | |
| 2011/0305673 A1 | 12/2011 | Spees | |
| 2012/0021482 A1 | 1/2012 | Zuba-Surma et al. | |
| 2012/0028355 A1 | 2/2012 | Sato et al. | |
| 2012/0034194 A1 | 2/2012 | Wang | |
| 2012/0177670 A1 | 7/2012 | Wang | |
| 2013/0095077 A1 | 4/2013 | Wang | |
| 2013/0189327 A1 | 7/2013 | Ortega et al. | |
| 2013/0236485 A1 | 9/2013 | Wang | |

(Continued)

FOREIGN PATENT DOCUMENTS

| | | |
|---|---|---|
| CN | 102008650 | 4/2011 |
| EP | 1632563 | 3/2006 |

(Continued)

OTHER PUBLICATIONS

Tennis et al. Neoplasia 2012;12:244-53.*
Trubiani et al. J Cell Physiol 2010;225:123-31.*
Naotsugu Haraguchi et al: "CD13 is a therapeutic target in human liver cancer stem cells",Journal of Clinical Investigation,vol. 120, No. 9, Sep. 1, 2010 (Sep. 1, 2010), pp. 3326-3339, XP055107319.
Janet Helen Fitton. "Therapies from Fucoidan; Multifunctional Marine Polymets",Marine Drugs, vol. 9, No. 12, Dec. 30, 2011 (Dec. 30, 2011), pp. 1731-1760, XP055107645.
Irhimeh M R et al. "Fucoidan ingestion increases the expression of CXCR4 on human CD34 +cells", Experimental Hematology,vol. 35, No. 6, Jun. 1, 2007 (Jun. 1, 2007), pp. 989-994, XP025319723.
Sweeney E A et al: "Mobilization of stem/progenitor cells by sulfated polysaccharides does not require selectin presence", Proceedings of the National Academy of Sciences, National Academy of Sciences, US,vol. 97, No. 12, Jun. 6, 2000 (Jun. 6, 2000), pp. 6544-6549, XP008119556, ISSN: 0027-8424, DOI: 10.1073/PNAS. 97.12.6544.

(Continued)

*Primary Examiner* — Janice Li
(74) *Attorney, Agent, or Firm* — Cesari and McKenna, LLP

(57) ABSTRACT

A method of evaluating an action includes (1) obtaining a first stem-cell data related to a subject before performing the action, (2) performing the action on the subject, (3) obtaining a second stem-cell data related to the subject after performing the action, and (4) identifying the effect of the action on the subject based on the first stem-cell data and the second stem-cell data. The subject may be a human or an animal. The action may be taking a drug or taking a nutrient or dietary supplement, which may include fucoidan. Each of the first and second stem-cell data may include the count of a type or types of stem cells and/or the percentage of the type or types of stem cells and may be obtained by the same method including counting cells using a cell counter or cell counting device such as flow cytometer.

14 Claims, 26 Drawing Sheets

(56) References Cited

U.S. PATENT DOCUMENTS

| | | |
|---|---|---|
| 2014/0161774 A1 | 6/2014 | Wang |
| 2014/0219952 A1 | 8/2014 | Cameron |
| 2014/0377760 A1 | 12/2014 | Wang et al. |
| 2016/0166611 A1 | 6/2016 | Wang |

FOREIGN PATENT DOCUMENTS

| | | | |
|---|---|---|---|
| EP | 2818544 A1 | 12/2014 | |
| JP | H0391491 A | 4/1991 | |
| JP | 2001/128660 A | 5/2001 | |
| WO | 9926639 | 6/1999 | |
| WO | WO-2006/028723 | 3/2006 | |
| WO | WO-2006/070370 | 7/2006 | |
| WO | WO-2007/026353 | 3/2007 | |
| WO | 2007087367 | 8/2007 | |
| WO | WO-2007/100845 | 9/2007 | |
| WO | WO-2008/148105 | 12/2008 | |
| WO | WO-2009/012357 | 1/2009 | |
| WO | WO-2009/059032 | 5/2009 | |
| WO | WO-2009/061024 | 5/2009 | |
| WO | WO-2009/136283 | 11/2009 | |
| WO | WO-2010/039241 | 4/2010 | |
| WO | WO-2010/083203 | 7/2010 | |
| WO | 2010099044 | 9/2010 | |
| WO | 2011137540 | 11/2011 | |
| WO | 2012019002 | 2/2012 | |
| WO | WO-2013/049459 | 4/2013 | |

OTHER PUBLICATIONS

Karaoz et al "Characterization of Mesenchymal Stem Cells from Rat Bone Marrow: Ultrastructural Properties, Differentiation Potential and Immunophenotypic Markers" Histochemistry and Cell Biology vol. 132, pp. 533-546, 2009.

Phadnis et al "Mesenchymal Stem Cells Derived from Bone Marrow of Diabetic Patients Portrait Unique Markers Influenced by the Diabetic Microenvironment" The Review of Diabetic Studies vol. 6, pp. 260-270, 2009.

Zhao et al "Embryonic Stem Cell Markers" Molecules vol. 17, pp. 6196-6236, 2012.

http://stemcells.nih.gov/info/glossary.asp.

Abeyta, et al., 2004, Human Molecular Genetics, vol. 13, No. 6, pp. 601-608.

Aiuti, et al., "Expression of CXCR4, the Receptor for Stromal Cell-derived Factor-1 on Fetal and Adult Human Lympho-hematopoietic Progenitors", European Journal of Immunology. Published 1999. Wiley-VCH Verlag GmbH, Weinheim. pp. 1823-1831.

Allergrucci, et al., 2006, Human Reproduction Update, Vol. Advance Access published on Aug. 26, 2006, p. 1-18.

Amit, et al., "Feeder Layer-and Serum-Free Culture of Human Embryonic Stem Cells", Biology of Reproduction, 2004, vol. 70, pp. 837-845.

Aoyama et al. "Stromal cell CD9 regulates differentiation of hematopoietic stem/progenitor cells" Hematopoiesis, Blood, 93(8):2586-2594, 1999.

Arechaga et al.; "Characterisation of new intracellular membranes in *Escherichia coli* accompanying large scale over-production of the b subunit of F1F0 ATP synthase"; FEBS Letters 482:215-219 (2000).

Banerjee et al. "An antibody to the tetraspan membrane protein CD9 promotes neurite formation in a partially α3β1 integrin-dependent manner" The Journal of Neuroscience 17(8):2756-2765, 1997.

Barker, et al., "Identification of stem cells in small intestine and colon by marker gene Lgr5", Articles, Nature Publishing Group, Oct. 2007.

Barker, et al., "Lgr5+ve Stem Cells Drive Self-Renewal in the Stomach and Build Long-Lived Gastric Units In Vitro", Cell Stem Cell, vol. 6, Jan. 2010.

Battula, et al. "Prospective isolation and characterization of mesenchymal stem cells from human placenta using a frizzled-9-specific monoclonal antibody", Differentiation, 2008, vol. 76, pp. 326-336.

Battula, et al., "Human placenta and bone marrow derived MSC cultured in serum-free, b-FGF-containing medium express cell surface frizzled-9 and SSEA-4 and give rise to multilinelage differentiation", Differentiation, Spinger Verlag, DE, col. 75, No. 4, Apr. 2007.

Bellato, et al., Pain Research and Treatment vol. 2012 pp. 1-7.

Bizzetto et al.; "Outcomes after related and unrelated umbilical cord blood transplantation for hereditary bone marrow failure syndromes other than fanconi anemia"; Haematologica 96(1)134-141 (2011).

Buhring et al. "Novel markers for the prospective isolation of human MSC" Ann. N.Y. Acad. Sci. 1106:262-271, 2007.

Cai, et al., (NeuroMolecular Medicine, 2002, vol. 2, pp. 233-249).

Cui et al. "Spatial distribution and initial changes of SSEA-1 and other cell adhesion-related molecules on mouse embryonic stem cells before and during differentiation" Journal of H Istochemistry & Cytochemistry, 52(11):1447-1457, 2004.

Dolcetti, et al., "Myeloid-Derived Suppressor Cell Rolse in Tumor-Related Inflammation", Cancer Letters; 267:216-225 (2008).

Fickert et al. "Identification of subpopulations with characteristics of mesenchymal progenitor cells from human osteoarthritic cartilage using triple staining for cell surface markers" Arthritis Research & Therapy, 6(5):R422-R432, 2004.

Furusawa et al. "Embryonic stem cells expressing both platelet endothelial cell adhesion molecule-1 and stage-specific embryonic antigen-1 differentiate predominantly into epiblast cells in a chimeric embryo" Biology of Reproduction, 70:1452-1457 (2004).

Gabrilovich, et al., "Myeloid-Derived-Suppressor Cells as Regulators of the Immune System", Nat. Rev. Immunol.; 9(3):162-176 (2009).

Gang et al. Prospective isolation of MSC with SSEA-4; Blood First Edition Paper, prepublished on line Oct. 24, 2006: DOI 10.1182/blood-2005-11-010504.

Gang et al. "SSEA-4 identifies mesenchymal stem cells from bone marrow", Stem Cells in Hematology, Blood, 109(4):1743-1751, 2007.

Glazar et al. "IgSF8 (EWI-2) and CD9 in fertilization: Evidence of distinct functions for CD9 and a CD9-associated protein in mammalian sperm-egg interaction" Reprod Fertil Dev. 21(2):293-303, 2009.

Hamman, et al. 2005, Biodrugs, vol. 19, No. 3, pp. 165-177.

Huang et al. "Isolation and characterization of cell subpopulation with stem cell properties in human and monkey intervertebral disc (IVD)" EMC Journal 2009 p. 28.

Hung, et al., "Isolation and characterization of size-sieved stem cells from human bone marrow", Stem Cells, Alphamed Press, vol. 20, No. 3, 2002.

Hur, "Highly Angiogenic CXCR4 and CD31 monocyte subset derived from 3D culture of human peripheral blood", Biomaterials, 2013, pp. 1929-1941.

Jaks, et al, "Lgr5 marks cycling, yet long-lived, hair follicle stem cells," Nature Genetics, vol. 40, No. 11, 1291-1299 (2008).

Jensen, et al., "Mobilization of human CD34<+>CD133<+> and CD34<+>CD133<-> stem cells in vivo by consumption of an extract from Aphanizomenon flos-aquae-related to modulation of CXCR4 expression by an L-selectin ligand?", Cardiovascular Revascularization Medicine, Elsevier, NL, vol. 8, No. 3, Aug. 29, 2007 pp. 189-202.

Kadam et al. "Islet neogenesis from the constitutively nestin expressing human umbilical cord matrix derived mesenchmal stem cells" Islets 2:2, 112-120, 2010.

Kim et al. "Role of CD9 in proliferation and proangiogenic action of human adipose-derived mesenchymal stem cells" Cell and Molecular Physiology Eur. J. Physiol 455:283-296, 2007.

Kim, et al., "Generation of human induced pluripotent stem cells from osteoarthritis patient-derived synovial cells", Arthritis and Rheumatism, 6(10):3010-2021 (2011).

Kogler, et al., "A new human somatic stem cell from placental cord blood with intrinsic pluripotent differentiation potential", Journal of Experimental Medicine, vol. 200, No. 2, 2004.

(56) References Cited

OTHER PUBLICATIONS

Kucia et al. "Evidence that very small embryonic like (VSEL) stem cells are mobilized into peripheral blood" Stem Cells Express, published online Jun. 5, 2008; doi:10.1634/stemcells.2007-0922 p. 1-23.
Kucia, et al., "A population of very small embryonic-like (VSEL) CXCR4+SSEA=1+Oct4+ stem cells identified in adult bone marrow", Leukemia, vol. 20, 2006.
Kucia, et al., "Morphological and molecular characterization of novel population of CXCR4+ SSEA=+ very small embryonic-like cell purified from human cord blood-preliminary report", Leukemia, vol. 21, 2007.
Kucia, et al., "Physiological and pathological consequences of identification of very small embryonic like (VSEL) stem cells in adult bone marrow", Journal of Physiology and Pharmacology, 2006, 57, Supp 5, 5-18.
Li, et al., 2009, Transplant Immunology, vol. 21, pp. 70-74.
Lian et al. "Establishing clonal cell lines with endothelial-like potential from CD9hi, SSEA-1 Cells in embryonic stem cell-derived embryoid bodies" PLoS ONE 1:(e6)1-10, 2006.
Lindvall, et al., J. Clin Invest. Jan. 4, 2010; 120(1): 29-40.
Lv, et al., "Concise Review: The Surface Markers and Identity of Human Mesenchymal Stem Cells", Stem Cells vol. 32, pp. 1408-1419, 2014.
Magnus, et al., Philos Trans R Soc Lond B Biol Sci. Jan. 12, 2008; 363 (1489): 9-22.
Meng et al. "Endometrial regenerative cells: A novel stem cell population" Journal of Translational Medicine, 5:(57)1-10, 2007.
Meregalli, et al., BioDrugs 2010, vol. 24, Issue 4, pp. 237-247.
Muller et al. "A novel embryonic stem cell like derived from the common marmoset monkey (callithrix jacchus) exhibiting germ cell-like characteristics" Human Reproduction, 24(6):1359-1372, 2009.
Negroni, et al., Expert Opin Biol Ter. Feb. 2011; 11(2):157-176.
Noggle, et al., "Notch signaling is inactive but inducible in human embryonic stem cells", Stem Cells, vol. 24, No. 7, 2006.
Oka et al. "CD9 is associated with leukemia inhibitory factor-mediated maintenance of embryonic stem cells" Molecular Biology of the Cell, 13:1274-1281, 2002.
Ostrand-Rosenberg, et al., "Myeloid-Derived Suppressor Cells: Linking Inflammation and Cancer", J. Immunol.; 182:4499-4506 (2009).
Prowse et al. "Multiplexed staining of live human embryonic stem cells for flow cytometric analysis of pluripotency markers" Stem Cells and Development, 18(8): 1135-1139, 2009.
Ratajczak, et al., "Very small embryonic-like (VSEL) stem cells: purification from adult organs, characterization, and biological significance", Stem Cell Reviews, vol. 4, No. 2, 2008.
Sackstein, et al., "Ex vivo glycan engineering on cd44 programs human multipotent mesenchymal stromal cell trafficking to bone", Nat. Med., vol. 14, pp. 181-187, 2008.
Sato, et al., 2003, Developmental Biology, vol. 260 p. 404-413.
Sato, et al., "Paneth cells constitute the niche for Lgr5 stem cells in intestinal crypts", Nature, vol. 469, Jan. 2011.
Schuldiner, et al., "Effects of eight growth factors on the differentiation of cells derived from human embryonic stem cells", PNAS, 2000, vol. 97, pp. 11307-11312.
Serafini, et al., "Myeloid Suppressor Cells in Cancer: Recruitment, Phenotype, Properties, and Mechanisms of Immune Suppression", Seminars in Cancer Biology; 16:53-65 (2006).
Sharp III, et al., 2014, Frontiers in Oncology, vol. 4, Article 299, p. 1-13.
Shinohara et al. "CD9 is a surface marker on mouse and rat male germline stem cells", Biology of Reproduction, 70:70-75, 2004.
Shmilovici "Mammalian spore-like cells—A reservoir of spare parts for old-age?" Medical Hypotheses, 2007, 68:767-769.
Sinha et al.; "Prostaglandin E2 promotes tumor progression by inducing myeloid-derived suppressor cells"; Cancer Res, 67(9):4507-4513 (2007).
Sprangers, et al., 2008, Kidney Immunology, vol. 74, pp. 14-21.
Stemrx Bio Science, "Get Rid of Ankylosing Spondylitis with Stem Cell Treatment and Applied Therapies", 2013.
Stout et al. "Primitive stem cells residing in the skeletal muscle of adult pigs are mobilized into the peripheral blood after trauma" The American Surgeon, 73:1106-1110, 2007.
Taha, 2010, Current Stem Cell Research & Therapy, vol. 5, pp. 23-36.
Talmadge, "Pathways Mediating the Expansion and Immunosuppressive Activity of Myeloid-Derived Suppressor Cells and Their Relevance to Cancer Therapy", Clin. Cancer Res.; 13918:5243-5248 (2007).
Tole et al. "Distribution of CD9 in the developing and mature rat nervous system" Developmental dynamics 197:94-106, 1993.
Torchilin, et al., 2003, DDT, vol. 8, No. 6, pp. 259-266.
Tourandre, et al., Arthritis & Rheumatism vol. 64, No. 2, pp. 533-541, 2012.
Tu et al.; "Overexpression of interleukin-1 beta induces gastric inflammation and cancer and mobilizes myeloid-derived suppressor cells in mice"; Cancer Cell, 14(5):408-419 (2008).
Vacanti et al. "Identification and initial characterization of spore-like cells in adult mammals" Journal of Cellular Biochemistry, 80:455-460, 2001.
Wang, et al., "Effects and Safety of Allogenic Mecenchymal Stem Cell Intravenous Infusion in Active Ankylosing Spondylitis Patients Who Failed NSAIDs: A 20-Week Clinical Trial", Cell Transplantation, vol. 23, pp. 1293-1303, 2013.
Wojakowski et al "Very Small Embryonic-Like Stem Cells in Cardiovascular Repair" Pharmacology & Therapeutics vol. 129, pp. 21-28. 2011.
Wu, et al., 2012, Ageing Research Reveiws, vol. 11, pp. 32-40.
Young et al.: "Adult-derived stem cells and their potential for use in tissue repair and molecular medicine"; J. Cell. Mol. Med., 9(3):753-769 (2005).
Young "Existence of Reserve quiescent stem cells in adults, from amphibians to humans" Immunol., 280:71-109, 2004.
Young et al. "Cancer gene mechanisms and gene therapy" Reviews, Minerva Biotec. 17:55-63, 2005.
Yu, et al., Liver Transpl. Jan. 2012; 18 (1): 9-21.
Zhao, et al. "A human peripheral blood monocyt-derived subset acts as pluripotent stem cells", Proceedings of the National Academy of Sciences, National Academy of Sciences, vol. 100, No. 5, pp. 2426-2431, Mar. 4, 2003.
Zuba-Surma, et al., "'Small stem cells' in adult tissues: Very small embryonic-like stem cells stand up!", Cytometry Part A, vol. 75A, No. 1, 2009.
Zulewski et al. "Multipotential nestin-positive stem cells isolated from adult pancreatic islets differentiate ex vivo into pancreatic endocrine, exocrine, and hepatic phenotypes" Diabetes, 50:521-533, 2001.
Choi, "Adult Stem Cell Therapy for Autoimmune Disease", International Journal of Stem Cells vol. 2, No. 2, 2009.
Hsu, et al., "Characterization of Two LGR Genes Homologous to Gonadotropin and Thyrotopin Receptors with Extracellular Leucine-Rich Repeats and a G Protein-Coupled, Seven-Transmembrane Region", Mol. Endocrinology, 1998, vol. 12, No. 12, pp. 1830-1845).
Ratajczak, et al., "Bone Marrow—Home of Versatile Stem Cells", Transfuion Medicine and Hemotherapy 2008;35:248-259.

\* cited by examiner

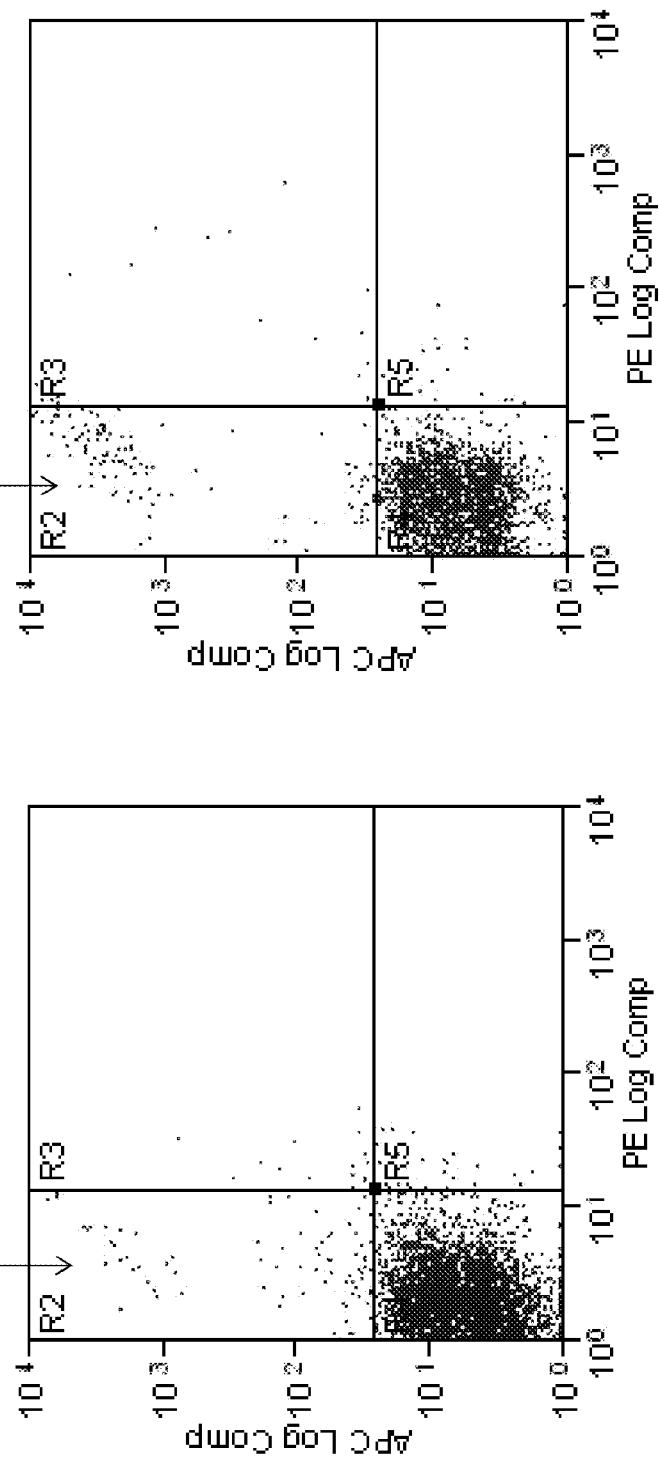

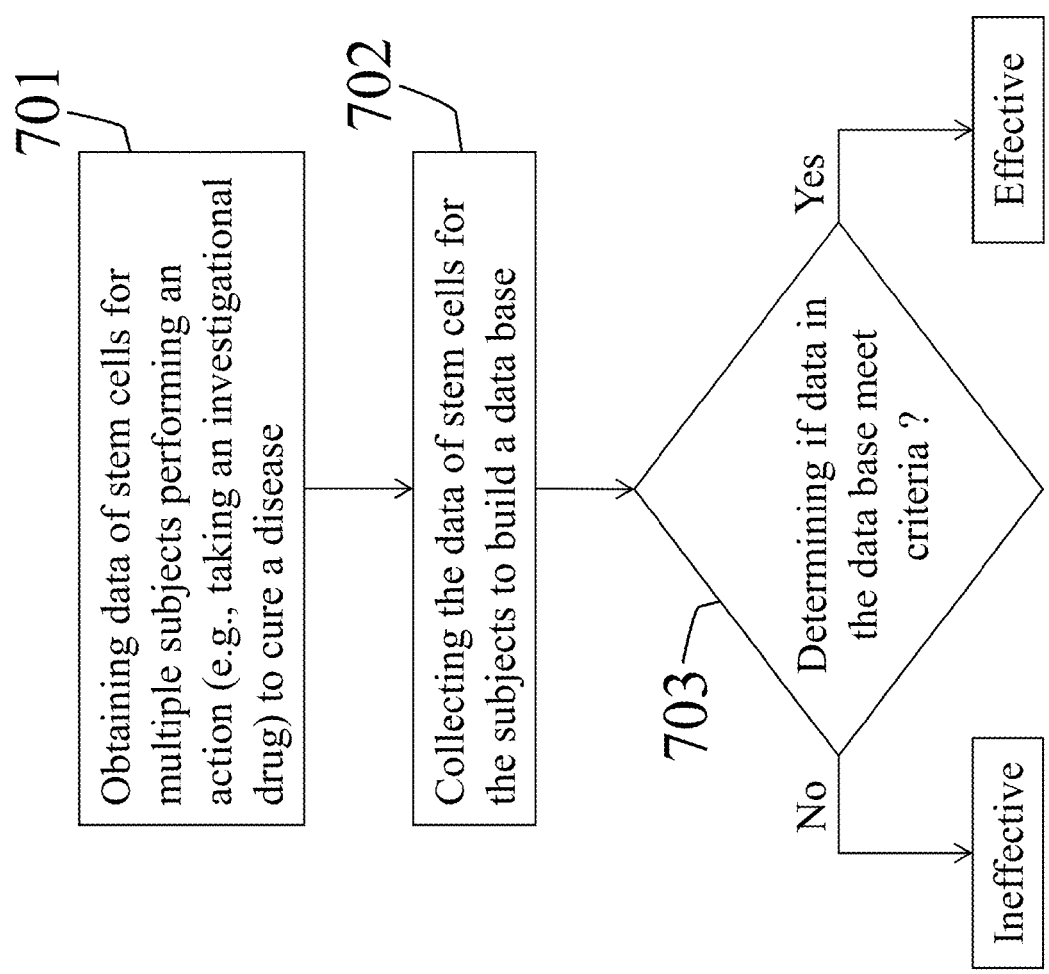

METHOD FOR INCREASING NUMBER OF STEM CELLS IN HUMAN OR ANIMAL BODIES

RELATED APPLICATION

This application claims priority to U.S. provisional application No. 61/740,507, filed on Dec. 21, 2012, and to U.S. provisional application No. 61/819,529, filed on May 3, 2013, all of which are incorporated herein by reference in their entirety.

BACKGROUND OF THE DISCLOSURE

Field of the Disclosure

The disclosure relates to a method of evaluating an action or a product, and more particularly, to a method of evaluating an action or a product based on information of stem cells.

Brief Description of the Related Art

Stem cells have the ability to self-renew to generate more stem cells and also to turn into other types of cells. Stem cell research is useful for learning about human development and is one of the most fascinating areas of contemporary biology. Therefore, stem cells offer exciting promise for future medical science.

SUMMARY OF THE DISCLOSURE

The present invention provides an approach of evaluating an action or a product (such as a drug, a nutrient, or a dietary supplement) based on information of stem cells.

The present invention provides another approach of establishing criteria or standards for evaluating an action or a product (such as a drug, a nutrient, or a dietary supplement).

The present invention provides the study of stem cell dynamics, measuring the change of the state or status of stem cells in, for example, the (human) blood, with respect to time, without or with external action or actions. By studying the stem cell dynamics, the effect of an external action or actions can be evaluated. The stem cell dynamics is just like quantum dynamics, electrodynamics or thermodynamics in the physical science, which study the changes of quantum states, electromagnetic fields, and thermo-states, respectively, with respect to time, without or with external interactions (forces), (electromagnetic) fields, disturbance (heat). The methodologies, theories, rules, laws, equations, skills, knowledge and experience in quantum dynamics, electrodynamics and thermodynamics for dealing, solving and understanding complex physical systems may be applied to stem cell dynamics in dealing, solving and understanding the complex human body system.

An exemplary embodiment of the present disclosure provides a method of evaluating an effect of an action including: (1) obtaining a first tissue sample from a subject; (2) analyzing the first tissue sample to obtain a first data related to information of a type or types of stem cells; (3) after obtaining the first tissue sample, performing the action on the subject; (4) after performing the action on the subject, obtaining a second tissue sample from the subject; (5) analyzing the second tissue sample to obtain a second data related to information of the type or types of stem cells; and (6) comparing the first and second data. This method may further include comparing a criterion for the type or types of stem cells with a change obtained by comparing the first and second data and/or comparing the criterion with the second data.

Another exemplary embodiment of the present disclosure provides a criterion establishing method including: establishing a criterion for a type or types of stem cells based on multiple first results and multiple second results, wherein each of the first results is obtained by analyzing a tissue sample taken from a correspond one of subjects before taking an action, and each of the second results is obtained by analyzing a tissue sample taken from a correspond one of the subjects after taking the action.

These, as well as other components, steps, features, benefits, and advantages of the present disclosure, will now become clear from a review of the following detailed description of illustrative embodiments, the accompanying drawings, and the claims.

BRIEF DESCRIPTION OF THE DRAWINGS

The drawings disclose illustrative embodiments of the present disclosure. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same reference number or reference indicator appears in different drawings, it may refer to the same or like components or steps.

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIGS. 18A and 18B show two flow cytometry results related to CD90(+) MSCs;

FIG. 20 shows a flow chart for identifying, evaluating or assessing the effect of an action or stimulus on curing or treating a disease according to a thirteenth embodiment of the present disclosure;

Figure 1:
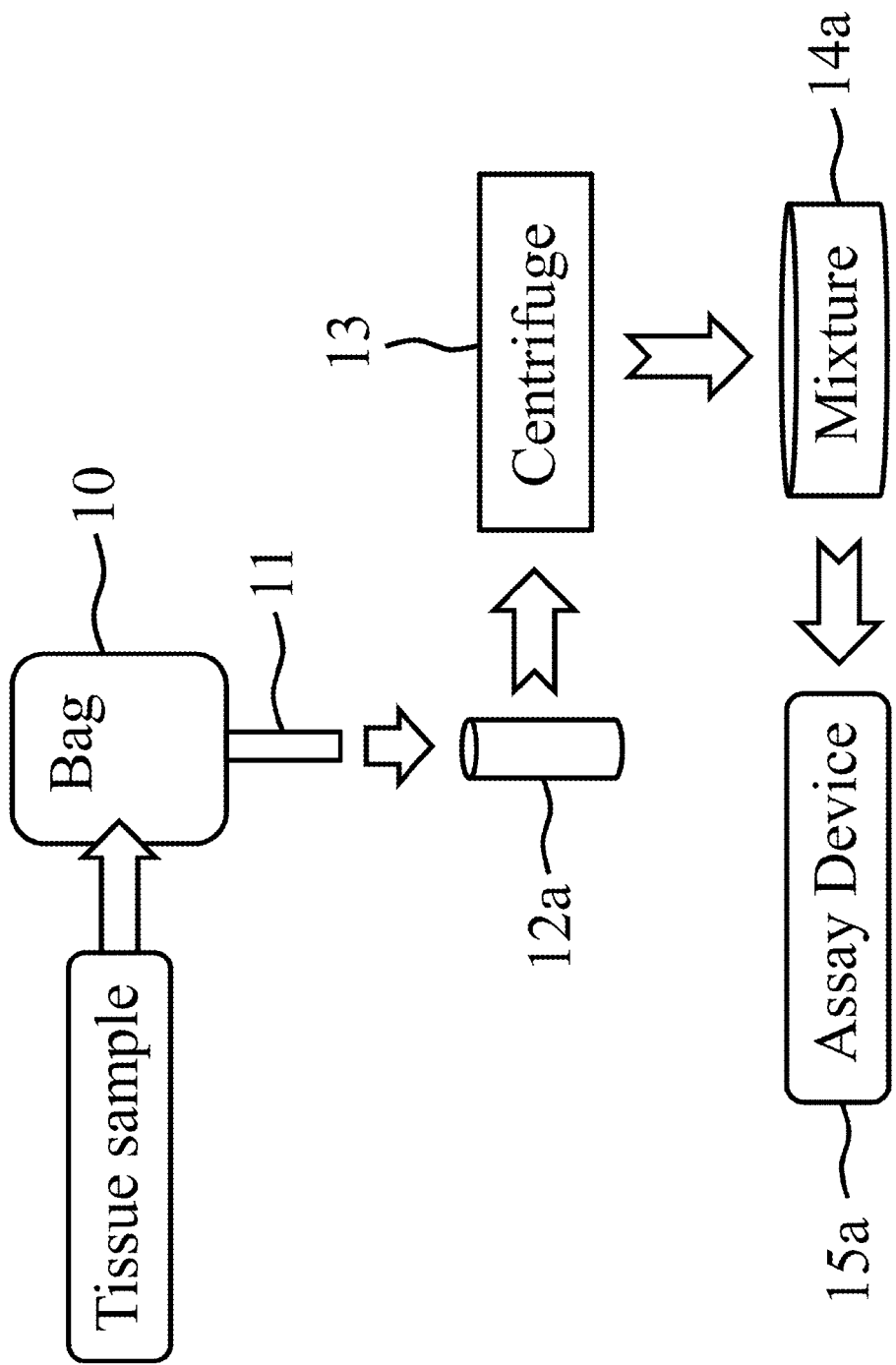
FIGS. 1-6 show various process flow diagrams of purification processes.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION OF THE INVENTION

Illustrative embodiments are now described. Other embodiments may be used in addition or instead. Details that may be apparent or unnecessary may be omitted to save space or for a more effective presentation. Conversely, some embodiments may be practiced without all of the details that are disclosed.

Before describing embodiments of the present invention, a definition or description has been included for these various terms. These definitions or descriptions are provided to assist in teaching a general understanding of the present invention.

Definition of Size (Z) of a Cell:

The size (Z) of a cell such as stem cell or biological cell, mentioned in all following paragraphs, of the present disclosure may be, but not limited to, described or defined as (1) the conventional definition of the size of a cell in the field of the cell biology or the field of stem cells, (2) the diameter of a cell especially when the cell is substantially with a shape of a sphere, (3) the length of the major axis of a cell especially when the cell is substantially with a shape of an ellipsoid, (4) the width of a cell when the shape of the cell is with an approximate shape of a square, (5) the length of a cell when the shape of the cell is with an approximate shape of a rectangle, or (6) the greatest cross-sectional or transverse dimension of a cell. The size (Z), either the diameter, length, width, or greatest cross-sectional or transverse dimension, may be, but not limited to, determined or measured, for example, using an image of the cell obtained from an optical microscope or from an electron microscope (e.g., scanning electron microscope (SEM)), or using data (e.g., two-dimensional dot, contour or density plot) of the cell obtained from a flow cytometer. The image of the cell obtained from the optical microscope or electron microscope may be a two-dimensional (2D) cross section or three-dimensional (3D) structure of the cell. As an example, the size (Z) of the cell may be obtained by, e.g., measuring the greatest cross-sectional or transverse dimension of the cell in a 2D cross-sectional image obtained from an optical microscope or an electron microscope (e.g., SEM).

Description of Stem Cells:

There are various types of stem cells, including totipotent stem cells, pluripotent stem cells, multipotent stem cells, and progenitor stem cells (also called unipotent stem cells). SB-1 cells, SB-2 cells, blastomere-like stem cells (BLSCs), and very small embryonic-like stem cells (VSELs) belong to pluripotent stem cells. Mesenchymal stem cells (MSCs), multipotent adult progenitor cells (MAPCs), bone marrow derived multipotent stem cells (BMSCs), and multipotent adult stem cells (MASCs) belong to multipotent stem cells. Neural stem cells, retina stem cells, olfactory bulbs stem cells, epidermal stem cells, muscle stem cells, intestine stem cells, pancreatic stem cells, heart stem cells, liver stem cells, kidney stem cells, endothelial stem cells, adipocyte or adipose-derived stem cells, marrow-isolated adult multilineage inducible (MIAMI) cells, pre mesenchymal stem cells (pre-MSCs), multipotent progenitor cells (MPPs), lineage-restricted progenitor cells (LRPs), common myeloid progenitor cells (CMPs) and common lymphocyte progenitor cells (CLPs) belong to progenitor stem cells.

In the following paragraphs the sign "+" following a cell (surface) marker means the stem cells can express the cell (surface) marker; in the other term, the cell (surface) marker existing in the cell surfaces of the stem cells may be detected by performing a flow cytometry using a (marker-specific) antibody. And, the sign "−" following a cell (surface) marker means the stem cells do not express the cell (surface) marker; in the other term, the cell (surface) marker, not existing in the cell surfaces of the stem cells, cannot be detected by performing a flow cytometry using a (marker-specific) antibody. The positive sign "+" is a positive expression of a cell (surface) marker for a stem cell, and the negative sign "−" is a negative expression of a cell (surface) marker for a stem cell.

A SB-1 cell described herein is a CD9(+), CD349(+) cell that is, but not limited to, smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). The SB-1 cell is a pluripotent stem cell having a nucleus and can express the two cell (surface) markers CD9 and CD349. The SB-1 cell may be characterized by CD9(+) and CD349(+).

A SB-2 cell described herein is a CD9(−), SSEA4(+) cell that is, but not limited to, smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). The SB-2 cell is a pluripotent stem cell having a nucleus. The SB-2 cell can express the cell (surface) marker SSEA4 and lacks expression of the cell (surface) marker CD9. The SB-2 cell may be characterized by CD9(−) and SSEA4(+).

A blastomere-like stem cell (BLSC) described herein may be a CD66e(+) pluripotent stem cell that is, but not limited to, smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). The BLSC is a pluripotent stem cell having a nucleus. The BLSC can express the cell (surface) marker CD66e. The BLSC may be characterized by CD66e(+).

A very small embryonic-like stem cell (VSEL) described herein may be a CD133(+), CD45(−), Lin(−) pluripotent stem cell or a CXCR4(+), CD45(−), Lin(−) pluripotent stem cell. The CD133(+), CD45(−), Lin(−) pluripotent stem cell or the CXCR4(+), CD45(−), Lin(−) pluripotent stem cell, i.e., the VSEL, may be, but not limited to, smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). The VSEL is a pluripotent stem cell having a nucleus. In the case of the CD133(+), CD45(−), Lin(−) pluripotent stem cell, the VSEL can express the cell (surface) marker CD133 and lacks expression of the two cell (surface) markers CD45 and Lin. In the case of the CXCR4(+), CD45(−), Lin(−) pluripotent stem cell, the VSEL can express the cell (surface) marker CXCR4 and lacks expression of the two cell (surface) markers CD45 and Lin. The VSEL may be characterized as CD133(+), CD45(−), and Lin(−) or as CXCR4(+), CD45(−), Lin(−). In addition, the VSEL may be described with the following characteristics: (1) are slightly smaller than red blood cells; and (2) are enriched in the CD133(+)CD45(−)Lin(−) cell fraction or CXCR4(+)CD45(−)Lin(−) cell fraction in humans.

A mesenchymal stem cell (MSC) described herein may be a CD13(+), CD29(+), CD44(+), CD73(+), CD90(+) or CD105(+) multipotent stem cell. The MSC is a multipotent stem cell having a nucleus. The MSC can express one or more of the cell (surface) markers CD13, CD29, CD44, CD73, CD90 and CD105 and may be characterized by one or more of CD13(+), CD29(+), CD44(+), CD73(+), CD90(+) and CD105(+).

Mesenchymal stem cells (MSCs) are very heterogeneous populations which mean to have various sizes and shapes. Some types of MSCs may be smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). Some types of MSCs may be greater than 6, 7 or 10 micrometers in size (as defined by the above-mentioned size (Z) of a cell).

A multipotent adult progenitor cell (MAPC), which is a multipotent stem cell having a nucleus, could be a CD13(+), SSEA1(+) multipotent stem cell. The MAPC can express the cell (surface) markers CD13 and SSEA1 and may be characterized by CD13(+) and SSEA1(+). A bone marrow derived multipotent stem cell (BMSC), which is a multipotent stem cell having a nucleus, could be a CD105(+) multipotent stem cell, a CD117(+) multipotent stem cell, or a CD13(+), SSEA3(+) multipotent stem cell. In the case of the CD105(+) multipotent stem cell, the BMSC can express the cell (surface) marker CD105 and may be characterized by CD105(+). In the case of the CD117(+) multipotent stem cell, the BMSC can express the cell (surface) marker CD117 and may be characterized by CD117(+). In the case of the CD13(+), SSEA3(+) multipotent stem cell, the BMSC can express the cell (surface) markers CD13 and SSEA3 and may be characterized by CD13(+) and SSEA3(+). A multipotent adult stem cell (MASC), which is a multipotent stem cell having a nucleus, could be a Oct4(+) multipotent stem cell, a Nanog(+) multipotent stem cell, or a RexI(+) multipotent stem cell. In the case of the Oct4(+) multipotent stem cell, the MASC can express the cell (surface) marker Oct4 and may be characterized by Oct4(+). In the case of the Nanog(+) multipotent stem cell, the MASC can express the cell (surface) marker Nanog and may be characterized by Nanog(+). In the case of the RexI(+) multipotent stem cell, the MASC can express the cell (surface) marker RexI and may be characterized by RexI(+). All the MAPC, the BMSC and the MASC may be, but not limited to, greater than 6, 7 or 10 micrometers, such as between 8 and 15 micrometers, in size (as defined by the above-mentioned size (Z) of a cell).

A hematopoietic stem cell (HSC) may be a CD34(+), cKit(−), CD38(−), Lin(−) multipotent or progenitor stem cell or a CD150(+), CD244(−), CD48(−) multipotent or progenitor stem cell. The CD34(+), cKit(−), CD38(−), Lin(−) multipotent or progenitor stem cell or the CD150(+), CD244(−), CD48(−) multipotent or progenitor stem cell, i.e., the HSC, may be, but not limited to, smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). The HSC is a multipotent or progenitor stem cell having a nucleus. In the case of the CD34(+), cKit(−), CD38(−), Lin(−) multipotent or progenitor stem cell, the HSC can express the cell (surface) marker CD34 and lacks expression of the cell (surface) markers cKit, CD38 and Lin. In the case of the CD150(+), CD244(−), CD48(−) multipotent or progenitor stem cell, the HSC can express the cell (surface) marker CD150 and lacks expression of the two cell (surface) markers CD244 and CD48. The HSC may be characterized by CD34(+), cKit(−), Lin(−) and CD38(−) or as CD150(+), CD244(−) and CD48(−).

A marrow-isolated adult multilineage inducible (MIAMI) cell, which is a progenitor stem cell having a nucleus, could be a CD29(+), CD63(+), CD81(+), CD122(+), CD164(+)

progenitor stem cell. The MIAMI cell can express the cell (surface) markers CD29, CD63, CD81, CD122 and CD164 and may be characterized by CD29(+), CD63(+), CD81(+), CD122(+) and CD164(+). A pre mesenchymal stem cell (pre-MSC), which is a progenitor stem cell having a nucleus, could be a SSEA1(+) progenitor stem cell. The pre-MSC can express the cell (surface) marker SSEA1 and may be characterized by SSEA1(+). Each of the MIAMI cell and the pre-MSC may be, but not limited to, greater than 6, 7 or 10 micrometers, such as between 8 and 15 micrometers, in size (as defined by the above-mentioned size (Z) of a cell).

A multipotent progenitor cell (MPP), which is a progenitor stem cell having a nucleus, could be a CD34(+), cKit(+), CD38(−), Lin(−) progenitor stem cell or a CD150(−), CD244(+), CD48(−) progenitor stem cell. The CD34(+), cKit(+), CD38(−), Lin(−) progenitor stem cell or the CD150(−), CD244(+), CD48(−) progenitor stem cell, i.e., the MPP, may be, but not limited to, greater than 6, 7 or 10 micrometers, such as between 8 and 15 micrometers, in size (as defined by the above-mentioned size (Z) of a cell). In the case of the CD34(+), cKit(+), CD38(−), Lin(−) progenitor stem cell, the MPP can express the two cell (surface) markers CD34 and cKit and lacks expression of the two cell (surface) markers CD38 and Lin. In the case of the CD150(−), CD244(+), CD48(−) progenitor stem cell, the MPP can express the cell (surface) marker CD244 and lacks expression of the two cell (surface) markers CD150 and CD48. The MPP may be characterized by CD34(+), cKit(+), CD38(−) and Lin(−) or as CD150(−), CD244(+) and CD48(−).

A lineage-restricted progenitor cell (LRP), which is a progenitor stem cell having a nucleus, could be a CD34(−), cKit(+), CD38(−), Lin(−) progenitor stem cell or a CD150(−), CD244(+), CD48(+) progenitor stem cell. The CD34(−), cKit(+), CD38(−), Lin(−) progenitor stem cell or the CD150(−), CD244(+), CD48(+) progenitor stem cell, i.e., the LRP, may be, but not limited to, greater than 6, 7 or 10 micrometers, such as between 8 and 15 micrometers, in size (as defined by the above-mentioned size (Z) of a cell). In the case of the CD34(−), cKit(+), CD38(−), Lin(−) progenitor stem cell, the LRP can express the cell (surface) marker cKit and lacks expression of the cell (surface) markers CD34, CD38 and Lin. In the case of the CD150(−), CD244(+), CD48(+) progenitor stem cell, the LRP can express the two cell (surface) markers CD244 and CD48 and lacks expression of the cell (surface) marker CD150. The LRP may be characterized by CD34(−), cKit(+), CD38(−) and Lin(−) or as CD150(−), CD244(+) and CD48(+).

A common myeloid progenitor cell (CMP) or common lymphocyte progenitor cell (CLP) is a progenitor stem cell having a nucleus and could be a CD90(+) progenitor stem cell. The CD90(+) progenitor stem cell, i.e., the CMP or CLP, may be, but not limited to, greater than 6, 7 or 10 micrometers, such as between 8 and 15 micrometers, in size (as defined by the above-mentioned size (Z) of a cell). The CMP or CLP could express the cell (surface) marker CD90 and may be characterized by CD90(+).

Description of Actions or Stimuli (X):

The actions or stimuli (X) include the following actions or stimuli (X1), (X2), (X3) and (X4).

The following items are examples of the actions or stimuli (X1). The items are generally believed to be good for a subject such as a human body or entity or a non-human body or entity, yet requiring further assessment and confirmation using more direct, convincing and quantitative measurements or tests provided by this invention.

A. Taking drugs such as synthetic drugs or drugs including extractions from nature;

B. Taking herbal or Chinese medicine such as *Cordyceps sinensis*, ginseng, Lycium Chinense Mill, *Ganoderma lucidum* (lingzhi), *Taiwanofungus camphoratus*, and/or Brazil mushroom;

C. Taking nutrients or dietary supplements, such as nutrition pills or powder, including or comprising the following materials or elements: vitamins (Vitamin A, B, B complex, $B_{12}$, D, $D_3$, E, etc.), macro and/or trace minerals (e.g., calcium, sodium, potassium, fluorine, bromine, chromium, iodine, silicon, selenium, beryllium, lithium, cobalt, vanadium and/or nickel), polysaccharides, high molecular weight fucose-containing glycoproteins, seaweed (including green algae, blue-green algae, brown algae, and etc.), fucose, fucoidan that is a major component of brown algae, oligo fucoidan, algae, brown algae containing fucoidan (for example, brown algae grown and produced in Okinawa, Japan), Japanese Mozuku, green algae, blue-green algae (or blue algae), brown algae (including mozuku, kelp, *undaria pinnatifida, sargassum fusiforme*, and etc.), green tea essence, phytochemical (e.g., isoflavones or phytoestrogen), lycopene, epigallocatechin gallate (EGCG), gluconutrients (e.g., Xylose, Galactose, Glucose, Mannose, N-acetyl glucosamine, N-acetyl galaetosanmine, or N-acetyl neuraminic acid), fish oil, China toona (*toona sinensis*), and/or nutrients extracted from plant, leaf, fruit, vegetable, fish, seaweed, or algae;

D. Practicing a vegetarian dietary;

E. Taking healthy food or organic food;

F. Taking alternative (non-traditional) medicine;

G. Being subjected to alternative therapy or treatment such as the Gerson therapy or the Breuss cancer cure;

H. Being subjected to acupuncture;

I. Being subjected to massage such as foot massage;

J. Exercising such as walking, jogging, dancing, gymnastics, Yuga, aerobic exercise, and/or Taijiquan (Chinese shadow exercise);

K. Sleeping (for purpose of measuring the quality of sleep);

L. Meditating;

M. Exercising a health improvement program or a disease curing program designed by an individual, a health professional, or a medical doctor;

N. Taking a certain nutrient for improving health of a certain organ in a body, for example, taking lycopene to improve the health of prostate;

O. Taking a rehabilitation program to heal the injury, or to heal the wounds caused by surgery, or to cure a disease;

P. Taking a medicinal liquor (or called medicinal wine, medicated liquor or medicated wine) made from, e.g., immersing one Chinese medicine or multiple Chinese medicines in liquor or wine for a period of time, such as ginseng wine made from immersing ginseng in a high alcohol concentration rice wine for a month;

Q. Taking one or more drugs approved by a government department or authority, such as U.S. food and drug administration (U.S. FDA), for curing a specific disease (e.g., a cancer, a skin disease, or a kidney disease);

R. Taking or being subjected to treatments or therapies approved by a government department for curing a specific disease (e.g., a cancer, a skin disease, or a kidney disease);

S. Exercising or participating a religious activity, such as praying for peace or worshiping God;

T. Being exposed directly or indirectly to sunshine or sunlight (in the morning between, for example, 10 minutes before sunrise and 50 minutes after sunrise (containing significant amount of infrared (IR) light); or around noon, for example, between 11:30 AM to 12:30 PM (containing significant amount of ultra-violet (UV) light); or in the afternoon, for example, between 50 minutes before sunset and 10 minutes after sunset (containing significant amount of infrared (IR) light));

U. Being exposed to the lamp light or the light emitting diode (LED) light. The lamp or LED light may comprise a whole spectrum of visible lights, IR light, red light, green light, blue light, or UV light, or a combination of more than one of the above lights;

V. Exercising or being subjected to programs, therapies, methods, apparatus and/or systems for improving body's self-healing, for example, a method or therapy (e.g., Hyperbaric oxygen therapy) performed after injury or surgery for improving self-healing; and W. Taking a nutrient, a nutrient product, a nutrient fluid, a nutrient drink, a nutrient liquid, or a nutrient food containing (1) varieties of amino acids (such as Arginine, Histidine, Lysine, Aspartic acid, Glutamic acid, Serine, Threonine, Asparagine, Glutamine, Cysteine, Selenocysteine, Glycine, Proline, Alanine, Valine, Isoleucine, Leucine, Methionine, Phenylalanine, Tyrosine, or Tryptophan), (2) balanced amino acids, or (3) 9 essential amino acids (i.e., Histidine, Isoleucine, Leucine, Lysine, Methionine, Phenylalanine, Threonine, Tryptophan and Valine) for human bodies. For examples: (a) Product produced or extracted from the fermentation of red, green, black beans; (b) Liquid, fluid, or drink produced from fermentation of a fruit or a combination of fruits, such as sugar beet, apple, guava, kiwi, grape, pineapple, red pitaya (dragon fruit), green papaya, tomato, and/or avocado, etc.; (c) A medicinal liquor (or called medicinal wine, medicated liquor, or medicated wine) made from, e.g., immersing one Chinese medicine or multiple Chinese medicines in liquor or wine for a period of time, such as ginseng wine made from immersing ginseng in a high alcohol concentration rice wine for a month.

The following items are examples of the actions or stimuli (X2). The items are generally believed to be hazardous or harmful for a subject such as a human body or entity or a non-human body or entity, yet requiring further assessment and confirmation using a more direct, convincing and quantitative measurement or test provided by this invention.

A. Taking food with preservatives including, e.g., sodium benzoate, artificial food color, additives, nitrate, and/or nitrite;

B. Taking food with left-over pesticides including, e.g., herbicides, insecticides, fungicides, rodenticides, pediculicides and/or biocides;

C. Taking food or drink with hazardous additives or contaminations including, e.g., sulfites, plasticizer, and/or dioxin;

D. Smoking tobacco or cigarette;

E. Being subjected to cancer curing treatment such as chemotherapy or radiation therapy;

F. Working in a highly polluted environment, such as working in an environment having polluted air with high-concentration of $CO_2$, NO, $NO_2$, and/or organic solvents;

G. Working in a night-shift;

H. Taking a high-stressed task;

I. Taking overdose drugs;

J. Taking toxic drugs such as amphetamine, heroin, or cocaine; and

K. Being exposed to intensive radiation (such as X-ray, γ-ray) or electromagnetic fields.

The following items are examples of the actions or stimuli (X3). The items are generally believed to be controversial for health of a subject such as a human body or entity or a non-human body or entity, yet requiring further assessment and clarification using a more direct, convincing and quantitative measurement or test provided by this invention.

A. Drinking coffee;

B. Drinking tea;

C. Drinking drinks containing caffeine;

D. Drinking red wine;

E. Taking melatonin;

F. Taking sleeping pills;

G. Eating egg; and

H. Being exposed to sunshine or sunlight, including ultra-violet (UV) light.

The following items are examples of the actions or stimuli (X4).

A. Taking a new drug or medicine still in (1) the research or development stage in a laboratory, an research institute or a research department or division of a university or a company; (2) the pilot or experimental run; or (3) the investigational or experimental stage;

B. Taking an investigational (or experimental) drug that is (1) in the research or development stage in a laboratory, an research institute or a research department or division of a university or a company; (2) in the pilot or experimental run; or (3) being tested but has not yet approved by a government department or authority (e.g., U.S. FDA);

C. Taking a generic drug still in (1) the research or development stage in a laboratory, an research institute or a research department or division of a university or a company; (2) the pilot or experimental run; or (3) the investigational or experimental stage;

D. Taking a new nutrient or dietary supplement still in (1) the research or development stage in a laboratory, an research institute or a research department or division of a university or a company; (2) the pilot or experimental run; or (3) the investigational or experimental stage;

E. Taking a new food (possibly made from a new preparing or cooking recipe) or a new genetically-modified (GM) food;

F. Being subjected to a new therapy or treatment still in the investigational or experimental stage; and G. Being subjected to a newly designed health program.

The above-mentioned actions or stimuli (X) may be performed based on the dose, intensity, duration, frequency (each action may comprise more than one sub-actions, for example, taking 1 pill of drug for three times with one hour apart), and/or the time (for example, the time of a day (in the morning, at noon, in the afternoon, in the evening, or in the night), the time before, with or after the meal, or the time of the year (spring, summer, autumn or winter)). As an example, when a subject (such as human or non-human body) is taking a drug or a nutrient, the dose (for example, the amount in grams) and the time (for example, before or after breakfast, or before sleep) are factors needed to be considered. As another example, when the subject is exposed to the sunshine or sunlight, the time of the day (morning, noon or afternoon), the time of seasons (spring, summer, autumn, or winter), and the exposing duration (30 minutes, 1 hour or 2 hours) are factors needed to be considered.

Description of Subject (S) and Tissue Sample (P):

A subject (S), which may be applied to all following paragraphs, may be a human body or entity, such as child, teenager, man, woman or graybeard. Alternatively, the subject (S) may be a non-human body or entity (creature), such as pet animal, farm animal, experimental animal, disease-model animal, or a type of an insect. Examples of the pet, farm, experimental or disease-model animal are as below: primate (e.g., monkey or gorilla), dog, rodent (e.g., mouse or guinea pig), cat, horse, cow, sheep, pig, chicken, duck, goose, bird, elephant, frog, and fish.

A tissue sample (P) containing various cells may be extracted, taken, obtained or derived from a bodily fluid or solid tissue of the subject (S). The bodily fluid of the subject (S) may be, but not limited to, blood (e.g., peripheral blood) or bone marrow. In the case of the subject (S) being a human body or entity, the bodily fluid may be human bone marrow or human blood such as peripheral blood. Peripheral blood is the flowing, circulating blood of the body. The solid tissue of the subject (S) may be, but not limited to, nerve, muscle, skin, gut, bone, kidney, liver, pancreas, thymus, adipocyte, or fat tissue. The tissue sample (P) may be a bodily fluid sample (e.g., peripheral-blood sample, whole-blood sample, or bone-marrow sample) when the tissue sample (P) is obtained from the bodily fluid of the subject (S). Whole blood may be collected from peripheral blood of the subject (S) such as human body or entity and then typically combined with an anticoagulant, but is generally otherwise unprocessed. The tissue sample (P) may be a solid tissue sample (e.g., muscle sample or adipocyte sample) when the tissue sample (P) is obtained from the solid tissue of the subject (S). In the case of the subject (S) being a human body or entity, the tissue sample (P) may be a human bone-marrow sample or a human blood sample such as peripheral-blood sample or whole-blood sample.

Description of Test, Assessment or Measurement (M0):

When a tissue sample extracted, taken, obtained or derived from a subject that may be referred to the above-mentioned subject (S) is a whole-blood sample, the test, assessment or measurement (M0) may be performed to obtain results or data related to one or more types of the above-mentioned stem cells from the whole-blood sample by steps of performing a purification process (Y0) and then performing an assay process (T0).

The purification process (Y0) may be performed in one of the following two ways to treat or process the whole-blood sample extracted, taken, obtained or derived from the subject.

In the first way, a blood-containing sample may be prepared by adding a cocktail (e.g., RosetteSep® Human Progenitor Enrichment Cocktail) to a tube containing the whole-blood sample (e.g., adding 100 μL of the Human Progenitor Enrichment Cocktail to 2 mL of the whole-blood sample) and then mixing the whole-blood sample and the cocktail well. Next, the blood-containing sample is incubated at room temperature for a suitable time period (e.g., about 20 minutes). After incubation, the blood-containing sample is diluted with a first medium (e.g., 2% fetal bovine serum (FBS)/phosphate-buffered saline (PBS)) and then mixed gently so as to form a diluted sample. Next, the diluted sample is poured into a tube containing a reagent such as Ficoll-Paque® slowly so as to be prevented from mixing with the reagent and to be overlaid or layered on top of the reagent. Next, by centrifuging the mixture of the diluted sample and the reagent at a suitable rotational speed (e.g., 3,000 rpm) for a suitable time period (e.g., 20 minutes) at room temperature, four distinct layers are formed. The four distinct layers can be, from the top to the bottom: a first layer of plasma, a second layer of multi-type cells, a third layer of the reagent, and a fourth layer of red blood cells. Next, the first and second layers and the top half of the third layer are transferred into a tube and then centrifuged at a suitable rotational speed (e.g., 3,000 rpm) for a suitable time period (e.g., 20 minutes) so as to from a centrifuged sample. Next, the supernatant of the centrifuged sample is discarded, and the multi-type cells of the centrifuged sample are re-suspended in a second medium (e.g., 2% FBS/PBS). Next, a suitable buffer (e.g., 3× red-blood-cell (RBC) lysis buffer) is added to the second medium. After being incubated in the second medium at room temperature for a suitable time period (e.g., 10 minutes), cells in the second medium added with the buffer are washed with a third medium (e.g., 2% FBS/PBS) twice and then re-suspended in a fourth medium (e.g., 2% bovine serum albumin (BSA)/PBS). Therefore, a test sample including the cells and the fourth medium is obtained and may be used in the following assay process (T0).

In the second way, a blood-containing sample may be prepared by adding one volume of 6% Hetastarch to five volumes of the whole-blood sample and then incubated at room temperature (e.g., about 27 degrees Celsius) for a suitable time period (e.g., between 30 minutes and 90 minutes). The 6% Hetastarch is a solution containing 6% of Hetastarch in a phosphate-buffered saline (PBS), wherein every 100 mL PBS contains 6 g of Hetastarch. Once the blood-containing sample is formed with two separate layers, the top layer (i.e., cell layer) of the blood-containing sample is pipetted out into a tube without disturbance of the underlying layer (i.e., RBC layer) of the blood-containing sample. Next, the top layer in the tube is centrifuged at a suitable rotational speed (e.g., 3,000 rpm) for a suitable time period (e.g., 15 minutes) so as to obtain a centrifuged sample. After centrifugation, the supernatant of the centrifuged sample is discarded, and cells of the centrifuged sample are washed with a first solution (e.g., PBS). Next, the cells can be re-suspended in a second solution (e.g., 2% BSA/PBS). Therefore, a test sample including the cells and the second solution is obtained and may be used in the following assay process (T0).

After the purification process (Y0) is performed to obtain one of the above-mentioned test samples, the assay process (T0) is performed to analyze the one of the above-mentioned test samples so as to obtain a set of results or data related to one or more types of the above-mentioned stem cells from the whole-blood sample descriptively, qualitatively or quantitatively. The assay process (T0) may be achieved by flow cytometry. The flow cytometry may be employed to analyze many parameters of the whole-blood sample using a flow cytometer, a type of assay device, to perform steps of cell counting, sorting, and biomarker detecting. The flow cytometer may be used to analyze the positive expression of specific cell (surface) markers of the whole-blood sample. The set of results or data related to the one or more types of the above-mentioned stem cells from the whole-blood sample include types of stem cells and parameters, such as the number, the percentage and/or the sizes, of the one or more types of the above-mentioned stem cells.

Description of Test, Assessment or Measurement (M1):

The test, assessment or measurement (M1) can be performed by steps of performing a purification process (Y1) and then performing an assay process (T1).

The purification process (Y1) may be performed in one of the following two ways to treat or process a tissue sample extracted, taken, obtained or derived from a subject that may be referred to the above-mentioned subject (S). The tissue sample may be referred to the above-mentioned tissue sample (P). For example, the tissue sample is a bodily fluid sample (e.g., peripheral-blood sample, whole-blood sample, or bone-marrow sample) when the tissue sample is obtained from a bodily fluid (e.g., human blood, peripheral blood, or bone marrow) of the subject. Alternatively, the tissue sample is a solid tissue sample (e.g., muscle sample or adipocyte sample) when the tissue sample is obtained from a solid tissue (e.g., muscle or adipocyte) of the subject.

If the tissue sample is obtained from the solid tissue of the subject, collagenase may be added to treat the tissue sample for at least 6 or 8 hours at a suitable temperature (e.g., about 37° C., greater than 30° C., between 35° C. and 39° C., or between 30° C. and 40° C.) prior to the purification process (Y1).

In the first way, referring to FIG. 1, the tissue sample is transferred to a bag 10 that contains an anti-clotting reagent such as divalent cation chelating agent. The divalent cation chelating agent can be, but not limited to, an ethylenediaminetetraacetic acid (EDTA). A filter 11 is attached to the bottom of the bag 10 and can be used to ensure that only small cells flow out of the bag 10 and are collected in a tube 12a. The small cells flowing through the filter 11 are smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). Next, the tube 12a is centrifuged by a centrifuge 13 at a suitable centrifugal force (e.g., 1,000 g, greater than 700 g, greater than 1,300 g, between 500 g and 2,500 g, or between 800 g and 1,600 g) for a suitable time period (e.g., about 18 minutes, longer than 12 minutes, longer than 16 minutes, between 10 minutes and 30 minutes, or between 15 minutes and 22 minutes) so as to isolate the small cells. Next, the small cells are placed in a medium, including phosphate-buffered saline (PBS) and bovine serum albumin (BSA) for example, and re-suspended in the medium so as to obtain a test sample 14a including the small cells and the medium. The test sample 14a may be used in the following assay process (T1).

Figure 2:
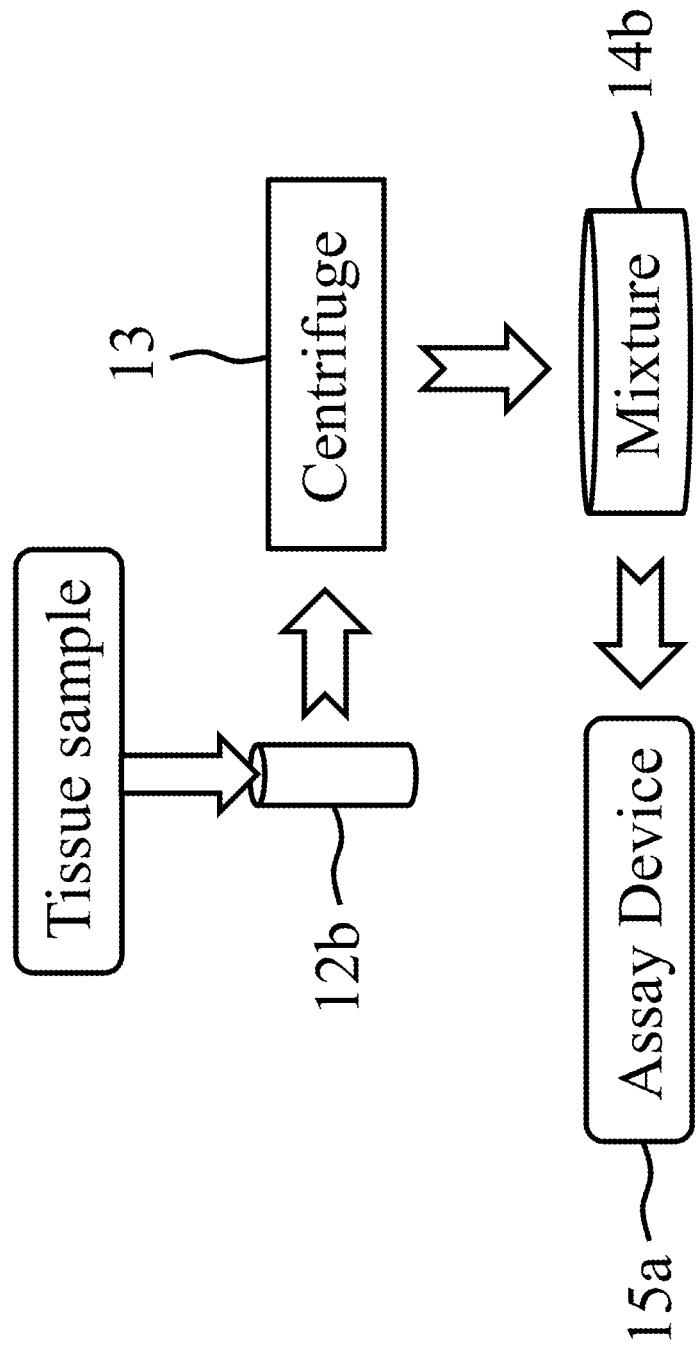

In the second way, referring to FIG. 2, if the tissue sample is obtained from the solid tissue, the tissue sample treated with the collagenase is placed into a tube 12b. Next, the tube 12b is centrifuged by the centrifuge 13 at a low speed of a suitable centrifugal force (e.g., 100 g, between 50 g and 450 g, or between 80 g and 250 g) for a suitable time period (e.g., about 10 minutes, longer than 8 minutes, longer than 12 minutes, between 8 minutes and 15 minutes, or between 9 minutes and 20 minutes) and then at a high speed of a suitable centrifugal force (e.g., 1,000 g, greater than 700 g, greater than 1,300 g, between 500 g and 2,500 g, or between 800 g and 1,600 g) for a suitable time period (e.g., about 18 minutes, longer than 12 minutes, longer than 16 minutes, between 10 minutes and 30 minutes, or between 15 minutes and 22 minutes) so as to isolate small cells from the tissue sample. The isolated small cells are smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). Next, the small cells are placed in a medium, including PBS and BSA for example, and re-suspended in the medium so as to obtain a test sample 14b including the small cells and the medium. The test sample 14b may be used in the following assay process (T1).

Figure 3:
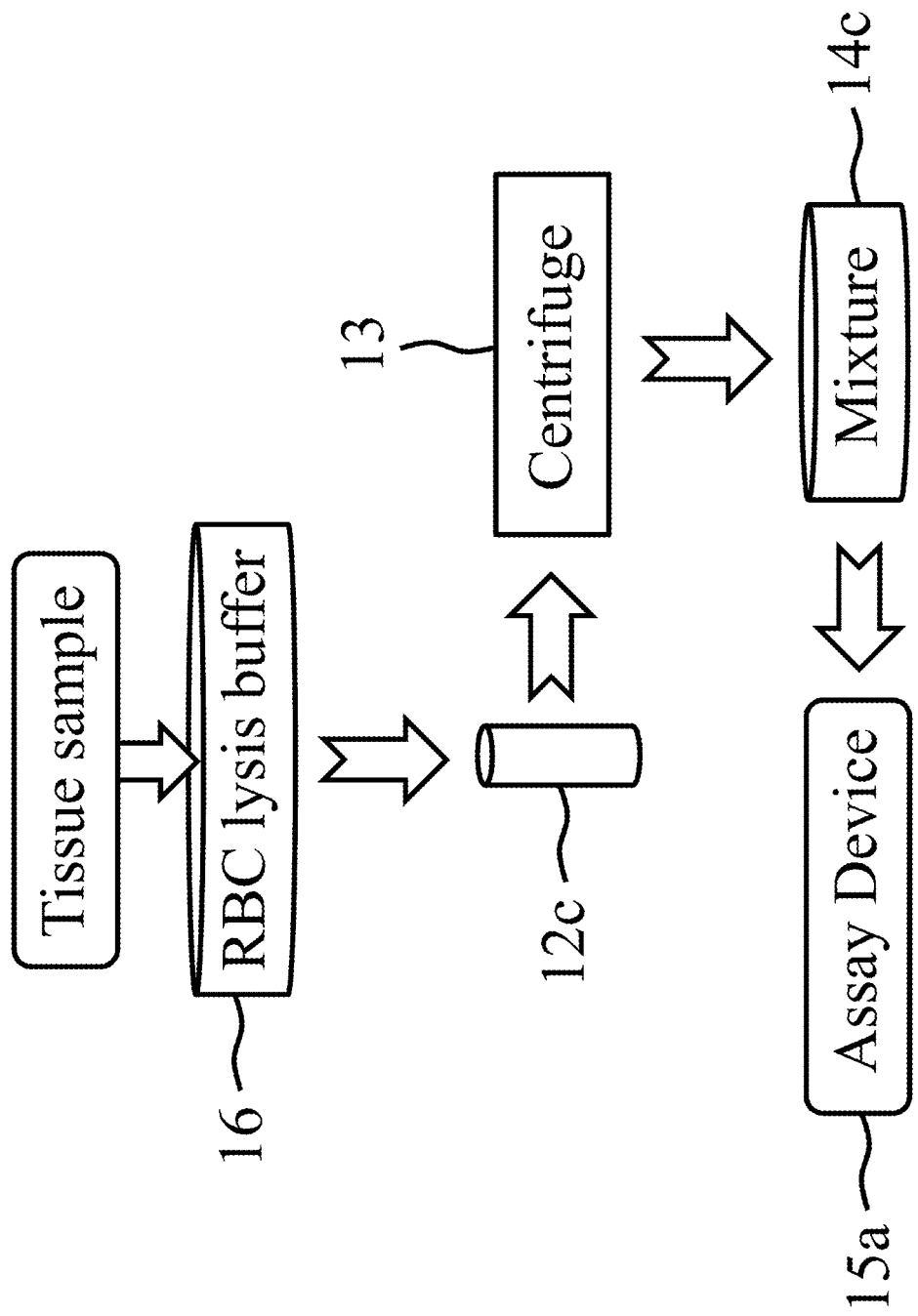

In the second way, referring to FIG. 3, if the tissue sample is obtained from the bodily fluid, the tissue sample is incubated with a red-blood-cell (RBC) lysis buffer 16 for a suitable time period (e.g., about 10 minutes, longer than 8 minutes, longer than 12 minutes, between 8 minutes and 15 minutes, or between 9 minutes and 20 minutes) in order to eliminate all of red blood cells of the tissue sample. Next, the mixture including the tissue sample and the buffer 16 is poured into a tube 12c. Next, the tube 12c is centrifuged by the centrifuge 13 at a low speed of a suitable centrifugal force (e.g., 100 g, between 50 g and 450 g, or between 80 g and 250 g) for a suitable time period (e.g., about 10 minutes, longer than 8 minutes, longer than 12 minutes, between 8 minutes and 15 minutes, or between 9 minutes and 20 minutes) and then at a high speed of a suitable centrifugal force (e.g., 1,000 g, greater than 700 g, greater than 1,300 g, between 500 g and 2,500 g, or between 800 g and 1,600 g) for a suitable time period (e.g., about 18 minutes, longer than 12 minutes, longer than 16 minutes, between 10 minutes and 30 minutes, or between 15 minutes and 22 minutes) so as to isolate small cells from the mixture including the tissue sample and the buffer 16. The isolated small cells are smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). Next, the small cells are placed in a medium, including PBS and BSA for example, and re-suspended in the medium so as to obtain a test sample 14c including the small cells and the medium. The test sample 14c may be used in the following assay process (T1).

After the purification process (Y1) is performed to obtain the test sample 14a, 14b or 14c, an assay device 15a, such as flow cytometer or RT-PCR device, as shown in FIG. 1, 2 or 3 is used to perform the assay process (T1) to analyze the test sample 14a, 14b and 14c so as to obtain a set of results or data of one or more types of small stem cells from the tissue sample descriptively, qualitatively or quantitatively. The set of results or data of the one or more types of small stem cells from the tissue sample include types of small stem cells and parameters, such as the number, the percentage and/or the sizes, of the one or more types of small stem cells. The one or more types of small stem cells from the tissue sample can be or may include, but not limited to, at least one type of totipotent stem cells, at least one type of pluripotent stem cells (e.g., SB-1 cells, SB-2 cells, BLSCs, VSELs, any other type of pluripotent stem cells, or any combination of the above-mentioned pluripotent stem cells), at least one type of multipotent stem cells (e.g., MSCs), hematopoietic stem cells (HSCs), and/or at least one type of progenitor stem cells, which can be, but not limited to, smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell).

The assay process (T1) may be achieved by flow cytometry or reverse transcription polymerase chain reaction (RT-PCR) analysis such as real-time RT-PCR analysis. The flow cytometry may be employed to analyze many parameters of a sample using a flow cytometer, a type of assay device 15a, to perform steps of cell counting, sorting, and biomarker detecting. The flow cytometer 15a may be used to analyze or look at the positive expression of specific cell (surface) markers of the sample. The RT-PCR analysis may be employed to detect and quantify gene expression in stem cells of a sample by using a (real-time) RT-PCR device, a type of assay device 15a. The RT-PCR results reveal that stem cells express various genes such as Oct4, Nanog, Nestin and alpha-feto protein.

Description of Test, Assessment or Measurement (M2):

The test, assessment or measurement (M2) can be performed by steps of performing a purification process (Y2) and then performing an assay process (T2).

The purification process (Y2) may be performed in one of the following two ways to treat or process a tissue sample extracted, taken, obtained or derived from a subject that may be referred to the above-mentioned subject (S). The tissue sample may be referred to the above-mentioned tissue sample (P). For example, the tissue sample is a bodily fluid sample (e.g., peripheral-blood sample, whole-blood sample, or bone-marrow sample) when the tissue sample is obtained from a bodily fluid (e.g., human blood, peripheral blood, or bone marrow) of the subject. Alternatively, the tissue sample is a solid tissue sample (e.g., muscle sample or adipocyte sample) when the tissue sample is obtained from a solid tissue (e.g., muscle or adipocyte) of the subject.

If the tissue sample is obtained from the solid tissue of the subject, collagenase may be added to treat the tissue sample for at least 6 or 8 hours at a suitable temperature (e.g., about 37° C., greater than 30° C., between 35° C. and 39° C., or between 30° C. and 40° C.) prior to the purification process (Y2).

Figure 4:
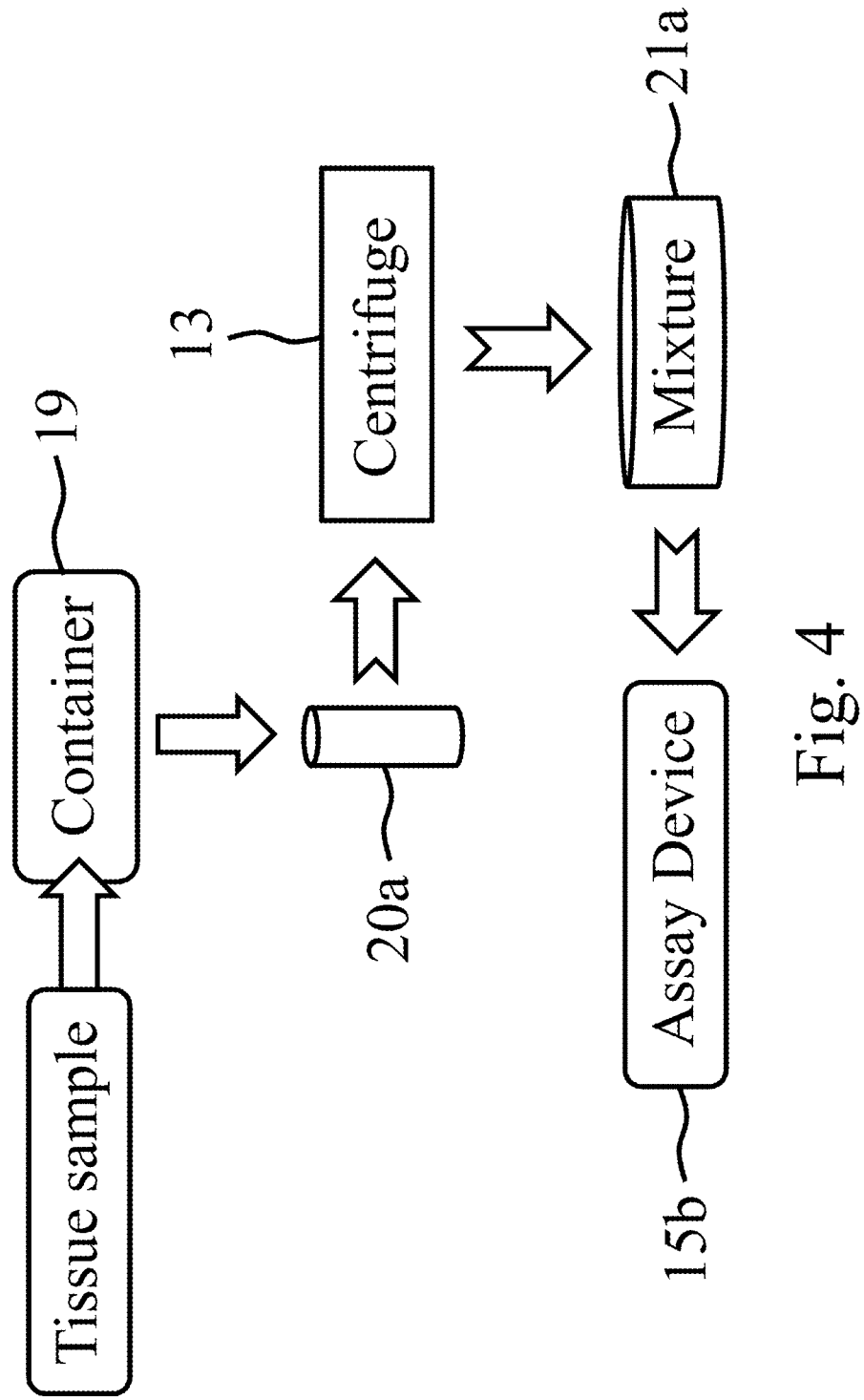

In the first way, referring to FIG. 4, the tissue sample is transferred to a container or bag 19 containing an anti-clotting reagent such as divalent cation chelating agent (e.g., EDTA) so as to obtain a mixture including the tissue sample and the anti-clotting reagent. The mixture is then poured into a tube 20a. Next, the tube 20a is centrifuged by a centrifuge 13 at a suitable centrifugal force (e.g., 1,000 g, greater than 700 g, greater than 1,300 g, between 500 g and 2,500 g, or between 800 g and 1,600 g) for a suitable time period (e.g., about 18 minutes, longer than 12 minutes, longer than 16 minutes, between 10 minutes and 30 minutes, or between 15 minutes and 22 minutes) so as to isolate all cells including small and large cells. The small cells may be, but not limited to, smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell). The large cells may be, but not limited to, greater than 6 micrometers in size (as defined by the above-mentioned size (Z) of a cell). Next, the cells including small and large cells are placed in a medium, including PBS and BSA for example, and re-suspended in the medium so as to obtain a test sample 21a that includes the medium and the cells including the small and large cells. The test sample 21a may be used in the following assay process (T2).

Figure 5:
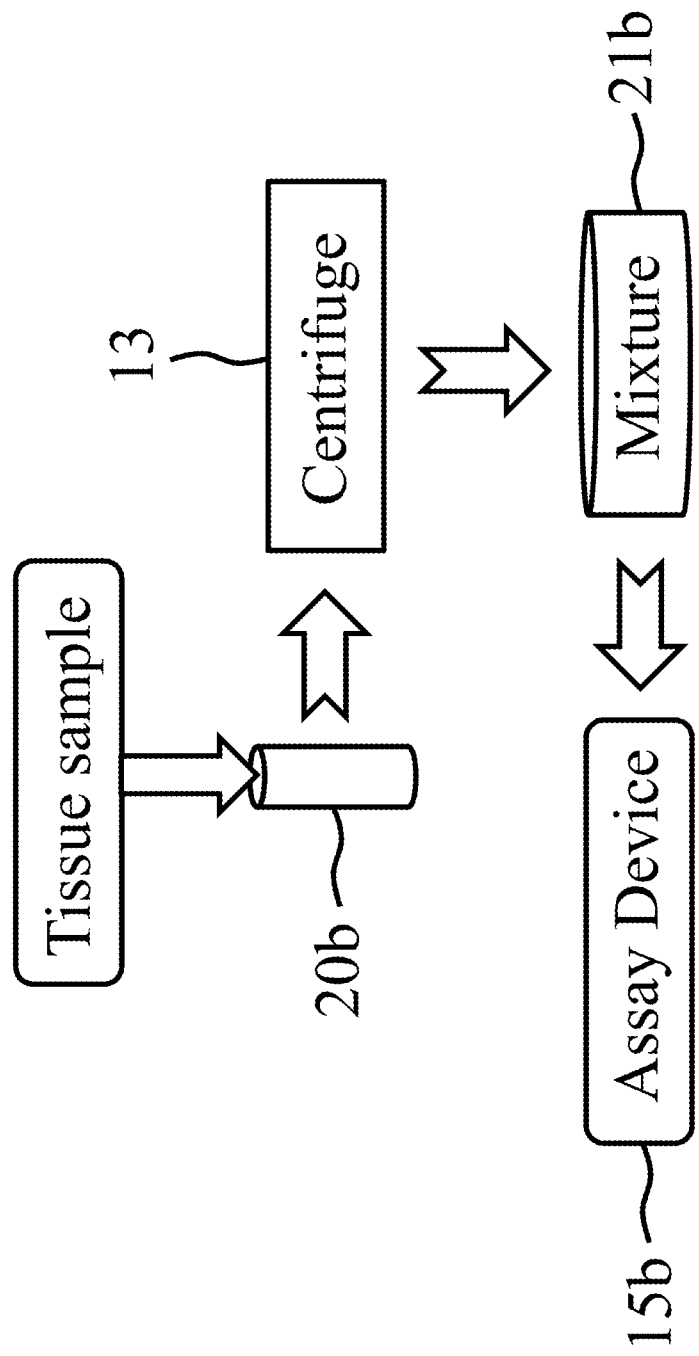

In the second way, referring to FIG. 5, if the tissue sample is obtained from the solid tissue, the tissue sample treated with the collagenase is placed into a tube 20b. Next, the tube 20b is centrifuged by the centrifuge 13 at a high speed of a suitable centrifugal force (e.g., 1,000 g, greater than 700 g, greater than 1,300 g, between 500 g and 2,500 g, or between 800 g and 1,600 g) for a suitable time period (e.g., about 18 minutes, longer than 12 minutes, longer than 16 minutes, between 10 minutes and 30 minutes, or between 15 minutes and 22 minutes) so as to isolate all cells including the small and large cells as defined in the first way of the purification process (Y2). Next, the cells including the small and large cells are placed in a medium, including PBS and BSA for example, and re-suspended in the medium so as to obtain a test sample 21b that includes the medium and the cells including the small and large cells. The test sample 21b may be used in the following assay process (T2).

Figure 6:
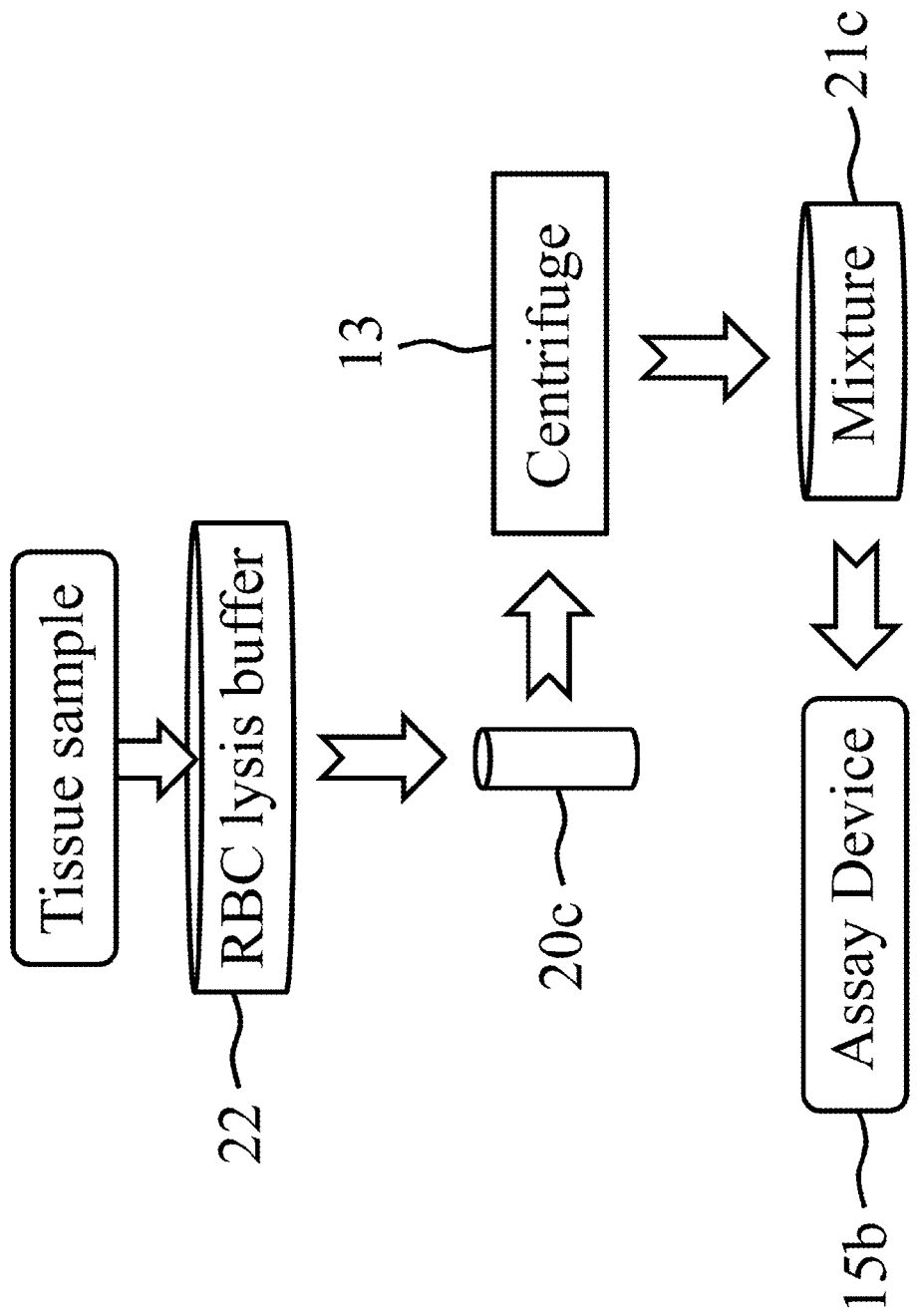

In the second way, referring to FIG. 6, if the tissue sample is obtained from the bodily fluid, the tissue sample is incubated with a RBC lysis buffer 22 for a suitable time period (e.g., about 10 minutes, longer than 8 minutes, longer than 12 minutes, between 8 minutes and 15 minutes, or between 9 minutes and 20 minutes) in order to eliminate all of red blood cells. Next, the mixture including the tissue sample and the buffer 22 is poured into a tube 20c. Next, the tube 20c is centrifuged by the centrifuge 13 at a high speed of a suitable centrifugal force (e.g., 1,000 g, greater than 700 g, greater than 1,300 g, between 500 g and 2,500 g, or between 800 g and 1,600 g) for a suitable time period (e.g., about 18 minutes, longer than 12 minutes, longer than 16 minutes, between 10 minutes and 30 minutes, or between 15 minutes and 22 minutes) so as to isolate all cells including the small and large cells as defined in the first way of the purification process (Y2). Next, the cells including the small and large cells are placed in a medium, including PBS and BSA for example, and re-suspended in the medium so as to obtain a test sample 21c that includes the medium and the cells including the small and large cells. The test sample 21c may be used in the following assay process (T2).

After the purification process (Y2) is performed to obtain the test sample 21a, 21b or 21c, an assay device 15b, such as flow cytometer or RT-PCR device, as shown in FIG. 4, 5 or 6 is used to perform the assay process (T2) to analyze the test sample 21a, 21b or 21c so as to obtain a set of results or data of one or more types of stem cells from the tissue sample descriptively, qualitatively or quantitatively. The set of results or data of the one or more types of stem cells from the tissue sample include types of stem cells and parameters, such as the number, the percentage and/or the sizes, of the one or more types of stem cells. The one or more types of stem cells from the tissue sample may be or may include the one or more types of small stem cells as mentioned or analyzed in the above assay process (T1) and/or one or more types of large stem cells, such as at least one type of multipotent stem cells (e.g., some types of MSCs), which may be greater than 6 micrometers in size (as defined by the above-mentioned size (Z) of a cell).

The assay process (T2) may be achieved by flow cytometry or RT-PCR analysis (e.g., real-time RT-PCR analysis). The flow cytometry may be employed to analyze many parameters of a sample using a flow cytometer, a type of assay device 15b, to perform steps of cell counting, sorting, and biomarker detecting. The flow cytometer 15b may be used to analyze or look at the positive expression of specific cell (surface) markers of the sample. The RT-PCR analysis may be employed to detect and quantify gene expression in stem cells of a sample by using a (real-time) RT-PCR device, a type of assay device 15b. The RT-PCR results reveal that stem cells express various genes such as Oct4, Nanog, Nestin and alpha-feto protein.

Description of Test, Assessment or Measurement (M3):

The test, assessment or measurement (M3) involves analyzing a tissue sample (usually blood sample) from a subject (such as human body) that may be referred to the above-mentioned subject (S) by measuring or detecting certain classes of antibodies (qualitatively) and/or the amount of certain classes of antibodies (quantitatively). Antibodies, also known as immunoglobulin proteins, are used by the immune system to identify and neutralize microscopic invaders such as viruses or bacteria. Antibodies recognize specific structures of invading foreign objects (such as such as viruses or bacteria). The specific structures that are recognized are called antigens. There are five different classes of antibodies: IgE, IgA, IgG, IgM, and IgD.

The present invention discloses multiple methods of identifying, evaluating or assessing an effect of one or more of the above-mentioned actions or stimuli (X) on a human body or entity or a non-human body or entity based on stem cells.

Immunity may be enhanced by increasing the number of (specific) stem cells in the body of a human since the presence of stem cells leads to a decrease in myeloid-derived suppressor cells (MDSCs) and a subsequent increase in natural killer cells (NK cells), T cells and B cells, aiding in the curing of a disease. The increasing number of stem cells also improves the body's repair function, contributing to anti-aging properties. Therefore, when a human or non-human (body) has more stem cells such as totipotent stem cells, pluripotent stem cells (e.g., SB-1 cells, SB-2 cells, BLSCs, or VSELs), multipotent stem cells (e.g., MSCs), progenitor stem cells or HSCs, the human or non-human (body) has a better immune system. The human or non-human (body) having a better immune system can be healthier and can be easily recovered from a disease.

First Embodiment

Figure 7:
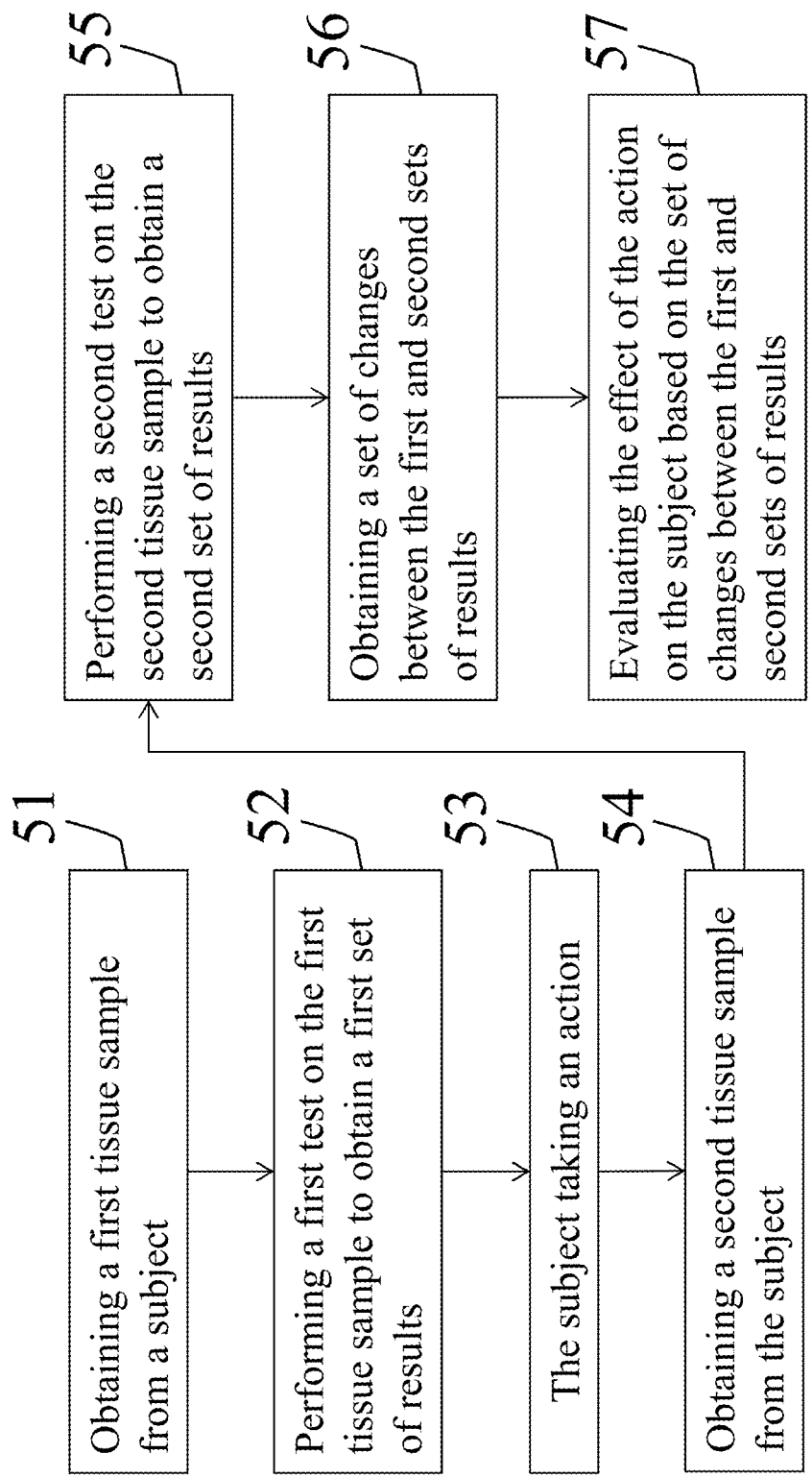
FIG. 7 shows a flow chart of identifying, evaluating or assessing the effect of at least one action or stimulus on a subject according to a first embodiment of the present disclosure.

FIG. 7 is a flow chart of identifying, evaluating or assessing the effect of one or more of the above-mentioned actions or stimuli (X) on a subject. Referring to FIG. 7, in step 51, a first tissue sample, which may be referred to the above-mentioned tissue sample (P), is extracted, taken, obtained or derived from the subject, which may be referred to the above-mentioned subject (S). Next, in step 52, a first test, assessment or measurement including extracting, characterizing, assessing and measuring stem cells is performed, referring to one of the above-mentioned tests, assessments or measurements (M0), (M1) and (M2), on the first tissue sample to obtain a first set of results or data related to one or more types of stem cells from the first tissue sample descriptively, qualitatively or quantitatively.

The first set of results or data include multiple results or data $R_{1,1}$-$R_{1,b}$, $R_{2,1}$-$R_{2,b}$, . . . , and $R_{a,1}$-$R_{a,b}$, where "a" is a positive integer such as one of the numbers from 3 to 14, and "b" is a positive integer such as 2 or 3. The notation $R_{1,1}$-$R_{1,b}$ means a series of results or data: $R_{1,1}$, $R_{1,2}$, . . . , to $R_{1,b}$. The notation $R_{2,1}$-$R_{2,b}$ means a series of results or data: $R_{2,1}$, $R_{2,2}$, . . . , to $R_{2,b}$. The notation $R_{a,1}$-$R_{a,b}$ means a series of results or data: $R_{a,1}$, $R_{a,2}$, . . . , to $R_{a,b}$. The first number in the subscript of R, i.e., the number immediately following the letter of R, i.e., from 1 to a, represents a certain selected type of stem cells or a group of selected two or more than two types of stem cells. The number a may be the number of all categories of stem cells or the number of all groups of stem cells. The second number in the subscript of R, i.e., the number immediately following the first number, i.e., from 1 to b, represents data types. The number b may be the number of data types.

With regard to the first number in the subscript of R, the results or data $R_{1,1}$-$R_{1,b}$ having the first number 1 in the subscript of R are results or data related to, for example, SB-1 cells. The results or data $R_{2,1}$-$R_{2,b}$ having the first number 2 in the subscript of R are results or data related to, for example, SB-2 cells. The results or data $R_{3,1}$-$R_{3,b}$ having the first number 3 in the subscript of R are results or data related to, for example, BLSCs. The results or data $R_{4,1}$-$R_{4,b}$ having the first number 4 in the subscript of R are results or data related to, for example, VSELs. The results or data $R_{5,1}$-$R_{5,b}$ having the first number 5 in the subscript of R are results or data related to, for example, one type of multipotent cells (e.g., MSCs, MAPCs or HSCs). The results or data $R_{6,1}$-$R_{6,b}$ having the first number 6 in the subscript of R are results or data related to, for example, another type of multipotent cells (e.g., BMSCs or MASCs). The results or data $R_{7,1}$-$R_{7,b}$ having the first number 7 in the subscript of R are results or data related to, for example, one or more types of totipotent stem cells. The results or data $R_{8,1}$-$R_{8,b}$ having the first number 8 in the subscript of R are results or data related to, for example, one or more types of progenitor stem cells, including, e.g., one, more or all of neural stem cells, retina stem cells, olfactory bulbs stem cells, epidermal stem cells, muscle stem cells, intestine stem cells, pancreatic stem cells, heart stem cells, liver stem cells, kidney stem cell, endothelial stem cells, adipocyte or adipose-derived stem cells, HSCs, MIAMI cells, pre-MSCs, MPPs, LRPs, CMPs, and CLPs). The results or data $R_{9,1}$-$R_{9,b}$ having the first number 9 in the subscript of R are results or data related to, for example, a combination or group of at least two types of pluripotent stem cells (e.g., SB-1 cells and SB-2 cells). The results or data $R_{10,1}$-$R_{10,b}$ having the first number 10 in the subscript of R are results or data related to, for example, a combination or group of one or more types of pluripotent stem cells (e.g., SB-1 cells and/or SB-2 cells) and one or more types of multipotent stem cells (e.g., MSCs, MAPCs, and/or HSCs). The results or data $R_{11,1}$-$R_{11,b}$ having the first number 11 in the subscript of R are results or data related to, for example, all types of stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)), which include one, more or all of SB-1 cells, SB-2 cells, BLSCs, VSELs, MSCs, MAPCs, BMSCs, MASCs, HSCs, MIAMI cells, pre-MSCs, MPPs, LRPs, CMPs, and CLPs. The number of all types of stem cells that can be detected or found (e.g., in the tissue sample) may be equal to or more than 3, 5, 10, 15, 20, 25, 50, 100 or 1,000 for cases requiring more information. The results or data $R_{12,1}$-$R_{12,b}$ having the first number 12 in the subscript of R are results or data related to, for example, a combination or group of at least two or three types of totipotent, pluripotent, multipotent and/or progenitor stem cells. The results or data $R_{13,1}$-$R_{13,b}$ having the first number 13 in the subscript of R are results or data related to, for example, a combination or group of selected two or more than two types of stem cells, which may include one, more or all of SB-1 cells, SB-2 cells, BLSCs, VSELs, MSCs, MAPCs, BMSCs, MASCs, HSCs, MIAMI cells, pre-MSCs, neural stem cells, retina stem cells, olfactory bulbs stem cells, epidermal stem cells, muscle stem cells, intestine stem cells, pancreatic stem cells, heart stem cells, liver stem cells, kidney stem cell, endothelial stem cells, adipocyte or adipose-derived stem cells, MPPs, LRPs, CMPs, and CLPs. For cases requiring more information for the human or non-human body health condition and stem cell dynamics, the combination or group of the selected two or more than two types of stem cells may include more than 3, 5, 10, 15, 20, 25, 50, 100 or 1,000 types of stem cells including one, more, or all of the above-mentioned types of stem cells. The results or data $R_{14,1}$-$R_{14,b}$ having the first number 14 in the subscript of R are results or data related to, for example, all of the stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)), which include more than 3, 5, 10, 15, 20, 25, 50, 100 or 1,000 types of stem cells containing one, more or all of SB-1 cells, SB-2 cells, BLSCs, VSELs, MSCs, MAPCs, BMSCs, MASCs, HSCs, MIAMI cells, pre-MSCs, MPPs, LRPs, CMPs, and CLPs.

With regard to the second number in the subscript of R, the results or data $R_{1,1}$-$R_{a,1}$ having the second number 1 in the subscript of R can be results or data related to, for example, the number of stem cells of a specific type or a combination or group of multiple types. The results or data $R_{1,2}$-$R_{a,2}$ having the second number 2 in the subscript of R can be results or data related to, for example, the percentage of the number of stem cells of a specific type or a combination or group of multiple types to the total number of (small) biological or stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)). The results or data $R_{1,3}$-$R_{a,3}$ having the second number 3 in the subscript of R can be results or data related to, for example, the sizes or size distribution (for example, the average size, the peak size, or the variation of the size distribution) of stem cells of a specific type or a combination or group of multiple types.

For further elaboration, the result $R_{1,1}$ shows (or indicates) the number of SB-1 cells. The result $R_{1,2}$ shows the percentage of the number of SB-1 cells to the total number of (small) biological or stem cells that can be detected or found (e.g., in the tissue sample). The result $R_{1,3}$ shows the sizes or size distribution (for example, the average size, the peak size, or the variation of the size distribution) of SB-1 cells. The result $R_{11,1}$ shows (or indicates) the number of stem cells of all types that can be detected or found (e.g., in the tissue sample). The result $R_{11,2}$ shows the percentage of the number of stem cells of all types that can be detected or found (e.g., in the tissue sample) to the total number of (small) biological cells that can be detected or found (e.g., in the tissue sample). The result $R_{13,1}$ shows (or indicates) the number of stem cells of the combination or group of the selected two or more than two types. The result $R_{13,2}$ shows the percentage of the number of stem cells of the combination or group of the selected two or more than two types to the total number of (small) biological or stem cells that can be detected or found (e.g., in the tissue sample). The result $R_{14,1}$ shows (or indicates) the number of all of the stem cells that can be detected or found (e.g., in the tissue sample). The result $R_{14,2}$ shows the percentage of the number of all of the stem cells that can be detected or found (e.g., in the tissue sample) to the total number of (small) biological cells that can be detected or found (e.g., in the tissue sample). Other notations can be considered in a similar way.

Referring to FIG. 7, after the step 51 or 52 is performed, step 53 is performed. In the step 53, the subject takes or is subjected to the one or more of the actions or stimuli (X), such as taking nutrients or dietary supplements, taking one or more drugs approved by a government department (e.g., U.S. FDA) for curing a specific disease (e.g., a cancer), and/or being exposed to sunshine or sunlight. The one or more actions or stimuli illustrated herein may be performed based on the dose, intensity, duration, frequency (each action may comprise more than one sub-actions, for example, taking one pill of drug for three times with one hour apart), and/or the time (for example, the time of a day (in the morning, at noon, in the afternoon, in the evening, or in the night), the time before, with or after the meal, or the time of the year (spring, summer, autumn or winter)). As an example, when the subject is taking a drug or a nutrient, the dose (for example, the amount in grams), the time (for example, before or after breakfast, or before sleep) are factors needed to be considered. As another example, when the subject is exposed to the sunshine or sunlight, the time of the day (morning, noon or afternoon), the time of seasons (spring, summer, autumn, or winter), or the exposing duration (30 minutes, 1 hour, 2 hours) are factors needed to be considered.

After a specific period of time, such as longer than or equal to 15, 30, 60, 90 or 120 minutes or one, two or thirty days, or, for example, between 30 and 120 minutes, step 54 is performed following the step 53. In the step 54, a second tissue sample, which may be referred to the above-mentioned tissue sample (P), is extracted, taken, obtained or derived from the subject. The first and second tissue samples are, but not limited to, two samples obtained from the same type of tissue of the subject. For example, both of the first and second tissue samples may be obtained from peripheral blood, bone marrow, muscle or adipocyte of the subject.

Next, in step 55, a second test, assessment or measurement including extracting, characterizing, assessing and measuring stem cells is performed, referring to one of the above-mentioned tests, assessments or measurements (M0), (M1) and (M2), on the second tissue sample to obtain a second set of results or data related to one or more types of stem cells from the second tissue sample descriptively, qualitatively or quantitatively. The second set of results or data include the same types of information as the first set of results or data illustrated in the step 52, that is, the second set of results or data include multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for the second set of results or data are defined, described or specified as the first set of results or data illustrated in the step 52, respectively.

For collecting the same types of information and reducing experimental errors, both of the first and second tests, assessments or measurements for the first and second sets of results or data illustrated herein may be performed using the same method described in the above-mentioned test, assessment or measurement (M0), (M1) or (M2). The first and second sets of results or data illustrated herein include types of small stem cells and parameters (such as the number, the percentage and/or the sizes) of one or more types of small stem cells, as described in the assay process (T1) when the test, assessment or measurement (M1) is performed. Alternatively, the first and second sets of results or data illustrated herein include types of stem cells and parameters (such as the number, the percentage and/or the sizes) of one or more types of stem cells, as described in the assay process (T2) when the test, assessment or measurement (M2) is performed. Alternatively, the first and second sets of results or data illustrated herein include types of stem cells and parameters (such as the number, the percentage and/or the sizes) of one or more types of stem cells, as described in the assay process (T0) when the test, assessment or measurement (M0) is performed.

Next, referring to FIG. 7, in step 56, by comparing the first and second sets of results or data, a set of changes between the first and second sets of results or data may be obtained. The set of changes between the first and second sets of results or data may be obtained by performing: (1) a first operation (i.e., subtraction operation), that is, the second set of results or data $R_{1,1}$-$R_{a,b}$ minus the first set of results or data $R_{1,1}$-$R_{a,b}$, or (2) a second operation of calculating the rates of change between the first and second sets of results or data $R_{1,1}$-$R_{a,b}$, which can be calculated by subtracting the first set of results or data $R_{1,1}$-$R_{a,b}$ from the second set of results or data $R_{1,1}$-$R_{a,b}$, then dividing the subtracted results by the first set of results or data $R_{1,1}$-$R_{a,b}$, and finally multiplying the divided results by 100% (which converts the divided results into percent figures). The first and second sets of results or data $R_{1,1}$-$R_{a,b}$ employed in the first or second operation have the same first and second numbers in the subscript.

The set of changes between the first and second sets of results or data include multiple changes $\Delta_{1,1}$-$\Delta_{1,c}$, $\Delta_{2,1}$-$\Delta_{2,c}$, ..., and $\Delta_{a,1}$-$\Delta_{a,c}$, where "a" is a positive integer such as one of the numbers from 3 to 14, and "c" is a positive integer such as 2, 3, 4 or 5. The notation $\Delta_{1,1}$-$\Delta_{1,c}$ means a series of data: $\Delta_{1,1}$, $\Delta_{1,2}$, ..., to $\Delta_{1,c}$. The notation $\Delta_{2,1}$-$\Delta_{2,c}$ means a series of data: $\Delta_{2,1}$, $\Delta_{2,2}$, ..., to $\Delta_{2,c}$. The notation $\Delta_{a,1}$-$\Delta_{a,c}$ means a series of data: $\Delta_{a,1}$, $\Delta_{a,2}$, ..., to $\Delta_{a,c}$. The first number in the subscript of $\Delta$, i.e., the number immediately following the sign $\Delta$, i.e., from 1 to a, represents a certain selected type of stem cells or a group of selected two or more than two types of stem cells. The number a may be the number of all categories of stem cells or the number of all groups of stem cells. The second number in the subscript of $\Delta$, i.e., the number immediately following the first number, i.e., from 1 to c, represents data types. The number c may be the number of data types.

With regard to the first number in the subscript of $\Delta$, the first number in the subscript of $\Delta_{1,1}$-$\Delta_{a,c}$ is as the same specification as that of $R_{1,1}$-$R_{a,c}$ for the first set of results or data illustrated in the step 52 described herein. For example, the changes $\Delta_{1,1}$-$\Delta_{1,c}$ having the first number 1 in the subscript of $\Delta$ are changes related to, for example, SB-1 cells. The changes $\Delta_{2,1}$-$\Delta_{2,c}$ having the first number 2 in the subscript of $\Delta$ are changes related to, for example, SB-2 cells. The changes $\Delta_{11,1}$-$\Delta_{11,c}$ having the first number 11 in the subscript of $\Delta$ are changes related to, for example, all types of stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)), which include one, more or all of SB-1 cells, SB-2 cells, BLSCs, VSELs, MSCs, MAPCs, BMSCs, MASCs, HSCs, MIAMI cells, pre-MSCs, MPPs, LRPs, CMPs, and CLPs. The number of all types of stem cells that can be detected or found (e.g., in the tissue sample) may be equal to or more than 3, 5, 10, 15, 20, 25, 50, 100 or 1,000 for cases requiring more information. The changes $\Delta_{13,1}$-$\Delta_{13,c}$ having the first number 13 in the subscript of $\Delta$ are changes related to, for example, a combination or group of selected two or more than two types of stem cells, which may include one, more or all of SB-1 cells, SB-2 cells, BLSCs, VSELs, MSCs, MAPCs, BMSCs, MASCs, HSCs, MIAMI cells, pre-MSCs, neural stem cells, retina stem cells, olfactory bulbs stem cells, epidermal stem cells, muscle stem cells, intestine stem cells, pancreatic stem cells, heart stem cells, liver stem cells, kidney stem cell, endothelial stem cells, adipocyte or adipose-derived stem cells, MPPs, LRPs, CMPs, and CLPs. For cases requiring more information for the human or non-human body health condition and stem cell dynamics, the combination or group of the selected two or more than two types of stem cells may include more than 3, 5, 10, 15, 20, 25, 50, 100 or 1,000 types of stem cells including one, more, or all of the above-mentioned types of stem cells. The changes $\Delta_{14,1}$-$\Delta_{14,c}$ having the first number 14 in the subscript of $\Delta$ are changes related to, for example, all of the stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)), which include more than 3, 5, 10, 15, 20, 25, 50, 100 or 1,000 types of stem cells including one, more or all of SB-1 cells, SB-2 cells, BLSCs, VSELs, MSCs, MAPCs, BMSCs, MASCs, HSCs, MIAMI cells, pre-MSCs, MPPs, LRPs, CMPs, and CLPs. Other notations can be considered in a similar way.

With regard to the second number in the subscript of $\Delta$, the changes $\Delta_{1,1}$-$\Delta_{a,1}$ having the second number 1 in the subscript of $\Delta$ are changes related to, for example, an increase or decrease in the number of stem cells of a specific type or a combination or group of multiple types. The changes $\Delta_{1,2}$-$\Delta_{a,2}$ having the second number 2 in the subscript of $\Delta$ are changes related to, for example, the increasing or decreasing rate of change, e.g., an increase of W percent or a decrease of K percent, in the percentage of the number of stem cells of a specific type or a combination or group of multiple types to the total number of (small) biological or stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)), where "W" is a positive number greater than or equal to 10, 20, 30, 40, 50, 60, 70, 80, 90, 100, 200, 300, 500 or 900, and "K" is a positive number greater than or equal to 10, 20, 30, 40, 50, 60, 70, 80, or 90. The changes $\Delta_{1,3}$-$\Delta_{a,3}$ having the second number 3 in the subscript of $\Delta$ are changes related to, for example, the sizes or size distribution (for example, the average size, the peak size, or the variation of the size distribution) of stem cells of a specific type or a combination or group of multiple types. The changes $\Delta_{1,4}$-$\Delta_{a,4}$ having the second number 4 in the subscript of $\Delta$ are changes related to, for example, the increasing or decreasing rate of change, e.g., the increase of W percent or the decrease of K percent, in the number of stem cells of a specific type or a combination or group of multiple types. The changes $\Delta_{1,5}$-$\Delta_{a,5}$ having the second number 5 in the subscript of $\Delta$ are changes related to, for example, an increase or decrease in the percentage of the number of stem cells of a specific type or a combination or group of multiple types to the total number of (small) biological or stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)).

For further elaboration, the change $\Delta_{1,1}$ between the two results $R_{1,1}$ in the first and second sets shows an increase or decrease in the number of SB-1 cells, which may be obtained by, e.g., performing a subtraction operation, that is, the result $R_{1,1}$ in the second set minus the result $R_{1,1}$ in the first set. The change $\Delta_{1,2}$ between the two results $R_{1,2}$ in the first and second sets shows the increasing or decreasing rate of change, e.g., the increase of W percent or the decrease of K percent, in the percentage of the number of SB-1 cells to the total number of (small) biological or stem cells that can be detected or found (e.g., in the tissue sample), which may be obtained by, e.g., subtracting the result $R_{1,2}$ in the first set from the result $R_{1,2}$ in the second set, then dividing the subtracted result by the result $R_{1,2}$ in the first set, and finally multiplying the divided result by 100% (which converts the divided result into a percent figure). The change $\Delta_{1,3}$ between the two results $R_{1,3}$ in the first and second sets shows the change of the sizes or size distribution related to SB-1 cells. The change $\Delta_{1,4}$ between the two results $R_{1,1}$ in the first and second sets shows the increasing or decreasing rate of change, e.g., the increase of W percent or the decrease of K percent, in the number of SB-1 cells, which may be obtained by, e.g., subtracting the result $R_{1,1}$ in the first set from the result $R_{1,1}$ in the second set, then dividing the subtracted result by the result $R_{1,1}$ in the first set, and finally multiplying the divided result by 100% (which converts the divided result into a percent figure). The change $\Delta_{1,5}$ between the two results $R_{1,2}$ in the first and second sets shows an increase or decrease in the percentage of the number of SB-1 cells to the total number of (small) biological or stem cells that can be detected or found (e.g., in the tissue sample), which may be obtained by, e.g., performing a subtraction operation, that is, the result $R_{1,2}$ in the second set minus the result $R_{1,2}$ in the first set.

The change $\Delta_{11,1}$ between the two results $R_{11,1}$ in the first and second sets shows an increase or decrease in the number of stem cells of all types that can be detected or found (e.g., in the tissue sample), which may be obtained by, e.g., performing a subtraction operation, that is, the result $R_{11,1}$ in the second set minus the result $R_{11,1}$ in the first set. The change $\Delta_{11,4}$ between the two results $R_{11,1}$ in the first and second sets shows the increasing or decreasing rate of change, e.g., the increase of W percent or the decrease of K percent, in the number of stem cells of all types that can be detected or found (e.g., in the tissue sample), which may be obtained by, e.g., subtracting the result $R_{11,1}$ in the first set from the result $R_{11,1}$ in the second set, then dividing the subtracted result by the result $R_{11,1}$ in the first set, and finally multiplying the divided result by 100% (which converts the divided result into a percent figure). The change $\Delta_{13,1}$ between the two results $R_{13,1}$ in the first and second sets shows an increase or decrease in the number of stem cells of the combination or group of the selected two or more than two types, which may be obtained by, e.g., performing a subtraction operation, that is, the result $R_{13,1}$ in the second set minus the result $R_{13,1}$ in the first set. The change $\Delta_{13,4}$ between the two results $R_{13,1}$ in the first and second sets shows the increasing or decreasing rate of change, e.g., the increase of W percent or the decrease of K percent, in the number of stem cells of the combination or group of the selected two or more than two types, which may be obtained by, e.g., subtracting the result $R_{13,1}$ in the first set from the result $R_{13,1}$ in the second set, then dividing the subtracted result by the result $R_{13,1}$ in the first set, and finally multiplying the divided result by 100% (which converts the divided result into a percent figure). The change $\Delta_{14,1}$ between the two results $R_{14,1}$ in the first and second sets shows an increase or decrease in the number of all of the stem cells that can be detected or found (e.g., in the tissue sample), which may be obtained by, e.g., performing a subtraction operation, that is, the result $R_{14,1}$ in the second set minus the result $R_{14,1}$ in the first set. The change $\Delta_{14,4}$ between the two results $R_{14,1}$ in the first and second sets shows the increasing or decreasing rate of change, e.g., the increase of W percent or the decrease of K percent, in the number of all of the stem cells that can be detected or found (e.g., in the tissue sample), which may be obtained by, e.g., subtracting the result $R_{14,1}$ in the first set from the result $R_{14,1}$ in the second set, then dividing the subtracted result by the result $R_{14,1}$ in the first set, and finally multiplying the divided result by 100% (which converts the divided result into a percent figure). Other notations can be considered in a similar way.

Next, referring to FIG. 7, in step 57, based on the set of changes between the first and second sets of results or data, the effect of the one or more of the actions or stimuli (X) in the step 53 on the subject may be identified, determined, evaluated or assessed as effective to health or immunity, as harmful to health or immunity, or as ineffective or harmless to health or immunity. The first and second sets of results or data and the set of changes can be written as an evaluation (or examination) report or card.

The one or more of the actions or stimuli (X) in the step 53 may be evaluated as "effective to health or immunity" based on, e.g., the result that a selected one of the changes $\Delta_{1,1}$-$\Delta_{a,c}$ in the set of changes between the first and second sets of results or data, such as the change $\Delta_{1,1}$, has significant increase, as "harmful to health or immunity" based on, e.g., the result that the selected one of the changes $\Delta_{1,1}$-$\Delta_{a,c}$ in the set of changes between the first and second sets of results or data, such as the change $\Delta_{1,1}$, has significant decrease, or as "ineffective or harmless to health or immunity" based on, e.g., the result that the selected one of the changes $\Delta_{1,1}$-$\Delta_{a,c}$ in the set of changes between the first and second sets of results or data, such as the change $\Delta_{1,1}$, has not significant decrease or not significant increase.

Alternatively, the one or more of the actions or stimuli (X) in the step 53 may be evaluated as "effective to health or immunity" based on, e.g., the result that selected ones of the changes $\Delta_{1,1}$-$\Delta_{a,c}$ in the set of changes between the first and second sets of results or data, such as the changes $\Delta_{1,1}$ and $\Delta_{2,1}$, have significant increases, as "harmful to health or immunity" based on, e.g., the result that the selected ones of the changes $\Delta_{1,1}$-$\Delta_{a,c}$ in the set of changes between the first and second sets of results or data, such as the changes $\Delta_{1,1}$ and $\Delta_{2,1}$, have significant decreases, or as "ineffective or harmless to health or immunity" based on, e.g., the result that the selected ones or all of the changes $\Delta_{1,1}$-$\Delta_{a,c}$ in the set of changes between the first and second sets of results or data, such as the changes $\Delta_{1,1}$ and $\Delta_{2,1}$, have not significant decreases or not significant increases. The number of the selected ones of the changes $\Delta_{1,1}$-$\Delta_{a,c}$ may be equal to or more than 2, 3, 4, 5 or 6.

Alternatively, the one or more of the actions or stimuli in the step 53 may be evaluated as "effective to health or immunity" based on, e.g., the result that more than or equal to a number "u1" of the changes $\Delta_{1,1}$-$\Delta_{a,c}$ in the set of changes between the first and second sets of results or data, such as the changes $\Delta_{1,1}$, $\Delta_{2,1}$ and $\Delta_{3,1}$, have significant increases, as "harmful to health or immunity" based on, e.g., the result that more than or equal to the number "u1" of the changes $\Delta_{1,1}$-$\Delta_{a,c}$ in the set of changes between the first and second sets of results or data, such as the changes $\Delta_{1,1}$, $\Delta_{2,1}$ and $\Delta_{3,1}$, have significant decreases, or as "ineffective or harmless to health or immunity" based on, e.g., the result that less than the number "u1" of the changes $\Delta_{1,1}$-$\Delta_{a,c}$ in the set of changes between the first and second sets of results or data, such as none of the changes $\Delta_{1,1}$-$\Delta_{a,c}$, have significant increases or significant increases. The number "u1" may be any positive integer such as 2, 3, 4, 5 or 6.

Alternatively, by (1) performing first comparisons between the set of changes obtained in the step 56, such as an increase or decrease in the number of SB-1 cells (i.e., $\Delta_{1,1}$), and corresponding ones of criteria or standards (G), such as the criterion for an increase in the number of SB-1 cells (i.e., $G_{1,4}$) and/or the criterion for a decrease in the number of SB-1 cells ($G_{1,5}$), built up in the following step 109 of FIG. 9 or the following step 208 of FIG. 10 and/or (2) performing second comparisons between the second set of results or data obtained in the step 55, such as the number of SB-1 cells (i.e., $R_{1,1}$), and corresponding ones of the criteria or standards (G), such as the criterion for the upper limit of a range of the number of SB-1 cells (i.e., $G_{1,1}$) and/or the criterion for the lower limit of a range of the number of SB-1 cells (i.e., $G_{1,7}$), the effect of the one or more of the actions or stimuli (X) in the step 53 on the subject may be identified, determined, evaluated or assessed as effective to health or immunity, as harmful to health or immunity, or as ineffective or harmless to health or immunity.

For ensuring the safety (no significant side-effects or damages to the human or non-human body, for example, organs such as liver or kidney) of the one or more of the actions or stimuli (X) in the step 53, data about liver and kidney functions related to the subject before and after taking or being subjected to the one or more of the actions or stimuli (X) in the step 53 may need to be obtained as an option. The data about liver and kidney functions related to the subject before taking or being subjected to the one or more of the actions or stimuli (X) in the step 53 are defined as first data LK1, and the data about liver and kidney functions related to the subject after taking or being subjected to the one or more of the actions or stimuli (X) in the step 53 are defined as second data LK2. Each piece of the first and second data LK1 and LK2 may include, but not limited to, (1) data about kidney functions (such as blood urea nitrogen (BUN), glomerular filtration rate (GFR), creatinine, creatinine clearance rate (CCR), albumin/urine creatinine ratio (ACR), cystatin C, uric acid, microalbumin, urine routine, and/or urine sediment), and (2) data about liver functions (such as aspartate aminotransferase (AST), alanine aminotransferase (ALT), α-fetoprotein (AFP), total bilirubin, direct bilirubin, indirect bilirubin, albumin, globulin, albumin/globulin ratio, γ-glutamyltranspeptidase (γ-GT), alkaline phosphatase (ALP), prothrombin time (PT), HBsAg, Anti-HBs, and/or Anti-HCV). AST is also called glutamic oxaloacetic transaminase (GOT) or serum glutamic-oxaloacetic transaminase (SGOT). ALT is also called serum glutamic-pyruvic transaminase (SGPT), or glutamic pyruvic transaminase (GPT).

By comparing the second data LK2 with the first data LK1, the difference between the first and second data LK1 and LK2 may be obtained to identify or evaluate the effect of the one or more of the actions or stimuli (X) in the step 53 on the liver and kidney of the subject, as mentioned below.

If there is no (significant) difference between the first and second data LK1 and LK2, it could mean the one or more of the actions or stimuli (X) in the step 53 are harmless to the liver and kidney of the subject. In this case, if one or more of the changes $\Delta_{1,1}$-$\Delta_{a,c}$ in the set of changes between the first and second sets of results or data, herein defined as change data SCD1, have significant increases, the one or more of the actions or stimuli (X) in the step 53 can be evaluated as "effective to immunity without impacts or damages on the liver and/or kidney" and may be repeated by the subject again. If the change data SCD1 have significant decreases, the one or more of the actions or stimuli (X) in the step 53 could be evaluated as "harmful to immunity without impacts or damages on the liver and/or kidney" and may not be repeated by the subject again. If the change data SCD1 have not significant increases or not significant decreases, the one or more of the actions or stimuli (X) in the step 53 could be evaluated as "ineffective or harmless to immunity without impacts or damages on the liver and/or kidney" and may or may not be repeated by the subject again.

If the second data LK2 are (much or significantly) better than the first data LK1, it could mean the one or more of the actions or stimuli (X) in the step 53 are harmless but beneficial to the liver and/or kidney of the subject. In this case, if the change data SCD1 have significant increases, the one or more of the actions or stimuli (X) in the step 53 can be evaluated as "effective to immunity and beneficial to the liver and/or kidney" and may be repeated by the subject again. If the change data SCD1 have significant decreases, the one or more of the actions or stimuli (X) in the step 53 could be evaluated as "harmful to immunity but beneficial to the liver and/or kidney" and may not be repeated by the subject again. If the change data SCD1 have not significant increases or not significant decreases, the one or more of the actions or stimuli (X) in the step 53 could be evaluated as "ineffective or harmless to immunity but beneficial to the liver and/or kidney" and may or may not be repeated by the subject again.

If the second data LK2 are a little worse than the first data LK1, it could mean the one or more of the actions or stimuli (X) in the step 53 are slightly harmful to the liver and/or kidney of the subject. In this case, if the change data SCD1 have significant increases, the one or more of the actions or stimuli (X) in the step 53 could be evaluated as "effective to immunity but slightly harmful to the liver and/or kidney" and may or may not be repeated by the subject again. If the change data SCD1 have significant decreases, the one or more of the actions or stimuli (X) in the step 53 could be evaluated as "harmful to immunity and to the liver and/or kidney" and may not be repeated by the subject again. If the change data SCD1 have not significant increases or not significant decreases, the one or more of the actions or stimuli (X) in the step 53 could be evaluated as "ineffective or harmless to immunity but slightly harmful to the liver and/or kidney" and may or may not be repeated by the subject again.

If the second data LK2 are much or significantly worse than the first data LK1, it could mean the one or more of the actions or stimuli (X) in the step 53 are significantly harmful to the liver and/or kidney of the subject. In this case, if the change data SCD1 have significant increases, the one or more of the actions or stimuli (X) in the step 53 could be evaluated as "effective to immunity but significantly harmful to the liver and/or kidney". Therefore, the subject cannot often take or be subject to or cannot take or be subject to the one or more of the actions or stimuli (X) in the step 53, or the one or more of the actions or stimuli (X) in the step 53 may be repeated by the subject with less dosage, amount or time than the current evaluation. If the change data SCD1 have significant decreases, the one or more of the actions or stimuli (X) in the step 53 could be evaluated as "harmful to immunity and to the liver and/or kidney" and may not be repeated by the subject again. If the change data SCD1 have not significant increases or not decreases, the one or more of the actions or stimuli (X) in the step 53 could be evaluated as "ineffective or harmless to immunity but significantly harmful to the liver and/or kidney" and may not be repeated by the subject again.

An evaluation or test results or data, analysis, assessment, summary and/or conclusion may be generated as an evaluation report or card for the above evaluation of this embodiment. This embodiment provides a method, an apparatus, or an integrated system combining methodology, software (tools) and hardware (equipments, machines, or devices for extraction, filtering, purification, analyzing stem cells), for evaluating actions or stimuli on a human or a non-human body by comparing the first and second sets of results or data $R_{1,1}$-$R_{a,b}$, obtained from tissue samples from the human or non-human body before and after performing the actions or stimuli respectively, as mentioned in accordance with this embodiment.

A method, in accordance with the first embodiment, of evaluating an effect of an action, comprises taking a first tissue sample from a subject; analyzing said first tissue sample to obtain a first result related to information of a type or types of stem cells; after said taking said first tissue sample, performing said action on said subject; after said performing said action on said subject, taking a second tissue sample from said subject; analyzing said second tissue sample to obtain a second result related to information of said type or types of stem cells; and comparing said first and second results.

Second Embodiment

Figure 8:
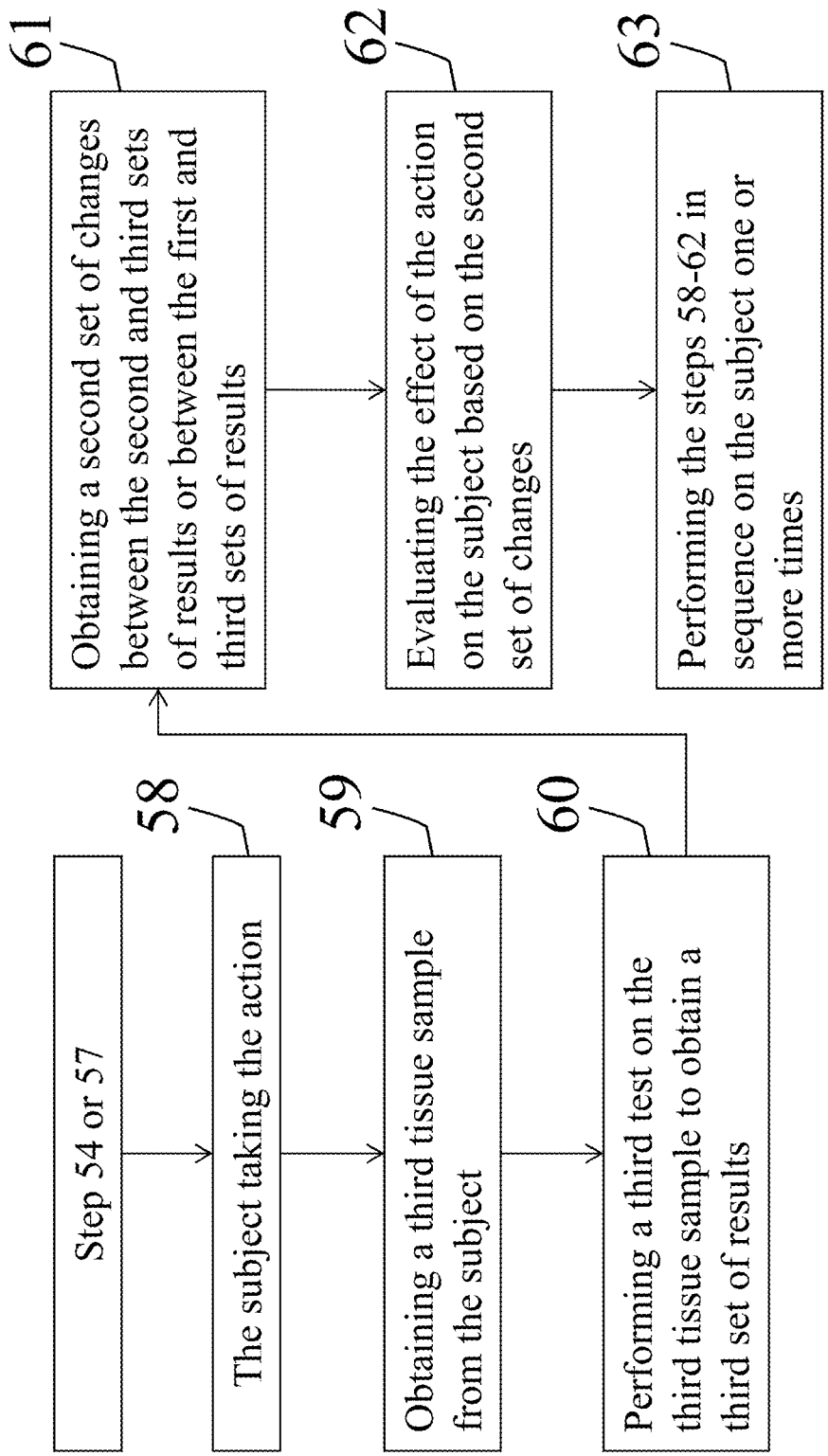
FIG. 8 shows a flow chart of identifying, evaluating or assessing the effect of a series of actions or stimuli on a subject according to a second embodiment of the present disclosure.

FIG. 8 is a flow chart of identifying, evaluating or assessing the effect of a plurality of one of the above-mentioned actions or stimuli (X), or repeating the above-mentioned one or more of the actions or stimuli (X), on a subject. Referring to FIG. 8, in step 58, after the second tissue sample is obtained as illustrated in the step 54 of FIG. 7 or the effect of the one or more of the actions or stimuli (X) on the subject is evaluated as illustrated in the step 57 of FIG. 7, the subject takes or is subjected to the same one or more of the actions or stimuli (X) in the step 53 again. Alternatively, the subject can take or can be subjected to different one or more of the actions or stimuli (X) from the previous last actions or stimuli (X). After a specific period of time, such as longer than or equal to 15, 30, 60, 90 or 120 minutes or one, two or thirty days, or between 30 and 120 minutes, step 59 is performed following the step 58. In the step 59, a third tissue sample, which may be referred to the above-mentioned tissue sample (P), is extracted, taken, obtained or derived from the subject. The first, second and third tissue samples may be three samples obtained from the same type of tissue of the subject. For example, all of the first, second and third tissue samples may be obtained from peripheral blood, bone marrow, muscle or adipocyte of the subject.

Next, in step 60, a third test, assessment or measurement including extracting, characterizing, assessing and measuring stem cells is performed on the third tissue sample to obtain a third set of results or data related to one or more types of stem cells from the third tissue sample descriptively, qualitatively or quantitatively. The third set of results or data include the same types of information as the first set of results or data illustrated in the step 52 of FIG. 7, that is, the third set of results or data include multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for the third set of results or data are defined, described or specified as the first set of results or data illustrated in the step 52 of FIG. 7, respectively. For collecting the same types of information and reducing experimental errors, all of the first, second and third tests, assessments or measurements for the first, second and third sets of results or data may be performed using the same method described in the above-mentioned test, assessment or measurement (M0), (M1) or (M2).

Next, referring to FIG. 8, in step 61, a second set of changes between the second and third sets of results or data or between the first and third sets of results or data may be obtained by comparing the second and third sets of results or data when the second set of changes are made between the second and third sets of results or data or by comparing the first and third sets of results or data when the second set of changes are made between the first and third sets of results or data.

In the case that the second set of changes are made between the second and third sets of results or data, the second set of changes may be obtained by performing: (1) a first operation (i.e., subtraction operation), that is, the third set of results or data $R_{1,1}$-$R_{a,b}$ minus the second set of results or data $R_{1,1}$-$R_{a,b}$, or (2) a second operation of calculating the rates of change between the second and third sets of results or data $R_{1,1}$-$R_{a,b}$, which may be calculated by subtracting the second set of results or data $R_{1,1}$-$R_{a,b}$ from the third set of results or data $R_{1,1}$-$R_{a,b}$, then dividing the subtracted results by the second set of results or data $R_{1,1}$-$R_{a,b}$, and finally multiplying the divided results by 100% (which converts the divided results into percent figures). The second and third sets of results or data $R_{1,1}$-$R_{a,b}$ employed in the first or second operation have the same first and second numbers in the subscript.

In the case that the second set of changes are made between the first and third sets of results or data, the second set of changes may be obtained by performing: (1) a first operation (i.e., subtraction operation), that is, the third set of results or data $R_{1,1}$-$R_{a,b}$ minus the first set of results or data $R_{1,1}$-$R_{a,b}$, or (2) a second operation of calculating the rates of change between the first and third sets of results or data $R_{1,1}$-$R_{a,b}$, which may be calculated by subtracting the first set of results or data $R_{1,1}$-$R_{a,b}$ from the third set of results or data $R_{1,1}$-$R_{a,b}$, then dividing the subtracted results by the first set of results or data $R_{1,1}$-$R_{a,b}$, and finally multiplying the divided results by 100% (which converts the divided results into percent figures). The first and third sets of results or data $R_{1,1}$-$R_{a,b}$ employed in the first or second operation have the same first and second numbers in the subscript.

The second set of changes illustrated herein include the same types of information as the set of changes illustrated in the step 56 of FIG. 7, that is, the second set of changes illustrated herein include multiple changes $\Delta_{1,1}$-$\Delta_{1,c}$, $\Delta_{2,1}$-$\Delta_{2,c}$, . . . , and $\Delta_{a,1}$-$\Delta_{a,c}$, wherein the first and second numbers in the subscript of $\Delta_{1,1}$-$\Delta_{a,c}$ for the second set of changes are defined, described or specified as the set of changes illustrated in the step 56 of FIG. 7, respectively.

Next, referring to FIG. 8, in step 62, based on the second set of changes illustrated herein, the effect of the one or more of the actions or stimuli (X), illustrated in the step 58, on the subject may be identified, determined, evaluated or assessed as effective to health or immunity, as harmful to health or immunity, or as ineffective or harmless to health or immunity. The first and second sets of results or data illustrated in the steps 52 and 55 of FIG. 7, the third set of results or data illustrated herein, the first set of changes (i.e., the set of changes obtained in the step 56 of FIG. 7), and the second set of changes illustrated herein can be written as an evaluation (or examination) report or card.

The one or more of the actions or stimuli (X) in the step 58 or the series of the actions or stimuli (X) in the steps 53 and 58 may be evaluated as "effective to health or immunity" based on, e.g., the result that a selected one of the changes $\Delta_{1,1}$-$\Delta_{a,c}$ in the second set of changes, such as the change $\Delta_{1,1}$, has significant increase, as "harmful to health or immunity" based on, e.g., the result that the selected one of the changes $\Delta_{1,1}$-$\Delta_{a,c}$ in the second set of changes, such as the change $\Delta_{1,1}$, has significant decrease, or as "ineffective or harmless to health or immunity" based on, e.g., the result that the selected one of the changes $\Delta_{1,1}$-$\Delta_{a,c}$ in the second set of changes, such as the change $\Delta_{1,1}$, has not significant decrease or not significant increase.

Alternatively, the one or more of the actions or stimuli (X) in the step 58 or the series of the actions or stimuli in the steps 53 and 58 may be evaluated as "effective to health or immunity" based on, e.g., the result that selected ones of the changes $\Delta_{1,1}$-$\Delta_{a,c}$ in the second set of changes, such as the changes $\Delta_{1,1}$ and $\Delta_{2,1}$, have significant increases, as "harmful to health or immunity" based on, e.g., the result that the selected ones of the changes $\Delta_{1,1}$-$\Delta_{a,c}$ in the second set of changes, such as the changes $\Delta_{1,1}$ and $\Delta_{2,1}$, have significant decreases, or as "ineffective or harmless to health or immunity" based on, e.g., the result that the selected ones of the changes $\Delta_{1,1}$-$\Delta_{a,c}$ in the second set of changes, such as the changes $\Delta_{1,1}$ and $\Delta_{2,1}$, have not significant decreases or not significant increases. The number of the selected ones of the changes $\Delta_{1,1}$-$\Delta_{a,c}$ in the second set of changes may be equal to or more than 2, 3, 4, 5 or 6.

Alternatively, the one or more of the actions or stimuli (X) in the step 58 or the series of the actions or stimuli (X) in the steps 53 and 58 may be evaluated as "effective to health or immunity" based on, e.g., the result that more than or equal to a number "u1" of the changes $\Delta_{1,1}$-$\Delta_{a,c}$ in the second set of changes, such as the changes $\Delta_{1,1}$, $\Delta_{2,1}$ and $\Delta_{3,1}$, have significant increases, as "harmful to health or immunity" based on, e.g., the result that more than or equal to the number "u1" of the changes $\Delta_{1,1}$-$\Delta_{a,c}$ in the second set of changes, such as the changes $\Delta_{1,1}$, $\Delta_{2,1}$ and $\Delta_{3,1}$, have significant decreases, or as "ineffective or harmless to health or immunity" based on, e.g., the result that less than the number "u1" of the changes $\Delta_{1,1}$-$\Delta_{a,c}$ in the second set of changes, such as none of the changes $\Delta_{1,1}$-$\Delta_{a,c}$, have significant increases or significant decreases. The number "u1" may be any positive integer such as 2, 3, 4, 5 or 6.

Alternatively, by (1) performing first comparisons between the second set of changes obtained in the step 61, such as an increase or decrease in the number of SB-1 cells (i.e., $\Delta_{1,1}$), and corresponding ones of the criteria or standards (G), such as the criterion for an increase in the number of SB-1 cells (i.e., $G_{1,4}$) and/or the criterion for a decrease in the number of SB-1 cells ($G_{1,5}$), and/or (2) performing second comparisons between the third set of results or data obtained in the step 60, such as the number of SB-1 cells (i.e., $R_{1,1}$), and corresponding ones of the criteria or standards (G), such as the criterion for the upper limit of a range of the number of SB-1 cells (i.e., $G_{1,1}$) and/or the criterion for the lower limit of a range of the number of SB-1 cells (i.e., $G_{1,7}$), the effect of the one or more of the actions or stimuli (X), illustrated in the step 58, on the subject may be identified, determined, evaluated or assessed as effective to health or immunity, as harmful to health or immunity, or as ineffective or harmless to health or immunity.

For ensuring the safety (no significant side-effects or damages to the human or non-human body, for example, organs such as liver or kidney) of the one or more of the actions or stimuli (X) in the step 58 or the series of the actions or stimuli in the steps 53 and 58, data about liver and kidney functions, defined as third data LK3, may need to be optionally obtained from the subject after taking or being subjected to the one or more of the actions or stimuli (X) in the step 58 of FIG. 8. By comparing the third data LK3 with the second data LK2 illustrated in the first embodiment, the difference between the second and third data LK2 and LK3 about liver and kidney functions of the subject may be obtained to identify or evaluate the effect of the one or more of the actions or stimuli (X) in the step 58 or the series of the actions or stimuli in the steps 53 and 58 on the liver and/or kidney of the subject, as mentioned below.

If there is no (significant) difference between the second and third data LK2 and LK3, it could mean the one or more of the actions or stimuli (X) in the step 58 or the series of the actions or stimuli in the steps 53 and 58 are harmless to the liver and kidney of the subject. In this case, if one or more of the changes $\Delta_{1,1}$-$\Delta_{a,c}$ in the second set of changes between the second and third sets of results or data, herein defined as change data SCD2, have significant increases, the one or more of the actions or stimuli (X) in the step 58 or the series of the actions or stimuli in the steps 53 and 58 can be evaluated as "effective to immunity without impacts or damages on the liver and/or kidney" and may be repeated by the subject again. If the change data SCD2 have significant decreases, the one or more of the actions or stimuli (X) in the step 58 or the series of the actions or stimuli in the steps 53 and 58 could be evaluated as "harmful to immunity without impacts or damages on the liver and/or kidney" and may not be repeated by the subject again. If the change data SCD2 have not significant increases or not significant decreases, the one or more of the actions or stimuli (X) in the step 58 or the series of the actions or stimuli in the steps 53 and 58 could be evaluated as "ineffective or harmless to immunity without impacts or damages on the liver and/or kidney" and may or may not be repeated by the subject again.

If the third data LK3 are (much or significantly) better than the second data LK2, it could mean the one or more of the actions or stimuli (X) in the step 58 or the series of the actions or stimuli in the steps 53 and 58 are harmless but beneficial to the liver and/or kidney of the subject. In this case, if the change data SCD2 have significant increases, the one or more of the actions or stimuli (X) in the step 58 or the series of the actions or stimuli in the steps 53 and 58 can be evaluated as "effective to immunity and beneficial to the liver and/or kidney" and may be repeated by the subject again. If the change data SCD2 have significant decreases, the one or more of the actions or stimuli (X) in the step 58 or the series of the actions or stimuli in the steps 53 and 58 could be evaluated as "harmful to immunity but beneficial to the liver and/or kidney" and may not be repeated by the subject again. If the change data SCD2 have not significant increases or not significant decreases, the one or more of the actions or stimuli (X) in the step 58 or the series of the actions or stimuli in the steps 53 and 58 could be evaluated as "ineffective or harmless to immunity but beneficial to the liver and/or kidney" and may or may not be repeated by the subject again.

If the third data LK3 are a little worse than the second data LK2, it could mean the one or more of the actions or stimuli (X) in the step 58 or the series of the actions or stimuli in the steps 53 and 58 are slightly harmful to the liver and/or kidney of the subject. In this case, if the change data SCD2 have significant increases, the one or more of the actions or stimuli (X) in the step 58 or the series of the actions or stimuli in the steps 53 and 58 could be evaluated as "effective to immunity but slightly harmful to the liver and/or kidney" and may or may not be repeated by the subject again. If the change data SCD2 have significant decreases, the one or more of the actions or stimuli (X) in the step 58 or the series of the actions or stimuli in the steps 53 and 58 could be evaluated as "harmful to immunity and to the liver and/or kidney" and may not be repeated by the subject again. If the change data SCD2 have not significant increases or not significant decreases, the one or more of the actions or stimuli (X) in the step 58 or the series of the actions or stimuli in the steps 53 and 58 could be evaluated as "ineffective or harmless to immunity but slightly harmful to the liver and/or kidney" and may or may not be repeated by the subject again.

If the third data LK3 are much or significantly worse than the second data LK2, it could mean the one or more of the actions or stimuli (X) in the step 58 or the series of the actions or stimuli in the steps 53 and 58 are significantly harmful to the liver and/or kidney of the subject. In this case, if the change data SCD2 have significant increases, the one or more of the actions or stimuli (X) in the step 58 or the series of the actions or stimuli in the steps 53 and 58 could be evaluated as "effective to immunity but significantly harmful to the liver and/or kidney". Therefore, the subject cannot often take or be subject to or cannot take or be subject to the one or more of the actions or stimuli (X) in the step 58 or the series of the actions or stimuli in the steps 53 and 58, or the one or more of the actions or stimuli (X) in the step 58 or the series of the actions or stimuli in the steps 53 and 58 may be repeated by the subject with less dosage, amount or time than the current evaluation. If the change data SCD2 have significant decreases, the one or more of the actions or stimuli (X) in the step 58 or the series of the actions or stimuli in the steps 53 and 58 could be evaluated as "harmful to immunity and to the liver and/or kidney" and may not be repeated by the subject again. If the change data SCD2 have not significant increases or not significant decreases, the one or more of the actions or stimuli (X) in the step 58 or the series of the actions or stimuli in the steps 53 and 58 could be evaluated as "ineffective or harmless to immunity but significantly harmful to the liver and/or kidney" and may not be repeated by the subject again.

In this embodiment, the third data LK3 are the data about liver and kidney functions related to the subject after taking or being subjected to the one or more of the actions or stimuli (X) in the step 58 of FIG. 8, and the second data LK2 are the data about liver and kidney functions related to the subject after taking or being subjected to the one or more of the actions or stimuli (X) in the step 53 of FIG. 7 but before taking or being subjected to the one or more of the actions or stimuli (X) in the step 58 of FIG. 8. Each piece of the second and third data LK2 and LK3 may include, but not limited to, (1) data about kidney functions (such as BUN, GFR, CCR, ACR, cystatin C, uric acid, microalbumin, urine routine, and/or urine sediment), and (2) data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV).

Alternatively, by comparing the third data LK3 with the first data LK1 illustrated in the first embodiment, the difference between the first and third data LK1 and LK3 about liver and kidney functions of the subject may be obtained to identify or evaluate the effect of the one or more of the actions or stimuli (X) in the step 58 or the series of the actions or stimuli in the steps 53 and 58 on the liver and/or kidney of the subject, as mentioned below.

If there is no (significant) difference between the first and third data LK1 and LK3, it could mean the one or more of the actions or stimuli (X) in the step 58 or the series of the actions or stimuli in the steps 53 and 58 are harmless to the liver and/or kidney of the subject. In this case, if one or more of the changes $\Delta_{1,1}$-$\Delta_{a,c}$ in the second set of changes between the first and third sets of results or data, herein defined as change data SCD3, have significant increases, the one or more of the actions or stimuli (X) in the step 58 or the series of the actions or stimuli in the steps 53 and 58 can be evaluated as "effective to immunity without impacts or damages on the liver and/or kidney" and may be repeated by the subject again. If the change data SCD3 have significant decreases, the one or more of the actions or stimuli (X) in the step 58 or the series of the actions or stimuli in the steps 53 and 58 could be evaluated as "harmful to immunity without impacts or damages on the liver and/or kidney" and may not be repeated by the subject again. If the change data SCD3 have not significant increases or not significant decreases, the one or more of the actions or stimuli (X) in the step 58 or the series of the actions or stimuli in the steps 53 and 58 could be evaluated as "ineffective or harmless to immunity without impacts or damages on the liver and/or kidney" and may or may not be repeated by the subject again.

If the third data LK3 are (much or significantly) better than the first data LK1, it could mean the one or more of the actions or stimuli (X) in the step 58 or the series of the actions or stimuli in the steps 53 and 58 are harmless but beneficial to the liver and/or kidney of the subject. In this case, if the change data SCD3 have significant increases, the one or more of the actions or stimuli (X) in the step 58 or the series of the actions or stimuli in the steps 53 and 58 can be evaluated as "effective to immunity and beneficial to the liver and/or kidney" and may be repeated by the subject again. If the change data SCD3 have significant decreases, the one or more of the actions or stimuli (X) in the step 58 or the series of the actions or stimuli in the steps 53 and 58 could be evaluated as "harmful to immunity but beneficial to the liver and/or kidney" and may not be repeated by the subject again. If the change data SCD3 have not significant increases or not significant decreases, the one or more of the actions or stimuli (X) in the step 58 or the series of the actions or stimuli in the steps 53 and 58 could be evaluated as "ineffective or harmless to immunity but beneficial to the liver and/or kidney" and may or may not be repeated by the subject again.

If the third data LK3 are a little worse than the first data LK1, it could mean the one or more of the actions or stimuli (X) in the step 58 or the series of the actions or stimuli in the steps 53 and 58 are slightly harmful to the liver and/or kidney of the subject. In this case, if the change data SCD3 have significant increases, the one or more of the actions or stimuli (X) in the step 58 or the series of the actions or stimuli in the steps 53 and 58 could be evaluated as "effective to immunity but slightly harmful to the liver and/or kidney" and may or may not be repeated by the subject again. If the change data SCD3 have significant decreases, the one or more of the actions or stimuli (X) in the step 58 or the series of the actions or stimuli in the steps 53 and 58 could be evaluated as "harmful to immunity and to the liver and/or kidney" and may not be repeated by the subject again. If the change data SCD3 have not significant increases or not significant decreases, the one or more of the actions or stimuli (X) in the step 58 or the series of the actions or stimuli in the steps 53 and 58 could be evaluated as "ineffective or harmless to immunity but slightly harmful to the liver and/or kidney" and may or may not be repeated by the subject again.

If the third data LK3 are much or significantly worse than the first data LK1, it could mean the one or more of the actions or stimuli (X) in the step 58 or the series of the actions or stimuli in the steps 53 and 58 are significantly harmful to the liver and/or kidney of the subject. In this case, if the change data SCD3 have significant increases, the one or more of the actions or stimuli (X) in the step 58 or the series of the actions or stimuli in the steps 53 and 58 could be evaluated as "effective to immunity but significantly harmful to the liver and/or kidney". Therefore, the subject cannot often take or be subject to or cannot take or be subject to the one or more of the actions or stimuli (X) in the step 58 or the series of the actions or stimuli in the steps 53 and 58, or the one or more of the actions or stimuli (X) in the step 58 or the series of the actions or stimuli in the steps 53 and 58 could be repeated by the subject with less dosage, amount or time than the current evaluation. If the change data SCD3 have significant decreases, the one or more of the actions or stimuli (X) in the step 58 or the series of the actions or stimuli in the steps 53 and 58 could be evaluated as "harmful to immunity and to the liver and/or kidney" and may not be repeated by the subject again. If the change data SCD3 have not significant increases or not significant decreases, the one or more of the actions or stimuli (X) in the step 58 or the series of the actions or stimuli in the steps 53 and 58 could be evaluated as "ineffective or harmless to immunity but significantly harmful to the liver and/or kidney" and may not be repeated by the subject again.

Referring to FIG. 8, after the step 58 or 62 is performed, step 63 can be performed if necessary. In the step 63, the same steps as the steps 58-62 are performed on the same subject one or more times. During the step 63, each time when the step 59 is performed, a tissue sample is taken from the same subject after the step 58 is performed. During the step 63, each time when a test, assessment or measurement, like the test, assessment or measurement illustrated in the step 60, is performed, a set of results or data, which may be referred to the first set of results or data illustrated in the step 52 of FIG. 7, related to one or more types of stem cells from the corresponding tissue sample of the subject can be collected and thereby a set of changes between two sets of current and last previous results or data or between two sets of current and first results or data, which may be referred to the set of changes illustrated in the step 56 of FIG. 7, may be obtained.

Therefore, after the steps 51-63 are performed, N sets of results or data related to N tissue samples of the subject may be obtained after N tests, assessments or measurements are performed, and Q sets of changes may be obtained after the subject takes or is subjected to the same one or more of the actions or stimuli (X) Q times, where "N" is a positive integer equal to or greater than 4, 10, 20 or 50, and "Q" is a positive integer equal to or greater than 3, where Q=N−1. The N tissue samples include the first and second tissue samples illustrated in the steps 51 and 54 of FIG. 7 and the third tissue sample illustrated in the step 59 described herein. The N sets of results or data include the first and second sets of results or data, illustrated in the steps 52 and 55 of FIG. 7, related to the first and second tissue samples and the third set of results or data, illustrated in the step 60 described herein, related to the third tissue sample. The Q sets of changes include the first set of changes (i.e., the set of changes obtained in the step 56 of FIG. 7) and the second set of changes illustrated in the step 61 described herein. The N tests, assessments or measurements include the first and second tests, assessments or measurements illustrated in the steps 52 and 55 of FIG. 7 and the third test, assessment or measurement illustrated in the step 60 described herein. The N sets of results or data and the Q sets of changes may be written as an evaluation (or examination) report or card.

For collecting the same types of information and reducing experimental errors, the N tissue samples may be N samples obtained from the same type of tissue of the subject. For example, the N tissue samples may be obtained from peripheral blood, bone marrow, muscle or adipocyte of the subject. The N tests, assessments or measurements may be performed using the same method described in the above-mentioned test, assessment or measurement (M0), (M1) or (M2), for example.

Each of the N sets of results or data includes the same types of information as the first set of results or data illustrated in the step 52 of FIG. 7, that is, each of the N sets of results or data includes multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for each of the N sets of results or data are defined, described or specified as the first set of results or data illustrated in the step 52 of FIG. 7, respectively.

Each of the Q sets of changes includes the same types of information as the set of changes illustrated in the step 56 of FIG. 7, that is, each of the Q sets of changes includes multiple changes $\Delta_{1,1}$-$\Delta_{1,c}$, $\Delta_{2,1}$-$\Delta_{2,c}$, . . . , and $\Delta_{a,1}$-$\Delta_{a,c}$, wherein the first and second numbers in the subscript of $\Delta_{1,1}$-$\Delta_{a,c}$ for each of the Q sets of changes are defined, described or specified as the set of changes illustrated in the step 56 of FIG. 7, respectively.

The $J^{th}$ set of changes in the Q sets of changes may be made between the $J^{th}$ and $J+1^{th}$ sets of results or data in the N sets of results or data or between the $J+1^{th}$ and first sets of results or data in the N sets of results or data, where "J" is a positive integer starting from 1. The $J^{th}$ set of changes may be any of the Q sets of changes. For example, the $J^{th}$ set of changes may be the $Q^{th}$ (last) set of changes between the $N^{th}$ (last) set of results or data and the N−1$^{th}$ set of results or data or between the $N^{th}$ (last) set of results or data and the first set of results or data.

The effect of the one or more of the actions or stimuli (X) in the $J^{th}$ step 58 or the series of the actions or stimuli in the steps 53 and 58 on the subject may be identified, determined, evaluated or assessed as effective to health or immunity, harmful to health or immunity, or ineffective or harmless to health or immunity according to the $J^{th}$ set of changes. For example, the effect of the one or more of the actions or stimuli (X) in the $Q^{th}$ (last) step 58 or the series of the actions or stimuli in the steps 53 and 58 on the subject may be identified, determined, evaluated or assessed as effective to health or immunity, harmful to health or immunity, or ineffective or harmless to health or immunity according to the $Q^{th}$ (last) set of changes between the N−1$^{th}$ and $N^{th}$ (last) sets of results or data or between the first and $N^{th}$ (last) sets of results or data.

The one or more of the actions or stimuli (X) in the $J^{th}$ step 58 or the series of the actions or stimuli in the steps 53 and 58 may be evaluated as "effective to health or immunity" based on, e.g., the result that a selected one of the changes $\Delta_{1,1}$-$\Delta_{a,c}$ in the $J^{th}$ set of changes, such as the change $\Delta_{1,1}$ or $\Delta_{11,1}$, has significant increase, as "harmful to health or immunity" based on, e.g., the result that the selected one of the changes $\Delta_{1,1}$-$\Delta_{a,c}$ in the $J^{th}$ set of changes, such as the change $\Delta_{1,1}$ or $\Delta_{11,1}$, has significant decrease, or as "ineffective or harmless to health or immunity" based on, e.g., the result that the selected one of the changes $\Delta_{1,1}$-$\Delta_{a,c}$ in the $J^{th}$ set of changes, such as the change $\Delta_{1,1}$ or $\Delta_{11,1}$, has not significant decrease or not significant increase.

Alternatively, the one or more of the actions or stimuli (X) in the $J^{th}$ step 58 or the series of the actions or stimuli in the steps 53 and 58 may be evaluated as "effective to health or immunity" based on, e.g., the result that selected ones of the changes $\Delta_{1,1}$-$\Delta_{a,c}$ in the $J^{th}$ set of changes, such as the changes $\Delta_{1,1}$ and $\Delta_{2,1}$, have significant increases, as "harmful to health or immunity" based on, e.g., the result that the selected ones of the changes $\Delta_{1,1}$-$\Delta_{a,c}$ in the $J^{th}$ set of changes, such as the changes $\Delta_{1,1}$ and $\Delta_{2,1}$, have significant decreases, or as "ineffective or harmless to health or immunity" based on, e.g., the result that the selected ones of the changes $\Delta_{1,1}$-$\Delta_{a,c}$ in the $J^{th}$ set of changes, such as the changes $\Delta_{1,1}$ and $\Delta_{2,1}$, have not significant decreases or not significant increases. The number of the selected ones of the changes $\Delta_{1,1}$-$\Delta_{a,c}$ in the $J^{th}$ set of changes may be equal to or more than 2, 3, 4, 5 or 6.

During the step 63, each time after taking or being subjected to the current one or more of the actions or stimuli (X) illustrated in the step 58, the subject may be optionally examined to obtain current data about liver and kidney functions to be compared with the first data LK1 illustrated in the first embodiment or the last previous data about liver and kidney functions related to the subject before taking or being subjected to the current one or more of the actions or stimuli (X). Before the subject repeats the same step 58 again, difference data LKD between the current and last previous data or between the current data and the first data LK1 may be obtained by comparing the current data with the last previous data or the first data LK1 so as to identify or evaluate the effect of the current one or more of the actions or stimuli (X) or the series of the actions or stimuli in the steps 53 and 58 on the liver and/or kidney of the subject. Each piece of the current and last previous data may include, but not limited to, (1) data about kidney functions (such as BUN, GFR, CCR, ACR, cystatin C, uric acid, microalbumin, urine routine, and/or urine sediment), and (2) data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV).

In the case of the difference data LKD between the current and last previous data about liver and kidney functions, the effect of the current one or more of the actions or stimuli (X) or the series of the actions or stimuli in the steps 53 and 58 on the liver and/or kidney of the subject may be identified or evaluated as mentioned in the following descriptions.

If there is no (significant) difference of the difference data LKD between the current and last previous data, it could mean the current one or more of the actions or stimuli (X) or the series of the actions or stimuli in the steps 53 and 58 are harmless to the liver and/or kidney of the subject. In this case, if one or more of the changes $\Delta_{1,1}$-$\Delta_{a,c}$ between the current and last previous sets of results or data, herein defined as change data SCD4, have significant increases, the current one or more of the actions or stimuli (X) or the series of the actions or stimuli in the steps 53 and 58 can be evaluated as "effective to immunity without impacts or damages on the liver and/or kidney" and may be repeated by the subject again. If the change data SCD4 have significant decreases, the current one or more of the actions or stimuli (X) or the series of the actions or stimuli in the steps 53 and 58 could be evaluated as "harmful to immunity without impacts or damages on the liver and/or kidney" and may not be repeated by the subject again. If the change data SCD4 have not significant increases or not significant decreases, the current one or more of the actions or stimuli (X) or the series of the actions or stimuli in the steps 53 and 58 may be evaluated as "ineffective or harmless to immunity without impacts or damages on the liver and/or kidney" and may or may not be repeated by the subject again.

If the difference data LKD between the current and last previous data show that the current data about liver and kidney functions are (much or significantly) better than the last previous data about liver and kidney functions, it could mean the current one or more of the actions or stimuli (X) or the series of the actions or stimuli in the steps 53 and 58 are harmless but beneficial to the liver and/or kidney of the subject. In this case, if the change data SCD4 have significant increases, the current one or more of the actions or stimuli (X) or the series of the actions or stimuli in the steps 53 and 58 can be evaluated as "effective to immunity and beneficial to the liver and/or kidney" and may be repeated by the subject again. If the change data SCD4 have significant decreases, the current one or more of the actions or stimuli (X) or the series of the actions or stimuli in the steps 53 and 58 could be evaluated as "harmful to immunity but beneficial to the liver and/or kidney" and may not be repeated by the subject again. If the change data SCD4 have not significant increases or not significant decreases, the current one or more of the actions or stimuli (X) or the series of the actions or stimuli in the steps 53 and 58 could be evaluated as "ineffective or harmless to immunity but beneficial to the liver and/or kidney" and may or may not be repeated by the subject again.

If the difference data LKD between the current and last previous data show that the current data about liver and kidney functions are a little worse than the last previous data about liver and kidney functions, it could mean the current one or more of the actions or stimuli (X) or the series of the actions or stimuli in the steps 53 and 58 are slightly harmful to the liver and/or kidney of the subject. In this case, if the change data SCD4 have significant increases, the current one or more of the actions or stimuli (X) or the series of the actions or stimuli in the steps 53 and 58 could be evaluated as "effective to immunity but slightly harmful to the liver and/or kidney" and may or may not be repeated by the subject again. If the change data SCD4 have significant decreases, the current one or more of the actions or stimuli (X) or the series of the actions or stimuli in the steps 53 and 58 could be evaluated as "harmful to immunity and to the liver and/or kidney" and may not be repeated by the subject again. If the change data SCD4 have not significant increases or not significant decreases, the current one or more of the actions or stimuli (X) or the series of the actions or stimuli in the steps 53 and 58 could be evaluated as "ineffective or harmless to immunity but slightly harmful to the liver and/or kidney" and may or may not be repeated by the subject again.

If the difference data LKD between the current and last previous data show that the current data about liver and kidney functions are much or significantly worse than the last previous data about liver and kidney functions, it could mean the current one or more of the actions or stimuli (X) or the series of the actions or stimuli in the steps 53 and 58 are significantly harmful to the liver and/or kidney of the subject. In this case, if the change data SCD4 have significant increases, the current one or more of the actions or stimuli (X) or the series of the actions or stimuli in the steps 53 and 58 could be evaluated as "effective to immunity but significantly harmful to the liver and/or kidney". Therefore, the subject cannot often take or be subject to or cannot take or be subject to the current one or more of the actions or stimuli (X) or the series of the actions or stimuli in the steps 53 and 58, or the current one or more of the actions or stimuli (X) or the series of the actions or stimuli in the steps 53 and 58 could be repeated by the subject with less dosage, amount or time than the current evaluation. If the change data SCD4 have significant decreases, the current one or more of the actions or stimuli (X) or the series of the actions or stimuli in the steps 53 and 58 could be evaluated as "harmful to immunity and to the liver and/or kidney" and mat not be repeated by the subject again. If the change data SCD4 have not significant increases or not significant decreases, the current one or more of the actions or stimuli (X) or the series of the actions or stimuli in the steps 53 and 58 could be evaluated as "ineffective or harmless to immunity but significantly harmful to the liver and/or kidney" and may not be repeated by the subject again.

In the case of the difference data LKD between the current data and the first data LK1, the effect of the current one or more of the actions or stimuli (X) or the series of the actions or stimuli in the steps 53 and 58 on the liver and/or kidney of the subject may be identified or evaluated as mentioned in the following descriptions.

If there is no (significant) difference of the difference data LKD between the current data and the first data LK1, it could mean the current one or more of the actions or stimuli (X) or the series of the actions or stimuli in the steps 53 and 58 are harmless to the liver and/or kidney of the subject. In this case, if one or more of the changes $\Delta_{1,1}$-$\Delta_{a,c}$ between the current set of results or data and the first set of results or data, herein defined as change data SCD5, have significant increases, the current one or more of the actions or stimuli (X) or the series of the actions or stimuli in the steps 53 and 58 can be evaluated as "effective to immunity without impacts or damages on the liver and/or kidney" and may be repeated by the subject again. If the change data SCD5 have significant decreases, the current one or more of the actions or stimuli (X) or the series of the actions or stimuli in the steps 53 and 58 could be evaluated as "harmful to immunity without impacts or damages on the liver and/or kidney" and may not be repeated by the subject again. If the change data SCD5 have not significant increases or not significant decreases, the current one or more of the actions or stimuli (X) or the series of the actions or stimuli in the steps 53 and 58 could be evaluated as "ineffective or harmless to immunity without impacts or damages on the liver and/or kidney" and may or may not be repeated by the subject again.

If the difference data LKD between the current data and the first data LK1 show that the current data about liver and kidney functions are (much or significantly) better than the first data LK1 about liver and kidney functions, it could mean the current one or more of the actions or stimuli (X) or the series of the actions or stimuli in the steps 53 and 58 are harmless but beneficial to the liver and/or kidney of the subject. In this case, if the change data SCD5 have significant increases, the current one or more of the actions or stimuli (X) or the series of the actions or stimuli in the steps 53 and 58 can be evaluated as "effective to immunity and beneficial to the liver and/or kidney" and may be repeated by the subject again. If the change data SCD5 have significant decreases, the current one or more of the actions or stimuli (X) or the series of the actions or stimuli in the steps 53 and 58 could be evaluated as "harmful to immunity but beneficial to the liver and/or kidney" and may not be repeated by the subject again. If the change data SCD5 have not significant increases or not significant decreases, the current one or more of the actions or stimuli (X) or the series of the actions or stimuli in the steps 53 and 58 could be evaluated as "ineffective or harmless to immunity but beneficial to the liver and/or kidney" and may or may not be repeated by the subject again.

If the difference data LKD between the current data and the first data LK1 show that the current data about liver and kidney functions are a little worse than the first data LK1 about liver and kidney functions, it could mean the current one or more of the actions or stimuli (X) or the series of the actions or stimuli in the steps 53 and 58 are slightly harmful to the liver and/or kidney of the subject. In this case, if the change data SCD5 have significant increases, the current one or more of the actions or stimuli (X) or the series of the actions or stimuli in the steps 53 and 58 could be evaluated as "effective to immunity but slightly harmful to the liver and/or kidney" and may or may not be repeated by the subject again. If the change data SCD5 have significant decreases, the current one or more of the actions or stimuli (X) or the series of the actions or stimuli in the steps 53 and 58 could be evaluated as "harmful to immunity and to the liver and/or kidney" and may not be repeated by the subject again. If the change data SCD5 have not significant increases or not significant decreases, the current one or more of the actions or stimuli (X) or the series of the actions or stimuli in the steps 53 and 58 could be evaluated as "ineffective or harmless to immunity but slightly harmful to the liver and/or kidney" and may or may not be repeated by the subject again.

If the difference data LKD between the current data and the first data LK1 show that the current data about liver and kidney functions are much or significantly worse than the first data LK1 about liver and kidney functions, it could mean the current one or more of the actions or stimuli (X) or the series of the actions or stimuli in the steps 53 and 58 are significantly harmful to the liver and/or kidney of the subject. In this case, if the change data SCD5 have significant increases, the current one or more of the actions or stimuli (X) or the series of the actions or stimuli in the steps 53 and 58 could be evaluated as "effective to immunity but significantly harmful to the liver and/or kidney". Therefore, the subject cannot often take or be subject to or cannot take or be subject to the current one or more of the actions or stimuli (X) or the series of the actions or stimuli in the steps 53 and 58, or the current one or more of the actions or stimuli (X) or the series of the actions or stimuli in the steps 53 and 58 could be repeated by the subject with less dosage, amount or time than the current evaluation. If the change data SCD5 have significant decreases, the current one or more of the actions or stimuli (X) or the series of the actions or stimuli in the steps 53 and 58 could be evaluated as "harmful to immunity and to the liver and/or kidney" and may not be repeated by the subject again. If the change data SCD5 have not significant increases or not significant decreases, the current one or more of the actions or stimuli (X) or the series of the actions or stimuli in the steps 53 and 58 could be evaluated as "ineffective or harmless to immunity but significantly harmful to the liver and/or kidney" and may not be repeated by the subject again.

An evaluation or test results or data, analysis, assessment, summary and/or conclusion can be generated as an evaluation report or card for the above evaluation of this embodiment. This embodiment provides a method, an apparatus, or an integrated system combining methodology, software (tools) and hardware (equipments, machines, or devices for extraction, filtering, purification, analyzing stem cells), for continuously evaluating a repeated action (or stimulus) or actions (or stimuli) on a human or a non-human body by comparing the first and last sets of results or data $R_{1,1}$-$R_{a,b}$, obtained respectively from the first and last tests, assessments or measurements, and/or by comparing the previous last and last sets of results or data $R_{1,1}$-$R_{a,b}$, obtained respectively from the previous last and last tests, assessments or measurements, as mentioned in accordance with this embodiment.

A method, in accordance with the second embodiment, of evaluating an effect of a series of action, comprises taking a first tissue sample from a subject; analyzing said first tissue sample to obtain a first result related to information of a type or types of stem cells; after said taking said first tissue sample, performing a first action on said subject; after said performing said first action on said subject, taking a second tissue sample from said subject; analyzing said second tissue sample to obtain a second result related to information of said type or types of stem cells; after said taking said second tissue sample, performing a second action on said subject; after said performing said second action on said subject, taking a third tissue sample from said subject; analyzing said third tissue sample to obtain a third result related to information of said type or types of stem cells; and comparing said first and third results or said second and third results. In an aspect, said first action is substantially the same as said second action. In another aspect, said first action is different from said second action.

Third Embodiment

Figure 9:
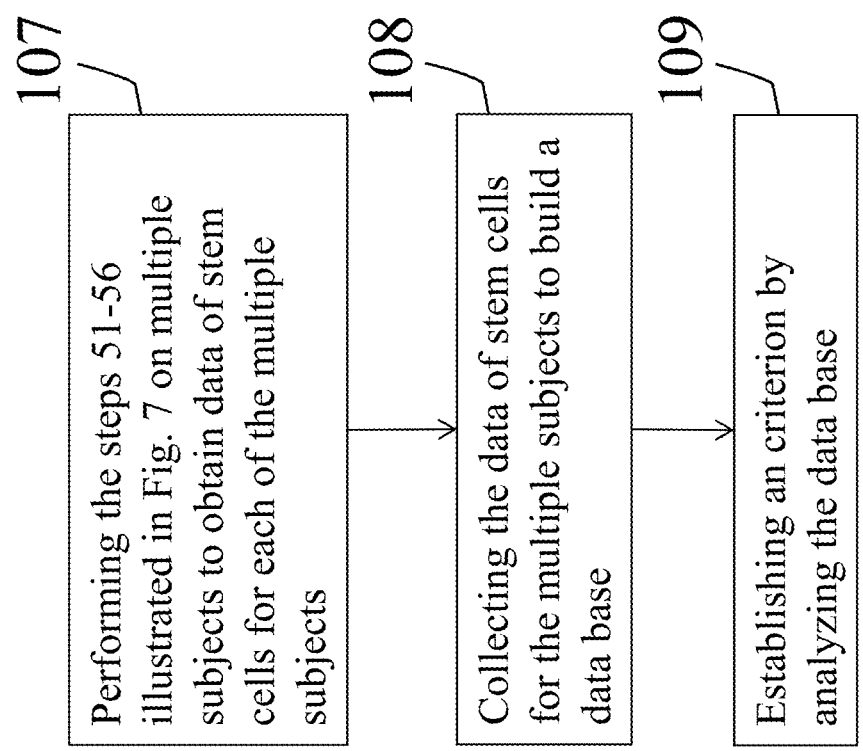
FIG. 9 shows a flow chart for establishing criteria or standards for one or more types of stem cells according to a third embodiment of the present disclosure.

FIG. 9 is a flow chart for establishing or obtaining criteria or standards (G). The third embodiment is based on collecting an amount of, with statistically significance, results or data obtained from multiple objects to build a data base. In this embodiment, N1 subjects, each of which may be referred to the above-mentioned subject (S), in an evaluation group are sampled or selected from species in the same biological category, and the steps illustrated in FIG. 9 may be performed on the N1 subjects, where "N1" is a positive integer equal to or greater than 2, 4, 6, 10, 20 or 50.

Referring to FIG. 9, in step 107, the steps 51-56 illustrated in FIG. 7 are performed on each of the N1 subjects in the evaluation group. Therefore, N1 first tissue samples, each of which may be referred to the above-mentioned tissue sample (P), are extracted, taken, obtained or derived from the N1 subjects using the method described in the step 51 of FIG. 7. Here the N1 first tissue samples are extracted, taken, obtained or derived from the N1 subjects before taking or being subjected to the one or more of the actions or stimuli (X) described in the step 53 of FIG. 7. The N1 first tissue samples are analyzed using the first test, assessment or measurement illustrated in the step 52 of FIG. 7, respectively. N1 second tissue samples are extracted, taken, obtained or derived from the N1 subjects after taking or being subjected to the one or more of the actions or stimuli (X) described in the step 53 of FIG. 7 using the method described in the step 54 of FIG. 7. The N1 second tissue samples are analyzed using the second test, assessment or measurement illustrated in the step 55 of FIG. 7, respectively.

N1 first sets of results or data related to the N1 subjects before taking or being subjected to the one or more of the actions or stimuli (X) described in the step 53 of FIG. 7 are obtained by performing the above first tests, assessments or measurements on the N1 first tissue samples, respectively, as mentioned in the step 52 of FIG. 7. N1 second sets of results or data related to the N1 respective subjects after taking or being subjected to the one or more of the actions or stimuli (X) described in the step 53 of FIG. 7 are obtained by performing the above second tests, assessments or measurements on the N1 second tissue samples, respectively, as mentioned in the step 55 of FIG. 7. N1 sets of changes in N1 respective pairs of results or data, each including one of the N1 first sets of results or data and a corresponding one of the N1 second sets of results or data for the same one of the N1 subjects in the evaluation group, may be obtained using the method described in the step 56 of FIG. 7.

The N1 first and N1 second sets of results or data related to the N1 subjects in the evaluation group include types of small stem cells and parameters (such as the number, the percentage and/or the sizes) of one or more types of small stem cells, as described in the above-mentioned assay process (T1), when each of the above first and second tests, assessments or measurements is performed using the above-mentioned test, assessment or measurement (M1). Alternatively, the N1 first and N1 second sets of results or data related to the N1 subjects in the evaluation group include types of stem cells and parameters (such as the number, the percentage and/or the sizes) of one or more types of stem cells, as described in the above-mentioned assay process (T2), when each of the above first and second tests, assessments or measurements is performed using the above-mentioned test, assessment or measurement (M2). Alternatively, the N1 first and N1 second sets of results or data related to the N1 subjects in the evaluation group include types of stem cells and parameters (such as the number, the percentage and/or the sizes) of one or more types of stem cells, as described in the above-mentioned assay process (T0), when each of the above first and second tests, assessments or measurements is performed using the above-mentioned test, assessment or measurement (M0).

Each of the N1 first sets of results or data illustrated herein includes the same types of information as the first set of results or data illustrated in the step 52 of FIG. 7, that is, each of the N1 first sets of results or data includes multiple results or data $R_{1,1}$-$R_{1,b}$, $R_{2,1}$-$R_{2,b}$, . . . , and $R_{a,1}$-$R_{a,b}$ related to a corresponding one of the N1 subjects in the evaluation group, wherein the first and second numbers in the subscript of $R_{1,1}$-$R_{a,b}$ for each of the N1 first sets of results or data are defined, described or specified as the first set of results or data illustrated in the step 52 of FIG. 7, respectively.

Each of the N1 second sets of results or data illustrated herein includes the same types of information as the first set of results or data illustrated in the step 52 of FIG. 7, that is, each of the N1 second sets of results or data includes multiple results or data $R_{1,1}$-$R_{1,b}$, $R_{2,1}$-$R_{2,b}$, . . . , and $R_{a,1}$-$R_{a,b}$ related to a corresponding one of the N1 subjects in the evaluation group, wherein the first and second numbers in the subscript of $R_{1,1}$-$R_{a,b}$ for each of the N1 second sets of results or data are defined, described or specified as the first set of results or data illustrated in the step 52 of FIG. 7, respectively.

The N1 sets of changes between the N1 first sets of results or data and the N1 second sets of results or data, related to the N1 subjects in the evaluation group, may be obtained by comparing the first and second sets of results or data $R_{1,1}$-$R_{a,b}$ having the same first and second numbers in the subscript for the N1 respective subjects in the evaluation group.

Each of the N1 sets of changes illustrated herein includes the same types of information as the set of changes illustrated in the step 56 of FIG. 7, that is, each of the N1 sets of changes includes multiple changes $\Delta_{1,1}$-$\Delta_{1,c}$, $\Delta_{2,1}$-$\Delta_{2,c}$, . . . , and $\Delta_{a,1}$-$\Delta_{a,c}$ related to a corresponding one of the N1 subjects in the evaluation group, wherein the first and second numbers in the subscript of $\Delta_{1,1}$-$\Delta_{a,c}$ for each of the N1 sets of changes are defined, described or specified as the set of changes illustrated in the step 56 of FIG. 7, respectively.

The step 107 may be performed in various sequences. For example, referring to FIG. 9, the step 107 may include performing the steps 51-55 on each of the N1 subjects, after which the step 56 described in FIG. 7 may be performed on each pair of results or data, including one of the N1 first sets of results or data $R_{1,1}$-$R_{a,b}$ and a corresponding one of the N1 second sets of results or data $R_{1,1}$-$R_{a,b}$ for the same one of the N1 subjects in the evaluation group, to obtain the N1 sets of changes in N1 respective pairs of results or data, each including one of the N1 first sets of results or data $R_{1,1}$-$R_{a,b}$ and a corresponding one of the N1 second sets of results or data $R_{1,1}$-$R_{a,b}$ for the same one of the N1 respective subjects in the evaluation group.

Referring to FIG. 9, in step 108, the N1 first and N1 second sets of results or data $R_{1,1}$-$R_{a,b}$ related to the N1 subjects and the N1 sets of changes $\Delta_{1,1}$-$\Delta_{a,c}$ related to the N1 subjects are collected to build a data base. The data base further includes the data of, for example, age, gender, race, height, weight, blood pressure, heartbeat, immunoglobulin (Ig), body mass index (BMI), data about kidney functions (such as BUN, GFR, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) for each of the N1 subjects in the evaluation group.

Next, in step 109, the data base built in the step 108 may be analyzed with a statistical significance such that criteria or standards (G) may be established for identifying, determining, evaluating or assessing the effect of one or more of the actions or stimuli (X), such as the one or more actions or stimuli described in the step 53 of FIG. 7. The analysis illustrated herein may include analyzing the N1 first and N1 second sets of results or data $R_{1,1}$-$R_{a,b}$ and the N1 sets of changes $\Delta_{1,1}$-$\Delta_{a,c}$ related to the N1 subjects in the evaluation group against age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) of the N1 subjects in the evaluation group.

Based on analysis of the N1 sets of changes $\Delta_{1,1}$-$\Delta_{a,c}$ related to the N1 subjects in the evaluation group and the N1 first and N1 second sets of results or data $R_{1,1}$-$R_{a,b}$ related to the N1 subjects in the evaluation group against age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) of the N1 subjects in the evaluation group, the distribution of some specific data, as X-axis, taken from the N1 first and/or N1 second sets of results or data $R_{1,1}$-$R_{a,b}$ related to the N1 subjects in the evaluation group and/or the N1 sets of changes $\Delta_{1,1}$-$\Delta_{a,c}$ related to the N1 subjects in the evaluation group may be plotted with the frequency of occurrence as Y-axis. For instance, the changes of the numbers of SB-1 cells, i.e., the N1 sets of change $\Delta_{1,1}$, related to the N1 subjects in the evaluation group may be taken to plot the distribution of the changes of the numbers of SB-1 cells related to the N1 subjects in the evaluation group with respect to the frequency of occurrence. In this example, all the N1 subjects in the evaluation group have a specific disease (e.g., a cancer, a skin disease, or a kidney disease). Other changes $\Delta_{1,2}$-$\Delta_{a,c}$ related to the N1 subjects in the evaluation group may be considered in a similar way.

The criteria or standards (G) may include multiple criteria or standards $G_{1,1}$-$G_{1,d}$, $G_{2,1}$-$G_{2,d}$, . . . , and $G_{a,1}$-$G_{a,d}$, where "a" is a positive integer such as one of the numbers from 3 to 14, and "d" is a positive integer such as 2, 3, 4, 5, or 6. The notation $G_{1,1}$-$G_{1,d}$ means a series of data: $G_{1,1}$, $G_{1,2}$, . . . , to $G_{1,d}$. The notation $G_{2,1}$-$G_{2,d}$ means a series of data: $G_{2,1}$, $G_{2,2}$, . . . , to $G_{2,d}$. The notation $G_{a,1}$-$G_{a,d}$ means a series of data: $G_{a,1}$, $G_{a,2}$, . . . , to $G_{a,d}$. The first number in the subscript of G, i.e., the number immediately following the letter of G, i.e., from 1 to a, represents a certain selected type of stem cells or a group of selected two or more than two types of stem cells. The number a may be the number of all categories of stem cells or the number of all groups of stem cells. The second number in the subscript of G, i.e., the number immediately following the first number, i.e., from 1 to d, represents data types. The number d may be the number of data types.

With regard to the first number in the subscript of G, the first number in the subscript of $G_{1,1}$-$G_{a,d}$ is as the same specification as that of $R_{1,1}$-$R_{a,b}$ for the first set of results or data illustrated in the step 52 of FIG. 7. For example, the criteria $G_{1,1}$-$G_{1,d}$ having the first number 1 in the subscript of G are criteria or standards related to, for example, SB-1 cells. The criteria $G_{2,1}$-$G_{2,d}$ having the first number 2 in the subscript of G are criteria or standards related to, for example, SB-2 cells. The criteria $G_{11,1}$-$G_{11,d}$ having the first number 11 in the subscript of G are criteria or standards related to, for example, all types of stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)), which include one, more or all of SB-1 cells, SB-2 cells, BLSCs, VSELs, MSCs, MAPCs, BMSCs, MASCs, HSCs, MIAMI cells, pre-MSCs, MPPs, LRPs, CMPs, and CLPs. The number of all types of stem cells that can be detected or found (e.g., in the tissue sample) may be equal to or more than 3, 5, 10, 15, 20, 25, 50, 100 or 1,000 for cases requiring more information. The criteria $G_{13,1}$-$G_{13,d}$ having the first number 13 in the subscript of G are criteria or standards related to, for example, a combination or group of selected two or more than two types of stem cells, which may include one, more or all of SB-1 cells, SB-2 cells, BLSCs, VSELs, MSCs, MAPCs, BMSCs, MASCs, HSCs, MIAMI cells, pre-MSCs, neural stem cells, retina stem cells, olfactory bulbs stem cells, epidermal stem cells, muscle stem cells, intestine stem cells, pancreatic stem cells, heart stem cells, liver stem cells, kidney stem cell, endothelial stem cells, adipocyte or adipose-derived stem cells, MPPs, LRPs, CMPs, and CLPs. For cases requiring more information for the human or non-human body health condition and stem cell dynamics, the combination or group of the selected two or more than two types of stem cells may include more than 3, 5, 10, 15, 20, 25, 50, 100 or 1,000 types of stem cells including one, more, or all of the above-mentioned types of stem cells. The criteria $G_{14,1}$-$G_{14,d}$ having the first number 14 in the subscript of G are criteria or standards related to, for example, all of the stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)), which include more than 3, 5, 10, 15, 20, 25, 50, 100 or 1,000 types of stem cells containing one, more or all of SB-1 cells, SB-2 cells, BLSCs, VSELs, MSCs, MAPCs, BMSCs, MASCs, HSCs, MIAMI cells, and pre-MSCs. Other notations can be considered in a similar way.

With regard to the second number in the subscript of G, the criteria $G_{1,1}$-$G_{a,1}$ having the second number 1 in the subscript of G are criteria or standards related to, for example, (1) the upper limit of a range of the number of stem cells of a specific type or a combination or group of multiple types that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)), or (2) the upper limit of a range of the percentage of the number of stem cells of the specific type or the combination or group of multiple types to the total number of (small) biological or stem cells that can be detected or found (e.g., in the tissue sample). The criteria $G_{1,2}$-$G_{a,2}$ having the second number 2 in the subscript of G are criteria or standards related to, for example, (1) the increasing rate of change, e.g., an increase of at least 10, 20, 30, 40, 50, 60, 70, 80, 90, 100, 200, 300, 500 or 900 percent, in the number of stem cells of the specific type or the combination or group of multiple types, or (2) the increasing rate of change, e.g., an increase of at least 10, 20, 30, 40, 50, 60, 70, 80, 90, 100, 200, 300, 500 or 900 percent, in the percentage of the number of stem cells of the specific type or the combination or group of multiple types to the total number of (small) biological or stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)). The criteria $G_{1,3}$-$G_{a,3}$ having the second number 3 in the subscript of G are criteria or standards related to, for example, the sizes or size distribution (for example, the average size, the peak size, or the variation of the size distribution) of stem cells of the specific type or the combination or group of multiple types. The criteria $G_{1,4}$-$G_{a,4}$ having the second number 4 in the subscript of G are criteria or standards related to, for example, (1) an increase in the number of stem cells of the specific type or the combination or group of multiple types, or (2) an increase in the percentage of the number of stem cells of the specific type or the combination or group of multiple types to the total number of (small) biological or stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)). The criteria $G_{1,5}$-$G_{a,5}$ having the second number 5 in the subscript of G are criteria or standards related to, for example, (1) a decrease in the number of stem cells of the specific type or the combination or group of multiple types, or (2) a decrease in the percentage of the number of stem cells of the specific type or the combination or group of multiple types to the total number of (small) biological or stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)). The criteria $G_{1,6}$-$G_{a,6}$ having the second number 6 in the subscript of G are criteria or standards related to, for example, (1) the decreasing rate of change, e.g., a decrease of at least 10, 20, 30, 40, 50, 60, 70, 80 or 90 percent, in the number of stem cells of the specific type or the combination or group of multiple types, or (2) the decreasing rate of change, e.g., a decrease of at least 10, 20, 30, 40, 50, 60, 70, 80 or 90 percent, in the percentage of the number of stem cells of the specific type or the combination or group of multiple types to the total number of (small) biological or stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)). The criteria $G_{1,7}$-$G_{a,7}$ having the second number 7 in the subscript of G are criteria or standards related to, for example, (1) the lower limit of a range of the number of stem cells of the specific type or the combination or group of multiple types that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)), or (2) the lower limit of a range of the percentage of the number of stem cells of the specific type or the combination or group of multiple types to the total number of (small) biological or stem cells that can be detected or found (e.g., in a tissue sample such as bodily fluid (e.g., human-blood sample, peripheral-blood sample, whole-blood sample, or bone-marrow sample) or solid tissue (e.g., muscle sample or adipocyte sample)).

For further elaboration, the criterion $G_{1,1}$ indicates a criterion or standard for (1) the upper limit of a range of the number of SB-1 cells, or (2) the upper limit of a range of the percentage of the number of SB-1 cells to the total number of (small) biological or stem cells. The criterion $G_{1,2}$ indicates a criterion or standard for (1) the increasing rate of change, e.g., an increase of at least 10, 20, 30, 40, 50, 60, 70, 80, 90, 100, 200, 300, 500 or 900 percent, in the number of SB-1 cells, or (2) the increasing rate of change, e.g., an increase of at least 10, 20, 30, 40, 50, 60, 70, 80, 90, 100, 200, 300, 500 or 900 percent, in the percentage of the number of SB-1 cells to the total number of (small) biological or stem cells. The criterion $G_{1,3}$ indicates a criterion or standard for the sizes or size distribution (for example, the average size, the peak size, or the variation of the size distribution) of SB-1 cells. The criterion $G_{1,4}$ indicates a criterion or standard for (1) an increase in the number of SB-1 cells, or (2) an increase in the percentage of the number of SB-1 cells to the total number of (small) biological or stem cells. The criterion $G_{1,5}$ indicates a criterion or standard for (1) a decrease in the number of SB-1 cells, or (2) a decrease in the percentage of the number of SB-1 cells to the total number of (small) biological or stem cells. The criterion $G_{1,6}$ indicates a criterion or standard for (1) the decreasing rate of change, e.g., a decrease of at least 10, 20, 30, 40, 50, 60, 70, 80 or 90 percent, in the number of SB-1 cells, or (2) the decreasing rate of change, e.g., a decrease of at least 10, 20, 30, 40, 50, 60, 70, 80 or 90 percent, in the percentage of the number of SB-1 cells to the total number of (small) biological or stem cells. The criterion $G_{1,7}$ indicates a criterion or standard for (1) the lower limit of a range of the number of SB-1 cells, or (2) the lower limit of a range of the percentage of the number of SB-1 cells to the total number of (small) biological or stem cells. Other notations can be considered in a similar way.

The criteria or standards (G) may further include a criterion or standard for a new type of stem cells. The criteria or standards (G) may further include a criterion or standard for a stem cell absent (not detected in the N1 first tests, assessments or measurements) in the N1 first sets of results or data, but present (detected in the N1 second tests, assessments or measurements) in the N1 second sets of results or data. The criteria or standards (G) may further include a criterion or standard for a stem cell absent (not detected in the N1 second tests, assessments or measurements) in the N1 second sets of results or data, but present (detected in the N1 first tests, assessments or measurements) in the N1 first sets of results or data.

The criteria or standards (G) may be, but not limited to, established with regards to the small stem cells smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell), which may be referred to the small stem cells as illustrated in the above-mentioned test, assessment or measurement (M1).

Alternatively, the criteria or standards (G) may be, but not limited to, established with regards to the stem cells including the small ones smaller than or equal to 4, 5 or 6 micrometers, such as between 0.1 and 6.0 micrometers, between 0.5 and 6.0 micrometers, between 1.0 and 6.0 micrometers, between 0.1 and 5.0 micrometers, between 0.5 and 5.0 micrometers, between 1.0 and 5.0 micrometers, between 0.1 and 4.0 micrometers, between 0.5 and 4.0 micrometers or between 1.0 and 4.0 micrometers, in size (as defined by the above-mentioned size (Z) of a cell) and including the large ones greater than 6 micrometers in size (as defined by the above-mentioned size (Z) of a cell), which may be referred to the stem cells including the small and large ones as illustrated in the above-mentioned test, assessment or measurement (M2).

The criteria or standards (G) may be, but not limited to, established against age, gender, race, weight, height, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) of the N1 subjects.

As mentioned above, the step 107 in FIG. 9 may be performed in various sequences. For example, the steps 51-55 may be performed on respective ones of the N1 subjects in different respective time periods that can be overlapped or non-overlapped. For example, the steps 51-55 may be performed on a first sub-group of the N1 subjects after the steps 51-55 are performed on a second sub-group of the N1 subjects but before the steps 51-55 are performed on a third sub-group of the N1 subjects.

For ensuring the safety (no significant side-effects or damages to the human or non-human body, for example, organs such as liver or kidney) of the one or more of the actions or stimuli (X) illustrated in the step 107, data about liver and kidney functions related to each of the N1 subjects before and after taking or being subjected to the one or more of the actions or stimuli (X) illustrated in the step 107 may need to be optionally obtained.

The data about liver and kidney functions related to the N1 subjects before taking or being subjected to the one or more of the actions or stimuli (X) illustrated in the step 107 are defined as data LKB9, and the data about liver and kidney functions related to the N1 subjects after taking or being subjected to the one or more of the actions or stimuli (X) illustrated in the step 107 are defined as data LKA9. By comparing the data LKA9 with the data LKB9, the differences between the data LKA9 and LKB9 may be obtained to identify or evaluate the effect of the one or more of the actions or stimuli (X) illustrated in the step 107 on their livers and kidneys of the N1 subjects. Each piece of the data LKA9 and LKB9 may include, but not limited to, (1) data about kidney functions (such as BUN, GFR, CCR, ACR, cystatin C, uric acid, microalbumin, urine routine, and/or urine sediment), and (2) data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV) for each of the N1 subjects.

If there is no (statistically significant) difference between the data LKA9 and LKB9 or the data LKA9 are (much or statistically significantly) better than the data LKB9, it could mean the one or more of the actions or stimuli (X) illustrated in the step 107 are harmless or even beneficial to their livers and/or kidneys of the N1 subjects and the criteria or standards (G) in the next step 109 may be allowed to be established due to the one or more of the actions or stimuli (X) illustrated in the step 107 having no negative impacts on their livers and/or kidneys of the N1 subjects. If the data LKA9 are (much or statistically significantly) worse than the data LKB9, it could mean the one or more of the actions or stimuli (X) illustrated in the step 107 are harmful to their livers and/or kidneys of the N1 subjects and the criteria or standards (G) in the next step 109 may not be allowed to be established due to the one or more of the actions or stimuli (X) illustrated in the step 107 having negative impacts on their livers and/or kidneys of the N1 subjects.

Figure 10:
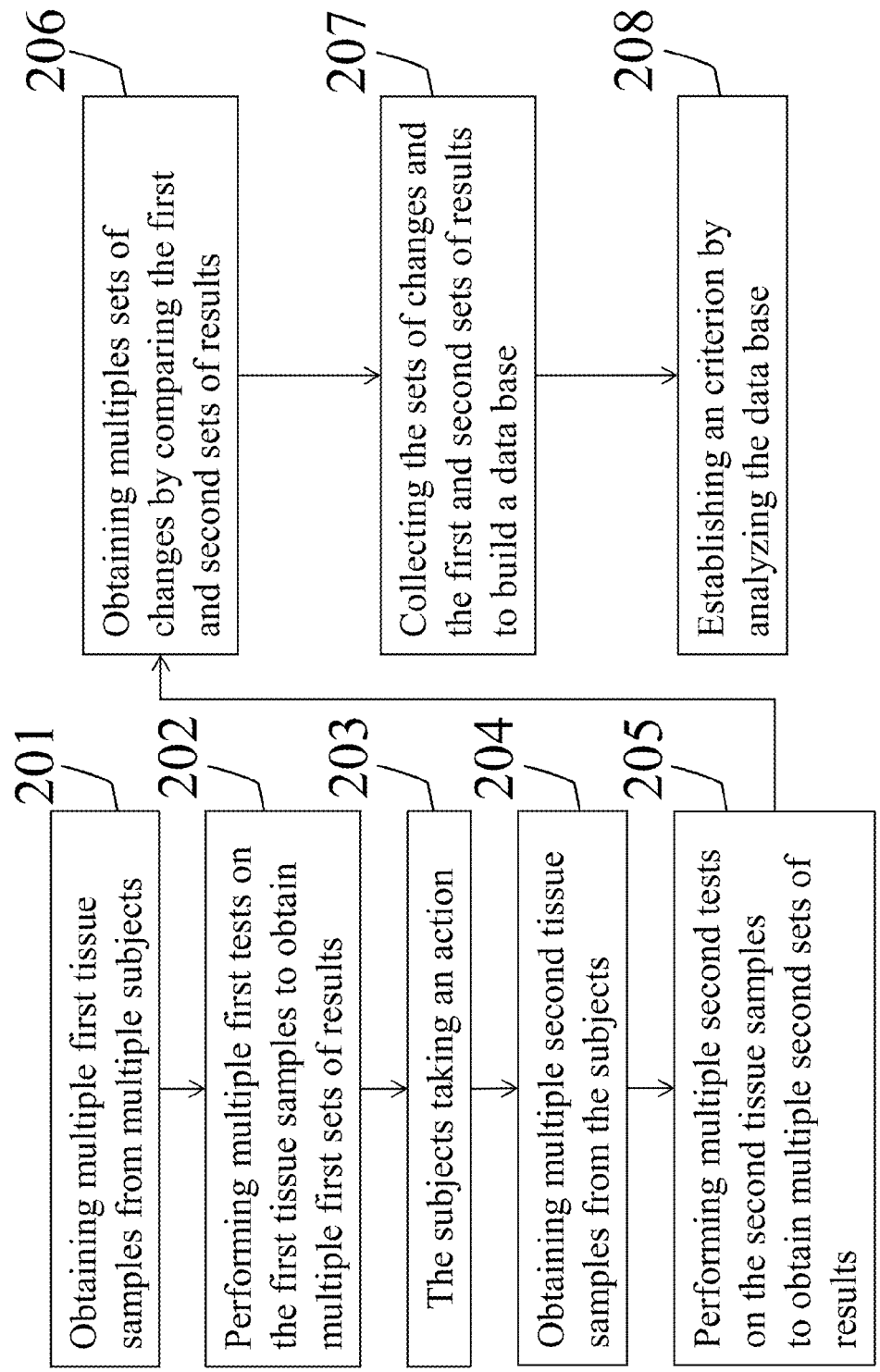
FIG. 10 shows a flow chart for establishing criteria or standards for one or more types of stem cells according to the third embodiment of the present disclosure.

FIG. 10 is another flow chart for establishing or obtaining the above-mentioned criteria or standards (G). Referring to FIG. 10, in step 201, the step 51 as illustrated in FIG. 7 may be performed on each of N1 subjects in an evaluation group in a first time period so as to obtain N1 first tissue samples from the N1 respective subjects in the first time period, such as in one day or two days or in a week, where "N1" is a positive integer equal to or greater than 2, 4, 6, 10, 20 or 50. The N1 subjects in the evaluation group illustrated herein may be referred to the N1 subjects in the evaluation group illustrated in FIG. 9, respectively. The N1 first tissue samples illustrated herein may be referred to the N1 first tissue samples illustrated in FIG. 9.

Next, referring to FIG. 10, in step 202, the step 52 as illustrated in FIG. 7 may be performed on the N1 respective first tissue samples such that the first test, assessment or measurement including extracting, characterizing, assessing and measuring stem cells may be performed, referring to one of the above-mentioned tests, assessments or measurements (M0), (M1) and (M2), on the respective N1 first tissue samples to obtain N1 first sets of results or data $R_{1,1}$-$R_{a,b}$ related to one or more types of stem cells from the N1 first tissue samples descriptively, qualitatively or quantitatively. The N1 first sets of results or data $R_{1,1}$-$R_{a,b}$ illustrated herein may be presented in the same way as those illustrated in the step 107 of FIG. 9.

Referring to FIG. 10, after the step 201 and/or the step 202 is/are performed, step 203 is performed. In the step 203, the step 53 as illustrated in FIG. 7 may be performed on the respective N1 subjects in the evaluation group in a second time period such that each of the N1 subjects takes or is subjected to the same one or more of the actions or stimuli (X) such as taking the same drug(s) approved by a government department (e.g., U.S. FDA) for curing a specific disease (e.g., a cancer) and/or taking the same nutrients or dietary supplements in the second time period.

Next, referring to FIG. 10, in step 204, the step 54 as illustrated in FIG. 7 may be performed on the respective N1 subjects in the evaluation group in a third time period, such as in one day or two days or in a week, so as to obtain N1 second tissue samples from the N1 subjects in the third time period. The first, second and third time periods are non-overlapped, for example. The N1 second tissue samples illustrated herein may be referred to the N1 second tissue samples illustrated in FIG. 9.

Next, referring to FIG. 10, in step 205, the step 55 as illustrated in FIG. 7 may be performed on the N1 respective second tissue samples such that the second test, assessment or measurement including extracting, characterizing, assessing and measuring stem cells can be performed, referring to one of the above-mentioned tests, assessments or measurements (M0), (M1) and (M2), on the respective N1 second tissue samples to obtain N1 second sets of results or data $R_{1,1}$-$R_{a,b}$ related to one or more types of stem cells from the N1 second tissue samples descriptively, qualitatively or quantitatively. The N1 second sets of results or data $R_{1,1}$-$R_{a,b}$ illustrated herein may be presented in the same way as those illustrated in the step 107 of FIG. 9.

Next, referring to FIG. 10, in step 206, the step 56 as illustrated in FIG. 7 may be performed so as to obtain N1 sets of changes $\Delta_{1,1}$-$\Delta_{a,c}$ by comparing the N1 first and N1 second sets of results or data $R_{1,1}$-$R_{a,b}$ having the same first and second numbers in the subscript with regard to the N1 respective subjects in the evaluation group. The N1 sets of changes $\Delta_{1,1}$-$\Delta_{a,c}$ illustrated herein may be presented in the same way as those illustrated in the step 107 of FIG. 9.

Next, referring to FIG. 10, in step 207, the N1 first and N1 second sets of results or data $R_{1,1}$-$R_{a,b}$ related to the N1 subjects and the N1 sets of changes $\Delta_{1,1}$-$\Delta_{a,c}$ related to the N1 subjects are collected to build a data base. The data base further includes the data of, for example, age, gender, race, height, weight, blood pressure, heartbeat, Ig, BMI, data about kidney functions (such as BUN, GFR, CCR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) for each of the N1 subjects in the evaluation group.

Next, referring to FIG. 10, in step 208, the data base built in the step 207 may be analyzed with a statistical significance such that the above-mentioned criteria or standards (G) may be established for identifying, determining, evaluating or assessing the effect of one or more of the actions or stimuli (X), as mentioned in the step 109 of FIG. 9.

Figure 10A:
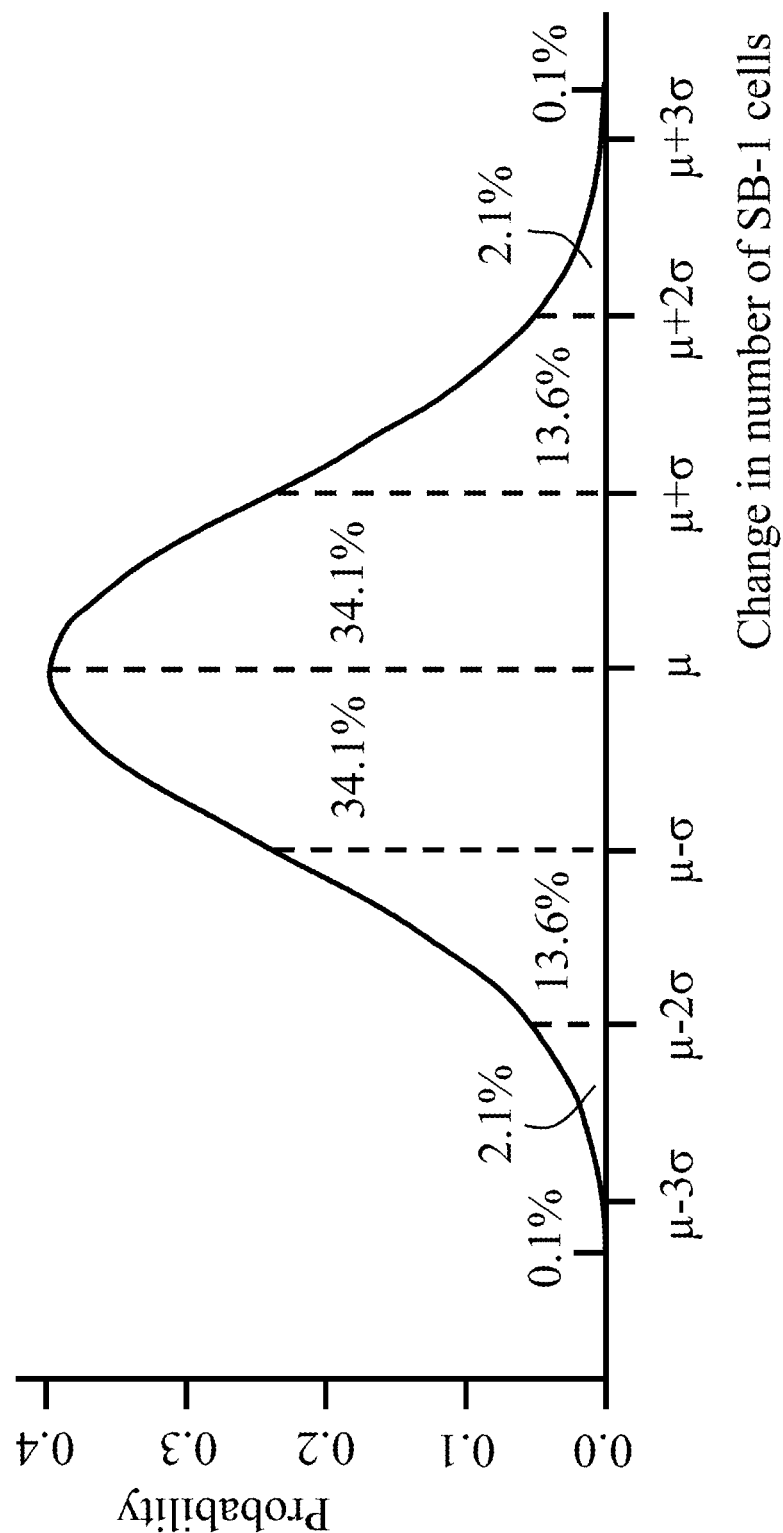
FIG. 10A shows a Gaussian distribution of change in number of SB-1 cells.

Statistically, Gaussian distribution can be employed for analyzing data in the data base built in the step 108 or 207 to establish the criteria or standards (G) for evaluating any one or more of actions or stimuli (X) or for determining if any one or more of actions or stimuli (X) can improve or cure a specific disease such as a cancer, a skin disease, or a kidney disease. For example, referring to FIG. 10A showing Gaussian distribution with relationship between the changes $\Delta_{1,1}$, in the N1 sets of changes $\Delta_{1,1}$-$\Delta_{a,c}$, related to the number of the SB-1 cells, as X-axis, and the probability of occurrence, as Y-axis, the Gaussian distribution may have the probability of 68.2% with the Gaussian peak at $\mu$ within a variance of $\sigma$ (i.e., width $2\sigma$ of the peak), the probability of 95.4% with Gaussian peak at $\mu$ within a variance of $2\sigma$ (i.e., width $4\sigma$ of the peak), and the probability of 99.8% with Gaussian peak at $\mu$ within a variance of $3\sigma$ (i.e., width $6\sigma$ of the peak). Based on the peaks and/or variances of Gaussian distributions for various types of results or data, such as the changes $\Delta_{1,1}$-$\Delta_{a,c}$ in the N1 sets, for each one or more types of stem cells, the criteria or standards (G) for each one or more types of stem cells may be established or obtained for identifying, determining, evaluating or assessing the effect of one or more of the actions or stimuli (X).

The data in the data base built in the step 108 may be analyzed to generate Gaussian distributions for the data in the data base built in the step 108, respectively. The data in the data base built in the step 207 may be analyzed to generate Gaussian distributions for the data in the data base built in the step 207, respectively.

For ensuring the safety (no significant side-effects or damages to the human or non-human body, for example, organs such as liver or kidney) of the one or more of the actions or stimuli (X) illustrated in the step 203, data about liver and kidney functions related to each of the N1 subjects before and after taking or being subjected to the one or more of the actions or stimuli (X) illustrated in the step 203 may need to be obtained as an option.

The data about liver and kidney functions related to the N1 subjects before taking or being subjected to the one or more of the actions or stimuli (X) illustrated in the step 203 are defined as data LKB10, and the data about liver and kidney functions related to the N1 subjects after taking or being subjected to the one or more of the actions or stimuli (X) illustrated in the step 203 are defined as data LKA10. By comparing the data LKA10 with the data LKB10, the differences between the data LKA10 and LKB10 may be obtained to identify or evaluate the effect of the one or more of the actions or stimuli (X) illustrated in the step 203 on their livers and kidneys of the N1 subjects. Each piece of the data LKA10 and LKB10 may include, but not limited to, (1) data about kidney functions (such as BUN, GFR, CCR, ACR, cystatin C, uric acid, microalbumin, urine routine, and/or urine sediment), and (2) data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV) for each of the N1 subjects.

If there is no (statistically significant) difference between the data LKA10 and LKB10 or the data LKA10 are (much or statistically significantly) better than the data LKB10, it could mean the one or more of the actions or stimuli (X) illustrated in the step 203 are harmless or even beneficial to their livers and/or kidneys of the N1 subjects and the criteria or standards (G) in the next step 208 may be allowed to be established due to the one or more of the actions or stimuli (X) illustrated in the step 203 having no negative impacts on their livers and/or kidneys of the N1 subjects. If the data LKA10 are (much or statistically significantly) worse than the data LKB10, it could mean the one or more of the actions or stimuli (X) illustrated in the step 203 are harmful to their livers and/or kidneys of the N1 subjects and the criteria or standards (G) in the next step 208 may not be allowed to be established due to the one or more of the actions or stimuli (X) illustrated in the step 203 having negative impacts on their livers and/or kidneys of the N1 subjects.

This embodiment provides a method, an apparatus, or an integrated system combining methodology, software (tools) and hardware (equipments, machines, or devices for extraction, filtering, purification, analyzing stem cells), for establishing the criteria or standards (G) by analyzing the N1 first and N1 second sets of results or data $R_{1,1}$-$R_{a,b}$ and the N1 sets of changes $\Delta_{1,1}$-$\Delta_{a,c}$, as mentioned in accordance with this embodiment.

After the criteria or standards (G) are established or obtained by the steps 107-109 illustrated in FIG. 9 or by the steps 201-208 illustrated in FIG. 10, the effect of one or more actions or stimuli (Xa) on a subject (Sa) that may be referred to the above-mentioned subject (S) may be identified, determined, evaluated or assessed by, e.g., (1) sequentially performing the above-mentioned steps 51-55 illustrated in FIG. 7, including performing the one or more actions or stimuli (Xa) in the step 53, on the subject (Sa) to obtain a first set of results or data $R_{1,1}$-$R_{a,b}$, such as the number of SB-1 cells (i.e., $R_{1,1}$), related to the subject (Sa) before taking or being subjected to the one or more actions or stimuli (Xa) in the step 53 and a second set of results or data $R_{1,1}$-$R_{a,b}$, such as the number of SB-1 cells (i.e., $R_{1,1}$), related to the subject (Sa) after taking or being subjected to the one or more actions or stimuli (Xa) in the step 53; (2) next comparing the first and second sets of results or data $R_{1,1}$-$R_{a,b}$ related to the subject (Sa) to obtain a set of changes $\Delta_{1,1}$-$\Delta_{a,c}$, such as an increase or decrease in the number of SB-1 cells (i.e., $\Delta_{1,1}$), related to the subject (Sa), as illustrated in the step 56 of FIG. 7; and (3) then comparing the set of changes $\Delta_{1,1}$-$\Delta_{a,c}$, such as an increase or decrease in the number of SB-1 cells (i.e., $\Delta_{1,1}$), with corresponding ones of the criteria or standards (G), such as the criterion for an increase or decrease in the number of SB-1 cells (i.e., $G_{1,4}$ or $G_{1,5}$), built up in the step 109 of FIG. 9 or the step 208 of FIG. 10 to determine whether the one or more actions or stimuli (Xa) in the step 53 are effective to health or immunity, harmful to health or immunity, or ineffective or harmless to health or immunity. The one or more actions or stimuli (Xa) may be, but not limited to, the one or more of the actions or stimuli (X) described in the step 53 of FIG. 7 or the step 203 of FIG. 10, or any other one of the actions or stimuli (X).

Accordingly, the one or more actions or stimuli (Xa) may be evaluated as "effective to health or immunity" based on the result that a selected one of the changes $\Delta_{1,1}$-$\Delta_{a,c}$ such as the change in the number of SB-1 cells (i.e., $\Delta_{1,1}$), related to the subject (Sa) meets a corresponding one of the criteria $G_{1,1}$-$G_{a,d}$, such as the criterion for an increase in the number of SB-1 cells (i.e., $G_{1,4}$), built up in the step 109 of FIG. 9 or the step 208 of FIG. 10, as "harmful to health or immunity" based on the result that the selected one of the changes $\Delta_{1,1}$-$\Delta_{a,c}$, such as the change in the number of SB-1 cells (i.e., $\Delta_{1,1}$), related to the subject (Sa) meets another corresponding one of the criteria $G_{1,1}$-$G_{a,d}$, such as the criterion for a decrease in the number of SB-1 cells (i.e., $G_{1,5}$), built up in the step 109 of FIG. 9 or the step 208 of FIG. 10, or as "ineffective or harmless to health or immunity" based on the result that the selected one of the changes $\Delta_{1,1}$-$\Delta_{a,c}$, such as the change in the number of SB-1 cells (i.e., $\Delta_{1,1}$), related to the subject (Sa) does not meet the two corresponding ones of the criteria $G_{1,1}$-$G_{a,d}$, such as the criterion for an increase in the number of SB-1 cells (i.e., $G_{1,4}$) and the criterion for a decreases in the number of SB-1 cells (i.e., $G_{1,5}$), built up in the step 109 of FIG. 9 or the step 208 of FIG. 10.

In the other application, after the criteria or standards (G) are established or obtained by the steps 107-109 illustrated in FIG. 9 or by the steps 201-208 illustrated in FIG. 10, the effect of the above-mentioned one or more actions or stimuli (Xa) on a subject (Sa) that may be referred to the above-mentioned subject (S) may be identified, determined, evaluated or assessed by, e.g., (1) sequentially performing the above-mentioned steps 53-55 illustrated in FIG. 7, including performing the one or more actions or stimuli (Xa) in the step 53 of FIG. 7, on the subject (Sa) to obtain a set of results or data $R_{a,1}$-$R_{a,b}$, such as the number of SB-1 cells (i.e., $R_{1,1}$), related to the subject (Sa) after taking or being subjected to the one or more actions or stimuli (Xa) in the step 53, and (2) then comparing the set of results or data $R_{a,1}$-$R_{a,b}$, such as the number of SB-1 cells (i.e., $R_{1,1}$), with corresponding ones of the criteria or standards (G), such as the criterion for the upper limit of a range of the number of SB-1 cells (i.e., $G_{1,1}$), built up in the step 109 of FIG. 9 or the step 208 of FIG. 10 to determine whether the one or more actions or stimuli (Xa) in the step 53 are effective to health or immunity, harmful to health or immunity, or ineffective or harmless to health or immunity.

Accordingly, the one or more actions or stimuli (Xa) may be evaluated as "effective to health or immunity" based on the result that a selected one of the results or data $R_{1,1}$-$R_{a,b}$, such as the number of SB-2 cells (i.e., $R_{2,1}$), related to the subject (Sa) is over a first corresponding one of the criteria $G_{1,1}$-$G_{a,d}$, such as the criterion for the upper limit of a range of the number of SB-2 cells (i.e., $G_{2,1}$), built up in the step 109 of FIG. 9 or the step 208 of FIG. 10, as "harmful to health or immunity" based on the result that the selected one of the results or data $R_{1,1}$-$R_{a,b}$, such as the number of SB-2 cells (i.e., $R_{2,1}$), related to the subject (Sa) is below or under a second corresponding one of the criteria $G_{1,1}$-$G_{a,d}$, such as the criterion for the lower limit of a range of the number of SB-2 cells (i.e., $G_{2,7}$), built up in the step 109 of FIG. 9 or the step 208 of FIG. 10, or as "ineffective or harmless to health or immunity" based on the result that the selected one of the results or data $R_{1,1}$-$R_{a,b}$, such as the number of SB-2 cells (i.e., $R_{2,1}$), related to the subject (Sa) is not over the first corresponding one of the criteria $G_{1,1}$-$G_{a,d}$, such as the criterion for the upper limit of a range of the number of SB-2 cells (i.e., $G_{2,1}$), and is not below or not under the second corresponding one of the criteria $G_{1,1}$-$G_{a,d}$, such as the criterion for the lower limit of a range of the number of SB-2 cells (i.e., $G_{2,7}$).

For ensuring the safety (no significant side-effects or damages to the human or non-human body, for example, organs such as liver or kidney) of the one or more actions or stimuli (Xa), data about liver and kidney functions related to the subject (Sa) before and after taking or being subjected to the one or more actions or stimuli (Xa) may need to be obtained as an option. The data about liver and kidney functions related to the subject (Sa) before taking or being subjected to the one or more actions or stimuli (Xa) are defined as data LKBa, and the data about liver and kidney functions related to the subject (Sa) after taking or being subjected to the one or more actions or stimuli (Xa) are defined as data LKAa. By comparing the data LKAa with the data LKBa, the differences between the data LKAa and LKBa may be obtained to identify or evaluate the effect of the one or more actions or stimuli (Xa) on the liver and kidney of the subject (Sa). Each piece of the data LKAa and LKBa may include, but not limited to, (1) data about kidney functions (such as BUN, GFR, CCR, ACR, cystatin C, uric acid, microalbumin, urine routine, and/or urine sediment), and (2) data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV).

If there is no (significant) difference between the data LKAa and LKBa, it could mean the one or more actions or stimuli (Xa) are harmless to the liver and/or kidney of the subject (Sa). In this case, if a selected one of the results or data $R_{1,1}$-$R_{a,b}$, such as the number of SB-2 cells (i.e., $R_{2,1}$), related to the subject (Sa) is over or meets a first corresponding one of the criteria $G_{1,1}$-$G_{a,d}$, such as the criterion for the upper limit of a range of the number of SB-2 cells (i.e., $G_{2,1}$), built up in the step 109 of FIG. 9 or the step 208 of FIG. 10, the one or more actions or stimuli (Xa) may be evaluated as "effective to immunity without impacts or damages on the liver and kidney". If the selected one of the results or data $R_{1,1}$-$R_{a,b}$, such as the number of SB-2 cells (i.e., $R_{2,1}$), related to the subject (Sa) is below or under or does not meet a second corresponding one of the criteria $G_{1,1}$-$G_{a,d}$, such as the criterion for the lower limit of a range of the number of SB-2 cells (i.e., $G_{2,7}$), built up in the step 109 of FIG. 9 or the step 208 of FIG. 10, the one or more actions or stimuli (Xa) may be evaluated as "harmful to immunity without impacts or damages on the liver and kidney". If the selected one of the results or data $R_{1,1}$-$R_{a,b}$, such as the number of SB-2 cells (i.e., $R_{2,1}$), related to the subject (Sa) is not over or does not meet the first corresponding one of the criteria $G_{1,1}$-$G_{a,d}$, such as the criterion for the upper limit of a range of the number of SB-2 cells (i.e., $G_{2,1}$), and is not below or not under or does not meet the second corresponding one of the criteria $G_{1,1}$-$G_{a,d}$, such as the criterion for the lower limit of a range of the number of SB-2 cells (i.e., $G_{2,7}$), the one or more actions or stimuli (Xa) may be evaluated as "ineffective or harmless to immunity without impacts or damages on the liver and kidney".

If the data LKAa are (much or significantly) better than the data LKBa, it could mean the one or more actions or stimuli (Xa) are beneficial to the liver and/or kidney of the subject (Sa). In this case, if a selected one of the results or data $R_{1,1}$-$R_{a,b}$, such as the number of SB-2 cells (i.e., $R_{2,1}$), related to the subject (Sa) is over or meets a first corresponding one of the criteria $G_{1,1}$-$G_{a,d}$, such as the criterion for the upper limit of a range of the number of SB-2 cells (i.e., $G_{2,1}$), built up in the step 109 of FIG. 9 or the step 208 of FIG. 10, the one or more actions or stimuli (Xa) may be evaluated as "effective to immunity and beneficial to the liver and/or kidney". If the selected one of the results or data $R_{1,1}$-$R_{a,b}$, such as the number of SB-2 cells (i.e., $R_{2,1}$), related to the subject (Sa) is below or under or does not meet a second corresponding one of the criteria $G_{1,1}$-$G_{a,d}$, such as the criterion for the lower limit of a range of the number of SB-2 cells (i.e., $G_{2,7}$), the one or more actions or stimuli (Xa) may be evaluated as "harmful to immunity but beneficial to the liver and/or kidney". If the selected one of the results or data $R_{1,1}$-$R_{a,b}$, such as the number of SB-2 cells (i.e., $R_{2,1}$), related to the subject (Sa) is not over or does not meet the first corresponding one of the criteria $G_{1,1}$-$G_{a,d}$, such as the criterion for the upper limit of a range of the number of SB-2 cells (i.e., $G_{2,1}$) and is not below or not under or does not meet the second corresponding one of the criteria $G_{1,1}$-$G_{a,d}$, such as the criterion for the lower limit of a range of the number of SB-2 cells (i.e., $G_{2,7}$), the one or more actions or stimuli (Xa) may be evaluated as "ineffective or harmless to immunity but beneficial to the liver and/or kidney".

If the data LKAa are little worse than the data LKBa, it could mean the one or more actions or stimuli (Xa) are slightly harmful to the liver and/or kidney of the subject (Sa). In this case, if a selected one of the results or data $R_{1,1}$-$R_{a,b}$, such as the number of SB-2 cells (i.e., $R_{2,1}$), related to the subject (Sa) is over or meets a first corresponding one of the criteria $G_{1,1}$-$G_{a,d}$, such as the criterion for the upper limit of a range of the number of SB-2 cells (i.e., $G_{2,1}$), built up in the step 109 of FIG. 9 or the step 208 of FIG. 10, the one or more actions or stimuli (Xa) may be evaluated as "effective to immunity but slightly harmful to the liver and/or kidney". If the selected one of the results or data $R_{1,1}$-$R_{a,b}$, such as the number of SB-2 cells (i.e., $R_{2,1}$), related to the subject (Sa) is below or under or does not meet a second corresponding one of the criteria $G_{1,1}$-$G_{a,d}$, such as the criterion for the lower limit of a range of the number of SB-2 cells (i.e., $G_{2,7}$), built up in the step 109 of FIG. 9 or the step 208 of FIG. 10, the one or more actions or stimuli (Xa) may be evaluated as "harmful to immunity and to the liver and/or kidney". If the selected one of the results or data $R_{1,1}$-$R_{a,b}$, such as the number of SB-2 cells (i.e., $R_{2,1}$), related to the subject (Sa) is not over or does not meet the first corresponding one of the criteria $G_{1,1}$-$G_{a,d}$, such as the criterion for the upper limit of a range of the number of SB-2 cells (i.e., $G_{2,1}$) and is not below or not under or does not meet the second corresponding one of the criteria $G_{1,1}$-$G_{a,d}$, such as the criterion for the lower limit of a range of the number of SB-2 cells (i.e., $G_{2,7}$), the one or more actions or stimuli (Xa) may be evaluated as "ineffective or harmless to immunity but slightly harmful to the liver and/or kidney".

If the data LKAa are much or significantly worse than the data LKBa, it could mean the one or more actions or stimuli (Xa) are significantly harmful to the liver and/or kidney of the subject (Sa). In this case, if a selected one of the results or data $R_{1,1}$-$R_{a,b}$, such as the number of SB-2 cells (i.e., $R_{2,1}$), related to the subject (Sa) is over or meets a first corresponding one of the criteria $G_{1,1}$-$G_{a,d}$, such as the criterion for the upper limit of a range of the number of SB-2 cells (i.e., $G_{2,1}$), built up in the step 109 of FIG. 9 or the step 208 of FIG. 10, the one or more actions or stimuli (Xa) may be evaluated as "effective to immunity but significantly harmful to the liver and/or kidney". If the selected one of the results or data $R_{1,1}$-$R_{a,b}$, such as the number of SB-2 cells (i.e., $R_{2,1}$), related to the subject (Sa) is below or under or does not meet a second corresponding one of the criteria $G_{1,1}$-$G_{a,d}$, such as the criterion for the lower limit of a range of the number of SB-2 cells (i.e., $G_{2,7}$), built up in the step 109 of FIG. 9 or the step 208 of FIG. 10, the one or more actions or stimuli (Xa) may be evaluated as "harmful to immunity and to the liver and/or kidney". If the selected one of the results or data $R_{1,1}$-$R_{a,b}$, such as the number of SB-2 cells (i.e., $R_{2,1}$), related to the subject (Sa) is not over or does not meet the first corresponding one of the criteria $G_{1,1}$-$G_{a,d}$, such as the criterion for the upper limit of a range of the number of SB-2 cells (i.e., $G_{2,1}$) and is not below or not under or does not meet the second corresponding one of the criteria $G_{1,1}$-$G_{a,d}$, such as the criterion for the lower limit of a range of the number of SB-2 cells (i.e., $G_{2,7}$), the one or more actions or stimuli (Xa) may be evaluated as "harmless to immunity but significantly harmful to the liver and/or kidney".

This embodiment further provides a method, an apparatus, or an integrated system combining methodology, software (tools) and hardware (equipments, machines, or devices for extraction, filtering, purification, analyzing stem cells), for evaluating the one or more actions or stimuli (Xa) on the subject (Sa) (such as a human or a non-human body) by comparing the set of changes $\Delta_{1,1}$-$\Delta_{a,c}$ related to the subject (Sa) with the criteria $G_{1,1}$-$G_{a,d}$ or by comparing the set of results or data $R_{1,1}$-$R_{a,b}$ related to the subject (Sa) with the criteria $G_{1,1}$-$G_{a,d}$, as mentioned in accordance with this embodiment.

A criterion establishing method, in accordance with the third embodiment, comprises taking a first tissue sample from a subject; analyzing said first tissue sample to obtain a first result related to information of a type or types of stem cells; after said taking said first tissue sample, performing an action on said subject; after said performing said action on said subject, taking a second tissue sample from said subject; analyzing said second tissue sample to obtain a second result related to information of said type or types of stem cells; comparing said first and second results to obtain a change; and establishing a criterion for said type or types of stem cells based on said change.

A method, in accordance with the third embodiment, of evaluating an effect of an action based on a criterion, comprises taking a first tissue sample from a subject; analyzing said first tissue sample to obtain a first result related to information of a type or types of stem cells; after said taking said first tissue sample, performing said action on said subject; after said performing said action on said subject, taking a second tissue sample from said subject; analyzing said second tissue sample to obtain a second result related to information of said type or types of stem cells; comparing said first and second results to obtain a change; and comparing said change with said criterion.

A criterion establishing method, in accordance with the third embodiment, comprises: performing an action on a subject; after said performing said action on said subject, taking a tissue sample from said subject; analyzing said tissue sample to obtain a result related to information of a type or types of stem cells; and establishing a criterion for said type or types of stem cells based on said result.

A method, in accordance with the third embodiment, of evaluating an effect of an action based on a criterion, comprises: performing said action on a subject; after said performing said action on said subject, taking a tissue sample from said subject; analyzing said tissue sample to obtain a result related to information of a type or types of stem cells; and comparing said result with said criterion.

A criterion establishing method, in accordance with the third embodiment, comprises: establishing a criterion for a type or types of stem cells based on multiple first results and multiple second results, wherein each of said first results is obtained by analyzing a tissue sample taken from a correspond one of subjects before taking an action, and each of said second results is obtained by analyzing a tissue sample taken from a correspond one of said subjects after taking said action.

Fourth Embodiment

Figure 11A:
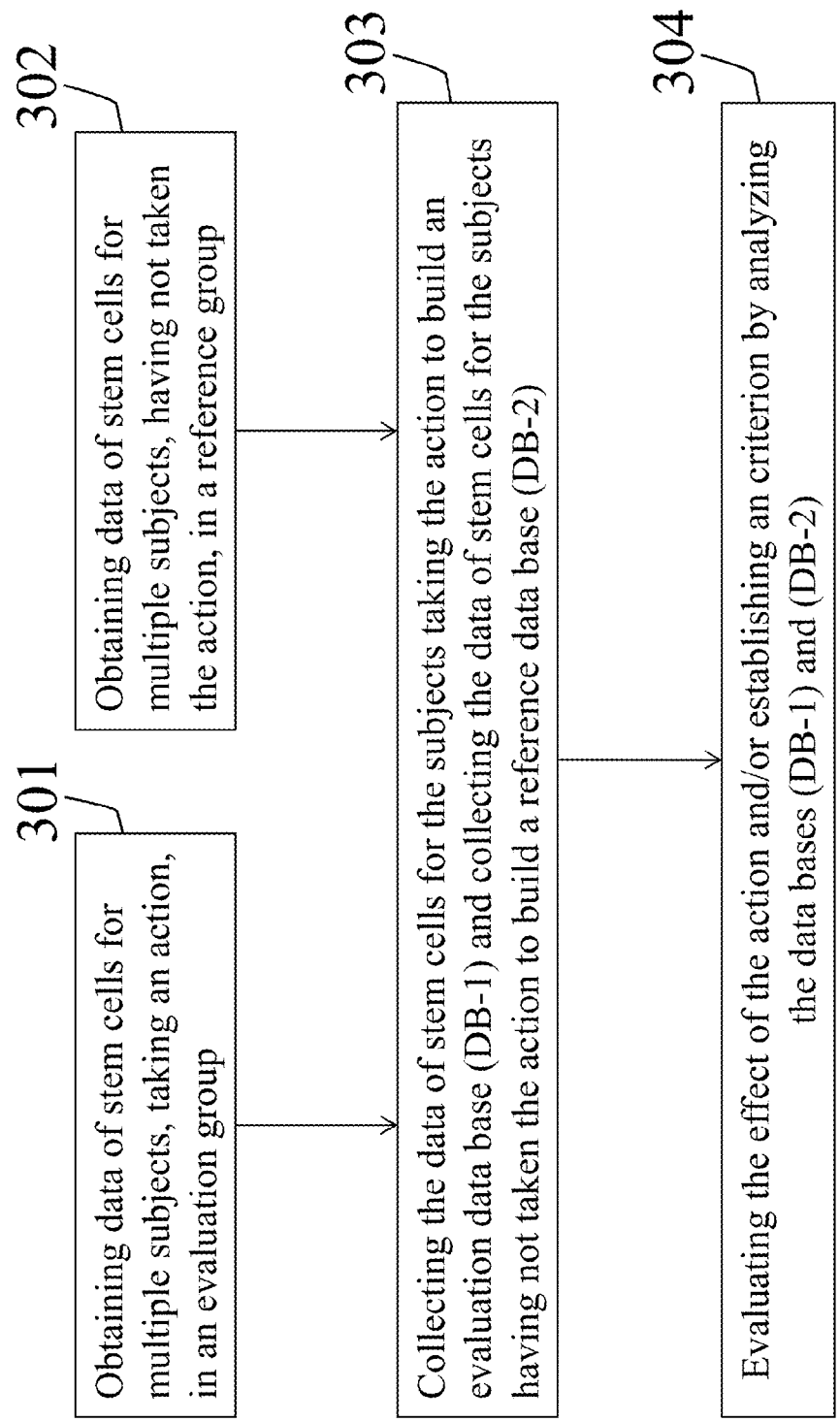
FIG. 11A shows a flow chart for evaluating the effect of one or more actions or stimuli performed on subjects in an evaluation group in comparison with data from subjects in a reference group according to a fourth embodiment of the present disclosure.

FIG. 11A is a flow chart for evaluating the effect of one or more actions or stimuli performed on subjects in an evaluation group in comparison with data from subjects in a reference group. Referring to FIG. 11A, in step 301, the step 107 illustrated in FIG. 9 or the steps 201-206 illustrated in FIG. 10 may be performed on the N1 subjects in the evaluation group to obtain data or information of stem cells, including the N1 first sets of results or data $R_{1,1}$-$R_{a,b}$, the N1 second sets of results or data $R_{1,1}$-$R_{a,b}$, and the N1 sets of changes $\Delta_{1,1}$-$\Delta_{a,c}$, as mentioned in FIG. 9 or 10, related to the N1 subjects in the evaluation group. For certain steps, the time period (period means duration, similar in all the followings) between them need to be controlled for a fair comparison between the evaluation group and the reference group. For example, the controlled time of periods between certain steps for the evaluation group may include: (1) in the step 107 illustrated in FIG. 9, the time period ($T_1$) between the steps 51 and 54, the time period ($T_2$) between the steps 51 and 52, and the time period ($T_3$) between the steps 54 and 55 (note: the steps 51, 52, 54 and 55 are illustrated in FIG. 7); or (2) in FIG. 10, the time period ($T_4$) between the steps 201 and 204, the time period ($T_5$) between the steps 201 and 202, the time period ($T_6$) between the steps 204 and 205.

The data or information of stem cells obtained from the step 301 may be compared with data or information of stem cells related to N2 subjects in a reference group illustrated in step 302 to establish the above-mentioned criteria or standards (G) and/or evaluate the effect of the one or more of the actions or stimuli (X) in the step 107 of FIG. 9 or the step 203 of FIG. 10. The N2 subjects, each of which may be referred to the above-mentioned subject (S), in the reference group may be sampled or selected from species in the same biological category, where "N2" is a positive integer equal to or greater than 2, 4, 6, 10, 20 or 50. The number of the N2 subjects in the reference group may be the same as or different from the number of the N1 subjects in the evaluation group illustrated in FIG. 9 or 10. The data or information of stem cells related to the N2 subjects in the reference group may be obtained by performing steps 311-316 illustrated in FIG. 11B on each of the N2 subjects in the reference group.

Figure 11B:
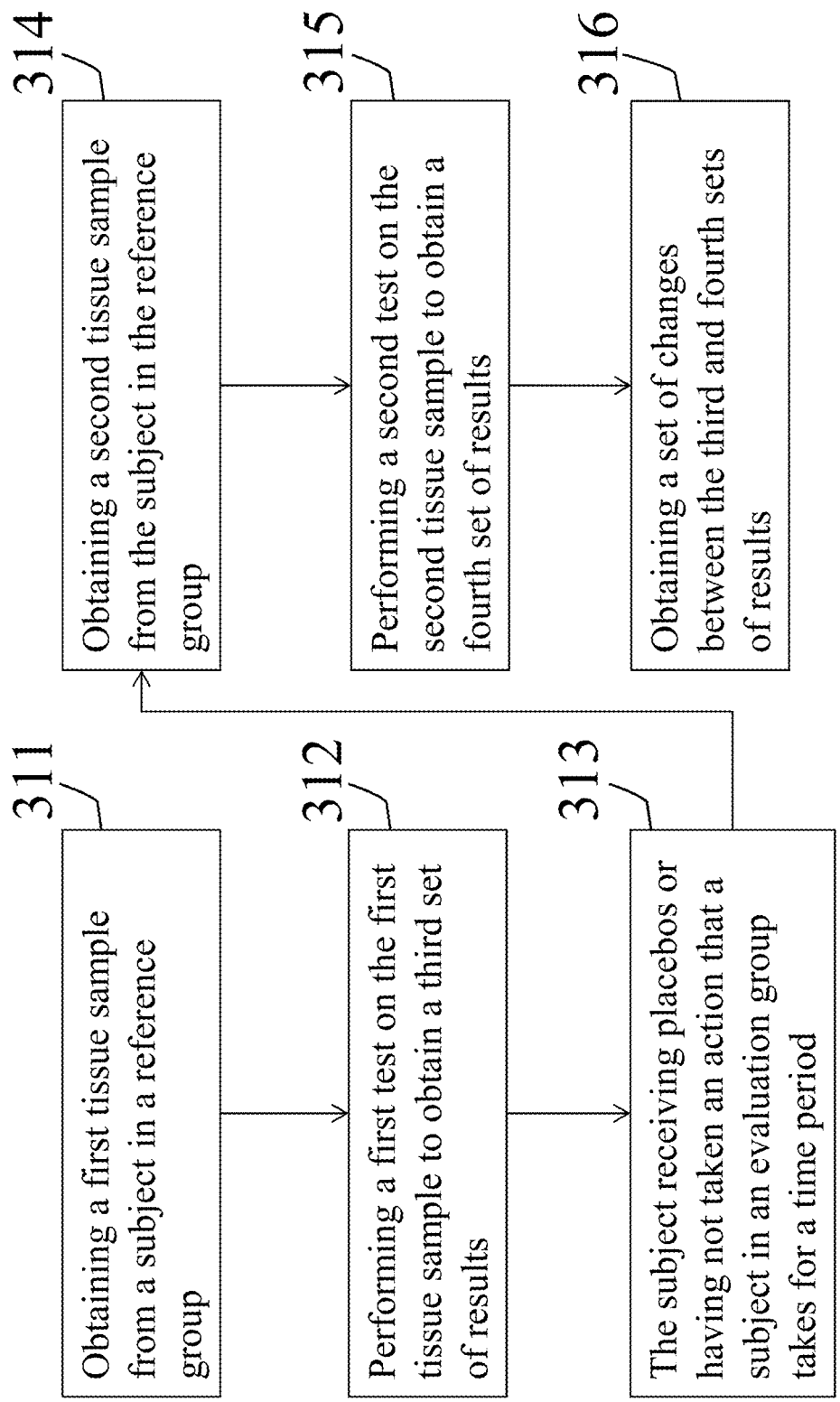
FIG. 11B shows a flow chart of obtaining stem-cell data related to a subject in a reference group according to the fourth embodiment of the present disclosure.

Referring to FIG. 11B, in the step 311, a first tissue sample, which may be referred to the above-mentioned tissue sample (P), is extracted, taken, obtained or derived from a subject, which may be referred to the above-mentioned subject (S), in the reference group. Next, in the step 312, a first test, assessment or measurement including extracting, characterizing, assessing and measuring stem cells is performed, referring to one of the above-mentioned tests, assessments or measurements (M0), (M1) and (M2), on the first tissue sample of the subject in the reference group to obtain a third set of results or data related to one or more types of stem cells from the first tissue sample of the subject in the reference group descriptively, qualitatively or quantitatively. The third set of results or data include the same types of information as the first set of results or data illustrated in the step 52 of FIG. 7, that is, the third set of results or data include multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for the third set of results or data are defined, described or specified as the first set of results or data illustrated in the step 52 of FIG. 7, respectively. For a fair comparison, the time period between the step 311 and the step 312 should be controlled and should be substantially the same as the time period ($T_2$) between the steps 51 and 52, (note the steps 51 and 52 are illustrated in FIG. 7), or the time period ($T_5$) between the steps 201 and 202, (note the steps 201 and 202 are illustrated in FIG. 10), in the evaluation group.

Next, in the step 313, after the step 311 or 312 is performed, the subject in the reference group receives placebos or has not taken or been not subjected to the one or more of the actions or stimuli that the N1 subjects in the evaluation group, as illustrated in the step 107 of FIG. 9 or the step 203 of FIG. 10, take or are subjected to for a suitable time period, such as 15 minutes, 30 minutes, 60 minutes, 90 minutes, 120 minutes, one day, thirty days, a week, or a month after the step 311 or 312 is performed.

Next, in the step 314, a second tissue sample, which may be referred to the above-mentioned tissue sample (P), is extracted, taken, obtained or derived from the subject in the reference group. The first and second tissue samples are, but not limited to, two samples obtained from the same type of tissue of the subject in the reference group. For example, both of the first and second tissue samples may be obtained from peripheral blood, bone marrow, muscle or adipocyte of the subject in the reference group. The first and second tissue samples obtained from the subject in the reference group have the same type as the first and second tissue samples obtained from the N1 subject in the evaluation group as illustrated in FIG. 9 or 10. For a fair comparison, the time period between the step 311 and the step 314 should be controlled and should be substantially the same as the time period ($T_1$) between the steps 51 and 54, (note the steps 51 and 54 are illustrated in FIG. 7), or the time period ($T_4$) between the steps 201 and 204, (note the steps 201 and 202 are illustrated in FIG. 10), in the evaluation group. The time period between the step 311 and the step 314 for the reference group and the time period between the steps 51 and 54 or between the steps 201 and 204 for the evaluation group may be overlapped (i.e., performed at the same time (schedule), or not-overlapped (i.e., performed at a different time (schedule), but with a same time period (duration)).

Next, in the step 315, a second test, assessment or measurement including extracting, characterizing, assessing and measuring stem cells is performed, referring to one of the above-mentioned tests, assessments or measurements (M0), (M1) and (M2), on the second tissue sample of the subject in the reference group to obtain a fourth set of results or data related to one or more types of stem cells from the second tissue sample of the subject in the reference group descriptively, qualitatively or quantitatively. The fourth set of results or data include the same types of information as the first set of results or data illustrated in the step 52 of FIG. 7, that is, the fourth set of results or data include multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for the fourth set of results or data are defined, described or specified as the first set of results or data illustrated in the step 52 of FIG. 7, respectively. For a fair comparison, the time period between the step 313 and the step 314 should be controlled and should be substantially the same as the time period ($T_3$) between the steps 54 and 55, (note the steps 54 and 55 are illustrated in FIG. 7), or the time period ($T_6$) between the steps 204 and 205, (note the steps 204 and 205 are illustrated in FIG. 10), in the evaluation group.

For collecting the same types of information and reducing experimental errors, both of the first and second tests, assessments or measurements illustrated in the step 312 and 315 are performed using the same method described in the above-mentioned test, assessment or measurement (M0), (M1) or (M2).

Next, in the step 316, by comparing the third and fourth sets of results or data obtained in the step 312 and 315, a set of changes between the third and fourth sets of results or data related to the subject in the reference group may be obtained. For example, the set of changes between the third and fourth sets of results or data may be obtained by performing: (1) a subtraction operation, that is, the fourth set of results or data minus the third set of results or data, or (2) an operation of calculating the rates of change between the third and fourth sets of results or data, which may be calculated by subtracting the third set of results or data from the fourth set of results or data, then dividing the subtracted results by the third set of results or data, and finally multiplying the divided results by 100% (which converts the divided results into percent figures). The set of changes include the same types of information as the set of changes illustrated in the step 56 of FIG. 7, that is, the set of changes include multiple changes $\Delta_{1,1}$-$\Delta_{1,c}$, $\Delta_{2,1}$-$\Delta_{2,c}$, . . . , and $\Delta_{a,1}$-$\Delta_{a,c}$, wherein the first and second numbers in the subscript of $\Delta_{1,1}$-$\Delta_{a,c}$ for the set of changes are defined, described or specified as the set of changes illustrated in the step 56 of FIG. 7, respectively.

Referring to FIG. 11A, in the step 302, the steps 311-316 illustrated in FIG. 11B are performed on each of the N2 subjects in the reference group. Therefore, N2 first tissue samples, each of which may be referred to the above-mentioned tissue sample (P), are extracted, taken, obtained or derived, employing the method described in the step 311 of FIG. 11B, from the N2 subjects before performing the step 313 of FIG. 11B and are analyzed using the first test, assessment or measurement illustrated in the step 312 of FIG. 11B, respectively. N2 second tissue samples, each of which may be referred to the above-mentioned tissue sample (P), are extracted, taken, obtained or derived, employing the method described in the step 314 of FIG. 11B, from the N2 subjects after performing the step 313 of FIG. 11B and are analyzed using the second test, assessment or measurement illustrated in the step 314 of FIG. 11B, respectively.

N2 third sets of results or data related to the N2 respective subjects before performing the step 313 of FIG. 11B may be obtained by performing the above first tests, assessments or measurements on the N2 first tissue samples, respectively, as mentioned in the step 312 of FIG. 11B. N2 fourth sets of results or data related to the N2 respective subjects after performing the step 313 of FIG. 11B are obtained by performing the above second tests, assessments or measurements on the N2 second tissue samples, respectively, as mentioned in the step 314 of FIG. 11B. N2 sets of changes between the N2 third sets of results or data and the N2 fourth sets of results or data, related to the N2 respective subjects in the reference group, may be obtained applying the method described in the step 316 of FIG. 11B.

The N2 third and N2 fourth sets of results or data related to the N2 respective subjects in the reference group include types of small stem cells and parameters (such as the number, the percentage and/or the sizes) of one or more types of small stem cells, as described in the above-mentioned assay process (T1), when each of the above first and second tests, assessments or measurements is performed using the above-mentioned test, assessment or measurement (M1). Alternatively, the N2 third and N2 fourth sets of results or data related to the N2 subjects in the reference group include types of stem cells and parameters (such as the number, the percentage and/or the sizes) of one or more types of stem cells, as described in the above-mentioned assay process (T2), when each of the above first and second tests, assessments or measurements is performed using the above-mentioned test, assessment or measurement (M2). Alternatively, the N2 third and N2 fourth sets of results or data related to the N2 subjects in the reference group include types of stem cells and parameters (such as the number, the percentage and/or the sizes) of one or more types of stem cells, as described in the above-mentioned assay process (T0), when each of the above first and second tests, assessments or measurements is performed using the above-mentioned test, assessment or measurement (M0).

Each of the N2 third sets of results or data includes the same types of information as the first set of results or data illustrated in the step 52 of FIG. 7, that is, each of the N2 third sets of results or data includes multiple results or data $R_{1,1}$-$R_{1,b}$, $R_{2,1}$-$R_{2,b}$, . . . , and $R_{a,1}$-$R_{a,b}$ related to a corresponding one of the N2 subjects in the reference group, wherein the first and second numbers in the subscript of $R_{1,1}$-$R_{a,b}$ for each of the N2 third sets of results or data are defined, described or specified as the first set of results or data illustrated in the step 52 of FIG. 7, respectively.

Each of the N2 fourth sets of results or data includes the same types of information as the first set of results or data illustrated in the step 52 of FIG. 7, that is, each of the N2 fourth sets of results or data includes multiple results or data $R_{1,1}$-$R_{1,b}$, $R_{2,1}$-$R_{2,b}$, . . . , and $R_{a,1}$-$R_{a,b}$ related to a corresponding one of the N2 subjects in the reference group, wherein the first and second numbers in the subscript of $R_{1,1}$-$R_{a,b}$ for each of the N2 fourth sets of results or data are defined, described or specified as the first set of results or data illustrated in the step 52 of FIG. 7, respectively.

The N2 sets of changes between the N2 third sets of results or data and the N2 fourth sets of results or data, related to the N2 respective subjects in the reference group, may be obtained by comparing the third and fourth sets of results or data $R_{1,1}$-$R_{a,b}$ having the same first and second numbers in the subscript for the N2 respective subjects in the reference group.

Each of the N2 sets of changes illustrated herein includes the same types of information as the set of changes illustrated in the step 56 of FIG. 7, that is, each of the N2 sets of changes includes multiple changes $\Delta_{1,1}$-$\Delta_{1,c}$, $\Delta_{2,1}$-$\Delta_{2,c}$, ..., and $\Delta_{a,1}$-$\Delta_{a,c}$ related to a corresponding one of the N2 subjects in the reference group, wherein the first and second numbers in the subscript of $\Delta_{1,1}$-$\Delta_{a,c}$ for each of the N2 sets of changes are defined, described or specified as the set of changes illustrated in the step 56 of FIG. 7, respectively.

Alternatively, referring to FIG. 11B, the steps 311-315 may be performed on the N2 respective subjects, after which the step 316 may be performed on each pair of results or data, including one of the N2 third sets of results or data $R_{1,1}$-$R_{a,b}$ and a corresponding one of the N2 fourth sets of results or data $R_{1,1}$-$R_{a,b}$ for the same one of the N2 subjects in the reference group, to obtain the N2 sets of changes in N2 respective pairs of results or data, each including one of the N2 third sets of results or data $R_{1,1}$-$R_{a,b}$ and a corresponding one of the N2 fourth sets of results or data $R_{1,1}$-$R_{a,b}$ for the same one of the N2 respective subjects in the reference group.

Referring to FIG. 11A, in step 303, the N1 first and N1 second sets of results or data $R_{1,1}$-$R_{a,b}$ and the N1 sets of changes $\Delta_{1,1}$-$\Delta_{a,c}$ related to the N1 subjects in the evaluation group are collected to build an evaluation data base, defined as a data base (DB-1), and the N2 third and N2 fourth sets of results or data $R_{1,1}$-$R_{a,b}$ and the N2 sets of changes $\Delta_{1,1}$-$\Delta_{a,c}$ related to the N2 subjects in the reference group are collected to build a reference data base, defined as a data base (DB-2). The data base (DB-1) may further include the data of, for example, age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) for each of the N1 subjects in the evaluation group. The data base (DB-2) may further include the data of, for example, age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) for each of the N2 subjects in the reference group.

Next, in step 304, the data bases (DB-1) and (DB-2) built in the step 303 may be analyzed by a suitable method (such as statistical analysis) to identify, determine, evaluate or assess the effect of the one or more of the actions or stimuli (X) in the step 107 of FIG. 9 or the step 203 of FIG. 10.

Based on analysis of the N1 sets of changes $\Delta_{1,1}$-$\Delta_{a,c}$ related to the N1 subjects in the evaluation group and the N1 first and N1 second sets of results or data $R_{1,1}$-$R_{a,b}$ related to the N1 subjects in the evaluation group against age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) of the N1 subjects in the evaluation group, the distribution of some specific data, as X-axis, taken from the N1 first and N1 second sets of results or data $R_{1,1}$-$R_{a,b}$ related to the N1 subjects in the evaluation group and/or the N1 sets of changes $\Delta_{1,1}$-$\Delta_{a,c}$ related to the N1 subjects in the evaluation group may be plotted with the frequency of occurrence as Y-axis.

Based on analysis of the N2 sets of changes $\Delta_{1,1}$-$\Delta_{a,c}$ related to the N2 subjects in the reference group and the N2 third and N2 fourth sets of results or data $R_{1,1}$-$R_{a,b}$ related to the N2 subjects in the reference group against age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) of the N2 subjects in the reference group, the distribution of some specific data, as X-axis, taken from the N2 third and N2 fourth sets of results or data $R_{1,1}$-$R_{a,b}$ related to the N2 subjects in the reference group and/or the N2 sets of changes $\Delta_{1,1}$-$\Delta_{a,c}$ related to the N2 subjects in the reference group can be plotted with the frequency of occurrence as Y-axis.

For instance, the changes of the numbers of SB-1 cells, i.e., the sets of change $\Delta_{1,1}$, related to the N1 subjects in the evaluation group or the N2 subjects in the reference group may be taken to plot the distribution of the changes of the numbers of SB-1 cells related to the N1 subjects in the evaluation group or the N2 subjects in the reference group with respect to the frequency of occurrence. In this example, all the N1 subjects in the evaluation group have a specific disease (e.g., a cancer, a skin disease, or a kidney disease) and take or are subjected to the same action or stimulus (e.g., taking the same drugs) depicted in the step 53 or 203, and all the N2 subjects in the reference group also have the specific disease but, in the step 313, do not take or are not subjected to any action or stimulus as the N1 subjects in the evaluation group take or are subjected to. Other changes $\Delta_{1,2}$-$\Delta_{a,c}$ related to the N1 and N2 subjects may be considered in a similar way.

If the distribution for the N1 sets of changes $\Delta_{1,1}$-$\Delta_{a,c}$, related to the N1 subjects in the evaluation group, in the data base (DB-1) show, with statistical significance, more effective or better than the distribution for the N2 sets of changes $\Delta_{1,1}$-$\Delta_{a,c}$, related to the N2 subjects in the reference group, in the data base (DB-2), the one or more of the actions or stimuli (X) performed, in the step 107 of FIG. 9 or the step 203 of FIG. 10, on the N1 subjects in the evaluation group may be evaluated as "effective to health or immunity". If the distribution for the N1 sets of changes $\Delta_{1,1}$-$\Delta_{a,c}$, related to the N1 subjects in the evaluation group, in the data base (DB-1) show, with statistical significance, more ineffective or worse than the distribution for the N2 sets of changes $\Delta_{1,1}$-$\Delta_{a,c}$, related to the N2 subjects in the reference group, in the data base (DB-2), the one or more of the actions or stimuli (X) performed, in the step 107 of FIG. 9 or the step 203 of FIG. 10, on the N1 subjects in the evaluation group may be evaluated as "harmful to health or immunity". If there is no statistically significant difference between the distribution for the N1 sets of changes $\Delta_{1,1}$-$\Delta_{a,c}$, related to the N1 subjects in the evaluation group, in the data base (DB-1) and the distribution for the N2 sets of changes $\Delta_{1,1}$-$\Delta_{a,c}$, related to the N2 subjects in the reference group, in the data base (DB-2), the one or more of the actions or stimuli (X) performed, in the step 107 of FIG. 9 or the step 203 of FIG. 10, on the N1 subjects in the evaluation group may be evaluated as "ineffective or harmless to health or immunity".

Statistically, Gaussian distribution may be employed for analyzing data in the data bases (DB-1) and (DB-2) built in the step 303 to evaluate the effect of the one or more of the actions or stimuli (X) performed, in the step 107 of FIG. 9 or the step 203 of FIG. 10, on the N1 subjects in the evaluation group or to determine if the one or more of the actions or stimuli (X) performed, in the step 107 of FIG. 9 or the step 203 of FIG. 10, on the N1 subjects in the evaluation group can improve or cure a specific disease such as a cancer, a skin disease, or a kidney disease.

The data in the data bases (DB-1) and (DB-2) may be analyzed to generate Gaussian distributions for the data in the data bases (DB-1) and (DB-2), respectively. Next, the peak and variance of the Gaussian distribution for the data in the data base (DB-1) may be compared with those for data in the data base (DB-2).

For example, if the peak of the Gaussian distribution for the changes $\Delta_{1,1}$, related to the N1 subjects in the evaluation group, in the data base (DB-1) is statistically significantly more effective or better than that for the changes $\Delta_{1,1}$, related to the N2 subjects in the reference group, in the data base (DB-2), the one or more of the actions or stimuli (X) performed, in the step 107 of FIG. 9 or the step 203 of FIG. 10, on the N1 subjects in the evaluation group may be evaluated as effective to health or immunity. If the peak of the Gaussian distribution for the changes $\Delta_{1,1}$, related to the N1 subjects in the evaluation group, in the data base (DB-1) is statistically significantly more ineffective or worse than that for the changes $\Delta_{1,1}$, related to the N2 subjects in the reference group, in the data base (DB-2), the one or more of the actions or stimuli (X) performed, in the step 107 of FIG. 9 or the step 203 of FIG. 10, on the N1 subjects in the evaluation group may be evaluated as harmful to health or immunity. If the peak of the Gaussian distribution for the changes $\Delta_{1,1}$, related to the N1 subjects in the evaluation group, in the data base (DB-1) is not statistically significantly different from that for the changes $\Delta_{1,1}$, related to the N2 subjects in the reference group, in the data base (DB-2), the one or more of the actions or stimuli (X) performed, in the step 107 of FIG. 9 or the step 203 of FIG. 10, on the N1 subjects in the evaluation group may be evaluated as ineffective or harmless to health or immunity. Other changes $\Delta_{1,2}$-$\Delta_{a,c}$ related to the N1 and N2 subjects may be considered in a similar way.

In addition, by comparing the peaks and variances of Gaussian distributions for each type of results or data, such as any one of the changes $\Delta_{1,1}$-$\Delta_{a,c}$, for each one or more types of stem cells among the data bases (DB-1) and (DB-2), the above-mentioned criteria or standards (G) may be established or generated. In the case that the one or more actions or stimuli (Xa) as mentioned in the third embodiment are to be evaluated, the effect of the one or more actions or stimuli (Xa) on a specific subject, which may be referred to the above-mentioned subject (S), may be identified, determined, evaluated or assessed based on the criteria or standards (G) established herein.

This embodiment provides a method, an apparatus, or an integrated system combining methodology, software (tools) and hardware (equipments, machines, or devices for extraction, filtering, purification, analyzing stem cells), for evaluating the one or more of the actions or stimuli (X) performed in the step 107 of FIG. 9 or the step 203 of FIG. 10 by comparing the data in the data bases (DB-1) and (DB-2) built in the step 303, as mentioned in accordance with this embodiment.

For ensuring the safety (no significant side-effects or damages to the human or non-human body, for example, organs such as liver or kidney) of the one or more of the actions or stimuli (X) performed, in the step 107 of FIG. 9 or the step 203 of FIG. 10, on the N1 subjects in the evaluation group, data about liver and kidney functions related to each of the N1 subjects in the evaluation group before and after taking or being subjected to the one or more of the actions or stimuli (X) may need to be optionally obtained. The data about liver and kidney functions related to the N1 subjects in the evaluation group before taking or being subjected to the one or more of the actions or stimuli (X) illustrated in the step 107 of FIG. 9 or the step 203 of FIG. 10 are defined as data LKB11, and the data about liver and kidney functions related to the N1 subjects in the evaluation group after taking or being subjected to the one or more of the actions or stimuli (X) illustrated in the step 107 of FIG. 9 or the step 203 of FIG. 10 are defined as data LKA11. By comparing the data LKA11 with the data LKB11 with respect to the N1 subjects, the differences between the data LKA11 and LKB11 may be obtained to identify or evaluate the effect of the one or more of the actions or stimuli (X) illustrated in the step 107 of FIG. 9 or the step 203 of FIG. 10 on their livers and kidneys of the N1 subjects in the evaluation group. Each piece of the data LKA11 and LKB11 may include, but not limited to, (1) data about kidney functions (such as BUN, GFR, CCR, ACR, cystatin C, uric acid, microalbumin, urine routine, and/or urine sediment), and (2) data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV) for each of the N1 subjects in the evaluation group.

If there is no (statistically significant) difference between the data LKA11 and LKB11 or the data LKA11 are (much or statistically significantly) better than the data LKB11, it could mean the one or more of the actions or stimuli (X) performed, in the step 107 of FIG. 9 or the step 203 of FIG. 10, on the N1 subjects in the evaluation group are harmless or even beneficial to their livers and/or kidneys of the N1 subjects in the evaluation group and the criteria or standards (G) in the next step 304 may be considered to be established with beneficial impacts or no impacts on the liver and kidney. If the data LKA11 are much or statistically significantly worse than the data LKB11, it could mean the one or more of the actions or stimuli (X) performed, in the step 107 of FIG. 9 or the step 203 of FIG. 10, on the N1 subjects in the evaluation group are harmful to their livers and/or kidneys of the N1 subjects in the evaluation group and the criteria or standards (G) in the next step 304 may not be considered to be established with negative impacts on the liver and/or kidney.

This embodiment further provides a method, an apparatus, or an integrated system combining methodology, software (tools) and hardware (equipments, machines, or devices for extraction, filtering, purification, analyzing stem cells), for establishing the above-mentioned criteria or standards (G) by comparing the data in the data bases (DB-1) and (DB-2), as mentioned in accordance with this embodiment.

A method, in accordance with the fourth embodiment, of evaluating an effect of an action, comprises: taking a first tissue sample from a first subject; analyzing said first tissue sample to obtain a first result related to information of a type or types of stem cells; after said taking said first tissue sample, performing said action on said first subject; after said performing said action on said first subject, taking a second tissue sample from said first subject; analyzing said second tissue sample to obtain a second result related to information of said type or types of stem cells; taking a third tissue sample from a second subject; analyzing said third tissue sample to obtain a third result related to information of said type or types of stem cells; after said taking said third tissue sample, not performing said action on said second subject until taking a fourth tissue sample from said second subject; analyzing said fourth tissue sample to obtain a fourth result related to information of said type or types of stem cells; comparing said first and second results to obtain a first change; comparing said third and fourth results to obtain a second change; and performing a comparison based on said first and second changes.

A criterion establishing method, in accordance with the fourth embodiment, comprises taking a first tissue sample from a first subject; analyzing said first tissue sample to obtain a first result related to information of a type or types of stem cells; after said taking said first tissue sample, performing said action on said first subject; after said performing said action on said first subject, taking a second tissue sample from said first subject; analyzing said second tissue sample to obtain a second result related to information of said type or types of stem cells; taking a third tissue sample from a second subject; analyzing said third tissue sample to obtain a third result related to information of said type or types of stem cells; after said taking said third tissue sample, not performing said action on said second subject until taking a fourth tissue sample from said second subject; analyzing said fourth tissue sample to obtain a fourth result related to information of said type or types of stem cells; comparing said first and second results to obtain a first change; comparing said third and fourth results to obtain a second change; and establishing a criterion for said type or types of stem cells based on said first and second changes.

Fifth Embodiment

Figure 12A:
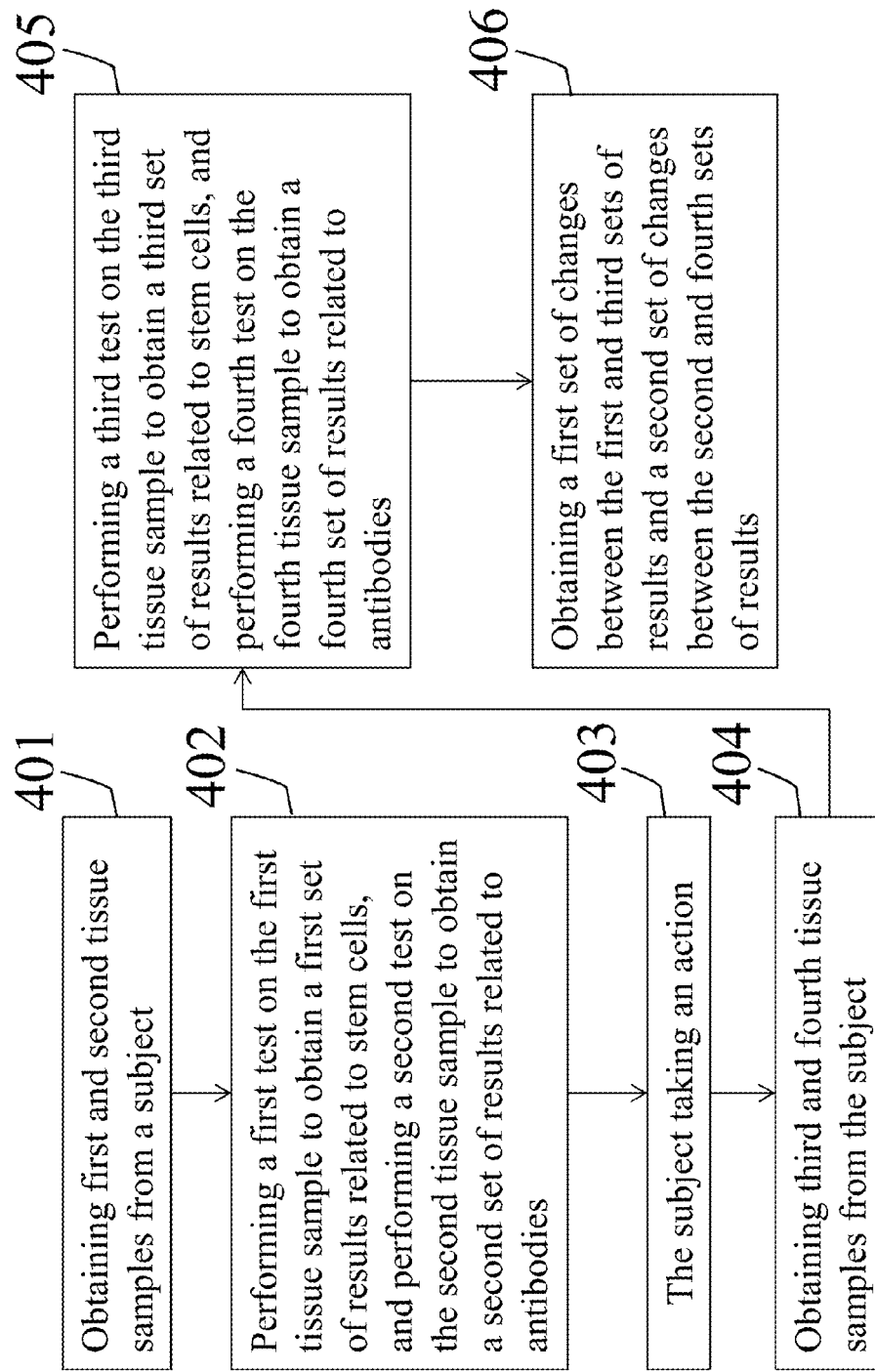
FIG. 12A shows a flow chart for obtaining data or information of stem cells and antibodies related to a subject according to a fifth embodiment of the present disclosure.

FIG. 12A is a flow chart for obtaining data or information of stem cells and antibodies related to a subject. Referring to FIG. 12A, in step 401, first and second tissue samples, each of which may be referred to the above-mentioned tissue sample (P), are extracted, taken, obtained or derived from a subject that may be referred to the above-mentioned subject (S). Next, in step 402, a first test, assessment or measurement including extracting, characterizing, assessing and measuring stem cells is performed, referring to one of the above-mentioned tests, assessments or measurements (M0), (M1) and (M2), on the first tissue sample to obtain a first set of results or data related to one or more types of stem cells from the first tissue sample descriptively, qualitatively or quantitatively. Furthermore, a second test, assessment or measurement including extracting, characterizing, assessing and measuring antibodies is performed, referring to the above-mentioned test, assessment or measurement (M3), on the second tissue sample to obtain a second set of results or data related to one or more classes of antibodies from the second tissue sample descriptively, qualitatively or quantitatively. The one or more classes of antibodies may include immunoglobulin G (IgG), immunoglobulin A (IgA), immunoglobulin M (IgM), immunoglobulin E (IgE), immunoglobulin D (IgD), and/or circulating immune complex, i.e., C3 or C4 complement component. The first set of results or data include types of (small) stem cells and parameters (such as the number, the percentage and/or the sizes) of one or more types of (small) stem cells. The second set of results or data include classes of antibodies and parameters (such as the concentration, e.g., in mg/ml, and/or the number) of one or more classes of antibodies.

The first set of results or data illustrated herein include the same types of information as the first set of results or data illustrated in the step 52 of FIG. 7, that is, the first set of results or data include multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for the first set of results or data are defined, described or specified as the first set of results or data illustrated in the step 52 of FIG. 7, respectively.

The second set of results or data illustrated herein include multiple results or data $I_{1,1}$-$I_{1,f}$, $I_{2,1}$-$I_{2,f}$, . . . , and $I_{e,1}$-$I_{e,f}$, where "e" is a positive integer such as one of the numbers from 3 to 10, and "f" is a positive integer such as 1 or 2. The notation $I_{1,1}$-$I_{1,f}$ means a series of results or data: $I_{1,1}$, $I_{1,2}$, . . . , to $I_{1,f}$. The notation $I_{2,1}$-$I_{2,f}$ means a series of results or data: $I_{2,1}$, $I_{2,2}$, . . . , to $I_{2,f}$. The notation $I_{e,1}$-$I_{e,f}$ means a series of results or data: $I_{e,1}$, $I_{e,2}$, . . . , to $I_{e,f}$. The first number in the subscript of I, i.e., the number immediately following the letter of I, i.e., from 1 to e, represents a certain selected class of antibodies or a group of selected two or more than two classes of antibodies. The number e may be the number of all categories of antibodies or the number of all groups of antibodies. The second number in the subscript of I, i.e., the number immediately following the first number, i.e., from 1 to f, represents data types. The number f may be the number of data types.

With regard to the first number in the subscript of I, the results or data $I_{1,1}$-$I_{1,f}$ having the first number 1 in the subscript of I are results or data related to, for example, immunoglobulin G (IgG). The results or data $I_{2,1}$-$I_{2,f}$ having the first number 2 in the subscript of I are results or data related to, for example, immunoglobulin A (IgA). The results or data $I_{3,1}$-$I_{3,f}$ having the first number 3 in the subscript of I are results or data related to, for example, immunoglobulin M (IgM). The results or data $I_{4,1}$-$I_{4,f}$ having the first number 4 in the subscript of I are results or data related to, for example, immunoglobulin E (IgE). The results or data $I_{5,1}$-$I_{5,f}$ having the first number 5 in the subscript of I are results or data related to, for example, circulating immune complex, i.e., C3 complement component. The results or data $I_{6,1}$-$I_{6,f}$ having the first number 6 in the subscript of I are results or data related to, for example, a combination or group of two classes of antibodies, which may include two of IgG, IgA, IgM, IgE, IgD, C3 complement component, and C4 complement component. The results or data $I_{7,1}$-$I_{7,f}$ having the first number 7 in the subscript of I are results or data related to, for example, all classes of antibodies that can be detected or found (e.g., in a tissue sample such as bodily fluid (e.g., human-blood sample, peripheral-blood sample, or whole-blood sample)), which include one, more or all of IgG, IgA, IgM, IgE, IgD, C3 complement component, and C4 complement component. The number of all classes of antibodies that can be detected or found (e.g., in the tissue sample) may be more than 3, 5 or 7 for cases requiring more information. The results or data $I_{8,1}$-$I_{8,f}$ having the first number 8 in the subscript of I are results or data related to, for example, circulating immune complex, i.e., C4 complement component. The results or data $I_{9,1}$-$I_{9,f}$ having the first number 9 in the subscript of I are results or data related to, for example, a combination or group of more than two or five classes of antibodies, which may include one, more or all of IgG, IgA, IgM, IgE, IgD, C3 complement component, and C4 complement component. The results or data $I_{10,1}$-$I_{10,f}$ having the first number 10 in the subscript of I are results or data related to, for example, immunoglobulin D (IgD).

With regard to the second number in the subscript of I, the results or data $I_{1,1}$-$I_{e,1}$ having the second number 1 in the subscript of I may be results or data related to the number of antibodies of a specific class or a combination or group of multiple classes. The results or data $I_{1,2}$-$I_{e,2}$ having the second number 2 in the subscript of I may be results or data related to the concentration, for example, in mg/ml, of antibodies of a specific class or a combination or group of multiple classes.

For further elaboration, the result $I_{1,1}$ shows the number of IgG. The result $I_{1,2}$ shows the concentration, for example, in mg/ml, of IgG. The result $I_{2,1}$ shows the number of IgA. The result $I_{2,2}$ shows the concentration, for example, in mg/ml, of IgA. The result $I_{3,1}$ shows the number of IgM. The result $I_{3,2}$ shows the concentration, for example, in mg/ml, of IgM. The result $I_{4,1}$ shows the number of IgE. The result $I_{4,2}$ shows the concentration, for example, in mg/ml, of IgE. The result $I_{5,1}$ shows the number of circulating immune complex C3. The result $I_{5,2}$ shows the concentration, for example, in mg/ml, of circulating immune complex C3. The result $I_{6,1}$ shows the number of antibodies of the combination or group of two classes. The result $I_{6,2}$ shows the concentration, for example, in mg/ml, of antibodies of the combination or group of two classes. The result $I_{7,1}$ shows the number of antibodies of all classes that can be detected or found (e.g., in a tissue sample such as bodily fluid (e.g., human-blood sample, peripheral-blood sample, or whole-blood sample)). The result $I_{7,2}$ shows the concentration, for example, in mg/ml, of antibodies of all classes that can be detected or found (e.g., in a tissue sample such as bodily fluid (e.g., human-blood sample, peripheral-blood sample, or whole-blood sample)). The result $I_{8,1}$ shows the number of circulating immune complex C4. The result $I_{8,2}$ shows the concentration, for example, in mg/ml, of circulating immune complex C4. The result $I_{9,1}$ shows the number of antibodies of the combination or group of more than two or five classes. The result $I_{9,2}$ shows the concentration, for example, in mg/ml, of antibodies of the combination or group of more than two or five classes. The result $I_{10,1}$ shows the number of IgD. The result $I_{10,2}$ shows the concentration, for example, in mg/ml, of IgD.

Referring to FIG. 12A, after the step 401 or 402 is performed, step 403 is performed. In the step 403, the subject takes or is subjected to one or more of the above-mentioned actions or stimuli (X), such as taking nutrients or dietary supplements, taking one or more drugs approved by a government department (e.g., U.S. FDA) for curing a specific disease (e.g., a cancer), and/or being exposed to sunshine or sunlight. The one or more actions or stimuli illustrated herein may be performed based on the dose, intensity, duration, frequency (each action may include more than one sub-actions, for example, taking one pill of drug for three times with one hour apart), and/or the time (for example, the time of a day (in the morning, at noon, in the afternoon, in the evening, or in the night), the time before, with or after the meal, or the time of the year (spring, summer, autumn or winter)). As an example, when the subject is taking a drug or a nutrient, the dose (for example, the amount in grams), the time (for example, before or after breakfast, or before sleep) are factors needed to be considered. As another example, when the subject is exposed to the sunshine or sunlight, the time of the day (morning, noon or afternoon), the time of seasons (spring, summer, autumn, or winter), or the exposing duration (30 minutes, 1 hour, 2 hours) are factors needed to be considered.

After a specific period of time, such as longer than or equal to 15, 30, 60, 90 or 120 minutes or one, two or thirty days, or, for example, between 30 and 120 minutes, step 404 is performed following the step 403. In the step 404, third and fourth tissue samples, each of which may be referred to the above-mentioned tissue sample (P), are extracted, taken, obtained or derived from the subject. The first, second, third and fourth tissue samples may be, but not limited to, four samples obtained from the same type of tissue of the subject. For example, all of the first, second, third and fourth tissue samples may be obtained from (peripheral) blood of the subject. Alternatively, the first and third tissue samples may have a different type of tissue from that of the second and fourth tissue samples. For example, the first and third tissue samples may be bone marrow, but the second and fourth tissue samples may be (peripheral) blood.

Next, referring to FIG. 12A, in step 405, a third test, assessment or measurement including extracting, characterizing, assessing and measuring stem cells is performed, referring to one of the above-mentioned tests, assessments or measurements (M0), (M1) and (M2), on the third tissue sample to obtain a third set of results or data related to one or more types of stem cells from the third tissue sample descriptively, qualitatively or quantitatively. Furthermore, a fourth test, assessment or measurement including extracting, characterizing, assessing and measuring antibodies is performed, referring to the above-mentioned test, assessment or measurement (M3), on the fourth tissue sample to obtain a fourth set of results or data related to one or more classes of antibodies from the fourth tissue sample descriptively, qualitatively or quantitatively. The third set of results or data include types of (small) stem cells and parameters (such as the number, the percentage and/or the sizes) of one or more types of (small) stem cells. The fourth set of results or data include classes of antibodies and parameters (such as the concentration, e.g., in mg/ml, and/or the number) of one or more classes of antibodies.

The third set of results or data illustrated herein include the same types of information as the first set of results or data illustrated in the step 52 of FIG. 7, that is, the third set of results or data include multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for the third set of results or data are defined, described or specified as the first set of results or data illustrated in the step 52 of FIG. 7, respectively. The fourth set of results or data illustrated herein include the same types of information as the second set of results or data illustrated in the step 402, that is, the fourth set of results or data include multiple results or data $I_{1,1}$-$I_{1,f}$, $I_{2,1}$-$I_{2,f}$, . . . , and $I_{e,1}$-$I_{e,f}$, wherein the first and second numbers in the subscript of $I_{1,1}$-$I_{e,f}$ for the fourth set of results or data are defined, described or specified as the second set of results or data illustrated in the step 402, respectively.

For collecting the same types of information and reducing experimental errors, both of the first and third tests, assessments or measurements for the first and third sets of results or data may be performed using the same method described in the above-mentioned test, assessment or measurement (M0), (M1) or (M2).

Next, referring to FIG. 12A, in step 406, a first set of changes between the first and third sets of results or data may be obtained by comparing the first and third sets of results or data, and a second set of changes between the second and fourth sets of results or data may be obtained by comparing the second and fourth sets of results or data.

For example, the first set of changes between the first and third sets of results or data may be obtained by performing: (1) a first operation (i.e., subtraction operation), that is, the third set of results or data $R_{1,1}$-$R_{a,b}$ minus the first set of results or data $R_{1,1}$-$R_{a,b}$, or (2) a second operation of calculating the rates of change between the first and third sets of results or data $R_{1,1}$-$R_{a,b}$, which may be calculated by subtracting the first set of results or data $R_{1,1}$-$R_{a,b}$ from the third set of results or data $R_{1,1}$-$R_{a,b}$, then dividing the subtracted results by the first set of results or data $R_{1,1}$-$R_{a,b}$, and finally multiplying the divided results by 100% (which converts the divided results into percent figures). The first and third sets of results or data $R_{1,1}$-$R_{a,b}$ employed in the first or second operation have the same first and second numbers in the subscript. The second set of changes between the second and fourth sets of results or data may be obtained by performing: (1) a third operation (i.e., subtraction operation), that is, the fourth set of results or data $I_{1,1}$-$I_{e,f}$ minus the second set of results or data $I_{1,1}$-$I_{e,f}$, or (2) a fourth operation of calculating the rates of change between the second and fourth sets of results or data $I_{1,1}$-$I_{e,f}$, which may be calculated by subtracting the second set of results or data $I_{1,1}$-$I_{e,f}$ from the fourth set of results or data $I_{1,1}$-$I_{e,f}$, then dividing the subtracted results by the second set of results or data $I_{1,1}$-$I_{e,f}$, and finally multiplying the divided results by 100% (which converts the divided results into percent figures). The second and fourth sets of results or data $I_{1,1}$-$I_{e,f}$ employed in the third or fourth operation have the same first and second numbers in the subscript.

The first set of changes between the first and third sets of results or data include the same types of information as the set of changes illustrated in the step 56 of FIG. 7, that is, the first set of changes illustrated herein include multiple changes $\Delta_{1,1}$-$\Delta_{1,c}$, $\Delta_{2,1}$-$\Delta_{2,c}$, . . . , and $\Delta_{a,1}$-$\Delta_{a,c}$, wherein the first and second numbers in the subscript of $\Delta_{1,1}$-$\Delta_{a,c}$ for the first set of changes are defined, described or specified as the set of changes illustrated in the step 56 of FIG. 7, respectively.

The second set of changes between the second and fourth sets of results or data include multiple changes $\delta_{1,1}$-$\delta_{1,h}$, $\delta_{2,1}$-$\delta_{2,h}$, . . . , and $\delta_{e,1}$-$\delta_{e,h}$, where "e" is a positive integer such as one of the numbers from 3 to 10, and "h" is a positive integer such as 2, 3, or 4. The notation $\delta_{1,1}$-$\delta_{1,h}$ means a series of data: $\delta_{1,1}$, $\delta_{1,2}$, . . . , to $\delta_{1,h}$. The notation $\delta_{2,1}$-$\delta_{2,h}$ means a series of data: $\delta_{2,1}$, $\delta_{2,2}$, . . . , to $\delta_{2,h}$. The notation $\delta_{e,1}$-$\delta_{e,h}$ means a series of data: $\delta_{e,1}$, $\delta_{e,2}$, . . . , to $\delta_{e,h}$. The first number in the subscript of $\delta$, i.e., the number immediately following the sign $\delta$, i.e., from 1 to e, represents a certain selected class of antibodies or a group of selected two or more than two classes of antibodies. The number e may be the number of all categories of antibodies or the number of all groups of antibodies. The second number in the subscript of $\delta$, i.e., the number immediately following the first number, i.e., from 1 to h, represents data types. The number h may be the number of data types.

With regard to the first number in the subscript of $\delta$, the first number in the subscript of $\delta_{1,1}$-$\delta_{e,h}$ is as the same specification as that of $I_{1,1}$-$I_{e,f}$ for the second set of results or data illustrated in the step 402. For example, the changes $\delta_{1,1}$-$\delta_{1,h}$ having the first number 1 in the subscript of $\delta$ are changes related to, for example, IgG. The changes $\delta_{2,1}$-$\delta_{2,h}$ having the first number 2 in the subscript of $\delta$ are changes related to, for example, IgA. The changes $\delta_{7,1}$-$\delta_{7,h}$ having the first number 7 in the subscript of $\delta$ are changes related to, for example, all classes of antibodies that can be detected or found (e.g., in a tissue sample such as bodily fluid (e.g., human-blood sample, peripheral-blood sample, or whole-blood sample)), which include one, more or all of IgG, IgA, IgM, IgE, IgD, C3 complement component, and C4 complement component. The number of all classes of antibodies that can be detected or found (e.g., in the tissue sample) may be equal to or more than 3, 5 or 7 for cases requiring more information. The changes $\delta_{9,1}$-$\delta_{9,h}$ having the first number 9 in the subscript of $\delta$ are changes related to, for example, a combination or group of more than two or five classes of antibodies, which may include one, more or all of IgG, IgA, IgM, IgE, IgD, C3 complement component, and C4 complement component. The changes $\delta_{10,1}$-$\delta_{10,h}$ having the first number 10 in the subscript of $\delta$ are changes related to, for example, IgD. Other notations can be considered in a similar way.

With regard to the second number in the subscript of $\delta$, the changes $\delta_{1,1}$-$\delta_{e,1}$ having the second number 1 in the subscript of $\delta$ are changes related to, for example, an increase or decrease in the number of antibodies of a specific class or a combination or group of multiple classes. The changes $\delta_{1,2}$-$\delta_{e,2}$ having the second number 2 in the subscript of $\delta$ are changes related to, for example, the increasing or decreasing rate of change, e.g., an increase of L1 percent or a decrease of L2 percent, in the number of antibodies of a specific class or a combination or group of multiple classes, where "L1" is a positive number greater than or equal to 10, 20, 30, 40, 50, 60, 70, 80, 90, 100, 200, 300, 500 or 900, and "L2" is a positive number greater than or equal to 10, 20, 30, 40, 50, 60, 70, 80, or 90. The changes $\delta_{1,3}$-$\delta_{e,3}$ having the second number 3 in the subscript of $\delta$ are changes related to, for example, an increase or decrease in the concentration, e.g., in mg/ml, of antibodies of a specific class or a combination or group of multiple classes. The changes $\delta_{1,4}$-$\delta_{e,4}$ having the second number 4 in the subscript of $\delta$ are changes related to, for example, the increasing or decreasing rate of change, e.g., an increase of L1 percent or a decrease of L2 percent, in the concentration, e.g., in mg/ml, of antibodies of a specific class or a combination or group of multiple classes.

For further elaboration, the change $\delta_{1,1}$ between the two results $I_{1,1}$ in the second and fourth respective sets of results or data shows an increase or decrease in the number of IgG, which may be obtained by, e.g., performing a subtraction operation, that is, the result $I_{1,1}$ in the fourth set of results or data minus the result $I_{1,1}$ in the second set of results or data. The change 61,2 between the two results $I_{1,1}$ in the second and fourth respective sets of results or data shows the increasing or decreasing rate of the change, e.g., an increase of L1 percent or a decrease of L2 percent, in the number of IgG, which may be obtained by, e.g., subtracting the result $I_{1,1}$ in the second set of results or data from the result $I_{1,1}$ in the fourth set of results or data, then dividing the subtracted result by the result $I_{1,1}$ in the second set of results or data, and finally multiplying the divided result by 100% (which converts the divided result into a percent figure). The change $\delta_{1,3}$ between the two results $I_{1,2}$ in the second and fourth respective sets of results or data shows an increase or decrease in the concentration of IgG, which may be obtained by, e.g., performing a subtraction operation, that is, the result $I_{1,2}$ in the fourth set of results or data minus the result $I_{1,2}$ in the second set of results or data. The change $\delta_{1,4}$ between the two results $I_{1,2}$ in the second and fourth respective sets of results or data shows the increasing or decreasing rate of the change, e.g., an increase of L1 percent or a decrease of L2 percent, in the concentration of IgG, which may be obtained by, e.g., subtracting the result $I_{1,2}$ in the second set of results or data from the result $I_{1,2}$ in the fourth set of results or data, then dividing the subtracted result by the result $I_{1,2}$ in the second set of results or data, and finally multiplying the divided result by 100% (which converts the divided result into a percent figure). Other notations can be considered in a similar way.

Figure 12B:
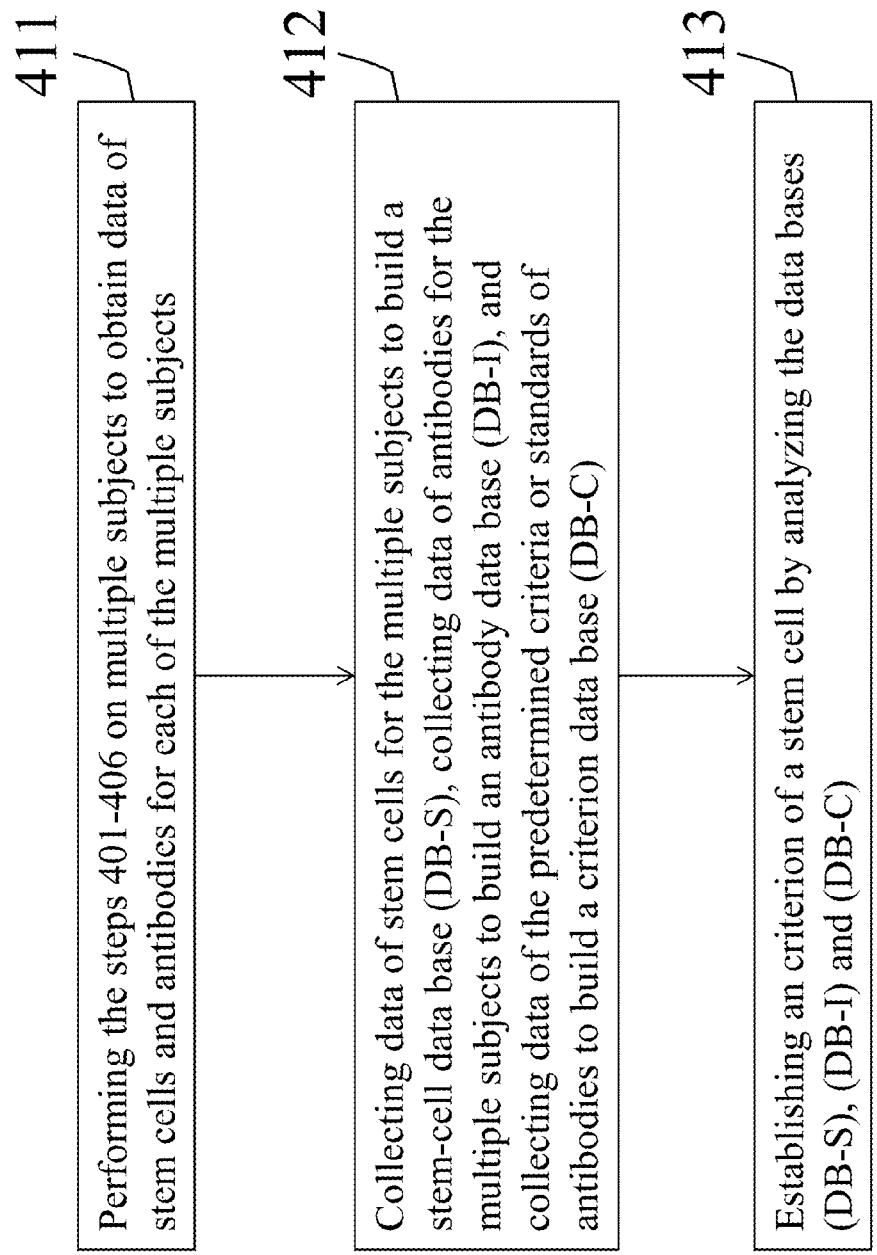
FIG. 12B shows a flow chart of establishing criteria or standards for one or more types of stem cells based on information related to one or more classes of antibodies according to the fifth embodiment of the present disclosure.

FIG. 12B is a flow chart for establishing or obtaining the above-mentioned criteria or standards (G) based on one or more classes of antibodies. The one or more classes of antibodies may include IgG, IgA, IgM, IgE, IgD, and/or circulating immune complex, i.e., C3 or C4 complement component. In this embodiment, N3 subjects, each of which may be referred to the above-mentioned subject (S), may be sampled or selected from species in the same biological category, and the steps illustrated in FIG. 12B may be performed on the N3 subjects, where "N3" is a positive integer equal to or greater than 2, 4, 6, 10, 20 or 50.

Referring to FIG. 12B, in step 411, the steps 401-406 illustrated in FIG. 12A are performed on each of the N3 subjects. Therefore, N3 first tissue samples are extracted, taken, obtained or derived from the N3 respective subjects using the method of obtaining the first tissue sample as described in the step 401 of FIG. 12A. The N3 first tissue samples are analyzed using the first test, assessment or measurement illustrated in the step 402 of FIG. 12A, respectively. N3 second tissue samples are extracted, taken, obtained or derived from the N3 respective subjects using the method of obtaining the second tissue sample as described in the step 401 of FIG. 12A. The N3 second tissue samples are analyzed using the second test, assessment or measurement illustrated in the step 402 of FIG. 12A, respectively. The N3 first tissue samples and the N3 second tissue samples are extracted, taken, obtained or derived from the N3 subjects before taking or being subjected to the one or more of the actions or stimuli (X), as described in the step 403 of FIG. 12A.

N3 third tissue samples are extracted, taken, obtained or derived from the N3 respective subjects after taking or being subjected to the one or more of the actions or stimuli (X) described in the step 403 of FIG. 12A using the method of obtaining the third tissue sample as described in the step 404 of FIG. 12A. The N3 third tissue samples are analyzed using the third test, assessment or measurement illustrated in the step 405 of FIG. 12A, respectively. N3 fourth tissue samples are extracted, taken, obtained or derived from the N3 respective subjects after taking or being subjected to the one or more of the actions or stimuli (X) described in the step 403 of FIG. 12A using the method of obtaining the fourth tissue sample as described in the step 404 of FIG. 12A. The N3 fourth tissue samples are analyzed using the fourth test, assessment or measurement illustrated in the step 405 of FIG. 12A, respectively. Each of the N3 first, N3 second, N3 third and N3 fourth tissue samples may be referred to the above-mentioned tissue sample (P).

N3 first sets of results or data related to one or more types of stem cells from the N3 first tissue samples are obtained by performing the above first tests, assessments or measurements on the N3 first tissue samples, respectively, using the method of obtaining the first set of results or data as described in the step 402 of FIG. 12A. N3 second sets of results or data related to one or more classes of antibodies from the N3 second tissue samples are obtained by performing the above second tests, assessments or measurements on the N3 second tissue samples, respectively, using the method of obtaining the second set of results or data as described in the step 402 of FIG. 12A. N3 third sets of results or data related to one or more types of stem cells from the N3 third tissue samples are obtained by performing the above third tests, assessments or measurements on the N3 third tissue samples, respectively, using the method of obtaining the third set of results or data as described in the step 405 of FIG. 12A. N3 fourth sets of results or data related to one or more classes of antibodies from the N3 fourth tissue samples are obtained by performing the above fourth tests, assessments or measurements on the N3 fourth tissue samples, respectively, using the method of obtaining the fourth set of results or data as described in the step 405 of FIG. 12A.

The N3 first and N3 third sets of results or data related to the N3 subjects include types of small stem cells and parameters (such as the number, the percentage and/or the sizes) of one or more types of small stem cells, as described in the above-mentioned assay process (T1), when each of the above first and third tests, assessments or measurements is performed using the above-mentioned test, assessment or measurement (M1). Alternatively, the N3 first and N3 third sets of results or data related to the N3 subjects include types of stem cells and parameters (such as the number, the percentage and/or the sizes) of one or more types of stem cells, as described in the above-mentioned assay process (T2), when each of the above first and third tests, assessments or measurements is performed using the above-mentioned test, assessment or measurement (M2). Alternatively, the N3 first and N3 third sets of results or data related to the N3 subjects include types of stem cells and parameters (such as the number, the percentage and/or the sizes) of one or more types of stem cells, as described in the above-mentioned assay process (T0), when each of the above first and third tests, assessments or measurements is performed using the above-mentioned test, assessment or measurement (M0).

Each of the N3 first and N3 third sets of results or data illustrated herein includes the same types of information as the first set of results or data illustrated in the step 52 of FIG. 7, that is, each of the N3 first and N3 third sets of results or data includes multiple results or data $R_{1,1}$-$R_{1,b}$, $R_{2,1}$-$R_{2,b}$, ..., and $R_{a,1}$-$R_{a,b}$ related to a corresponding one of the N3 subjects, wherein the first and second numbers in the subscript of $R_{1,1}$-$R_{a,b}$ for each of the N3 first and N3 third sets of results or data are defined, described or specified as the first set of results or data illustrated in the step 52 of FIG. 7, respectively.

Each of the N3 second and N3 fourth sets of results or data illustrated herein includes the same types of information as the second set of results or data illustrated in the step 402 of FIG. 12A, that is, each of the N3 second and N3 fourth sets of results or data includes multiple results or data $I_{1,1}$-$I_{1,f}$, $I_{2,1}$-$I_{2,f}$, ..., and $I_{e,1}$-$I_{e,f}$ related to a corresponding one of the N3 subjects, wherein the first and second numbers in the subscript of $I_{1,1}$-$I_{e,f}$ for each of the N3 second and N3 fourth sets of results or data are defined, described or specified as the second set of results or data illustrated in the step 402 of FIG. 12A, respectively.

N3 first sets of changes in N3 respective first pairs of results or data, each including one of the N3 first sets of results or data and a corresponding one of the N3 third sets of results or data for the same one of the N3 subjects, may be obtained by comparing the N3 first and N3 third sets of results or data $R_{1,1}$-$R_{a,b}$ having the same first and second numbers in the subscript for the N3 respective subjects, which may be referred to the method of obtaining the first set of changes as described in the step 406 of FIG. 12A. N3 second sets of changes in N3 respective second pairs of results or data, each including one of the N3 second sets of results or data and a corresponding one of the N3 fourth sets of results or data for the same one of the N3 subjects, may be obtained by comparing the N3 second and N3 fourth sets of results or data $I_{1,1}$-$I_{e,f}$ having the same first and second numbers in the subscript for the N3 respective subjects, which may be referred to the method of obtaining the second set of changes as described in the step 406 of FIG. 12A.

Each of the N3 first sets of changes illustrated herein includes the same types of information as the set of changes illustrated in the step 56 of FIG. 7, that is, each of the N3 first sets of changes includes multiple changes $\Delta_{1,1}$-$\Delta_{1,c}$, $\Delta_{2,1}$-$\Delta_{2,c}$, . . . , and $\Delta_{a,1}$-$\Delta_{a,c}$ related to a corresponding one of the N3 subjects, wherein the first and second numbers in the subscript of $\Delta_{1,1}$-$\Delta_{a,c}$ for each of the N3 first sets of changes are defined, described or specified as the set of changes illustrated in the step 56 of FIG. 7, respectively. Each of the N3 second sets of changes illustrated herein includes the same types of information as the second set of changes illustrated in the step 406 of FIG. 12A, that is, each of the N3 second sets of changes includes multiple changes $\delta_{1,1}$-$\delta_{1,h}$, $\delta_{2,1}$-$\delta_{2,h}$, . . . , and $\delta_{e,1}$-$\delta_{e,h}$ related to a corresponding one of the N3 subjects, wherein the first and second numbers in the subscript of $\delta_{1,1}$-$\delta_{e,h}$ for each of the N3 second sets of changes are defined, described or specified as the second set of changes illustrated in the step 406 of FIG. 12A, respectively.

Alternatively, referring to FIG. 12B, the step 411 may include performing the steps 401-405 on each of the N3 subjects, after which the step 406 performed in FIG. 12A may be performed on each first pair of results or data, including one of the N3 first sets of results or data $R_{1,1}$-$R_{a,b}$ and a corresponding one of the N3 third sets of results or data $R_{1,1}$-$R_{a,b}$ for the same one of the N3 subjects, to obtain the N3 first sets of changes in N3 respective first pairs of results or data, each including one of the N3 first sets of results or data $R_{1,1}$-$R_{a,b}$ and a corresponding one of the N3 third sets of results or data $R_{1,1}$-$R_{a,b}$ for the same one of the N3 respective subjects, and performed on each second pair of results or data, including one of the N3 second sets of results or data $I_{1,1}$-$I_{e,f}$ and a corresponding one of the N3 fourth sets of results or data $I_{1,1}$-$I_{e,f}$ for the same one of the N3 subjects, to obtain the N3 second sets of changes in N3 respective second pairs of results or data, each including one of the N3 second sets of results or data $I_{1,1}$-$I_{e,f}$ and a corresponding one of the N3 fourth sets of results or data $I_{1,1}$-$I_{e,f}$ for the same one of the N3 respective subjects.

Referring to FIG. 12B, in step 412, the N3 first and N3 third sets of results or data $R_{1,1}$-$R_{a,b}$ and the N3 first sets of changes $\Delta_{1,1}$-$\Delta_{a,c}$ related to information of stem cells from the N3 subjects illustrated herein are collected to build a stem-cell data base (DB-S). The N3 second and N3 fourth sets of results or data $I_{1,1}$-$I_{e,f}$ and the N3 second sets of changes $\delta_{1,1}$-$\delta_{e,h}$ related to information of antibodies from the N3 subjects illustrated herein are collected to build an antibody data base (DB-I). Each of the data bases (DB-S) and (DB-I) may further include the data of, for example, age, gender, race, height, weight, blood pressure, heartbeat, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) for each of the N3 subjects. The data of the predetermined criteria or standards of antibodies for the biological category of the N3 subjects are collected to build a criterion data base (DB-C).

Next, in step 413, the data in the data bases (DB-S) and (DB-I) built in the step 412 may be compared to obtain correlations between the data in the data bases (DB-S) and (DB-I). In the case that high correlation, with a statistical significance, between data, for specific one or more types of stem cells as listed in the specification for the first numbers 1-a in the subscript of R as described in step 52 of FIG. 7, in the data base (DB-S) and those, for specific one or more classes of antibodies as listed in the specification for the first numbers 1-e in the subscript of I as described in step 402 of FIG. 12A, in the data base (DB-I) is found, criteria or standards for the specific one or more types of stem cells may be established based on the predetermined criteria or standards for the specific one or more classes of antibodies, collected in the data base (DB-C). The criteria or standards established herein for the specific one or more types of stem cells include the same types of information as the criteria or standards (G) defined, specified or described in the third embodiment. The effect of the one or more actions or stimuli (Xa), such as the one or more actions or stimuli performed in the step 403 of FIG. 12A, on the subject (Sa), as mentioned in the third embodiment, may be evaluated or determined by comparing a specific one of the changes $\Delta_{1,1}$-$\Delta_{a,c}$, for the specific one or more types of stem cells, from the subject (Sa) to the criteria or standards, for the specific one or more types of stem cells, built up in this embodiment, or by comparing a specific one in the second set of results or data $R_{1,1}$-$R_{a,b}$, for the specific one or more types of stem cells, from the subject (Sa) to the criteria or standards, for the specific one or more types of stem cells, built up in this embodiment.

The correlations between data in the data bases (DB-S) and (DB-I) may be established by a suitable method including, e.g., (1). comparing one or more of the changes $\Delta_{1,1}$-$\Delta_{a,c}$ between the first and third sets of results or data $R_{1,1}$-$R_{a,b}$ and one or more of the changes $\delta_{1,1}$-$\delta_{e,h}$ between the second and fourth sets of results or data $I_{1,1}$-$I_{e,f}$; (2). comparing one or more of the results or data $R_{1,1}$-$R_{a,b}$ in the N3 third sets and one or more of the results or data $I_{1,1}$-$I_{e,f}$ in the N3 fourth sets; and/or (3). comparing one or more of the results or data $R_{1,1}$-$R_{a,b}$ in the N3 first sets and one or more of the results or data $I_{1,1}$-$I_{e,f}$ in the N3 second sets. For example, in the case that high correlations with statistical significance are found between one of the changes $\Delta_{1,2}$ and $\Delta_{1,4}$ in the N3 first sets of changes $\Delta_{1,1}$-$\Delta_{a,c}$ and one of the changes $\delta_{1,2}$ and $\delta_{1,4}$ in the N3 second sets of changes $\delta_{1,1}$-$\delta_{e,h}$ for the N3 subjects, the above-mentioned criterion $G_{1,2}$ and/or $G_{1,4}$ may be established based on the predetermined criterion of immunoglobulin G (IgG) for evaluating the effect of one or more of the actions or stimuli (e.g., X1, X3 and/or X4) on a human body or for determining if any one or more of the actions or stimuli (e.g., X1, X3 and/or X4) can improve immunity of the human body or enhance the number of antibodies. Other notations may be considered in a similar way.

This embodiment provides a method, an apparatus, or an integrated system combining methodology, software (tools) and hardware (equipments, machines, or devices for extraction, filtering, purification, analyzing stem cells), for establishing the above-mentioned criteria or standards (G) based on reference of (predetermined) criteria of antibodies in the data base (DB-C) and correlations between data in the data bases (DB-S) and (DB-I), as mentioned in accordance with this embodiment.

For ensuring the safety (no significant side-effects or damages to the human or non-human body, for example, organs such as liver or kidney) of the one or more of the above-mentioned actions or stimuli (X) illustrated in the step 403, data about liver and kidney functions related to each of the N3 subjects before and after taking or being subjected to the one or more of the actions or stimuli (X) illustrated in the step 403 may need to be obtained as an option. The data about liver and kidney functions related to the N3 subjects before taking or being subjected to the one or more of the actions or stimuli (X) illustrated in the step 403 are defined as data LKB12, and the data about liver and kidney functions related to the N3 subjects after taking or being subjected to the one or more of the actions or stimuli (X) illustrated in the step 403 are defined as data LKA12. By comparing the data LKA12 with the data LKB12, the differences between the data LKA12 and LKB12 may be obtained to identify or evaluate the effect of the one or more of the actions or stimuli (X) illustrated in the step 403 on their livers and kidneys of the N3 subjects.

If there is no (statistically significant) difference between the data LKA12 and LKB12 or the data LKA12 are (much or statistically significantly) better than the data LKB12, it could mean the one or more of the actions or stimuli (X) illustrated in the step 403 are harmless or even beneficial to their livers and/or kidneys of the N3 subjects and the criteria or standards for the specific one or more types of stem cells in the step 413 may be allowed to be established due to the one or more of the actions or stimuli (X) illustrated in the step 403 having no negative impacts on their livers and/or kidneys of the N3 subjects. If the data LKA12 are (much or statistically significantly) worse than the data LKB12, it could mean the one or more of the actions or stimuli (X) illustrated in the step 403 are harmful to their livers and/or kidneys of the N3 subjects and the criteria or standards for the specific one or more types of stem cells in the step 413 may not be allowed to be established due to the one or more of the actions or stimuli (X) illustrated in the step 403 having negative impacts on their livers and/or kidneys of the N3 subjects. Each piece of the data LKA12 and LKB12 may include, but not limited to, (1) data about kidney functions (such as BUN, GFR, CCR, ACR, cystatin C, uric acid, microalbumin, urine routine, and/or urine sediment), and (2) data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV) for each of the N3 subjects.

A criterion establishing method, in accordance with the fifth embodiment, comprises taking a first tissue sample and a second tissue sample from a subject; analyzing said first tissue sample to obtain a first result related to information of a type or types of stem cells; analyzing said second tissue sample to obtain a second result related to information of a class or classes of antibodies; after said taking said first and second tissue samples, performing an action on said subject; after said performing said action on said subject, taking a third tissue sample and a fourth tissue sample from said subject; analyzing said third tissue sample to obtain a third result related to information of said type or types of stem cells; analyzing said fourth tissue sample to obtain a fourth result related to information of said class or classes of antibodies; performing analysis to obtain a relationship between first data associated with said first and third results and second data associated with said second and fourth results; and establishing a criterion for said type or types of stem cells based on said relationship and a criterion for said class or classes of antibodies.

A criterion establishing method, in accordance with the fifth embodiment, comprises taking a first tissue sample and a second tissue sample from a subject; analyzing said first tissue sample to obtain a first result related to information of a type or types of stem cells; analyzing said second tissue sample to obtain a second result related to information of a class or classes of antibodies; after said taking said first and second tissue samples, performing an action on said subject; after said performing said action on said subject, taking a third tissue sample and a fourth tissue sample from said subject; analyzing said third tissue sample to obtain a third result related to information of said type or types of stem cells; analyzing said fourth tissue sample to obtain a fourth result related to information of said class or classes of antibodies; performing analysis to obtain a relationship between first data associated with said third result and second data associated with said fourth result; and establishing a criterion for said type or types of stem cells based on said relationship and a criterion for said class or classes of antibodies.

Sixth Embodiment

Figure 13:
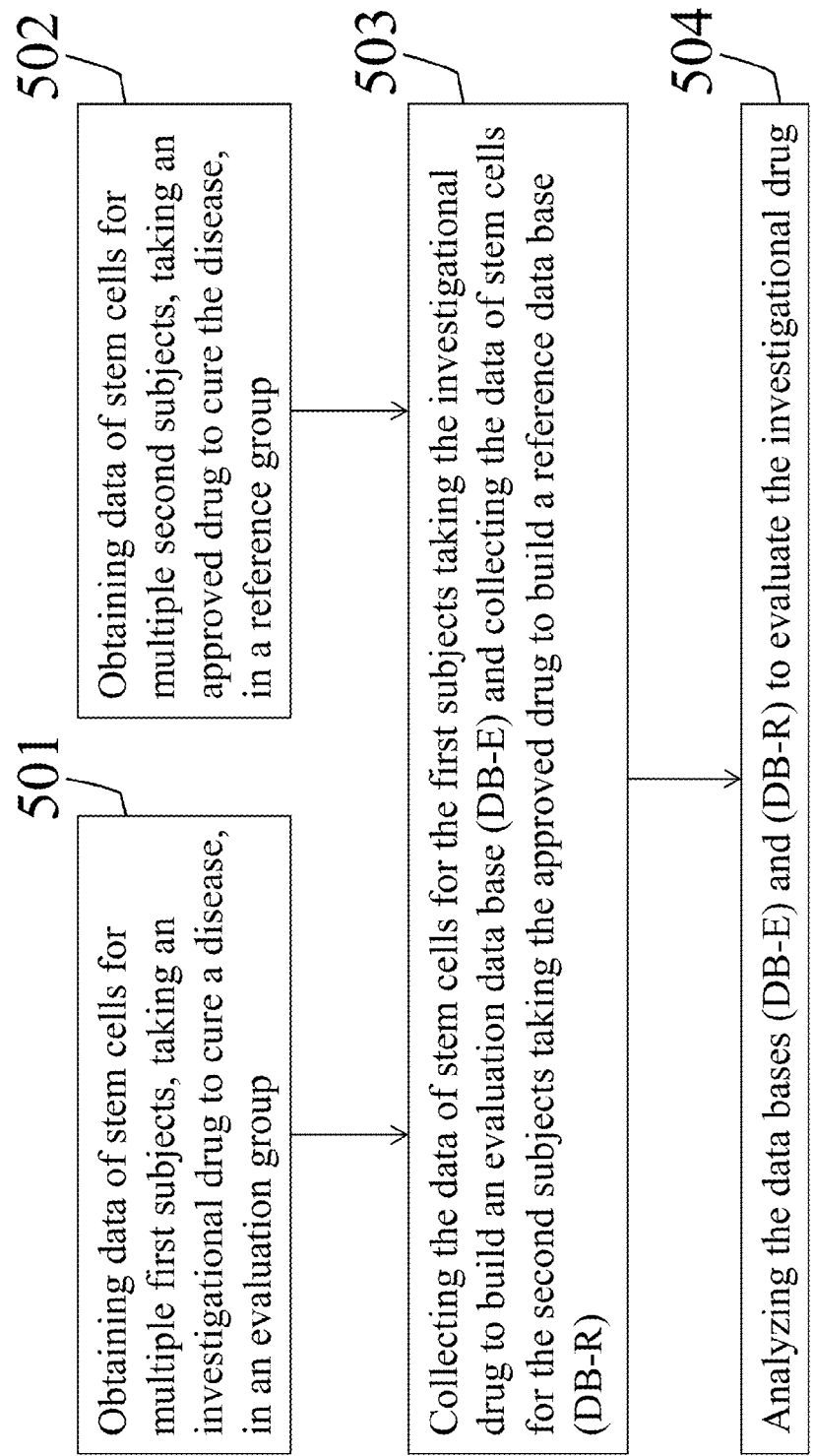
FIG. 13 shows a flow chart for identifying, evaluating or assessing the effect of an investigational (or experimental) drug on curing a disease according to a sixth embodiment of the present disclosure.

FIG. 13 is a flow chart for identifying, evaluating or assessing the effect of an investigational (or experimental) drug on curing a specific disease in comparison of the results obtained from the patients taking a drug that has been approved by a government department (e.g., U.S. FDA) for curing the specific disease.

In this embodiment, multiple first subjects in an evaluation group are sampled or selected from human or non-human bodies having a specific disease (such as a cancer, a skin disease, or a kidney disease), and multiple second subjects in a reference group are sampled or selected from human or non-human bodies having the same specific disease as the first subjects in the evaluation group have. The first and second subjects, each of which may be referred to the above-mentioned subject (S), illustrated herein are sampled or selected from species in the same biological category.

Referring to FIG. 13, in step 501, the steps 51-56 illustrated in FIG. 7 or the steps 201-206 illustrated in FIG. 10 may be performed on each of the first subjects in the evaluation group to obtain data or information of stem cells related to the first subjects in the case that each first subject in the evaluation group takes an investigational (or experimental) drug, in the step 53 of FIG. 7 or the step 203 of FIG. 10, to cure the specific disease. Related to the first subjects in the evaluation group, the data or information of stem cells includes (1) multiple first sets of results or data obtained by the method illustrated in the steps 51 and 52 of FIG. 7 or the steps 201 and 202 of FIG. 10, (2) multiple second sets of results or data obtained by the method illustrated in the steps 54 and 55 of FIG. 7 or the steps 204 and 205 of FIG. 10, and (3) multiple first sets of changes in multiple respective first pairs of results or data, each including one of the first set of results or data and a corresponding one of the second set of results or data for the same one of the first subjects, obtained by the method illustrated in the step 56 of FIG. 7 or the step 206 of FIG. 10. A (new) drug that is (1) in the research or development stage in a laboratory, an research institute or a research department or division of a university or a company; (2) in the pilot or experimental run; or (3) being tested but has not yet approved by a government department or authority (e.g., U.S. FDA), may be called an investigational (or experimental) drug.

For certain steps, the time period (period means duration, similar in all the followings) between them need to be controlled for a fair comparison between the evaluation group and the reference group. For example, the controlled time of periods between certain steps for the evaluation group may include: (1) in the steps 51-56 performed in the step 501, the time period ($T_a$) between the steps 51 and 52, the time period ($T_b$) between the steps 51 and 53, the time period ($T_c$) between the steps 53 and 54, and the time period ($T_d$) between the steps 54 and 55; or (2) in the steps 201-206 performed in the step 501, the time period ($T_e$) between the steps 201 and 202, the time period ($T_f$) between the steps 201 and 203, the time period ($T_g$) between the steps 203 and 204, and the time period ($T_h$) between the steps 204 and 205.

Each of the first sets of results or data related to a corresponding one of the first subjects in the evaluation group includes the same types of information as the first set of results or data illustrated in the step 52 of FIG. 7, that is, each of the first sets of results or data illustrated herein includes multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for each of the first sets of results or data illustrated herein are defined, described or specified as the first set of results or data illustrated in the step 52 of FIG. 7, respectively. Each of the second sets of results or data related to a corresponding one of the first subjects in the evaluation group includes the same types of information as the first set of results or data illustrated in the step 52 of FIG. 7, that is, each of the second sets of results or data illustrated herein includes multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for each of the second sets of results or data illustrated herein are defined, described or specified as the first set of results or data illustrated in the step 52 of FIG. 7, respectively.

Each of the first sets of changes related to a corresponding one of the first subjects in the evaluation group includes the same types of information as the set of changes illustrated in the step 56 of FIG. 7, that is, each of the first sets of changes illustrated herein includes multiple changes $\Delta_{1,1}$-$\Delta_{1,c}$, $\Delta_{2,1}$-$\Delta_{2,c}$, . . . , and $\Delta_{a,1}$-$\Delta_{a,c}$, wherein the first and second numbers in the subscript of $\Delta_{1,1}$-$\Delta_{a,c}$ for each of the first sets of changes illustrated herein are defined, described or specified as the set of changes illustrated in the step 56 of FIG. 7, respectively.

Referring to FIG. 13, in step 502, the steps 51-56 illustrated in FIG. 7 or the steps 201-206 illustrated in FIG. 10 may be performed on each of the second subjects in the reference group to obtain data or information of stem cells related to the second subjects in the case that each second subject in the reference group takes a drug that has been approved by the government department (also called an approved drug), in the step 53 of FIG. 7 or the step 203 of FIG. 10, to cure the specific disease. Related to the second subjects in the reference group, the data or information of stem cells includes (1) multiple third sets of results or data obtained by the method illustrated in the steps 51 and 52 of FIG. 7 or the steps 201 and 202 of FIG. 10, (2) multiple fourth sets of results or data obtained by the method illustrated in the steps 54 and 55 of FIG. 7 or the steps 204 and 205 of FIG. 10, and (3) multiple second sets of changes in multiple respective second pairs of results or data, each including one of the third set of results or data and a corresponding one of the fourth set of results or data for the same one of the second subjects, obtained by the method illustrated in the step 56 of FIG. 7 or the step 206 of FIG. 10.

Each of the third sets of results or data related to a corresponding one of the second subjects in the reference group includes the same types of information as the first set of results or data illustrated in the step 52 of FIG. 7, that is, each of the third sets of results or data illustrated herein includes multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for each of the third sets of results or data illustrated herein are defined, described or specified as the first set of results or data illustrated in the step 52 of FIG. 7, respectively. Each of the fourth sets of results or data related to a corresponding one of the second subjects in the reference group includes the same types of information as the first set of results or data illustrated in the step 52 of FIG. 7, that is, each of the fourth sets of results or data illustrated herein includes multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for each of the fourth sets of results or data illustrated herein are defined, described or specified as the first set of results or data illustrated in the step 52 of FIG. 7, respectively.

Each of the second sets of changes related to a corresponding one of the second subjects in the reference group includes the same types of information as the set of changes illustrated in the step 56 of FIG. 7, that is, each of the second sets of changes illustrated herein includes multiple changes $\Delta_{1,1}$-$\Delta_{1,c}$, $\Delta_{2,1}$-$\Delta_{2,c}$, . . . , and $\Delta_{a,1}$-$\Delta_{a,c}$, wherein the first and second numbers in the subscript of $\Delta_{1,1}$-$\Delta_{a,c}$ for each of the second sets of changes illustrated herein are defined, described or specified as the set of changes illustrated in the step 56 of FIG. 7, respectively.

For a fair comparison, the time period between the steps 51 and 52 performed in the step 502 or between the steps 201 and 202 performed in the step 502 may be controlled and may be substantially the same as the time period ($T_a$) between the steps 51 and 52 performed in the step 501 or the time period ($T_e$) between the steps 201 and 202 performed in the step 501. For a fair comparison, the time period between the steps 51 and 53 performed in the step 502 or between the steps 201 and 203 performed in the step 502 may be controlled and may be substantially the same as the time period ($T_b$) between the steps 51 and 53 performed in the step 501 or the time period ($T_f$) between the steps 201 and 203 performed in the step 501. The time period between the steps 51 and 53 performed in the step 502 or between the steps 201 and 203 performed in the step 502 for the reference group and the time period between the steps 51 and 53 performed in the step 501 or between the steps 201 and 203 performed in the step 501 for the evaluation group may be overlapped (i.e., the steps 51 and 53 performed in the step 502 for the reference group and the steps 51 and 53 performed in the step 501 for the evaluation group may be performed at the same time (schedule), or the steps 201 and 203 performed in the step 502 for the reference group and the steps 201 and 203 performed in the step 501 for the evaluation group may be performed at the same time (schedule)), or not-overlapped (i.e., the steps 51 and 53 performed in the step 502 for the reference group and the steps 51 and 53 performed in the step 501 for the evaluation group may be performed at different time (schedule), but with the same time period (duration), or the steps 201 and 203 performed in the step 502 for the reference group and the steps 201 and 203 performed in the step 501 for the evaluation group may be performed at a different time (schedule), but with the same time period (duration)).

For a fair comparison, the time period between the steps 53 and 54 performed in the step 502 or between the steps 203 and 204 performed in the step 502 may be controlled and may be substantially the same as the time period ($T_c$) between the steps 53 and 54 performed in the step 501 or the time period ($T_g$) between the steps 203 and 204 performed in the step 501. The time period between the steps 53 and 54 performed in the step 502 or between the steps 203 and 204 performed in the step 502 for the reference group and the time period between the steps 53 and 54 performed in the step 501 or between the steps 203 and 204 performed in the step 501 for the evaluation group may be overlapped (i.e., the steps 53 and 54 performed in the step 502 for the reference group and the steps 53 and 54 performed in the step 501 for the evaluation group may be performed at the same time (schedule), or the steps 203 and 204 performed in the step 502 for the reference group and the steps 203 and 204 performed in the step 502 for the evaluation group may be performed at the same time (schedule)), or not-overlapped (i.e., the steps 53 and 54 performed in the step 502 for the reference group and the steps 53 and 54 performed in the step 501 for the evaluation group may be performed at a different time (schedule), but with the same time period (duration), or the steps 203 and 204 performed in the step 502 for the reference group and the steps 203 and 204 performed in the step 501 for the evaluation group may be performed at different time (schedule), but with the same time period (duration)). For a fair comparison, the time period between the steps 54 and 55 performed in the step 502 or between the steps 204 and 205 performed in the step 502 may be controlled and may be substantially the same as the time period ($T_d$) between the steps 54 and 55 performed in the step 501 or the time period ($T_h$) between the steps 204 and 205 performed in the step 501.

Referring to FIG. 13, in step 503, the first and second sets of results or data $R_{1,1}$-$R_{a,b}$ and the first sets of changes $\Delta_{1,1}$-$\Delta_{a,c}$ related to the first subjects in the evaluation group illustrated herein are collected to build an evaluation data base (DB-E). The evaluation data base (DB-E) may further include the data of, for example, age, gender, race, height, weight, blood pressure, heartbeat, immunoglobulin (Ig), BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and one or more diseases (e.g., a cancer, a skin disease, and/or a kidney disease) for each of the first subjects in the evaluation group illustrated herein. Furthermore, the third and fourth sets of results or data $R_{1,1}$-$R_{a,b}$ and the second sets of changes $\Delta_{1,1}$-$\Delta_{a,c}$ related to the second subjects in the reference group illustrated herein are collected to build a reference data base (DB-R). The reference data base (DB-R) may further include the data of, for example, age, gender, race, height, weight, blood pressure, heartbeat, immunoglobulin (Ig), BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and one or more diseases (e.g., a cancer, a skin disease, and/or a kidney disease) for each of the second subjects in the reference group illustrated herein.

Next, in step 504, the two data bases (DB-E) and (DB-R) built in the step 503 may be analyzed by a suitable method (such as statistical analysis) to identify, determine, evaluate or assess the effect of the investigational (or experimental) drug on curing the specific disease. If the data in the evaluation data base (DB-E) show, with statistical significance, more effective or better than or substantially equal to the data in the reference data base (DB-R), the investigational (or experimental) drug can be approved to cure the specific disease. Otherwise, the investigational (or experimental) drug cannot be approved to cure the specific disease.

Based on analysis of the first sets of changes $\Delta_{1,1}$-$\Delta_{a,c}$ related to the first subjects in the evaluation group and the first and second sets of results or data $R_{1,1}$-$R_{a,b}$ related to the first subjects in the evaluation group against age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) of the first subjects in the evaluation group, the distribution of some specific data, as X-axis, taken from the first and second sets of results or data $R_{1,1}$-$R_{a,b}$ related to the first subjects in the evaluation group and/or the first sets of changes $\Delta_{1,1}$-$\Delta_{a,c}$ related to the first subjects in the evaluation group may be plotted with the frequency of occurrence as Y-axis. Based on analysis of the second sets of changes $\Delta_{1,1}$-$\Delta_{a,c}$ related to the second subjects in the reference group and the third and fourth sets of results or data $R_{1,1}$-$R_{a,b}$ related to the second subjects in the reference group against age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) of the second subjects in the reference group, the distribution of some specific data, as X-axis, taken from the third and fourth sets of results or data $R_{1,1}$-$R_{a,b}$ related to the second subjects in the reference group and/or the second sets of changes $\Delta_{1,1}$-$\Delta_{a,c}$ related to the second subjects in the reference group can be plotted with the frequency of occurrence as Y-axis.

For instance, the changes of the numbers of SB-1 cells, i.e., the first or second sets of changes $\Delta_{1,1}$, related to the first or second subjects in the evaluation or reference group may be taken to plot the distribution of the changes of the numbers of SB-1 cells related to the first or second subjects in the evaluation or reference group with respect to the frequency of occurrence. Other changes $\Delta_{1,2}$-$\Delta_{a,c}$ related to the first or second subjects may be considered in a similar way.

Statistically, Gaussian distribution may be employed for analyzing data in the data bases (DB-E) and (DB-R) built in the step 503 to evaluate the effect of the investigational (or experimental) drug performed, in the step 501, on the first subjects in the evaluation group or to determine if the investigational (or experimental) drug performed, in the step 501, on the first subjects in the evaluation group can improve or cure the specific disease. For example, if changes for a specific stem cell in the first sets of changes $\Delta_{1,1}$-$\Delta_{a,c}$, related to the first subjects in the evaluation group, in the data base (DB-E) show, with statistical significance, more effective or better than changes for the specific stem cell in the second sets of changes $\Delta_{1,1}$-$\Delta_{a,c}$, related to the second subjects in the reference group, in the data base (DB-R), the investigational (or experimental) drug may be approved by the government department (e.g., U.S. FDA). Otherwise, if changes for the specific stem cell in the first sets of changes $\Delta_{1,1}$-$\Delta_{a,c}$, related to the first subjects in the evaluation group, in the data base (DB-E) show, with statistical significance, more ineffective or worse than changes for the specific stem cell in the second sets of changes $\Delta_{1,1}$-$\Delta_{a,c}$, related to the second subjects in the reference group, in the data base (DB-R), the investigational (or experimental) drug cannot be approved by the government department (e.g., U.S. FDA). If changes for the specific stem cell in the first sets of changes $\Delta_{1,1}$-$\Delta_{a,c}$, related to the first subjects in the evaluation group, in the data base (DB-E) do not show, with statistical significance, more effective or ineffective than changes for the specific stem cell in the second sets of changes $\Delta_{1,1}$-$\Delta_{a,c}$, related to the second subjects in the reference group, in the data base (DB-R), the investigational (or experimental) drug means to have substantially equal effects to the approved drug and may also be approved by the government department (e.g., U.S. FDA).

The data in the data bases (DB-E) and (DB-R) may be analyzed to generate Gaussian distributions for the data in the data bases (DB-E) and (DB-R), respectively. Next, the peak and variance of the Gaussian distribution for the data in the data base (DB-E) can be compared with those for data in the data base (DB-R).

For example, if the peak of the Gaussian distribution for the changes $\Delta_{1,1}$, related to the first subjects in the evaluation group, in the data base (DB-E) is statistically significantly more effective or better than that for the changes $\Delta_{1,1}$, related to the second subjects in the reference group, in the data base (DB-R), the investigational (or experimental) can be approved by the government department (e.g., U.S. FDA). Otherwise, if the peak of the Gaussian distribution for the changes $\Delta_{1,1}$, related to the first subjects in the evaluation group, in the data base (DB-E) is statistically significantly more ineffective or worse than that for the changes $\Delta_{1,1}$, related to the second subjects in the reference group, in the data base (DB-R), the investigational (or experimental) cannot be approved by the government department (e.g., U.S. FDA). If the peak of the Gaussian distribution for the changes $\Delta_{1,1}$, related to the first subjects in the evaluation group, in the data base (DB-E) is not statistically significantly different from that for the changes $\Delta_{1,1}$, related to the second subjects in the reference group, in the data base (DB-R), the investigational (or experimental) drug means to have substantially equal effects to the approved drug and may also be approved by the government department (e.g., U.S. FDA). Other change $\Delta_{1,2}$-$\Delta_{a,c}$ related to the first or second subjects can be considered in a similar way.

In addition, by comparing the peaks and variances of Gaussian distributions for each type of results or data, such as any one of the changes $\Delta_{1,1}$-$\Delta_{a,c}$, for each one or more types of stem cells in the data base (DB-R), the above-mentioned criteria or standards (G) can be established or generated. In the case that the one or more actions or stimuli (Xa) as mentioned in the third embodiment are to be evaluated, the effect of the one or more actions or stimuli (Xa) on a specific subject, which may be referred to the above-mentioned subject (S), may be identified, determined, evaluated or assessed based on the criteria or standards (G) established herein.

For ensuring the safety (no significant side-effects or damages to the human or non-human body, for example, organs such as liver or kidney) of the investigational drug in the step 501, data about liver and kidney functions related to each of the first subjects before and after taking the investigational drug in the step 501 may need to be optionally obtained. The data about liver and kidney functions related to the first subjects in the evaluation group before taking the investigational drug in the step 501 are defined as data LKB13, and the data about liver and kidney functions related to the first subjects in the evaluation group after taking the investigational drug in the step 501 are defined as data LKA13. By comparing the data LKA13 with the data LKB13, the differences between the data LKA13 and LKB13 may be obtained to identify or evaluate the effect of the investigational drug in the step 501 on their livers and kidneys of the first subjects in the evaluation group.

If there is no (statistically significant) difference between the data LKA13 and LKB13 or the data LKA13 are (much or statistically significantly) better than the data LKB13, it could mean the investigational drug in the step 501 is harmless or even beneficial to their livers and/or kidneys of the first subjects. In this case, if the data in the evaluation data base (DB-E) show, with statistical significance, more effective or better than or substantially equal to the data in the reference data base (DB-R), the investigational drug in the step 501 can be approved for use in humans or non-humans and treatment of the specific disease with beneficial impacts or no impacts on the liver or kidney. If the data in the evaluation data base (DB-E) do not show, with statistical significance, more effective or better than or substantially equal to the data in the reference data base (DB-R), the investigational drug in the step 501 cannot be approved for use in humans or non-humans and treatment of the specific disease.

If the data LKA13 are (much or statistically significantly) worse than the data LKB13, it could mean the investigational drug in the step 501 is harmful to their livers and/or kidneys of the first subjects. In this case, if the data in the evaluation data base (DB-E) show, with statistical significance, more effective or better than or substantially equal to the data in the reference data base (DB-R), the investigational drug in the step 501 may not be approved for use in humans or non-humans and treatment of the specific disease or may be approved for use in humans or non-humans and treatment of the specific disease with notations of negative impacts on the liver and/or kidney.

Each piece of the data LKA13 and LKB13 may include, but not limited to, (1) data about kidney function (such as BUN, GFR, CCR, ACR, cystatin C, uric acid, microalbumin, urine routine, and/or urine sediment), and (2) data about liver function (such as AST, ALT, AFP, total bilirubin, direct bilirubin, indirect bilirubin, albumin, globulin, albumin/globulin ratio, $\gamma$-GT, ALP, PT, HBsAg, Anti-HBs, and/or Anti-HCV).

This embodiment provides a method, an apparatus, or an integrated system combining methodology, software (tools) and hardware (equipments, machines, or devices for extraction, filtering, purification, analyzing stem cells), for evaluating the effect of the investigational (or experimental) drug on curing the specific disease by comparing the data in the data bases (DB-E) and (DB-R) built in the step 503, as mentioned in accordance with this embodiment. This embodiment further provides a method, an apparatus, or an integrated system combining methodology, software (tools) and hardware (equipments, machines, or devices for extraction, filtering, purification, analyzing stem cells), for establishing the above-mentioned criteria or standards (G) by analyzing the data in the data base (DB-R), as mentioned in accordance with this embodiment.

A method, in accordance with the sixth embodiment, of evaluating an effect of an investigational drug on curing a disease, comprises: taking a first tissue sample from a first subject having said disease; analyzing said first tissue sample to obtain a first result related to information of a type or types of stem cells; after said taking said first tissue sample, said first subject taking said investigational drug; after said first subject taking said investigational drug, taking a second tissue sample from said first subject; analyzing said second tissue sample to obtain a second result related to information of said type or types of stem cells; taking a third tissue sample from a second subject having said disease; analyzing said third tissue sample to obtain a third result related to information of said type or types of stem cells; after said taking said third tissue sample, said second subject taking an approved drug; after said second subject taking said approved drug, taking a fourth tissue sample from said second subject; analyzing said fourth tissue sample to obtain a fourth result related to information of said type or types of stem cells; comparing said first and second results to obtain a first change; comparing said third and fourth results to obtain a second change; and performing a comparison based on said first and second changes.

Seventh Embodiment

Figure 14:
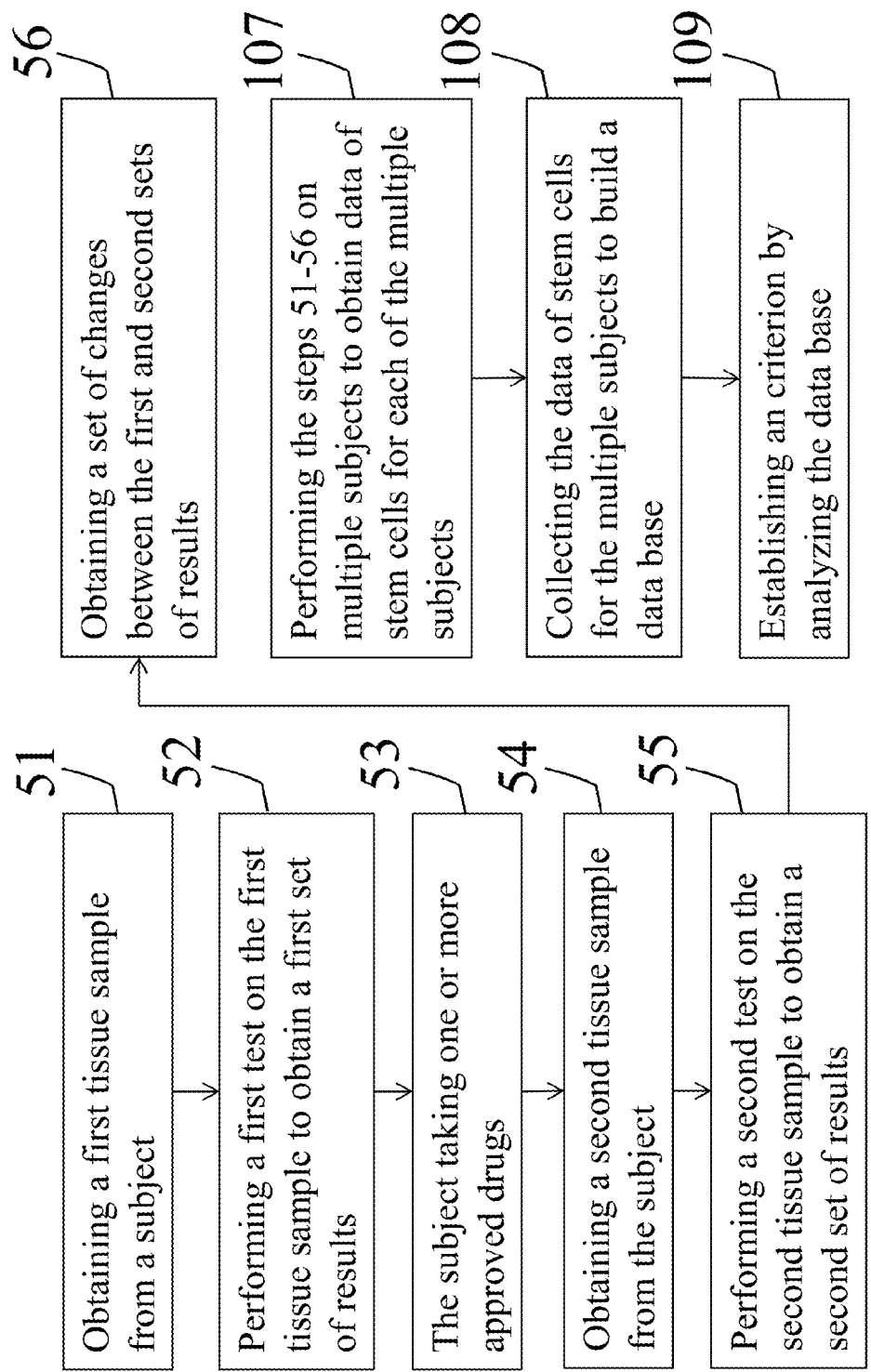
FIG. 14 shows flow charts for establishing universal criteria or standards for evaluating, qualifying or approving at least one action or stimulus for curing a disease according to a seventh embodiment of the present disclosure.
Figure 15:
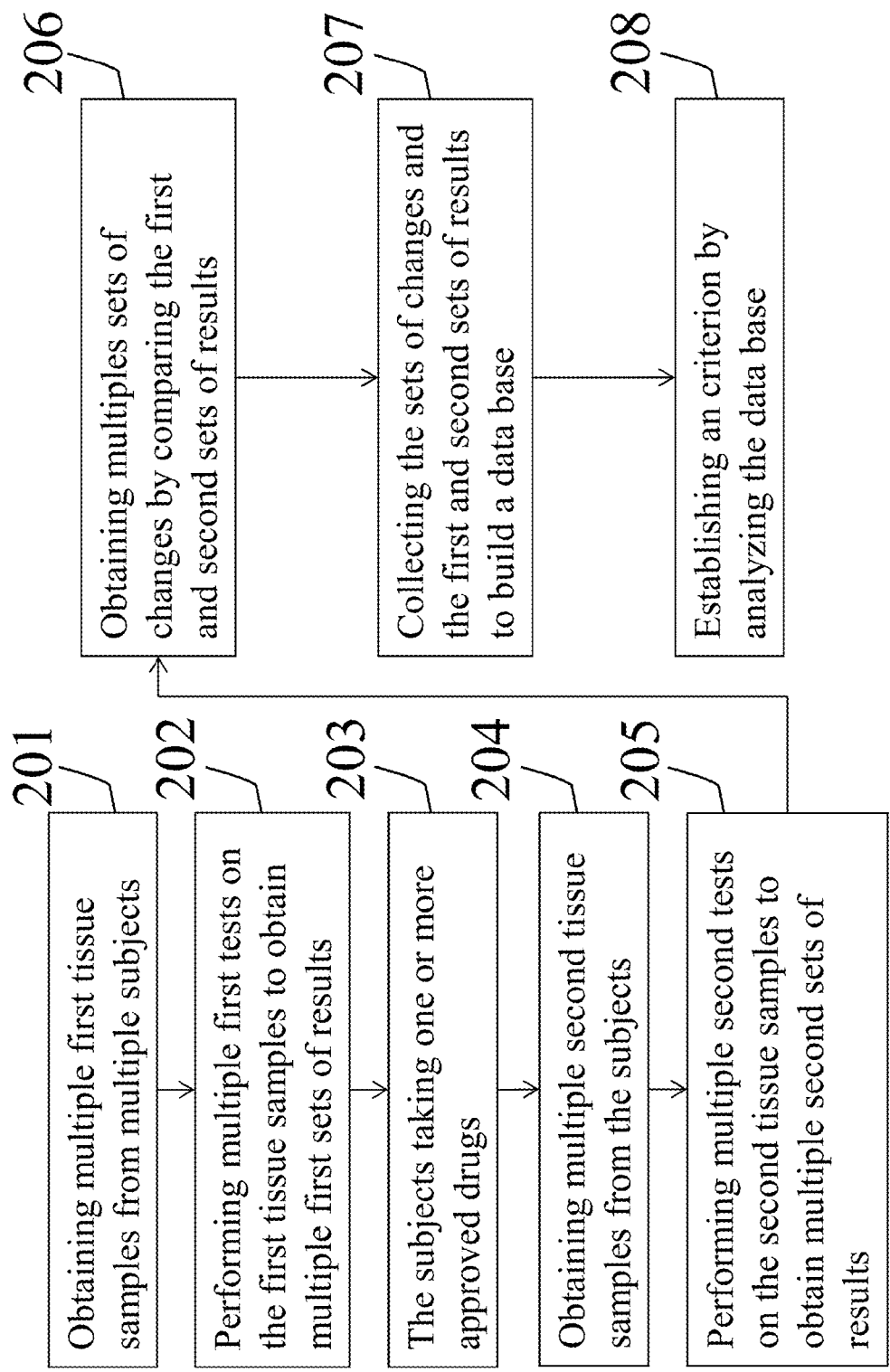
FIG. 15 shows a flow chart for establishing universal criteria or standards for evaluating, qualifying or approving at least one action or stimulus for curing a disease according to the seventh embodiment of the present disclosure.

FIGS. 14 and 15 are two examples used to establish or generate one or more universal criteria or standards for evaluating, qualifying or approving one or more of the above-mentioned actions or stimuli (X) for curing a specific disease such as a cancer, a skin disease, or a kidney disease. In this embodiment, N1 subjects may be sampled or selected from human or non-human bodies having a specific disease (such as a cancer, a skin disease, or a kidney disease). The N1 subjects, each of which may be referred to the above-mentioned subject (S), are sampled or selected from species in the same biological category.

Referring to FIG. 14, as the step 107 illustrated in FIG. 9, the steps 51-56 illustrated in FIG. 7 may be performed on each of the N1 subjects to obtain data or information of stem cells related to the N1 subjects in the case that each of the N1 subjects takes the same one or more drugs approved by a government department (e.g., U.S. FDA) or different one or more drugs approved by the government department, in the step 53, to cure the specific disease. A drug that has been approved by the government department (e.g., U.S. FDA) is called an approved drug. The steps 51-56, including the N1 subjects taking the same or different one or more approved drugs in the step 53, and the step 107 are also shown in FIG. 14. Related to the N1 subjects illustrated herein, the data or information of stem cells includes (1) N1 first sets of results or data obtained by the method illustrated in the steps 51 and 52, (2) N1 second sets of results or data obtained by the method illustrated in the steps 54 and 55, and (3) N1 sets of changes in N1 respective pairs of results or data, each including one of the N1 first sets of results or data and a corresponding one of the N1 second sets of results or data for the same one of the N1 subjects, obtained by the method illustrated in the step 56, as mentioned in the step 107 of FIG. 9. After the information of stem cells related to the N1 subjects is obtained by the step 107, the information of stem cells related to the N1 subjects is collected to build a data base, as mentioned in the step 108 of FIG. 9. The data base further includes the data of, for example, age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) for each of the N1 subjects. Next, the data base may be analyzed, with a statistical significance, to establish the above-mentioned criteria or standards (G) for identifying, determining, evaluating or assessing the effect of one or more of the actions or stimuli (X), such as the one or more actions or stimuli performed in the step 53, as mentioned in the step 109 of FIG. 9.

As mentioned above, the step 107 in FIG. 14 may be performed in various sequences. For example, the steps 51-55 may be performed on respective ones of the N1 subjects in different respective time periods that may be overlapped or non-overlapped. Alternatively, the steps 51-55 may be performed on a first sub-group of the N1 subjects after the steps 51-55 are performed on a second sub-group of the N1 subjects but before the steps 51-55 are performed on a third sub-group of the N1 subjects.

Referring to FIG. 15, the steps 201-206 illustrated in FIG. 10 may be performed on each of the N1 subjects to obtain data or information of stem cells related to the N1 subjects in the case that each of the N1 subjects takes the same one or more drugs approved by a government department (e.g., U.S. FDA) or different one or more drugs approved by the government department, in the step 203, to cure the specific disease. Related to the N1 subjects illustrated herein, the data or information of stem cells includes (1) N1 first sets of results or data obtained by the method illustrated in the steps 201 and 202, (2) N1 second sets of results or data obtained by the method illustrated in the steps 204 and 205, and (3) N1 sets of changes in N1 respective pairs of results or data, each including one of the N1 first sets of results or data and a corresponding one of the N1 second sets of results or data for the same one of the N1 subjects, obtained by the method illustrated in the step 206. After the information of stem cells related to the N1 subjects is obtained by the steps 201-206, the information of stem cells related to the N1 subjects is collected to build a data base, as mentioned in the step 207 of FIG. 10. The data base further includes the data of, for example, age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) for each of the N1 subjects. Next, the data base may be analyzed, with a statistical significance, to establish the above-mentioned criteria or standards (G) for identifying, determining, evaluating or assessing the effect of one or more of the actions or stimuli (X), such as the one or more actions or stimuli performed in the step 203, as mentioned in the step 208 of FIG. 10. The steps 201-208, including the N1 subjects taking the same or different one or more approved drugs in the step 203, are also shown in FIG. 15.

Universal criteria or standards, including information defined as that of the criteria or standards (G) in the third embodiment, may be generated or established by, e.g., (1) determining if any one or more of the changes $\Delta_{1,1}$-$\Delta_{a,c}$ in the N1 sets related to the N1 subjects illustrated in FIG. 14 or 15 exceeds a (predetermined) threshold or (2) finding or identifying significant or dramatic one(s) of the changes $\Delta_{1,1}$-$\Delta_{a,c}$ in the N1 sets related to the N1 subjects illustrated in FIG. 14 or 15. Based on the peaks and/or variances of Gaussian distributions for the one or more of the changes $\Delta_{1,1}$-$\Delta_{a,c}$ in the N1 sets exceeding the (predetermined) threshold or for the significant or dramatic one(s) of the changes $\Delta_{1,1}$-$\Delta_{a,c}$ in the N1 sets, a corresponding universal criteria or standards may be established or obtained for identifying, determining, evaluating or assessing the effect of one or more of the actions or stimuli (X) on a specific subject having the specific disease. For example, the universal criteria like the criteria $G_{1,2}$ and $G_{1,4}$ may be established for evaluating the effect of one or more of the actions or stimuli (X) on a specific subject having the specific disease in the case that the changes $\Delta_{1,1}$, $\Delta_{1,2}$, $\Delta_{1,4}$ and $\Delta_{1,5}$ in the N1 sets related to the N1 subjects illustrated in FIG. 14 or 15 are identified to be (statistically) significant for samples as the N1 subjects having the specific disease.

Accordingly, the universal criteria or standards may be established for evaluating the effects of one or more of the action or stimuli (X) on curing the specific disease or for determining if the one or more of the action or stimuli (X) can improve or cure the specific disease. For example, if the changes $\Delta_{1,1}$, $\Delta_{1,2}$, $\Delta_{1,4}$ and/or $\Delta_{1,5}$, obtained from the steps 51-56 of FIG. 7, related to a patient taking nutrients extracted from algae in the step 53, meet the universal criteria or standards $G_{1,2}$ and/or $G_{1,4}$, the action of taking nutrients extracted from algae may be considered to be a therapy against the specific disease for the patient. Otherwise, the action of taking nutrients extracted from algae would be considered to be ineffective to cure the specific disease for the patient.

One or more types of (common) stem cells, found for the one or more approved drugs for curing the specific disease, for establishing the universal criteria or standards illustrated in FIG. 14 or 15 may be at an upper stream or level in the hierarchical chain of stem cells. That means the one or more types of (common) stem cells may be relatively primitive or generic; other stem cells may be derived from the one or more types of (common) stem cells.

This embodiment provides a method, an apparatus, or an integrated system combining methodology, software (tools) and hardware (equipments, machines, or devices for extraction, filtering, purification, analyzing stem cells), for establishing the universal criteria or standards by finding or identifying significant or dramatic one(s) of the changes $\Delta_{1,1}$-$\Delta_{a,c}$ in the N1 sets related to the N1 subjects illustrated in FIG. 14 or 15, as mentioned in accordance with this embodiment.

A criterion establishing method, in accordance with the seventh embodiment, comprises: taking a first tissue sample from a subject having a disease; analyzing said first tissue sample to obtain a first result related to information of a type or types of stem cells; after said taking said first tissue sample, said subject taking a drug to cure said disease; after said subject taking said drug, taking a second tissue sample from said subject; analyzing said second tissue sample to obtain a second result related to information of said type or types of stem cells; comparing said first and second results to obtain a change; determining if said change exceeds a threshold; and establishing a criterion to cure said disease based on said change.

A criterion establishing method, in accordance with the seventh embodiment, comprises: taking a first tissue sample from a subject having a disease; analyzing said first tissue sample to obtain a first result related to information of a first type or types of stem cells and a second result related to information of a second type or types of stem cells; after said taking said first tissue sample, said subject taking a drug to cure said disease; after said subject taking said drug, taking a second tissue sample from said subject; analyzing said second tissue sample to obtain a third result related to information of said first type or types of stem cells and a fourth result related to information of said second type or types of stem cells; comparing said first and third results to obtain a first change; comparing said second and fourth results to obtain a second change; establishing a criterion to cure said disease based on a significant one of said first and second changes.

Eighth Embodiment

Figure 16:
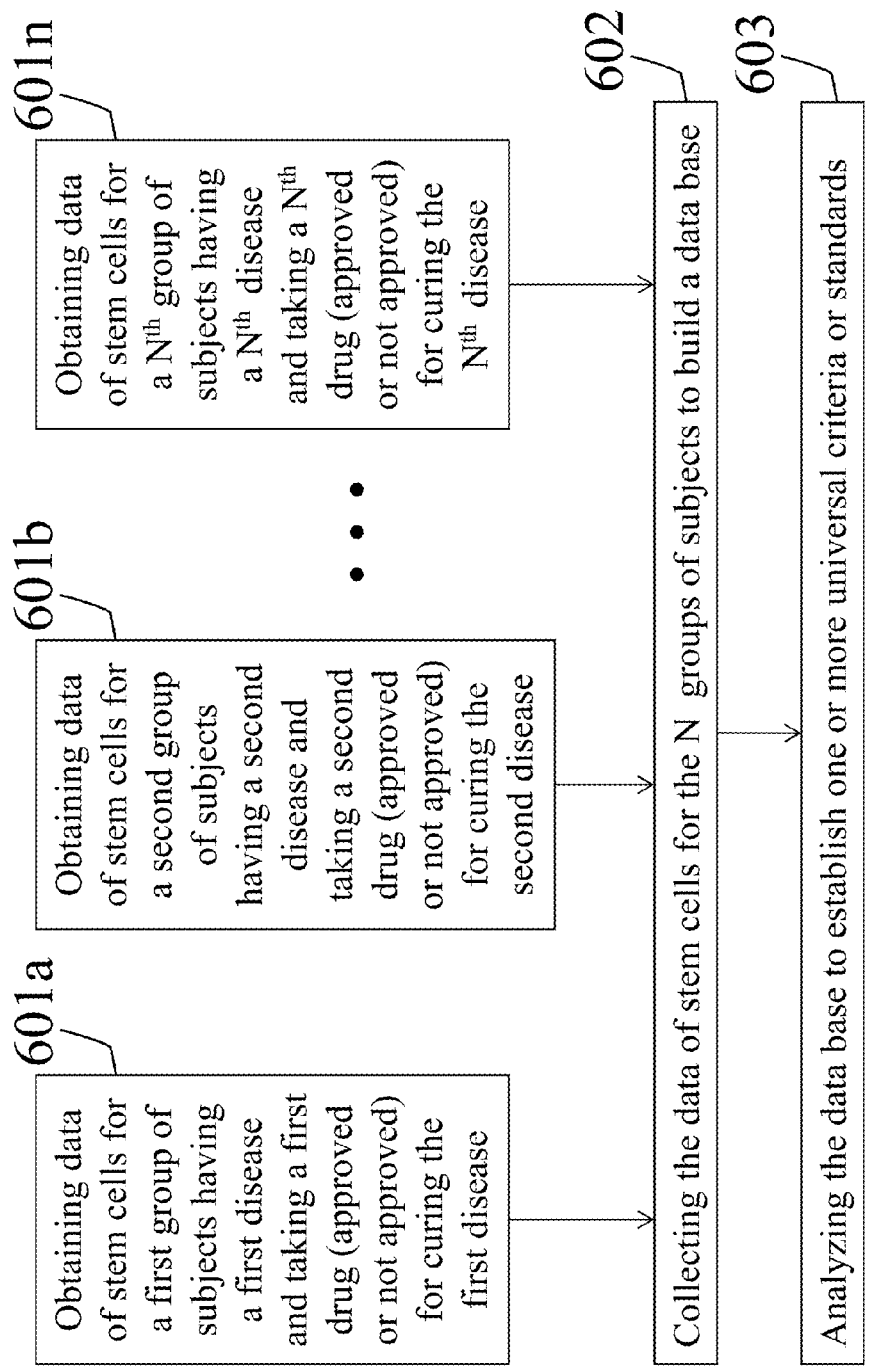
FIG. 16 shows a flow chart of establishing universal criteria or standards for evaluating, qualifying or approving at least one action or stimulus for curing various diseases according to an eighth embodiment of the present disclosure.

FIG. 16 is a flow chart of establishing one or more universal criteria or standards for evaluating, qualifying or approving one or more of the above-mentioned actions or stimuli (X) for curing at least two, three, four, five or ten various diseases, such as two types of cancers.

In this embodiment, N groups of subjects are sampled or selected from human or non-human bodies having N various diseases, respectively, where "N" is a positive integer equal to or greater than 2, 3, 4, 5 or 10. For example, the first group of subjects is sampled or selected from human or non-human bodies having the first disease; the $N^{th}$ group of subjects is sampled or selected from human or non-human bodies having the $N^{th}$ disease. Each of the N groups may include at least two, five, ten, twenty or fifty subjects. Each subject in the N groups may be referred to the above-mentioned subject (S). The N groups of subjects are sampled or selected from species in the same biological category.

N steps 601a-601n in FIG. 16 are performed on the N groups of subjects, respectively. For example, the step 601a is performed on the first group of subjects; the step 601n is performed on the $N^{th}$ group of subjects. The N steps 601a-601n may be performed, as illustrated in the steps 51-56 of FIG. 7 or the steps 201-206 of FIG. 10, on the N respective groups of subjects to obtain information of stem cells related to the N respective groups of subjects. For example, the step 601a including the steps 51-56 of FIG. 7 or the steps 201-206 of FIG. 10 may be performed on the first group of subjects having the first disease, wherein the subjects are taking or subjected to a first action or stimulus (for example, taking a first U.S. FDA approved drug, or a first drug not approved by U.S. FDA), to obtain information of stem cells related to the first group of subjects; the step 601n including the steps 51-56 of FIG. 7 or the steps 201-206 of FIG. 10 may be performed on the $N^{th}$ group of subjects having the $N^{th}$ disease, wherein the subjects are taking or subjected to a $N^{th}$ action or stimulus (for example, taking a $N^{th}$ U.S. FDA approved drug, or a $N^{th}$ drug not approved by U.S. FDA), to obtain information of stem cells related to the $N^{th}$ group of subjects.

In the N steps 601a-601n, in each of the N groups, the subjects may take, for example, the same one or more approved drugs or different one or more approved drugs to cure the corresponding one of the N diseases in the step 53 of FIG. 7 or the step 203 of FIG. 10. For example, in the step 601a, the first group of subjects may take one or more approved first drugs or different one or more approved first drugs to cure the first disease in the step 53 of FIG. 7 or the step 203 of FIG. 10; in the step 601n, the $N^{th}$ group of subjects may take one or more approved $N^{th}$ drugs or different one or more approved $N^{th}$ drugs to cure the $N^{th}$ disease in the step 53 of FIG. 7 or the step 203 of FIG. 10. A drug that has been approved by the government department (e.g., U.S. FDA) is called an approved drug.

The information of stem cells related to each of the N groups of subjects include (1) multiple first sets of the results or data $R_{1,1}$-$R_{a,b}$ obtained by the method illustrated in the steps 51 and 52 of FIG. 7 or the steps 201 and 202 of FIG. 10, (2) multiple second sets of results or data $R_{1,1}$-$R_{a,b}$ obtained by the method illustrated in the steps 54 and 55 of FIG. 7 or the steps 204 and 205 of FIG. 10, and (3) multiple sets of changes $\Delta_{1,1}$-$\Delta_{a,c}$ in multiple respective pairs of results or data, each including one of the first set of results or data and a corresponding one of the second set of results or data for the same one of the subjects, obtained by the method illustrated in the step 56 of FIG. 7 or the step 206 of FIG. 10.

Referring to FIG. 16, in step 602, the information of stem cells, obtained by the N steps 601a-601n, related to the N groups of subjects may be collected to build a broad data base (B-DB). The broad data base (B-DB) may further include the data of, for example, age, gender, race, height, weight, blood pressure, heartbeat, immunoglobulin (Ig), BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and one or more diseases (e.g., a cancer, a skin disease, and/or a kidney disease) for each subject in the N groups.

Next, referring to FIG. 16, in step 603, the broad data bases (B-DB) may be analyzed by a suitable method (such as statistical analysis) to generate or establish multiple criteria or standards as the criteria or standards (G) defined, specified or described in the third embodiment.

In one case, for each of the N groups of subjects the analysis may include analyzing the first and second sets of results or data $R_{1,1}$-$R_{a,b}$ and the sets of changes $\Delta_{1,1}$-$\Delta_{a,c}$ against age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), or one or more diseases (e.g., a cancer, a skin disease, and/or a kidney disease) of the subjects in the corresponding one of the N groups.

For one of the N groups of subjects the distribution of some specific data, as X-axis, taken from the first and/or second sets of results or data $R_{1,1}$-$R_{a,b}$ related to said one of the N groups of subjects and/or the sets of changes $\Delta_{1,1}$-$\Delta_{a,c}$ related to said one of the N groups of subjects may be plotted with the frequency of occurrence as Y-axis. For instance, the changes of the numbers of SB-1 cells, i.e., the changes $\Delta_{1,1}$, related to said one of the N groups of subjects may be taken to plot the distribution of the changes of the numbers of SB-1 cells related to said one of the N groups of subjects (in X-axis) with respect to the frequency of occurrence (in Y-Axis); herein all the subjects in said one of the N groups of subjects have the same specific disease (e.g., a cancer, a skin disease, or a kidney disease) and take the same or different drugs in the step 53 or 203. Other changes $\Delta_{1,2}$-$\Delta_{a,c}$ related to said one of the N groups of subjects may be considered in a similar way.

Statistically, Gaussian distribution may be employed for analyzing data in the broad data bases (B-DB) built in the step 602 to generate or establish criteria or standards, which may be referred to the criteria or standards (G) defined, specified or described in the third embodiment, for each group of subjects. The data in the broad data base (B-DB) may be analyzed to generate Gaussian distributions for the data in the broad data base (B-DB). Alternatively, criteria or standards including information defined as that the criteria or standards (G) in the third embodiment, for each group of subjects, may be generated or established by, e.g., (1) determining if any one or more of the changes $\Delta_{1,1}$-$\Delta_{a,c}$ for said each group of subjects exceeds a (predetermined) threshold or (2) finding or identifying significant or dramatic one(s) of the changes $\Delta_{1,1}$-$\Delta_{a,c}$ for said each group of subjects. Alternatively, based on the peaks and/or variances of Gaussian distributions for the significant or dramatic one(s) of the changes $\Delta_{1,1}$-$\Delta_{a,c}$ for said each group of subjects, the criteria or standards may be established or obtained.

By finding or determining which of the criteria or standards that may be established by the above Gaussian distributions for the broad data bases (B-DB) are frequently established among all or most of the N groups of subjects, by determining if said one or more of the changes $\Delta_{1,1}$-$\Delta_{a,c}$ exceeding the (predetermined) threshold is frequently found among all or most of the N groups of subjects or by determining if said significant or dramatic one or more of the changes $\Delta_{1,1}$-$\Delta_{a,c}$ is frequently found among all or most of the N groups of subjects, universal criteria or standards may be established based on the frequently established criteria or standards, on said one or more of the changes $\Delta_{1,1}$-$\Delta_{a,c}$ exceeding the (predetermined) threshold, frequently found among all or most of the N groups of subjects, or on said significant or dramatic one or more of the changes $\Delta_{1,1}$-$\Delta_{a,c}$, frequently found among all or most of the N groups of subjects. For example, universal criteria or standards can be established based on the criteria $G_{1,2}$ and $G_{1,4}$, if established among all or most of the N groups of subjects. Alternatively, one or more of the other criteria or standards $G_{1,1}$, $G_{1,3}$, and $G_{1,5}$-$G_{a,d}$ may be defined as universal criteria or standards in the case that the one or more of the other criteria or standards $G_{1,1}$, $G_{1,3}$, and $G_{1,5}$-$G_{a,d}$ can be established among all or most of the N groups of subjects.

Accordingly, the universal criteria or standards, such as the criteria $G_{1,2}$ and $G_{1,4}$, may be used for evaluating the effects of one or more of the actions or stimuli (X) on curing various diseases or for determining if the one or more of the actions or stimuli (X) can improve or cure various diseases. For example, if the changes $\Delta_{1,1}$, $\Delta_{1,2}$, $\Delta_{1,4}$ and/or $\Delta_{1,5}$, obtained from the steps 51-56 of FIG. 7, related to a patient taking nutrients extracted from algae in the step 53, meet the universal criteria or standards $G_{1,2}$ and/or $G_{1,4}$, the action of taking nutrients extracted from algae may be considered to be a universal therapy against various diseases for the patient. Otherwise, the action of taking nutrients extracted from algae would be not considered to be a universal therapy against various diseases for the patient.

Besides, the one or more universal criteria or standards, such as the criteria $G_{1,2}$ and $G_{1,4}$, may be used for many applications, for examples, (1) it may become a routine procedure in a medical hospital for evaluating effectiveness of a medical treatment; (2) it may be included in items in the routine medical check-ups or routine physical examinations to show the body's health condition. In addition, one or more types of (common) stem cells, found for the one or more approved (or investigational) drugs for curing the N various diseases, for establishing the universal criteria or standards illustrated in FIG. 16 may be at an upper stream or level in the hierarchical chain of stem cells. That means the one or more types of (common) stem cells may be relatively primitive or generic; other stem cells may be derived from the one or more types of (common) stem cells. This embodiment provides a method, an apparatus, or an integrated system combining methodology, software (tools) and hardware (equipments, machines, or devices for extraction, filtering, purification, analyzing stem cells), to determine or identify the position, level or status of stem cells in the hierarchical chain of stem cells. For example, the stem cells may be found in the following hierarchical chain (from upper stream/more primitive/more generic to lower stream/less primitive/less generic): (1) Stem Cell A found in all 5 groups (GA, GB, GC, GD and GE) of subjects having Diseases (DA, DB, DC, DD and DE), respectively, and taking Drugs (DGA, DGB and DGC); (2) Stem Cell B found in 4 groups (GA, GB, GC and GD) of subjects having Diseases (DA, DB, DC and DD), respectively, and taking Drugs (DGA, DGB and DGC); (3) Stem Cell C found in 4 groups (GA, GB, GC and GD) of subjects having Diseases (DA, DB, DC and DD), respectively, and taking Drugs (DGA and DGB); (4) Stem Cell D found in the group (GA) of subjects having Disease (DA) and taking Drugs (DGA and DGB); and (5) Stem Cell E found in the group (GA) of subjects having Disease (DA) and taking Drug (DGA). More specifically, Stem cell B can be derived from Stem cell A; Stem cell C can be derived from Stem cell A and/or Stem cell B; Stem cell D can be derived from Stem cell A, Stem cell B and/or Stem cell C; Stem cell E can be derived from Stem cell A, Stem cell B, Stem cell C, and/or Stem cell D.

This embodiment further provides a method, an apparatus, or an integrated system combining methodology, software (tools) and hardware (equipments, machines, or devices for extraction, filtering, purification, analyzing stem cells), for establishing the universal criteria or standards by, e.g., finding or determining which criteria or standards are frequently established among the N groups of subjects, as mentioned in accordance with this embodiment.

A criterion establishing method, in accordance with the eighth embodiment, comprises: taking a first tissue sample from a first subject having a first disease; analyzing said first tissue sample to obtain a first result related to information of a type or types of stem cells; after said taking said first tissue sample, said first subject taking a first drug to cure said first disease; after said first subject taking said first drug, taking a second tissue sample from said first subject; analyzing said second tissue sample to obtain a second result related to information of said type or types of stem cells; comparing said first and second results to obtain a first change; determining if said first change exceeds a threshold; taking a third tissue sample from a second subject having a second disease; analyzing said third tissue sample to obtain a third result related to information of said type or types of stem cells; after said taking said third tissue sample, said second subject taking a second drug to cure said second disease; after said second subject taking said second drug, taking a fourth tissue sample from said second subject; analyzing said fourth tissue sample to obtain a fourth result related to information of said type or types of stem cells; comparing said third and fourth results to obtain a second change; determining if said second change exceeds said threshold; and establishing a criterion based on said first and second changes when said first and second changes exceed said threshold.

A criterion establishing method, in accordance with the eighth embodiment, comprises: taking a first tissue sample from a first subject having a first disease; analyzing said first tissue sample to obtain a first result related to information of a first type or types of stem cells and a second result related to information of a second type or types of stem cells; after said taking said first tissue sample, said first subject taking a first drug to cure said first disease; after said first subject taking said first drug, taking a second tissue sample from said first subject; analyzing said second tissue sample to obtain a third result related to information of said first type or types of stem cells and a fourth result related to information of said second type or types of stem cells; comparing said first and third results to obtain a first change; comparing said second and fourth results to obtain a second change; taking a third tissue sample from a second subject having a second disease; analyzing said third tissue sample to obtain a fifth result related to information of said first type or types of stem cells and a sixth result related to information of said second type or types of stem cells; after said taking said third tissue sample, said second subject taking a second drug to cure said second disease; after said second subject taking said second drug, taking a fourth tissue sample from said second subject; analyzing said fourth tissue sample to obtain a seventh result related to information of said first type or types of stem cells and an eighth result related to information of said second type or types of stem cells; comparing said fifth and seventh results to obtain a third change; comparing said sixth and eighth results to obtain a fourth change; and establishing a criterion based on a significant one of said first and second changes and on a significant one of said third and fourth changes.

Ninth Embodiment

Figure 17A:
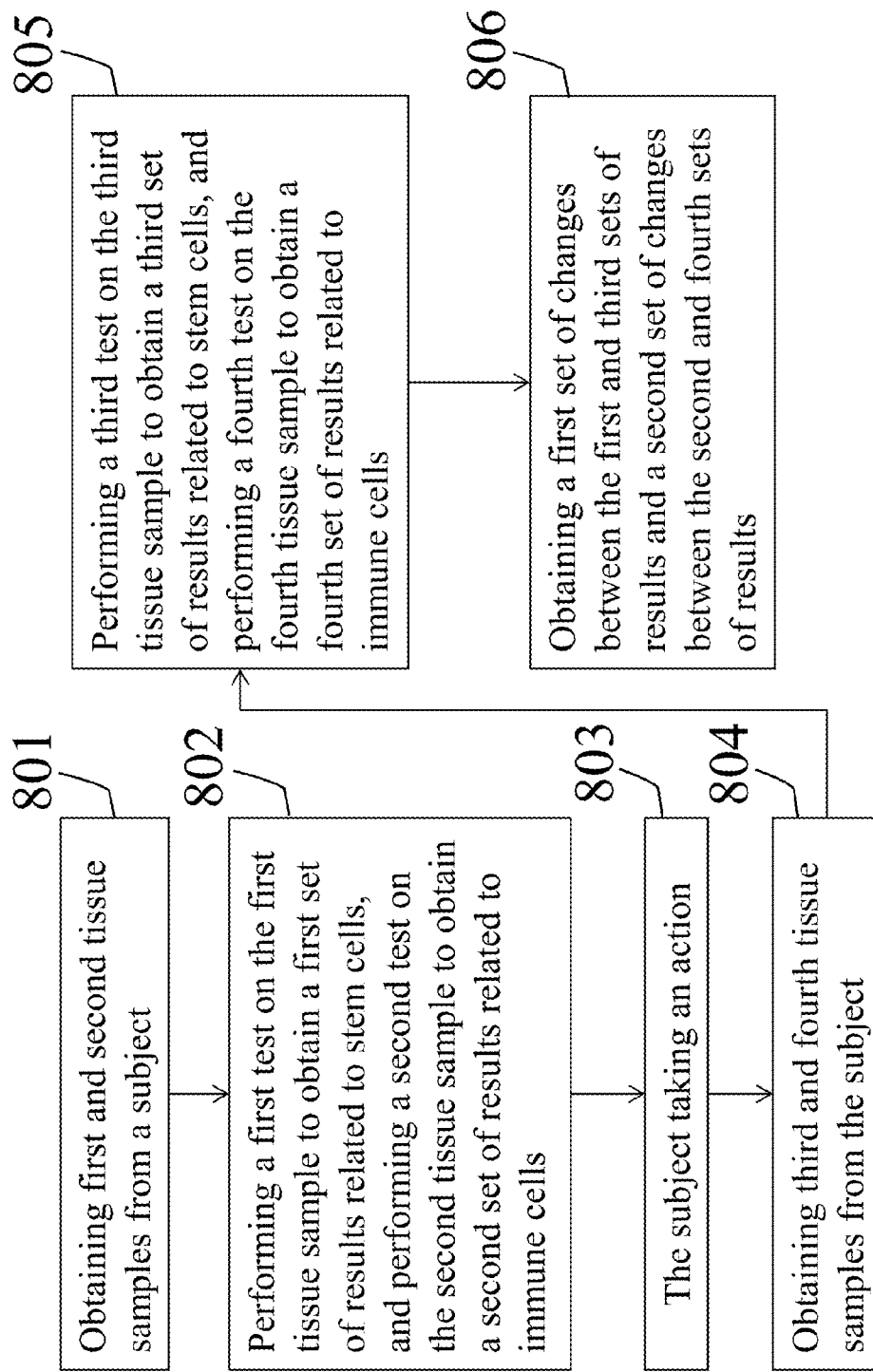
FIG. 17A shows a flow chart for obtaining data or information of stem cells and immune cells related to a subject according to a ninth embodiment of the present disclosure.

FIG. 17A is a flow chart for obtaining data or information of stem cells and immune cells related to a subject. Referring to FIG. 17A, in step 801, first and second tissue samples, each of which may be referred to the above-mentioned tissue sample (P), are extracted, taken, obtained or derived from a subject that may be referred to the above-mentioned subject (S). Next, in step 802, a first test, assessment or measurement including extracting, characterizing, assessing and measuring stem cells is performed, referring to one of the above-mentioned tests, assessments or measurements (M0), (M1) and (M2), on the first tissue sample to obtain a first set of results or data related to one or more types of stem cells from the first tissue sample descriptively, qualitatively or quantitatively. Furthermore, a second test, assessment or measurement including extracting, characterizing, assessing and measuring immune cells is performed on the second tissue sample to obtain a second set of results or data related to one or more types of immune cells from the second tissue sample descriptively, qualitatively or quantitatively.

The first set of results or data illustrated herein may include parameters, such as the number, the percentage and/or the sizes, of the one or more types of (small) stem cells. For example, the first set of results or data illustrated herein include the same types of information as the first set of results or data illustrated in the step 52 of FIG. 7, that is, the first set of results or data illustrated herein include multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for the first set of results or data illustrated herein are defined, described or specified as the first set of results or data illustrated in the step 52 of FIG. 7, respectively.

The second test, assessment or measurement illustrated herein may include using flow cytometry, cytometric bead assay or hematology analysis to obtain the second set of results or data related to immune cells from the second tissue sample. The second set of results or data may include types of immune cells and parameters (such as the count (number) and/or the percentage) of the one or more types of immune cells. The one or more types of immune cells may include, but not limited to, lymphocytes, T cells (or T lymphocytes), T helper cells, cytotoxic T cells, regulatory T cells (or suppressor T cells), active T cells, B cells (or B lymphocytes), natural killer cells (NK cells), dendritic cells, granulocytes, and/or macrophages. Lymphocytes are a type of white blood cell produced by the immune system and include T cells, B cells, and natural killer cells. The three major types of T cells are T helper cells ($T_H$ cells), cytotoxic T cells ($T_C$ cells), and regulatory T cells ($T_{reg}$ cells). T cells could be also known as CD3(+) cells because they can express the cell (surface) marker CD3. T helper cells could be also known as CD3(+), CD4(+) cells because they can express the two cell (surface) markers CD3 and CD4. Cytotoxic T cells could be also known as CD3(+), CD8(+) cells because they can express the two cell (surface) markers CD3 and CD8. Active T cells can express the cell (surface) marker HLA-DR. Natural killer cells can express the two cell (surface) markers CD16 and CD56 and can be characterized by CD16(+) and CD56 (+). Alternatively, natural killer cells can express the cell (surface) marker CD57 and can be characterized as CD57(+). B cells could be also known as CD20(+) cells because they can express the cell (surface) marker CD20. Granulocytes could be also known as Gr-1(+) cells because they can express the cell (surface) marker Gr-1. Macrophages could be also known as CD80(+) cells because they can express the cell (surface) marker CD80.

The second set of results or data illustrated herein, for example, may include multiple results or data $U_{1,1}$-$U_{1,y}$, $U_{2,1}$-$U_{2,y}$, . . . , and $U_{x,1}$-$U_{x,y}$, where "x" is a positive integer such as one of the numbers from 2 to 12, and "y" is a positive integer such as 1 or 2. The notation $U_{1,1}$-$U_{1,3}$, means a series of results or data: $U_{1,1}$, $U_{1,2}$, . . . , to $U_{1,y}$. The notation $U_{2,1}$-$U_{2,y}$ means a series of results or data: $U_{2,1}$, $U_{2,2}$, . . . , to $U_{2,y}$. The notation $U_{x,1}$-$U_{x,y}$ means a series of results or data: $U_{x,1}$, $U_{x,2}$, . . . , to $U_{x,y}$. The first number in the subscript of U, i.e., the number immediately following the letter of U, i.e., from 1 to x, represents a certain selected type of immune cells or a group of several types of immune cells. The number x may be the number of all categories of immune cells or the number of all groups of immune cells. The second number in the subscript of U, i.e., the number immediately following the first number, i.e., from 1 to y, represents data types. The number y may be the number of the data types.

With regard to the first number in the subscript of U, the results or data $U_{1,1}$-$U_{1,y}$ having the first number 1 in the subscript of U are results or data related to, for example, lymphocytes. The results or data $U_{2,1}$-$U_{2,y}$ having the first number 2 in the subscript of U are results or data related to, for example, T cells. The results or data $U_{3,1}$-$U_{3,y}$ having the first number 3 in the subscript of U are results or data related to, for example, T helper cells. The results or data $U_{4,1}$-$U_{4,y}$ having the first number 4 in the subscript of U are results or data related to, for example, cytotoxic T cells. The results or data $U_{5,1}$-$U_{5,y}$ having the first number 5 in the subscript of U are results or data related to, for example, regulatory T cells. The results or data $U_{6,1}$-$U_{6,y}$ having the first number 6 in the subscript of U are results or data related to, for example, active T cells. The results or data $U_{7,1}$-$U_{7,y}$ having the first number 7 in the subscript of U are results or data related to, for example, B cells. The results or data $U_{8,1}$-$U_{8,y}$ having the first number 8 in the subscript of U are results or data related to, for example, natural killer cells. The results or data $U_{9,1}$-$U_{9,y}$ having the first number 9 in the subscript of U are results or data related to, for example, dendritic cells. The results or data $U_{10,1}$-$U_{10,y}$ having the first number 10 in the subscript of U are results or data related to, for example, two selected types of immune cells (e.g., T helper cells and cytotoxic T cells). The results or data $U_{11,1}$-$U_{11,y}$ having the first number 11 in the subscript of U are results or data related to, for example, granulocytes. The results or data $U_{12,1}$-$U_{12,y}$ having the first number 12 in the subscript of U are results or data related to, for example, macrophages.

With regard to the second number in the subscript of U, the results or data $U_{1,1}$-$U_{x,1}$ having the second number 1 in the subscript of U are results or data related to, for example, the count (number) of immune cells of a specific type or a group of several types. The results or data $U_{1,2}$-$U_{x,2}$ having the second number 2 in the subscript of U are results or data related to, for example, the percentage of the count (number) of immune cells of a specific type or a group of several types to the total count (total number) of biological or immune cells, such as lymphocytes.

For further elaboration, the result $U_{1,1}$ shows the count of lymphocytes. The result $U_{2,1}$ shows the count of T cells. The result $U_{2,2}$ shows the percentage of the count of T cells to the total count of biological or immune cells (e.g., lymphocytes). The result $U_{3,1}$ shows the count of T helper cells. The result $U_{3,2}$ shows the percentage of the count of T helper cells to the total count of biological or immune cells (e.g., lymphocytes). The result $U_{4,1}$ shows the count of cytotoxic T cells. The result $U_{4,2}$ shows the percentage of the count of cytotoxic T cells to the total count of biological or immune cells (e.g., lymphocytes). The result $U_{5,1}$ shows the count of regulatory T cells. The result $U_{5,2}$ shows the percentage of the count of regulatory T cells to the total count of biological or immune cells (e.g., lymphocytes). The result $U_{6,1}$ shows the count of active T cells. The result $U_{6,2}$ shows the percentage of the count of active T cells to the total count of biological or immune cells (e.g., lymphocytes).

The result $U_{7,1}$ shows the count of B cells. The result $U_{7,2}$ shows the percentage of the count of B cells to the total count of biological or immune cells (e.g., lymphocytes). The result $U_{8,1}$ shows the count of natural killer cells. The result $U_{8,2}$ shows the percentage of the count of natural killer cells to the total count of biological or immune cells (e.g., lymphocytes). The result $U_{9,1}$ shows the count of dendritic cells. The result $U_{9,2}$ shows the percentage of the count of dendritic cells to the total count of biological or immune cells (e.g., lymphocytes). The result $U_{10,1}$ shows the count of immune cells of the group of the two selected types (e.g., T helper cells and cytotoxic T cells). The result $U_{10,2}$ shows the percentage of the count of immune cells of the group of the two selected types (e.g., T helper cells and cytotoxic T cells) to the total count of biological or immune cells (e.g., lymphocytes). The result $U_{10,3}$ shows the ratio of immune cells of one type (e.g., T helper cells) to immune cells of another type (e.g., cytotoxic T cells). The result $U_{11,1}$ shows the count of granulocytes. The result $U_{11,2}$ shows the percentage of the count of granulocytes to the total count of biological or immune cells (e.g., lymphocytes). The result $U_{12,1}$ shows the count of macrophage cells. The result $U_{12,2}$ shows the percentage of the count of macrophage cells to the total count of biological or immune cells (e.g., lymphocytes).

Referring to FIG. 17A, after the step 801 or 802 is performed, step 803 is performed. In the step 803, the subject takes or is subjected to one or more of the above-mentioned actions or stimuli (X), such as taking nutrients or dietary supplements, taking one or more drugs approved by a government department (e.g., U.S. FDA) for curing a specific disease (e.g., cancer), and/or being exposed to sunshine or sunlight. The one or more actions or stimuli illustrated herein may be performed based on the dose, intensity, duration, frequency (each action may include more than one sub-actions, for example, taking one pill of drug for three times with one hour apart), and/or the time (for example, the time of a day (in the morning, at noon, in the afternoon, in the evening, or in the night), the time before, with or after the meal, or the time of the year (spring, summer, autumn or winter)). As an example, when the subject is taking a drug or a nutrient, the dose (for example, the amount in grams), the time (for example, before or after breakfast, or before sleep) are factors needed to be considered. As another example, when the subject is exposed to the sunshine or sunlight, the time of the day (morning, noon or afternoon), the time of seasons (spring, summer, autumn, or winter), or the exposing duration (30 minutes, 1 hour, 2 hours) are factors needed to be considered.

After a specific period of time, such as longer than or equal to 15, 30, 60, 90 or 120 minutes or one, two or thirty days, or, for example, between 30 and 120 minutes, step 804 is performed following the step 803. In the step 804, third and fourth tissue samples, each of which may be referred to the above-mentioned tissue sample (P), are extracted, taken, obtained or derived from the subject. The first, second, third and fourth tissue samples may be, but not limited to, four samples obtained from the same type of tissue of the subject. For example, all of the first, second, third and fourth tissue samples may be obtained from (peripheral) blood of the subject. Alternatively, the first and third tissue samples may have a different type of tissue from that of the second and fourth tissue samples. For example, the first and third tissue samples may be bone marrow, but the second and fourth tissue samples may be (peripheral) blood.

Next, referring to FIG. 17A, in step 805, a third test, assessment or measurement including extracting, characterizing, assessing and measuring stem cells is performed, referring to one of the above-mentioned tests, assessments or measurements (M0), (M1) and (M2), on the third tissue sample to obtain a third set of results or data related to one or more types of stem cells from the third tissue sample descriptively, qualitatively or quantitatively. Furthermore, a fourth test, assessment or measurement including extracting, characterizing, assessing and measuring immune cells is performed on the fourth tissue sample to obtain a fourth set of results or data related to one or more types of immune cells from the fourth tissue sample descriptively, qualitatively or quantitatively. The one or more types of stem cells measured in the step 802 may be the same as the respective one or more types of stem cells measured in the step 805, and the one or more types of immune cells measured in the step 802 may be the same as the respective one or more types of immune cells measured in the step 805.

The third set of results or data illustrated herein may include parameters, such as the number, the percentage and/or the sizes, of the one or more types of (small) stem cells. For example, the third set of results or data illustrated herein include the same types of information as the first set of results or data illustrated in the step 52 of FIG. 7, that is, the third set of results or data illustrated herein include multiple results or data $R_{1,1}$-$R_{1,b}$, $R_{2,1}$-$R_{2,b}$, ..., and $R_{a,1}$-$R_{a,b}$, wherein the first and second numbers in the subscript of $R_{1,1}$-$R_{a,b}$ for the third set of results or data illustrated herein are defined, described or specified as the first set of results or data illustrated in the step 52 of FIG. 7, respectively.

The fourth test, assessment or measurement illustrated herein may include using flow cytometry, cytometric bead assay or hematology analysis to obtain the fourth set of results or data related to immune cells from the fourth tissue sample. The fourth set of results or data illustrated herein may include parameters, such as the count and/or the percentage, of the one or more types of immune cells. For example, the fourth set of results or data illustrated herein could include the same types of information as the second set of results or data illustrated in the step 802, that is, the fourth set of results or data illustrated herein include multiple results or data $U_{1,1}$-$U_{1,y}$, $U_{2,1}$-$U_{2,y}$, ..., and $U_{x,1}$-$U_{x,y}$, wherein the first and second numbers in the subscript of $U_{1,1}$-$U_{x,y}$ for the fourth set of results or data illustrated herein are defined, described or specified as the second set of results or data illustrated in the step 802, respectively.

For collecting the same types of information and reducing experimental errors, both of the first and third tests, assessments or measurements for the first and third sets of results or data may be performed using the same method described in the above-mentioned test, assessment or measurement (M0), (M1) or (M2), and both of the second and fourth tests, assessments or measurements for the second and fourth sets of results or data may be performed using the same method.

Next, referring to FIG. 17A, in step 806, a first set of changes between the first and third sets of results or data may be obtained by comparing the first and third sets of results or data, and a second set of changes between the second and fourth sets of results or data may be obtained by comparing the second and fourth sets of results or data.

The first set of changes between the first and third sets of results or data could be obtained by performing: (1) a first operation (i.e., subtraction operation), that is, the third set of results or data $R_{1,1}$-$R_{a,b}$ minus the first set of results or data $R_{1,1}$-$R_{a,b}$, or (2) a second operation of calculating the rates of change between the first and third sets of results or data $R_{1,1}$-$R_{a,b}$, which can be calculated by subtracting the first set of results or data $R_{1,1}$-$R_{a,b}$ from the third set of results or data $R_{1,1}$-$R_{a,b}$, then dividing the subtracted results by the first set of results or data $R_{1,1}$-$R_{a,b}$, and finally multiplying the divided results by 100% (which converts the divided results into percent figures). The first and third sets of results or data $R_{1,1}$-$R_{a,b}$ employed in the first or second operation have the same first and second numbers in the subscript.

The second set of changes between the second and fourth sets of results or data could be obtained by performing: (1) a third operation (i.e., subtraction operation), that is, the fourth set of results or data $U_{1,1}$-$U_{x,y}$ minus the second set of results or data $U_{1,1}$-$U_{x,y}$, or (2) a fourth operation of calculating the rates of change between the second and fourth sets of results or data $U_{1,1}$-$U_{x,y}$, which may be calculated by subtracting the second set of results or data $U_{1,1}$-$U_{x,y}$ from the fourth set of results or data $U_{1,1}$-$U_{x,y}$, then dividing the subtracted results by the second set of results or data $U_{1,1}$-$U_{x,y}$, and finally multiplying the divided results by 100% (which converts the divided results into percent figures). The second and fourth sets of results or data $U_{1,1}$-$U_{x,y}$ employed in the third or fourth operation have the same first and second numbers in the subscript.

The first set of changes between the first and third sets of results or data could include the same types of information as the set of changes illustrated in the step 56 of FIG. 7, that is, the first set of changes illustrated herein include multiple changes $\Delta_{1,1}$-$\Delta_{1,c}$, $\Delta_{2,1}$-$\Delta_{2,c}$, ..., and $\Delta_{a,1}$-$\Delta_{a,c}$, wherein the first and second numbers in the subscript of $\Delta_{1,1}$-$\Delta_{a,c}$ for the first set of changes illustrated herein are defined, described or specified as the set of changes illustrated in the step 56 of FIG. 7, respectively.

The second set of changes between the second and fourth sets of results or data could include multiple changes $\theta_{1,1}$-$\theta_{1,z}$, $\theta_{2,1}$-$\theta_{2,z}$, ..., and $\theta_{x,1}$-$\theta_{x,z}$, where "x" is a positive integer such as one of the numbers from 2 to 12, and "z" is a positive integer such as 2, 3, or 4. The notation $\theta_{1,1}$-$\theta_{1,z}$ means a series of data: $\theta_{1,1}$, $\theta_{1,2}$, ..., to $\theta_{1,z}$. The notation $\theta_{2,1}$-$\theta_{2,z}$ means a series of data: $\theta_{2,1}$, $\theta_{2,2}$, ..., to $\theta_{2,z}$. The notation $\theta_{x,1}$-$\theta_{x,z}$ means a series of data: $\theta_{x,1}$, $\theta_{x,2}$, ..., to $\theta_{x,z}$. The first number in the subscript of $\theta$, i.e., the number immediately following the letter $\theta$, i.e., from 1 to x, represents a certain selected type of immune cells or a group of several types of immune cells. The number x may be the number of all categories of immune cells or the number of all groups of immune cells. The second number in the subscript of $\theta$, i.e., the number immediately following the first number, i.e., from 1 to z, represents data types. The number z may be the number of data types.

With regard to the first number in the subscript of $\theta$, the first number in the subscript of $\theta_{1,1}$-$\theta_{x,z}$ is as the same specification as that of $U_{1,1}$-$U_{x,y}$ for the second set of results or data illustrated in the step 802. For example, the changes $\theta_{1,1}$-$\theta_{1,z}$ having the first number 1 in the subscript of $\theta$ are changes related to, for example, lymphocytes. The changes $\theta_{2,1}$-$\theta_{2,z}$ having the first number 2 in the subscript of $\theta$ are changes related to, for example, T cells. The changes $\theta_{3,1}$-$\theta_{3,z}$ having the first number 3 in the subscript of $\theta$ are changes related to, for example, T helper cells. Other notations can be considered in a similar way.

With regard to the second number in the subscript of $\theta$, the changes $\theta_{1,1}$-$\theta_{x,1}$ having the second number 1 in the subscript of $\theta$ are changes related to, for example, an increase or decrease in the count (number) of immune cells of a specific type or a group of several types. The changes $\theta_{1,2}$-$\theta_{x,2}$ having the second number 2 in the subscript of $\theta$ are changes related to, for example, the increasing or decreasing rate of change, e.g., an increase of W1 percent or a decrease of W2 percent, in the count (number) of immune cells of a specific type or a group of several types, where "W1" is a positive number greater than or equal to one of the numbers 10, 20, 30, 40, 50, 60, 70, 80, 90, 100, 200, 300, 500 or 900, and "W2" is a positive number greater than or equal to 10, 20, 30, 40, 50, 60, 70, 80, or 90. The changes $\theta_{1,3}$-$\theta_{x,3}$ having the second number 3 in the subscript of $\theta$ are changes related to, for example, an increase or decrease in the percentage of the count (number) of immune cells of a specific type or a group of several types to the total count (total number) of biological or immune cells (e.g., lymphocytes). The changes $\theta_{1,4}$-$\theta_{x,4}$ having the second number 4 in the subscript of $\theta$ are changes related to, for example, the increasing or decreasing rate of change, e.g., an increase of W1 percent or a decrease of W2 percent, in the percentage of the count (number) of immune cells of a specific type or several types to the total count (total number) of biological or immune cells (e.g., lymphocytes).

For further elaboration, the change $\theta_{1,1}$ between the two results $U_{1,1}$ in the second and fourth respective sets of results or data shows an increase or decrease in the count of lymphocytes, which may be obtained by, e.g., performing a subtraction operation, that is, the result $U_{1,1}$ in the fourth set of results or data minus the result $U_{1,1}$ in the second set of results or data. The change $\theta_{1,2}$ between the two results $U_{1,1}$ in the second and fourth respective sets of results or data shows the increasing or decreasing rate of change, e.g., an increase of W1 percent or a decrease of W2 percent, in the count of lymphocytes, which may be obtained by, e.g., subtracting the result $U_{1,1}$ in the second set of results or data from the result $U_{1,1}$ in the fourth set of results or data, then dividing the subtracted result by the result $U_{1,1}$ in the second set of results or data, and finally multiplying the divided result by 100% (which converts the divided result into a percent figure). The change $\theta_{2,3}$ between the two results $U_{2,2}$ in the second and fourth respective sets of results or data shows an increase or decrease in the percentage of the count of T cells to the total number of biological or immune cells (e.g., lymphocytes), which may be obtained by, e.g., performing a subtraction operation, that is, the result $U_{2,2}$ in the fourth set of results or data minus the result $U_{2,2}$ in the second set of results or data. The change $\theta_{2,4}$ between the two results $U_{2,2}$ in the second and fourth respective sets of results or data shows the increasing or decreasing rate of change, e.g., an increase of W1 percent or a decrease of W2 percent, in the percentage of the count of T cells to the total number of biological or immune cells (e.g., lymphocytes), which may be obtained by, e.g., subtracting the result $U_{2,2}$ in the second set of results or data from the result $U_{2,2}$ in the fourth set of results or data, then dividing the subtracted result by the result $U_{2,2}$ in the second set of results or data, and finally multiplying the divided result by 100% (which converts the divided result into a percent figure). The change $\theta_{10,5}$ between the two results $U_{10,3}$ in the second and fourth respective sets of results or data shows an increase or decrease in the ratio of immune cells of one type (e.g., T helper cells) to immune cells of another type (e.g., cytotoxic T cells), which may be obtained by, e.g., performing a subtraction operation, that is, the result $U_{10,3}$ in the fourth set of results or data minus the result $U_{10,3}$ in the second set of results or data. The change $\theta_{10,6}$ between the two results $U_{10,3}$ in the second and fourth respective sets of results or data shows the increasing or decreasing rate of change, e.g., an increase of W1 percent or a decrease of W2 percent, in the ratio of immune cells of one type (e.g., T helper cells) to immune cells of another type (e.g., cytotoxic T cells), which may be obtained by, e.g., subtracting the result $U_{10,3}$ in the second set of results or data from the result $U_{10,3}$ in the fourth set of results or data, then dividing the subtracted result by the result $U_{10,3}$ in the second set of results or data, and finally multiplying the divided result by 100% (which converts the divided result into a percent figure). Other notations can be considered in a similar way.

Figure 17B:
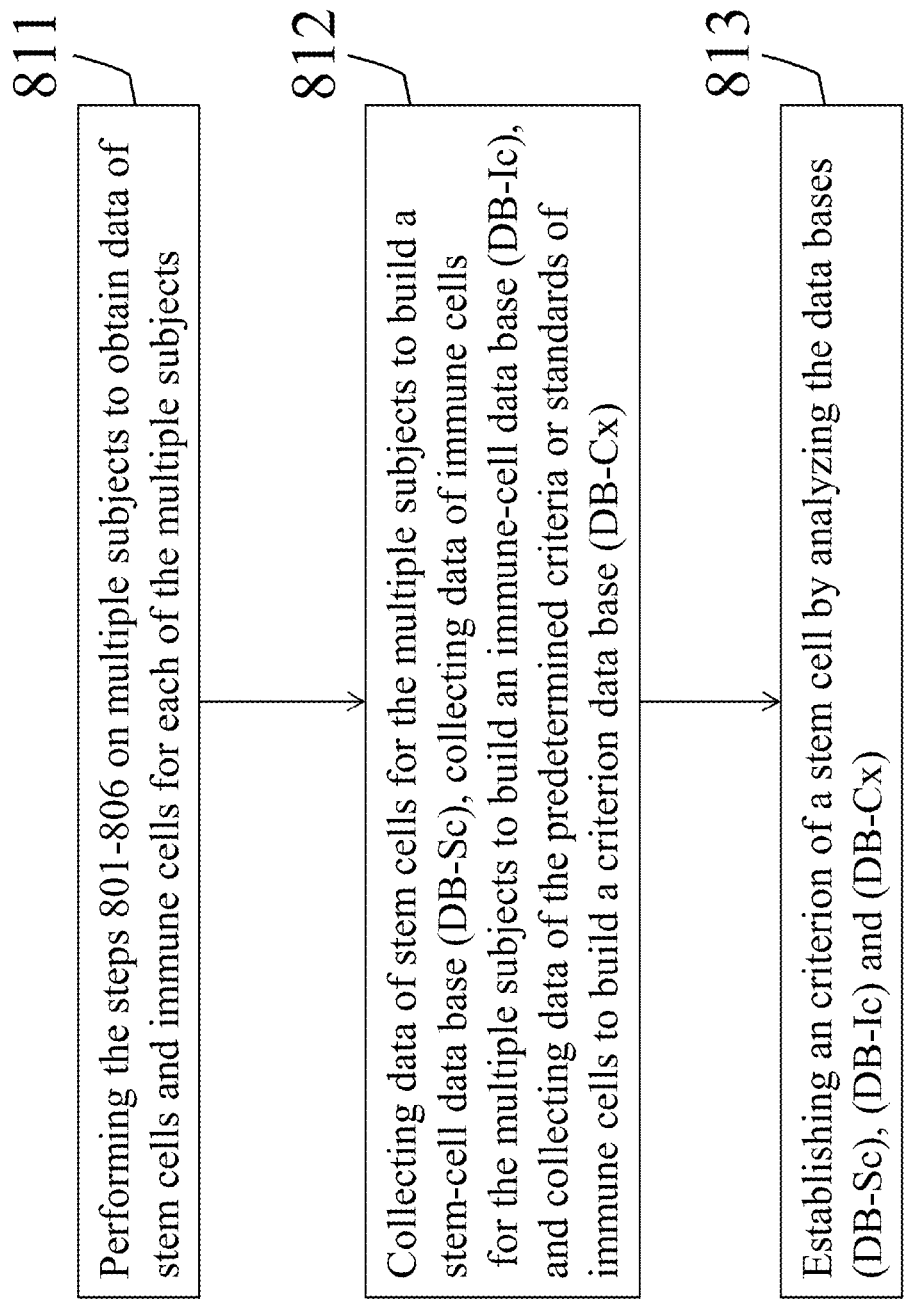
FIG. 17B shows a flow chart for establishing criteria or standards for one or more types of stem cells based on information related to one or more types of immune cells according to the ninth embodiment of the present disclosure.

FIG. 17B is a flow chart for establishing or obtaining the above-mentioned criteria or standards (G) based on the one or more types of immune cells described in FIG. 17A. In this embodiment, N4 subjects, each of which may be referred to the above-mentioned subject (S), may be sampled or selected from species in the same biological category, where "N4" is a positive integer equal to or greater than 2, 4, 6, 10, 20 or 50. The steps illustrated in FIG. 17B may be performed on the N4 subjects.

Referring to FIG. 17B, in step 811, the steps 801-806 illustrated in FIG. 17A are performed on each of the N4 subjects. Therefore, N4 first tissue samples are extracted, taken, obtained or derived from the N4 respective subjects using the method of obtaining the first tissue sample as described in the step 801 of FIG. 17A. The N4 first tissue samples are analyzed using the first test, assessment or measurement illustrated in the step 802 of FIG. 17A, respectively. N4 second tissue samples are extracted, taken, obtained or derived from the N4 respective subjects using the method of obtaining the second tissue sample as described in the step 801 of FIG. 17A. The N4 second tissue samples are analyzed using the second test, assessment or measurement illustrated in the step 802 of FIG. 17A, respectively. The N4 first tissue samples and the N4 second tissue samples are extracted, taken, obtained or derived from the N4 subjects before taking or being subjected to the one or more of the actions or stimuli (X), as described in the step 803 of FIG. 17A.

N4 third tissue samples are extracted, taken, obtained or derived from the N4 respective subjects after taking or being subjected to the one or more of the actions or stimuli (X) described in the step 803 of FIG. 17A using the method of obtaining the third tissue sample as described in the step 804 of FIG. 17A. The N4 third tissue samples are analyzed using the third test, assessment or measurement illustrated in the step 805 of FIG. 17A, respectively. N4 fourth tissue samples are extracted, taken, obtained or derived from the N4 respective subjects after taking or being subjected to the one or more of the actions or stimuli (X) described in the step 803 of FIG. 17A using the method of obtaining the fourth tissue sample as described in the step 804 of FIG. 17A. The N4 fourth tissue samples are analyzed using the fourth test, assessment or measurement illustrated in the step 805 of FIG. 17A, respectively. Each of the N4 first, N4 second, N4 third and N4 fourth tissue samples may be referred to the above-mentioned tissue sample (P).

N4 first sets of results or data related to the one or more types of stem cells from the N4 first tissue samples are obtained by performing the above first tests, assessments or measurements on the N4 first tissue samples, respectively, using the method of obtaining the first set of results or data as described in the step 802 of FIG. 17A. N4 second sets of results or data related to the one or more types of immune cells from the N4 second tissue samples are obtained by performing the above second tests, assessments or measurements on the N4 second tissue samples, respectively, using the method of obtaining the second set of results or data as described in the step 802 of FIG. 17A. N4 third sets of results or data related to the one or more types of stem cells from the N4 third tissue samples are obtained by performing the above third tests, assessments or measurements on the N4 third tissue samples, respectively, using the method of obtaining the third set of results or data as described in the step 805 of FIG. 17A. N4 fourth sets of results or data related to the one or more types of immune cells from the N4 fourth tissue samples are obtained by performing the above fourth tests, assessments or measurements on the N4 fourth tissue samples, respectively, using the method of obtaining the fourth set of results or data as described in the step 805 of FIG. 17A.

The N4 first and N4 third sets of results or data related to the N4 subjects include types of small stem cells and parameters (such as the number, the percentage and/or the sizes) of one or more types of small stem cells, as described in the above-mentioned assay process (T1), when each of the above first and third tests, assessments or measurements is performed using the above-mentioned test, assessment or measurement (M1). Alternatively, the N4 first and N4 third sets of results or data related to the N4 subjects include types of stem cells and parameters (such as the number, the percentage and/or the sizes) of one or more types of stem cells, as described in the above-mentioned assay process (T2), when each of the above first and third tests, assessments or measurements is performed using the above-mentioned test, assessment or measurement (M2). Alternatively, the N4 first and N4 third sets of results or data related to the N4 subjects include types of stem cells and parameters (such as the number, the percentage and/or the sizes) of one or more types of stem cells, as described in the above-mentioned assay process (T0), when each of the above first and third tests, assessments or measurements is performed using the above-mentioned test, assessment or measurement (M0).

For example, each of the N4 first and N4 third sets of results or data includes the same types of information as the first set of results or data illustrated in the step 52 of FIG. 7, that is, each of the N4 first and N4 third sets of results or data includes multiple results or data $R_{1,1}$-$R_{1,b}$, $R_{2,1}$-$R_{2,b}$, . . . , and $R_{a,1}$-$R_{a,b}$ related to a corresponding one of the N4 subjects, wherein the first and second numbers in the subscript of $R_{1,1}$-$R_{a,b}$ for each of the N4 first and N4 third sets of results or data are defined, described or specified as the first set of results or data illustrated in the step 52 of FIG. 7, respectively.

Each of the N4 second and N4 fourth sets of results or data, for example, includes the same types of information as the second set of results or data illustrated in the step 802 of FIG. 17A, that is, each of the N4 second and N4 fourth sets of results or data includes multiple results or data $U_{1,1}$-$U_{1,y}$, $U_{2,1}$-$U_{2,y}$, . . . , and $U_{x,1}$-$U_{x,y}$ related to a corresponding one of the N4 subjects, wherein the first and second numbers in the subscript of $U_{1,1}$-$U_{x,y}$ for each of the N4 second and N4 fourth sets of results or data are defined, described or specified as the second set of results or data illustrated in the step 802 of FIG. 17A, respectively.

N4 first sets of changes in N4 respective first pairs of results or data, each including one of the N4 first sets of results or data and a corresponding one of the N4 third sets of results or data for the same one of the N4 subjects, may be obtained by comparing the N4 first and N4 third sets of results or data $R_{1,1}$-$R_{a,b}$ having the same first and second numbers in the subscript for the N4 respective subjects, which may be referred to the method of obtaining the first set of changes as described in the step 806 of FIG. 17A. N4 second sets of changes in N4 respective second pairs of results or data, each including one of the N4 second sets of results or data and a corresponding one of the N4 fourth sets of results or data for the same one of the N4 subjects, may be obtained by comparing the N4 second and N4 fourth sets of results or data $U_{1,1}$-$U_{x,y}$ having the same first and second numbers in the subscript for the N4 respective subjects, which may be referred to the method of obtaining the second set of changes as described in the step 806 of FIG. 17A.

Each of the N4 first sets of changes, for example, includes the same types of information as the set of changes illustrated in the step 56 of FIG. 7, that is, each of the N4 first sets of changes includes multiple changes $\Delta_{1,1}$-$\Delta_{1,c}$, $\Delta_{2,1}$-$\Delta_{2,c}$, . . . , and $\Delta_{a,1}$-$\Delta_{a,c}$ related to a corresponding one of the N4 subjects, wherein the first and second numbers in the subscript of $\Delta_{1,1}$-$\Delta_{a,c}$ for each of the N4 first sets of changes are defined, described or specified as the set of changes illustrated in the step 56 of FIG. 7, respectively. Each of the N4 second sets of changes, for example, includes the same types of information as the second set of changes illustrated in the step 806 of FIG. 17A, that is, each of the N4 second sets of changes includes multiple changes $\theta_{1,1}$-$\theta_{1,z}$, $\theta_{2,1}$-$\theta_{2,z}$, . . . , and $\theta_{x,1}$-$\theta_{x,z}$ related to a corresponding one of the N4 subjects, wherein the first and second numbers in the subscript of $\theta_{1,1}$-$\theta_{x,z}$ for each of the N4 second sets of changes are defined, described or specified as the second set of changes illustrated in the step 806 of FIG. 17A, respectively.

Alternatively, referring to FIG. 17B, the step 811 may include performing the steps 801-805 on each of the N4 subjects, after which the step 806 performed in FIG. 17A may be performed on each first pair of results or data, including one of the N4 first sets of results or data $R_{1,1}$-$R_{a,b}$ and a corresponding one of the N4 third sets of results or data $R_{1,1}$-$R_{a,b}$ for the same one of the N4 subjects, to obtain the N4 first sets of changes in N4 respective first pairs of results or data, each including one of the N4 first sets of results or data $R_{1,1}$-$R_{a,b}$ and a corresponding one of the N4 third sets of results or data $R_{1,1}$-$R_{a,b}$ for the same one of the N4 respective subjects, and performed on each second pair of results or data, including one of the N4 second sets of results or data $U_{1,1}$-$U_{x,y}$ and a corresponding one of the N4 fourth sets of results or data $U_{1,1}$-$U_{x,y}$ for the same one of the N4 subjects, to obtain the N4 second sets of changes in N4 respective second pairs of results or data, each including one of the N4 second sets of results or data $U_{1,1}$-$U_{x,y}$ and a corresponding one of the N4 fourth sets of results or data $U_{1,1}$-$U_{x,y}$ for the same one of the N4 respective subjects.

Referring to FIG. 17B, in step 812, the N4 first and N4 third sets of results or data $R_{1,1}$-$R_{a,b}$ and the N4 first sets of changes $\Delta_{1,1}$-$\Delta_{a,c}$ related to information of stem cells from the N4 subjects are collected to build a stem-cell data base (DB-Sc). The N4 second and N4 fourth sets of results or data $U_{1,1}$-$U_{x,y}$ and the N4 second sets of changes $\theta_{1,1}$-$\theta_{x,z}$ related to information of immune cells from the N4 subjects are collected to build an immune-cell data base (DB-Ic). Each of the data bases (DB-Sc) and (DB-Ic) may further include the data of, for example, age, gender, race, height, weight, blood pressure, heartbeat, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) for each of the N4 subjects. The data of the predetermined criteria or standards of immune cells for the biological category of the N4 subjects are collected to build a criterion data base (DB-Cx).

Next, in step 813, the data in the data bases (DB-Sc) and (DB-Ic) built in the step 812 may be compared to obtain correlations between the data in the data bases (DB-Sc) and (DB-Ic). In the case that high correlation, with a statistical significance, between data, for specific one or more types of stem cells as listed in the specification for the first numbers 1-a in the subscript of R as described in step 52 of FIG. 7, in the data base (DB-Sc) and those, for specific one or more types of immune cells as listed in the specification for the first numbers 1-x in the subscript of U as described in step 802 of FIG. 17A, in the data base (DB-Ic) is found, criteria or standards for the specific one or more types of stem cells may be established based on the predetermined criteria or standards for the specific one or more types of immune cells, collected in the data base (DB-Cx). The criteria or standards established herein for the specific one or more types of stem cells include the same types of information as the criteria or standards (G) defined, specified or described in the third embodiment. The effect of the one or more actions or stimuli (Xa), such as the one or more actions or stimuli performed in the step 803 of FIG. 17A, on the subject (Sa), as mentioned in the third embodiment, may be evaluated or determined by comparing a specific one of the changes $\Delta_{1,1}$-$\Delta_{a,c}$, for the specific one or more types of stem cells, from the subject (Sa) to the criteria or standards, for the specific one or more types of stem cells, built up in this embodiment, or by comparing a specific one in the second set of results or data $R_{1,1}$-$R_{a,b}$, for the specific one or more types of stem cells, from the subject (Sa) to the criteria or standards, for the specific one or more types of stem cells, built up in this embodiment.

The correlations between data in the data bases (DB-Sc) and (DB-Ic) may be established by a suitable method including, e.g., (1) comparing one or more of the changes $\Delta_{1,1}$-$\Delta_{a,c}$ between the first and third sets of results or data $R_{1,1}$-$R_{a,b}$ and one or more of the changes $\theta_{1,1}$-$\theta_{x,z}$ between the second and fourth sets of results or data $U_{1,1}$-$U_{x,y}$; (2) comparing one or more of the results or data $R_{1,1}$-$R_{a,b}$ in the N4 third sets and one or more of the results or data $U_{1,1}$-$U_{x,y}$ in the N4 fourth sets; and/or (3) comparing one or more of the results or data $R_{1,1}$-$R_{a,b}$ in the N4 first sets and one or more of the results or data $U_{1,1}$-$U_{x,y}$ in the N4 second sets. For example, in the case that high correlations with statistical significance are found between one of the changes $\Delta_{1,2}$ and $\Delta_{1,4}$ in the N4 first sets of changes $\Delta_{1,1}$-$\Delta_{a,c}$ and one of the changes $\theta_{1,2}$ and $\theta_{1,4}$ in the N4 second sets of changes $\theta_{1,1}$-$\theta_{x,z}$, for the N4 subjects, the above-mentioned criterion $G_{1,2}$ and/or $G_{1,4}$ may be established based on the predetermined criterion of CD4(+) cells for evaluating the effect of one or more of the actions or stimuli (e.g., X1, X3 and/or X4) on a human body or for determining if any one or more of the actions or stimuli (e.g., X1, X3 and/or X4) can improve immunity of the human body or enhance the count of immune cells. Other notations may be considered in a similar way.

This embodiment provides a method, an apparatus, or an integrated system combining methodology, software (tools) and hardware (equipments, machines, or devices for extraction, filtering, purification, analyzing stem cells), for establishing the above-mentioned criteria or standards (G) based on reference of (predetermined) criteria of immune cells collected in the data base (DB-Cx) and correlations between data in the data bases (DB-Sc) and (DB-Ic), as mentioned in accordance with this embodiment.

For ensuring the safety (no significant side-effects or damages to the human or non-human body, for example, organs such as liver or kidney) of the one or more of the above-mentioned actions or stimuli (X) illustrated in the step 803, data about liver and kidney functions related to each of the N4 subjects before and after taking or being subjected to the one or more of the actions or stimuli (X) illustrated in the step 803 may need to be obtained as an option. The data about liver and kidney functions related to the N4 subjects before taking or being subjected to the one or more of the actions or stimuli (X) illustrated in the step 803 are defined as data LKB17, and the data about liver and kidney functions related to the N4 subjects after taking or being subjected to the one or more of the actions or stimuli (X) illustrated in the step 803 are defined as data LKA17. By comparing the data LKA17 with the data LKB17, the differences between the data LKA17 and LKB17 may be obtained to identify or evaluate the effect of the one or more of the actions or stimuli (X) illustrated in the step 803 on their livers and kidneys of the N4 subjects.

If there is no (statistically significant) difference between the data LKA17 and LKB17 for the N4 subjects or the data LKA17 are (much or statistically significantly) better than the data LKB17, it could mean the one or more of the actions or stimuli (X) illustrated in the step 803 are harmless or even beneficial to their livers and/or kidneys of the N4 subjects and the criteria or standards for the specific one or more types of stem cells in the step 813 may be allowed to be established due to the one or more of the actions or stimuli (X) illustrated in the step 803 having no negative impacts on their livers and/or kidneys of the N4 subjects. If the data LKA17 are (much or statistically significantly) worse than the data LKB17, it could mean the one or more of the actions or stimuli (X) illustrated in the step 803 are harmful to their livers and/or kidneys of the N4 subjects and the criteria or standards for the specific one or more types of stem cells in the step 813 may not be allowed to be established due to the one or more of the actions or stimuli (X) illustrated in the step 803 having negative impacts on their livers and/or kidneys of the N4 subjects. Each piece of the data LKA17 and LKB17 may include, but not limited to, (1) data about kidney functions (such as BUN, GFR, CCR, ACR, cystatin C, uric acid, microalbumin, urine routine, and/or urine sediment), and (2) data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV) for each of the N4 subjects.

In this embodiment, another two sets of results or data (defined as fifth and sixth sets of results or data) about one or more classes of antibodies related to each of the N4 subjects before and after taking or being subjected to the one or more of the actions or stimuli (X) in the step 803 may be further obtained using the method of obtaining the second and fourth sets of results or data about one or more classes of antibodies as illustrated in the steps 402 and 405 of FIG. 12A. The fifth set of results or data related to each of the N4 subjects before taking or being subjected to the one or more of the actions or stimuli (X) in the step 803 may include the same types of information as the second set of results or data illustrated in the step 402 of FIG. 12A, that is, the fifth set of results or data may include multiple results or data $I_{1,1}$-$I_{1,f}$, $I_{2,1}$-$I_{2,f}$, . . . , and $I_{e,1}$-$I_{e,f}$, wherein the first and second numbers in the subscript of $I_{1,1}$-$I_{e,f}$ for the fifth set of results or data are defined, described or specified as the second set of results or data illustrated in the step 402 of FIG. 12A, respectively. The sixth set of results or data related to each of the N4 subjects after taking or being subjected to the one or more of the actions or stimuli (X) in the step 803 may include the same types of information as the second set of results or data illustrated in the step 402 of FIG. 12A, that is, the sixth set of results or data may include multiple results or data $I_{1,1}$-$I_{1,f}$, $I_{2,1}$-$I_{2,f}$, . . . , and $I_{e,1}$-$I_{e,f}$, wherein the first and second numbers in the subscript of $I_{1,1}$-$I_{e,f}$ for the sixth set of results or data are defined, described or specified as the second set of results or data illustrated in the step 402 of FIG. 12A, respectively.

Therefore, N4 fifth sets of results or data and N4 sixth sets of results or data may be obtained. N4 third sets of changes in N4 respective third pairs of results or data, each including one of the N4 fifth sets of results or data and a corresponding one of the N4 sixth sets of results or data for the same one of the N4 subjects, may be obtained by comparing the N4 fifth and N4 sixth sets of results or data $I_{1,1}$-$I_{e,f}$ having the same first and second numbers in the subscript for the N4 respective subjects, which may be referred to the method of obtaining the second set of changes as described in the step 406 of FIG. 12A. Each of the N4 third sets of changes illustrated herein includes the same types of information as the second set of changes illustrated in the step 406 of FIG. 12A, that is, each of the N4 third sets of changes includes multiple changes $\delta_{1,1}$-$\delta_{1,h}$, $\delta_{2,1}$-$\delta_{2,h}$, . . . , and $\delta_{e,1}$-$\delta_{e,h}$ related to a corresponding one of the N4 subjects, wherein the first and second numbers in the subscript of $\delta_{1,1}$-$\delta_{e,h}$ for each of the N4 third sets of changes are defined, described or specified as the second set of changes illustrated in the step 406 of FIG. 12A, respectively.

The N4 fifth sets of results or data and N4 sixth sets of results or data $I_{1,1}$-$I_{e,f}$ and the N4 third sets of changes $\delta_{1,1}$-$\delta_{e,h}$ related to information of antibodies from the N4 subjects are collected to build an antibody data base (DB-Ig). The data base (DB-Ig) further include the data of, for example, age, gender, race, height, weight, blood pressure, heartbeat, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or one or more diseases (e.g., a cancer, a skin disease, and/or a kidney disease) for each of the N4 subjects. The data of the predetermined criteria or standards of antibodies for the biological category of the N4 subjects are collected to build a criterion data base (DB-Cg).

Next, the data in the data base (DB-Sc) may be compared with the data in a data base incorporating the data bases of both (DB-Ic) and (DB-Ig) to obtain correlations between the data in the data base (DB-Sc) and the data in the data base incorporating the data bases of (DB-Ic) and (DB-Ig). The correlations between (1) data in the data base (DB-Sc), for specific one or more types of stem cells as listed in the specification for the first numbers 1-a in the subscript of R as described in step 52 of FIG. 7, and (2) data in the data base (DB-Ic), for specific one or more types of immune cells as listed in the specification for the first numbers 1-x in the subscript of U as described in step 802 of FIG. 17A, incorporated with data in the data base (DB-Ig), for specific one or more classes of antibodies as listed in the specification for the first numbers 1-e in the subscript of I as described in step 402 of FIG. 12A, may be analyzed. If high correlations are found, criteria or standards for the specific one or more types of stem cells may be established based on the predetermined criteria or standards for the specific one or more types of immune cells, collected in the data base (DB-Cx), and/or the predetermined criteria or standards for the specific one or more antibodies, collected in the data base (DB-Cg), respectively.

The criteria or standards established herein for the specific one or more types of stem cells may include the same types of information as the criteria or standards (G) defined, specified or described in the third embodiment. The correlations of data in the data bases (DB-Sc) with respect to both (DB-Ic) and (DB-Ig) may be established by a suitable method including, e.g., (1) comparing one or more of the changes $\Delta_{1,1}$-$\Delta_{a,c}$ between the first and third sets of results or data $R_{1,1}$-$R_{a,b}$ and one or more of the changes $\theta_{1,1}$-$\theta_{x,z}$ between the second and fourth sets of results or data $U_{1,1}$-$U_{x,y}$ combined with one or more of the changes $\delta_{1,1}$-$\delta_{e,h}$ between the fifth and sixth sets of results or data $I_{1,1}$-$I_{e,f}$; (2) comparing one or more of the results or data $R_{1,1}$-$R_{a,b}$ in the N4 third sets and one or more of the results or data $U_{1,1}$-$U_{x,y}$ in the N4 fourth sets combined with one or more of the results or data $I_{1,1}$-$I_{e,f}$ in the N4 sixth sets; and/or (3) comparing one or more of the results or data $R_{1,1}$-$R_{a,b}$ in the N4 first sets and one or more of the results or data $U_{1,1}$-$U_{x,y}$ in the N4 second sets combined with one or more of the results or data $I_{1,1}$-$I_{e,f}$ in the N4 fifth sets.

A criterion establishing method, in accordance with the ninth embodiment, comprises taking a first tissue sample, a second tissue sample and a third tissue sample from a subject; analyzing said first tissue sample to obtain a first result related to information of a type or types of stem cells; analyzing said second tissue sample to obtain a second result related to information of a type or types of immune cells; analyzing said third tissue sample to obtain a third result related to information of a class or classes of antibodies; after said taking said first, second and third tissue samples, performing an action on said subject; after said performing said action on said subject, taking a fourth tissue sample, a fifth tissue sample and a sixth tissue sample from said subject; analyzing said fourth tissue sample to obtain a fourth result related to information of said type or types of stem cells; analyzing said fifth tissue sample to obtain a fifth result related to information of said type or types of immune cells; analyzing said sixth tissue sample to obtain a sixth result related to information of said class or classes of antibodies; performing analysis to obtain a relationship between first data associated with said first and fourth results and second data associated with said second and fifth results combined with third data associated with said third and sixth results; and establishing a criterion for said type or types of stem cells based on said relationship, a criterion for said type or types of immune cells, and a criterion for said class or classes of antibodies.

A criterion establishing method, in accordance with the ninth embodiment, comprises taking a first tissue sample, a second tissue sample and a third tissue sample from a subject; analyzing said first tissue sample to obtain a first result related to information of a type or types of stem cells; analyzing said second tissue sample to obtain a second result related to information of a type or types of immune cells; analyzing said third tissue sample to obtain a third result related to information of a class or classes of antibodies; after said taking said first, second and third tissue samples, performing an action on said subject; after said performing said action on said subject, taking a fourth tissue sample, a fifth tissue sample and a sixth tissue sample from said subject; analyzing said fourth tissue sample to obtain a fourth result related to information of said type or types of stem cells; analyzing said fifth tissue sample to obtain a fifth result related to information of said type or types of immune cells; analyzing said sixth tissue sample to obtain a sixth result related to information of said class or classes of antibodies; performing analysis to obtain a relationship between first data associated with said fourth result and second data associated with said fifth result combined with said sixth result; and establishing a criterion for said type or types of stem cells based on said relationship, a criterion for said type or types of immune cells, and a criterion for said class or classes of antibodies.

Tenth Embodiment

An example of identifying, evaluating or assessing the effect of a human taking two alga pills is described as below. In this case, a first blood sample is taken or obtained from the human before taking the two alga pills, as illustrated in the step 51 of FIG. 7. Next, a first test, assessment or measurement including extracting, characterizing, assessing and measuring stem cells is performed on the first blood sample to obtain the percentage of the number of CD90(+) MSCs to the total number of the small (biological) cells, as illustrated in the step 52 of FIG. 7. The percentage of the number of CD90(+) MSCs to the total number of the small (biological) cells related to the first blood sample is 1.56%, as shown in FIG. 18A. The data of FIG. 18A is obtained from a flow cytometer. Blue points in the plot of FIG. 18A stand for the small (biological) cells which may be referred to the small cells illustrated in the purification process (Y2) in FIG. 4, and black points in the plot of FIG. 18A stand for the large (biological) cells which may be referred to the large cells illustrated in the purification process (Y2) in FIG. 4. The blue points in the region R2 in the plot of FIG. 18A represent CD90(+) MSCs.

Next, the human takes the two alga pills totally including 1,000 mg of Aphanizomenon flos-aquae concentrate, as illustrated in the step 53 of FIG. 7. After about 60 minutes, a second blood sample is taken or obtained from the human, as illustrated in the step 54 of FIG. 7. Next, a second test, assessment or measurement including extracting, characterizing, assessing and measuring stem cells is performed on the second blood sample to obtain the percentage of the number of CD90(+) MSCs to the total number of the small (biological) cells, as illustrated in the step 55 of FIG. 7. The percentage of the number of CD90(+) MSCs to the total number of the small (biological) cells related to the second blood sample is 5.92%, as shown in FIG. 18B. The data of FIG. 18B is obtained from the same flow cytometer. Blue points in the plot of FIG. 18B stand for the small (biological) cells which may be referred to the small cells illustrated in the purification process (Y2) in FIG. 4, and black points in the plot of FIG. 18B stand for the large (biological) cells which may be referred to the large cells illustrated in the purification process (Y2) in FIG. 4. The blue points in the region R2 in the plot of FIG. 18B represent CD90(+) MSCs.

Accordingly, the action of taking two alga pills on the human may be evaluated as "effective to health or immunity" based on the increase of 4.36% calculated by subtracting 1.56%, obtained from the first blood sample, from 5.92%, obtained from the second blood sample, as illustrated in the steps 56 and 57 of FIG. 7.

Eleventh Embodiment

Figures 19A, 19B:
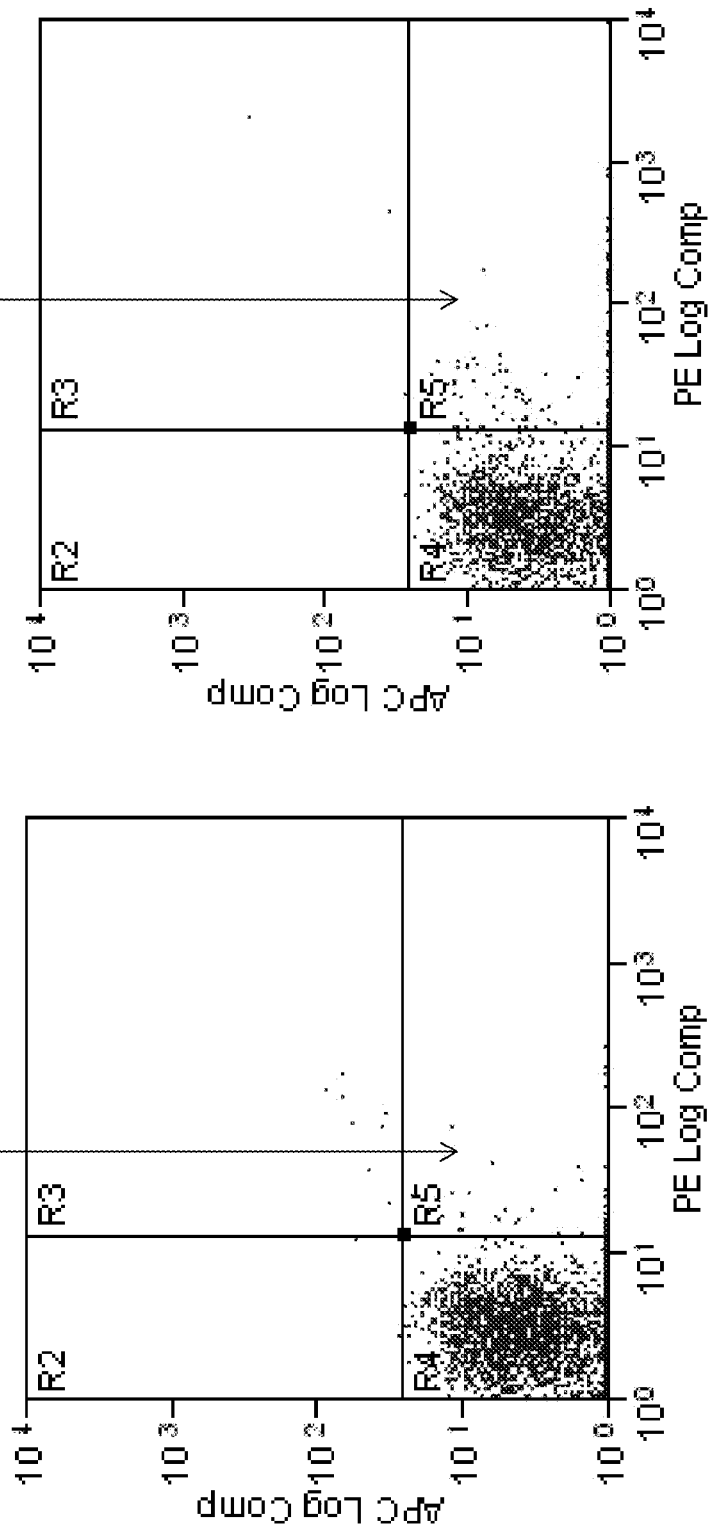
FIGS. 19A and 19B show two flow cytometry results related to CD66e (+) BLSCs.

Another example of identifying, evaluating or assessing the effect of a human taking two alga pills is described as below. In this case, a first blood sample is taken or obtained from the human before taking the two alga pills, as illustrated in the step 51 of FIG. 7. Next, a first test, assessment or measurement including extracting, characterizing, assessing and measuring stem cells is performed on the first blood sample to obtain the percentage of the number of CD66e(+) BLSCs to the total number of the small (biological) cells, as illustrated in the step 52 of FIG. 7. The percentage of the number of CD66e(+) BLSCs to the total number of the small (biological) cells related to the first blood sample is 1.26%, as shown in FIG. 19A. The data of FIG. 19A is obtained from a flow cytometer. Blue points in the plot of FIG. 19A stand for the small (biological) cells which may be referred to the small cells illustrated in the purification process (Y2) in FIG. 4, and black points in the plot of FIG. 19A stand for the large (biological) cells which may be referred to the large cells illustrated in the purification process (Y2) in FIG. 4. The blue points in the region R5 in the plot of FIG. 19A represent CD66e(+) BLSCs.

Next, the human takes the two alga pills totally including 1,000 mg of Aphanizomenon flos-aquae concentrate, as illustrated in the step 53 of FIG. 7. After about 60 minutes, a second blood sample is taken or obtained from the human, as illustrated in the step 54 of FIG. 7. Next, a second test, assessment or measurement including extracting, characterizing, assessing and measuring stem cells is performed on the second blood sample to obtain the percentage of the number of CD66e(+) BLSCs to the total number of the small (biological) cells, as illustrated in the step 55 of FIG. 7. The percentage of the number of CD66e(+) BLSCs to the total number of the small (biological) cells related to the second blood sample is 4.52%, as shown in FIG. 19B. The data of FIG. 19B is obtained from the same flow cytometer. Blue points in the plot of FIG. 19B stand for the small (biological) cells which may be referred to the small cells illustrated in the purification process (Y2) in FIG. 4, and black points in the plot of FIG. 19B stand for the large (biological) cells which may be referred to the large cells illustrated in the purification process (Y2) in FIG. 4. The blue points in the region R5 in the plot of FIG. 19B represent CD66e(+) BLSCs.

Accordingly, the action of taking two alga pills on the human may be evaluated as "effective to health or immunity" based on the increase of 3.26% calculated by subtracting 1.26%, obtained from the first blood sample, from 4.52%, obtained from the second blood sample, as illustrated in the steps 56 and 57 of FIG. 7.

Twelfth Embodiment

A system, apparatus or tool may be established for performing the steps 51-57 in FIG. 7. The system, apparatus or tool includes, but not limited to, a sample collection kit or device (such as blood collection kit or device) for performing the steps 51 and 54 illustrated in FIG. 7, a processing device for performing the first and second tests, assessments or measurements illustrated in the steps 52 and 55 of FIG. 7, a computer, a printer, and a display panel.

The processing device may include a sample purification device for performing the purification processes (Y1) or (Y2) for the first and second tests, assessments or measurements illustrated in the steps 52 and 55 of FIG. 7 and an assay device, which may be referred to the assay device 15a illustrated in FIG. 1, 2 or 3 or the assay device 15b illustrated in FIG. 4, 5 or 6, for performing the assay processes (T1) or (T2) for the first and second tests, assessments or measurements illustrated in the steps 52 and 55 of FIG. 7. The sample purification device may include the centrifuge 13 illustrated in FIG. 1, 2, 3, 4, 5 or 6. The assay device may be, but not limited to, a flow cytometer, a (real-time) RT-PCR device, or a device that can perform the same function as the flow cytometer or (real-time) RT-PCR device illustrated in FIG. 1, 2, 3, 4, 5 or 6.

The computer of the system, apparatus or tool may include a memory or storage and a processor. The memory or storage may be used for storing the first and second sets of the results or data $R_{1,1}$-$R_{a,b}$ obtained from the steps 52 and 55 in FIG. 7, storing the criteria or standards (G) established in the third, fourth, fifth, sixth or ninth embodiment, and storing the universal criteria or standards established in the seventh and/or eighth embodiments. The processor may be used for comparing the first and second sets of the results or data $R_{1,1}$-$R_{a,b}$ obtained from the steps 52 and 55 in FIG. 7 to obtain the set of changes $\Delta_{1,1}$-$\Delta_{a,c}$ illustrated in the step 56 in FIG. 7 to be stored in the memory or storage, and evaluating the effect of one or more of the actions or stimuli (X) performed in the step 53 of FIG. 7 on a user based on the set of changes $\Delta_{1,1}$-$\Delta_{a,c}$ illustrated in the step 56 in FIG. 7 to output final results or data to be displayed on the display panel or printed from the printer.

Alternatively, the processor of the computer also may be used for evaluating the effect of the one or more of the actions or stimuli (X) performed in the step 53 of FIG. 7 on the user based on comparing the set of changes $\Delta_{1,1}$-$\Delta_{a,c}$ illustrated in the step 56 of FIG. 7 with the criteria or standards (G) established in the third, fourth, fifth, sixth or ninth embodiment and/or based on comparing the second set of the results or data $R_{1,1}$-$R_{a,b}$ obtained from the step 55 of FIG. 7 with the criteria or standards (G) established in the third, fourth, fifth, sixth or ninth embodiment.

The processor of the computer also may be used for evaluating the effect of one or more of the actions or stimuli (X) performed in the step 53 of FIG. 7 on the user based on comparing the set of changes $\Delta_{1,1}$-$\Delta_{a,c}$ illustrated in the step 56 of FIG. 7 with the universal criteria or standards illustrated in the seventh or eighth embodiment and/or based on comparing the second set of the results or data $R_{1,1}$-$R_{a,b}$ obtained from the step 55 of FIG. 7 with the universal criteria or standards illustrated in the seventh or eighth embodiment.

Thirteen Embodiment

FIG. 20 is a flow chart for identifying, evaluating or assessing the effect of one of the above-mentioned actions or stimuli (X4) on curing or treating a specific disease (e.g., a cancer, a skin disease, or a kidney disease). A (new) drug that is (1) in the research or development stage in a laboratory, an research institute or a research department or division of a university or a company; (2) in the pilot or experimental run; or (3) being tested but has not yet approved by a government department or authority (e.g., U.S. FDA), may be called an investigational (or experimental) drug.

In this embodiment, there are N5 subjects sampled or selected from human or non-human bodies having a specific disease (e.g., a cancer, a skin disease, or a kidney disease), where "N5" is a positive integer equal to or greater than 2, 4, 6, 10, 20 or 50. The subjects, each of which may be referred to the above-mentioned subject (S), are sampled or selected from species in the same biological category.

Referring to FIG. 20, in step 701, the steps 51-56 illustrated in FIG. 7 or the steps 201-206 illustrated in FIG. 10 may be performed on each of the N5 subjects to obtain data or information of stem cells related to the N5 subjects in the case that each of the N5 subjects performs one of the above-mentioned actions or stimuli (X4) (e.g., taking an investigational (or experimental) drug), in the step 53 of FIG. 7 or the step 203 of FIG. 10, to cure the specific disease. Related to the N5 subjects, the data or information of stem cells include (1) N5 first sets of results or data obtained by the method illustrated in the steps 51 and 52 of FIG. 7 or the steps 201 and 202 of FIG. 10, (2) N5 second sets of results or data obtained by the method illustrated in the steps 54 and 55 of FIG. 7 or the steps 204 and 205 of FIG. 10, and (3) N5 sets of changes in N5 respective pairs of results or data, each including one of the N5 first set of results or data and a corresponding one of the N5 second set of results or data for the same one of the N5 subjects, obtained by the method illustrated in the step 56 of FIG. 7 or the step 206 of FIG. 10.

Each of the N5 first sets of results or data, related to a corresponding one of the N5 subjects, includes the same types of information as the first set of results or data illustrated in the step 52 of FIG. 7, that is, each of the N5 first sets of results or data illustrated herein includes multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for each of the N5 first sets of results or data illustrated herein are defined, described or specified as the first set of results or data illustrated in the step 52 of FIG. 7, respectively. Each of the N5 second sets of results or data, related to a corresponding one of the N5 subjects, includes the same types of information as the first set of results or data illustrated in the step 52 of FIG. 7, that is, each of the N5 second sets of results or data illustrated herein includes multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for each of the N5 second sets of results or data illustrated herein are defined, described or specified as the first set of results or data illustrated in the step 52 of FIG. 7, respectively.

Each of the N5 sets of changes, related to a corresponding one of the N5 subjects, includes the same types of information as the set of changes illustrated in the step 56 of FIG. 7, that is, each of the N5 sets of changes illustrated herein includes multiple changes $\Delta_{1,1}$-$\Delta_{1,c}$, $\Delta_{2,1}$-$\Delta_{2,c}$, . . . , and $\Delta_{a,1}$-$\Delta_{a,c}$, wherein the first and second numbers in the subscript of $\Delta_{1,1}$-$\Delta_{a,c}$ for each of the N5 sets of changes illustrated herein are defined, described or specified as the set of changes illustrated in the step 56 of FIG. 7, respectively.

Next, referring to FIG. 20, in step 702, the N5 first sets of result or data, the N5 second sets of results or data, and the N5 sets of changes are collected to build a data base. The data base further include the data of, for example, age, gender, race, height, weight, blood pressure, heartbeat, Ig, BMI, data about kidney functions (such as BUN, GFR, creatinine, CCR, ACR, cystatin C, uric acid, microalbumin, urine routine, and/or urine sediment), data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV), and/or other disease for each of the N5 subjects.

Next, referring to FIG. 20, in step 703, data in the data base built in the step 702 may be compared with the criteria or standards (G) or universal criteria or standards, as built up in the third through ninth embodiments, to determine whether the one of the above-mentioned actions or stimuli (X4) is effective or ineffective to the cure of the specific disease. The comparison may include comparing the N5 sets of changes $\Delta_{1,1}$-$\Delta_{a,c}$ and/or the N5 second sets of results or data $R_{1,1}$-$R_{a,b}$ with corresponding ones of the criteria or standards (G) or universal criteria or standards.

Accordingly, the one of the above-mentioned actions or stimuli (X4) may be evaluated as "effective to the cure of the specific disease" based on the result that the average of a specific one of the changes $\Delta_{1,1}$-$\Delta_{a,c}$, for all the N5 subjects, among the N5 sets thereof, such as the average of all the changes $\Delta_{1,1}$, for all the N5 subjects, among the N5 sets thereof, meets a corresponding one of the criteria $G_{1,1}$-$G_{a,d}$, such as the criterion for an increase in the number of SB-1 cells (i.e., $G_{1,4}$), and thus the one of the above-mentioned actions or stimuli (X4) may be approved by a government department or authority (e.g., U.S. FDA) based on the result, while the one of the above-mentioned actions or stimuli (X4) may be evaluated as "ineffective to the cure of the specific disease" based on the result that the average of a specific one of the changes $\Delta_{1,1}$-$\Delta_{a,c}$, for all the N5 subjects, among the N5 sets thereof, such as the average of all the changes $\Delta_{1,1}$, for all the N5 subjects, among the N5 sets thereof, does not meet the corresponding one of the criteria $G_{1,1}$-$G_{a,d}$, such as the criterion for an increase in the number of SB-1 cells (i.e., $G_{1,4}$), and thus the one of the above-mentioned actions or stimuli (X4) cannot be approved by the government department or authority based on the result.

Alternatively, the one of the above-mentioned actions or stimuli (X4) may be evaluated as "effective to the cure of the specific disease" based on the result that the average of a specific one of the results or data $R_{1,1}$-$R_{a,b}$, for all the N5 subjects, among the N5 second sets thereof, such as the average of all the results or data $R_{2,1}$, for all the N5 subjects, among the N5 second sets thereof, meets or is over a corresponding one of the criteria $G_{1,1}$-$G_{a,d}$, such as the criterion for the upper or lower limit of a range of the number of SB-2 cells (i.e., $G_{2,1}$ or $G_{2,7}$), and thus the one of the above-mentioned actions or stimuli (X4) may be approved by a government department or authority (e.g., U.S. FDA) based on the result, while the one of the above-mentioned actions or stimuli (X4) may be evaluated as "ineffective to the cure of the specific disease" based on the result that the average of a specific one of the results or data $R_{1,1}$-$R_{a,b}$, for all the N5 subjects, among the N5 second sets thereof, such as the average of all the results or data $R_{2,1}$, for all the N5 subjects, among the N5 second sets thereof, does not meet or is below or under the corresponding one of the criteria $G_{1,1}$-$G_{a,d}$, such as the criterion for the upper or lower limit of a range of the number of SB-2 cells (i.e., $G_{2,1}$ or $G_{2,7}$), such that the one of the above-mentioned actions or stimuli (X4) cannot be approved by the government department or authority based on the result.

For ensuring the safety (no significant side-effects or damages to the human or non-human body, for example, organs such as liver or kidney) of the one of the above-mentioned actions or stimuli (X4), data about liver and kidney functions related to each of the N5 subjects before and after taking or being subjected to the one of the above-mentioned actions or stimuli (X4) may be optionally obtained. The data about liver and kidney functions related to the N5 subjects before taking or being subjected to the one of the above-mentioned actions or stimuli (X4) are defined as data LKB20, and the data about liver and kidney functions related to the N5 subjects after taking or being subjected to the one of the above-mentioned actions or stimuli (X4) are defined as data LKA20. By comparing the data LKA20 with the data LKB20, the differences between the data LKA20 and LKB20 may be obtained to identify or evaluate the effect of the one of the above-mentioned actions or stimuli (X4) on their livers and kidneys of the N5 subjects.

If there is no (statistically significant) difference between the data LKA20 and LKB20 for the N5 subjects or the data LKA20 are (much or statistically significantly) better than the data LKB20, it could mean the one of the above-mentioned actions or stimuli (X4) is harmless or even beneficial to their livers and/or kidneys of the N5 subjects. In this case, the one of the above-mentioned actions or stimuli (X4) may be approved by a government department or authority (e.g., U.S. FDA) if being evaluated as "effective to the cure of the specific disease". If being evaluated as "ineffective to the cure of the specific disease", the one of the above-mentioned actions or stimuli (X4) may not be approved by the government department or authority.

If the data LKA20 are much or statistically significantly worse than the data LKB20, it could mean the one of the above-mentioned actions or stimuli (X4) is harmful to their livers and/or kidneys of the N5 subjects. In this case, the one of the above-mentioned actions or stimuli (X4) evaluated as "effective to the cure of the specific disease" may not be approved by the government department or authority due to the one of the actions or stimuli (X4) having negative impacts on their livers and/or kidneys of the N5 subjects or may be approved by the government department or authority with notations of negative impacts on the liver and/or kidney.

Each piece of the data LKA20 and LKB20 may include, but not limited to, (1) data about kidney functions (such as BUN, GFR, CCR, ACR, cystatin C, uric acid, microalbumin, urine routine, and/or urine sediment), and (2) data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV).

This embodiment provides a method, an apparatus, or an integrated system combining methodology, software (tools) and hardware (equipments, machines, or devices for extraction, filtering, purification, analyzing stem cells), for evaluating the effect of the one of the above-mentioned actions or stimuli (X4) on curing or treating the specific disease, by comparing the data in the data base built in the step 702 with the criteria or standards (G) or universal criteria or standards, as mentioned in accordance with this embodiment. Hence, this embodiment further provides a method, an apparatus, or an integrated system combining methodology, software (tools) and hardware (equipments, machines, or devices for extraction, filtering, purification, analyzing stem cells), for government authorities (for example, U.S. FDA) to approve or disapprove the above-mentioned actions or stimuli (X4), for example, a new drug.

A method, in accordance with the thirteen embodiment, of evaluating an effect of an action on a cure of a disease based on a criterion, comprises taking a first tissue sample from a subject having said disease; analyzing said first tissue sample to obtain a first result related to information of a type or types of stem cells; after said taking said first tissue sample, performing said action on said subject; after said performing said action on said subject, taking a second tissue sample from said subject; analyzing said second tissue sample to obtain a second result related to information of said type or types of stem cells; comparing said first and second results to obtain a change; and comparing said change with said criterion.

A method, in accordance with the thirteen embodiment, of evaluating an effect of an action on a cure of a disease based on a criterion, comprises: performing said action on a subject having said disease; after said performing said action on said subject, taking a tissue sample from said subject; analyzing said tissue sample to obtain a result related to information of a type or types of stem cells; and comparing said result with said criterion.

Fourteenth Embodiment

Figure 21:
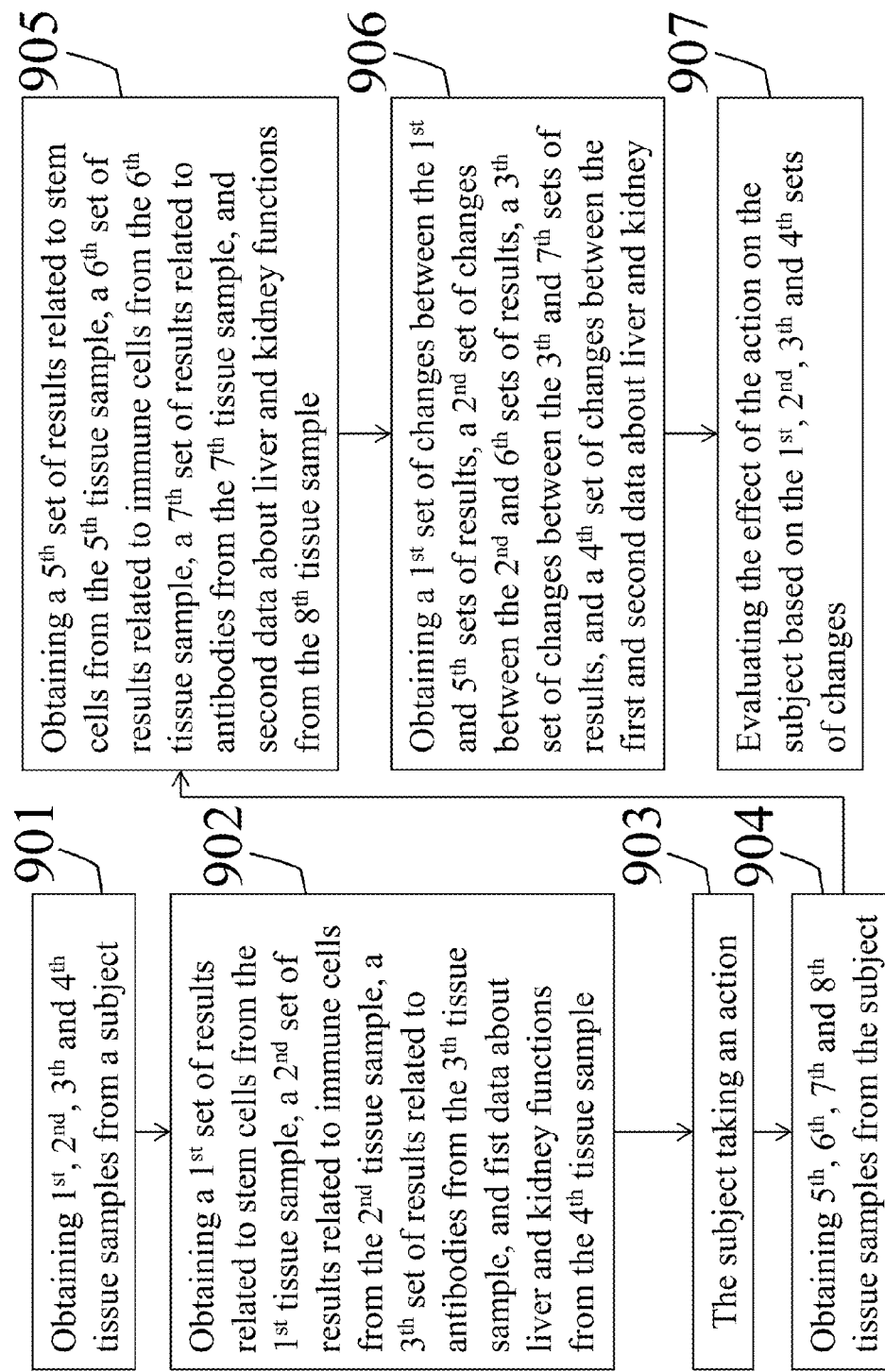
FIG. 21 shows a flow chart for identifying, evaluating or assessing the effect of one or more actions or stimuli on a subject according to a fourteenth embodiment of the present disclosure.

FIG. 21 is a flow chart for identifying, evaluating or assessing the effect of one or more of the actions or stimuli (X) on a subject that may be referred to the above-mentioned subject (S). Referring to FIG. 21, in step 901, first, second, third and fourth tissue samples, each of which may be referred to the above-mentioned tissue sample (P), are extracted, taken, obtained or derived from the subject.

Next, in step 902, a first test, assessment or measurement including extracting, characterizing, assessing and measuring stem cells, which may be referred to one of the above-mentioned tests, assessments or measurements (M0), (M1) and (M2), is performed on the first tissue sample to obtain a first set of results or data SR1 related to one or more types of stem cells, as listed in the above-mentioned description of stem cells and as discussed or described in the step 52 of FIG. 7, descriptively, qualitatively or quantitatively. A second test, assessment or measurement including extracting, characterizing, assessing and measuring immune cells is performed on the second tissue sample to obtain a second set of results or data SR2 related to one or more types of immune cells, as described in the step 802 of FIG. 17A, descriptively, qualitatively or quantitatively. A third test, assessment or measurement including extracting, characterizing, assessing and measuring antibodies, which may be referred to the above-mentioned test, assessment or measurement (M3), is performed on the third tissue sample to obtain a third set of results or data SR3 related to one or more classes of antibodies, as described in the step 402 of FIG. 12A, descriptively, qualitatively or quantitatively. One or more fourth tests, assessments or measurements may be performed on the fourth tissue sample(s) to obtain data LKD21a about liver and kidney functions related to the subject. The data LKD21a may include, but not limited to, data about kidney functions (such as BUN, GFR, CCR, ACR, cystatin C, uric acid, microalbumin, urine routine, and/or urine sediment) and data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV).

The first set of results or data SR1 may include parameters (such as the number, the percentage and/or the sizes) of the one or more types of stem cells. For example, the first set of results or data SR1 may include the same types of information as the first set of results or data illustrated in the step 52 of FIG. 7, that is, the first set of results or data SR1 include multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for the first set of results or data SR1 are defined, described or specified as the first set of results or data illustrated in the step 52 of FIG. 7, respectively. For cases required more information for the human or non-human body health condition and stem cell dynamics, the selected type or types of stem cells for the test may include more than 3, 5, 10, 15, 20, 25, 50, 100 or 1,000 types of stem cells including one, more, or all of above-mentioned types of stem cells.

The second test, assessment or measurement illustrated herein may include using flow cytometry, cytometric bead assay or hematology analysis to obtain the second set of results or data SR2 related to immune cells from the second tissue sample. The second set of results or data SR2 may include parameters (such as the count and/or the percentage) of the one or more types of immune cells. For example, the second set of results or data SR2 could include the same types of information as the second set of results or data illustrated in the step 802 of FIG. 17A, that is, the second set of results or data SR2 include multiple results or data $U_{1,1}$-$U_{1,y}$, $U_{2,1}$-$U_{2,y}$, . . . , and $U_{x,1}$-$U_{x,y}$, wherein the first and second numbers in the subscript of $U_{1,1}$-$U_{x,y}$ for the second set of results or data SR2 are defined, described or specified as the second set of results or data illustrated in the step 802 of FIG. 17A, respectively.

The third set of results or data SR3 may include parameters, such as the concentration, e.g., in mg/ml, and/or the number, of the one or more classes of antibodies. For example, the third set of results or data SR3 may include the same types of information as the second set of results or data illustrated in the step 402 of FIG. 12A, that is, the third set of results or data SR3 include multiple results or data $I_{1,1}$-$I_{1,f}$, $I_{2,1}$-$I_{2,f}$, . . . , and $I_{e,1}$-$I_{e,f}$, wherein the first and second numbers in the subscript of $I_{1,1}$-$I_{e,f}$ for the third set of results or data SR3 are defined, described or specified as the second set of results or data illustrated in the step 402 of FIG. 12A, respectively.

Referring to FIG. 21, after the step 901 or 902 is performed, step 903 is performed. In the step 903, the subject takes or is subjected to the one or more of the actions or stimuli (X), such as taking nutrients or dietary supplements, taking one or more drugs approved by a government department (e.g., U.S. FDA) for curing a specific disease (e.g., a cancer), and/or being exposed to sunshine or sunlight. The one or more actions or stimuli illustrated herein may be performed based on the dose, intensity, duration, frequency (each action may include more than one sub-actions, for example, taking one pill of drug for three times with one hour apart), and/or the time (for example, the time of a day (in the morning, at noon, in the afternoon, in the evening, or in the night), the time before, with or after the meal, or the time of the year (spring, summer, autumn or winter)). As an example, when the subject is taking a drug or a nutrient, the dose (for example, the amount in grams), the time (for example, before or after breakfast, or before sleep) are factors needed to be considered. As another example, when the subject is exposed to the sunshine or sunlight, the time of the day (morning, noon or afternoon), the time of seasons (spring, summer, autumn, or winter), or the exposing duration (30 minutes, 1 hour, 2 hours) are factors needed to be considered.

After a specific period of time, such as longer than or equal to 15, 30, 60, 90 or 120 minutes or one, two or thirty days, or, for example, between 30 and 120 minutes, step 904 is performed following the step 903. In the step 904, fifth, sixth, seventh and eighth tissue samples, each of which may be referred to the above-mentioned tissue sample (P), are extracted, taken, obtained or derived from the subject. The first through eighth tissue samples may be, but not limited to, obtained from the same type of tissue of the subject. For example, all of the first through eighth tissue samples may be obtained from (peripheral) blood of the subject. Alternatively, the first and fifth tissue samples may have a different type of tissue from that of the second, third, fourth, sixth, seventh and eighth tissue samples.

Next, in step 905, a fifth test, assessment or measurement including extracting, characterizing, assessing and measuring stem cells, which may be referred to one of the above-mentioned tests, assessments or measurements (M0), (M1) and (M2), may be performed on the fifth tissue sample to obtain a fifth set of results or data SR5 related to the one or more types of stem cells, as listed in the above-mentioned description of stem cells and as discussed or described in the step 52 of FIG. 7, descriptively, qualitatively or quantitatively. A sixth test, assessment or measurement including extracting, characterizing, assessing and measuring immune cells may be performed on the sixth tissue sample to obtain a sixth set of results or data SR6 related to the one or more types of immune cells, as described in the step 802 of FIG. 17A, descriptively, qualitatively or quantitatively. A seventh test, assessment or measurement including extracting, characterizing, assessing and measuring antibodies, which may be referred to the above-mentioned test, assessment or measurement (M3), may be performed on the seventh tissue sample to obtain a seventh set of results or data SR7 related to the one or more classes of antibodies, as described in the step 402 of FIG. 12A, descriptively, qualitatively or quantitatively. One or more eighth tests, assessments or measurements may be performed on the eighth tissue sample(s) to obtain data LKD21b about liver and kidney functions related to the subject. The data LKD21b may include, but not limited to, data about kidney functions (such as BUN, GFR, CCR, ACR, cystatin C, uric acid, microalbumin, urine routine, and/or urine sediment) and data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV).

The fifth set of results or data SR5 may include parameters (such as the number, the percentage and/or the sizes) of the one or more types of stem cells. For example, the fifth set of results or data SR5 may include the same types of information as the first set of results or data illustrated in the step 52 of FIG. 7, that is, the fifth set of results or data SR5 include multiple results or data $R_{1,1}$-$R_{1,b}$, $R_{2,1}$-$R_{2,b}$, . . . , and $R_{a,1}$-$R_{a,b}$, wherein the first and second numbers in the subscript of $R_{1,1}$-$R_{a,b}$ for the fifth set of results or data SR5 are defined, described or specified as the first set of results or data illustrated in the step 52 of FIG. 7, respectively. For cases required more information for the human body health condition and stem cell dynamics, the selected type or types of stem cells for the test may include more than 3, 5, 10, 15, 20, 25, 50, 100 or 1,000 types of stem cells including one, more, or all of above mentioned types of stem cells.

The sixth test, assessment or measurement illustrated herein may include using flow cytometry, cytometric bead assay or hematology analysis to obtain the sixth set of results or data SR6 related to immune cells from the sixth tissue sample. The sixth set of results or data SR6 may include parameters (such as the count and/or the percentage) of the one or more types of immune cells. For example, the sixth set of results or data SR6 may include the same types of information as the second set of results or data illustrated in the step 802 of FIG. 17A, that is, the sixth set of results or data SR6 include multiple results or data $U_{1,1}$-$U_{1,y}$, $U_{2,1}$-$U_{2,y}$, . . . , and $U_{x,1}$-$U_{x,y}$, wherein the first and second numbers in the subscript of $U_{1,1}$-$U_{x,y}$ for the sixth set of results or data SR6 are defined, described or specified as the second set of results or data illustrated in the step 802 of FIG. 17A, respectively.

The seventh set of results or data SR7 may include parameters (such as the concentration, e.g., in mg/ml, and/or the number) of one or more classes of antibodies. For example, the seventh set of results or data SR7 may include the same types of information as the second set of results or data illustrated in the step 402 of FIG. 12A, that is, the seventh set of results or data SR7 include multiple results or data $I_{1,1}$-$I_{1,f}$, $I_{2,1}$-$I_{2,f}$, . . . , and $I_{e,1}$-$I_{e,f}$, wherein the first and second numbers in the subscript of $I_{1,1}$-$I_{e,f}$ for the seventh set of results or data SR7 are defined, described or specified as the second set of results or data illustrated in the step 402 of FIG. 12A, respectively.

For collecting the same types of information and reducing experimental errors, both of the first and fifth tests, assessments or measurements for the first and fifth sets of results or data SR1 and SR5 may be performed using the same method such as the above-mentioned test, assessment or measurement (M0), (M1) or (M2). Both of the second and sixth tests, assessments or measurements for the second and sixth sets of results or data SR2 and SR6 may be performed using the same method. Both of the third and seventh tests, assessments or measurements for the third and seventh sets of results or data SR3 and SR7 may be performed using the same method such as the above-mentioned test, assessment or measurement (M3). The fourth and eighth tests, assessments or measurements for the data LKD21a and LKD21b may be performed using the same method.

Next, referring to FIG. 21, in step 906, a first set of changes FSC1 between the first and fifth sets of results or data SR1 and SR5 may be obtained by comparing the first and fifth sets of results or data SR1 and SR5. A second set of changes FSC2 between the second and sixth sets of results or data SR2 and SR6 may be obtained by comparing the second and sixth sets of results or data SR2 and SR6. A third set of changes FSC3 between the third and seventh sets of results or data SR3 and SR7 may be obtained by comparing the third and seventh sets of results or data SR3 and SR7. A fourth set of changes FSC4 between the data LKD21a and LKD21b may be obtained by comparing the data LKD21a and LKD21b.

The first set of changes FSC1 may be obtained by performing: (1) a first operation (i.e., subtraction operation), that is, the fifth set of results or data $R_{1,1}$-$R_{a,b}$ minus the first set of results or data $R_{1,1}$-$R_{a,b}$, or (2) a second operation of calculating the rates of change between the first and fifth sets of results or data $R_{1,1}$-$R_{a,b}$, which may be calculated by subtracting the first set of results or data $R_{1,1}$-$R_{a,b}$ from the fifth set of results or data $R_{1,1}$-$R_{a,b}$, then dividing the subtracted results by the first set of results or data $R_{1,1}$-$R_{a,b}$, and finally multiplying the divided results by 100% (which converts the divided results into percent figures). The first and fifth sets of results or data $R_{1,1}$-$R_{a,b}$ employed in the first or second operation have the same first and second numbers in the subscript.

The second set of changes FSC2 may be obtained by performing: (1) a third operation (i.e., subtraction operation), that is, the sixth set of results or data $U_{1,1}$-$U_{x,y}$ minus the second set of results or data $U_{1,1}$-$U_{x,y}$, or (2) a fourth operation of calculating the rates of change between the second and sixth sets of results or data $U_{1,1}$-$U_{x,y}$, which may be calculated by subtracting the second set of results or data $U_{1,1}$-$U_{x,y}$ from the sixth set of results or data $U_{1,1}$-$U_{x,y}$, then dividing the subtracted results by the second set of results or data $U_{1,1}$-$U_{x,y}$, and finally multiplying the divided results by 100% (which converts the divided results into percent figures). The second and sixth sets of results or data $U_{1,1}$-$U_{x,y}$ employed in the third or fourth operation have the same first and second numbers in the subscript.

The third set of changes FSC3 may be obtained by performing: (1) a fifth operation (i.e., subtraction operation), that is, the seventh set of results or data $I_{1,1}$-$I_{e,f}$ minus the third set of results or data $I_{1,1}$-$I_{e,f}$, or (2) a sixth operation of calculating the rates of change between the third and seventh sets of results or data $I_{1,1}$-$I_{e,f}$, which may be calculated by subtracting the third set of results or data $I_{1,1}$-$I_{e,f}$ from the seventh set of results or data $I_{1,1}$-$I_{e,f}$, then dividing the subtracted results by the third set of results or data $I_{1,1}$-$I_{e,f}$, and finally multiplying the divided results by 100% (which converts the divided results into percent figures). The third and seventh sets of results or data $I_{1,1}$-$I_{e,f}$ employed in the fifth or sixth operation have the same first and second numbers in the subscript.

The first set of changes FSC1 may include the same types of information as the set of changes illustrated in the step 56 of FIG. 7, that is, the first set of changes FSC1 may include multiple changes $\Delta_{1,1}$-$\Delta_{1,c}$, $\Delta_{2,1}$-$\Delta_{2,c}$, ..., and $\Delta_{a,1}$-$\Delta_{a,c}$, wherein the first and second numbers in the subscript of $\Delta_{1,1}$-$\Delta_{a,c}$ for the first set of changes FSC1 are defined, described or specified as the set of changes illustrated in the step 56 of FIG. 7, respectively. The second set of changes FSC2 may include the same types of information as the second set of changes illustrated in the step 806 of FIG. 17A, that is, the second set of changes FSC2 may include multiple changes $\theta_{1,1}$-$\theta_{1,z}$, $\theta_{2,1}$-$\theta_{2,z}$, ..., and $\theta_{x,1}$-$\theta_{x,z}$, wherein the first and second numbers in the subscript of $\theta_{1,1}$-$\theta_{x,z}$ for the second set of changes FSC2 are defined, described or specified as the second set of changes illustrated in the step 806 of FIG. 17A, respectively. The third set of changes FSC3 may include the same types of information as the second set of changes illustrated in the step 406 of FIG. 12A, that is, the third set of changes FSC3 may include multiple changes $\delta_{1,1}$-$\delta_{1,h}$, $\delta_{2,1}$-$\delta_{2,h}$, ..., and $\delta_{e,1}$-$\delta_{e,h}$, wherein the first and second numbers in the subscript of $\delta_{1,1}$-$\delta_{e,h}$ for the third set of changes FSC3 are defined, described or specified as the second set of changes illustrated in the step 406 of FIG. 12A, respectively.

Next, referring to FIG. 21, in step 907, based on the first, second, third and fourth sets of changes FSC1, FSC2, FSC3 and FSC4 and/or the data SR5, SR6, SR7 and LKD21b, the effect of the one or more actions or stimuli depicted in the step 903 on the subject may be identified, determined, evaluated or assessed.

Fifteenth Embodiment

Figure 22:
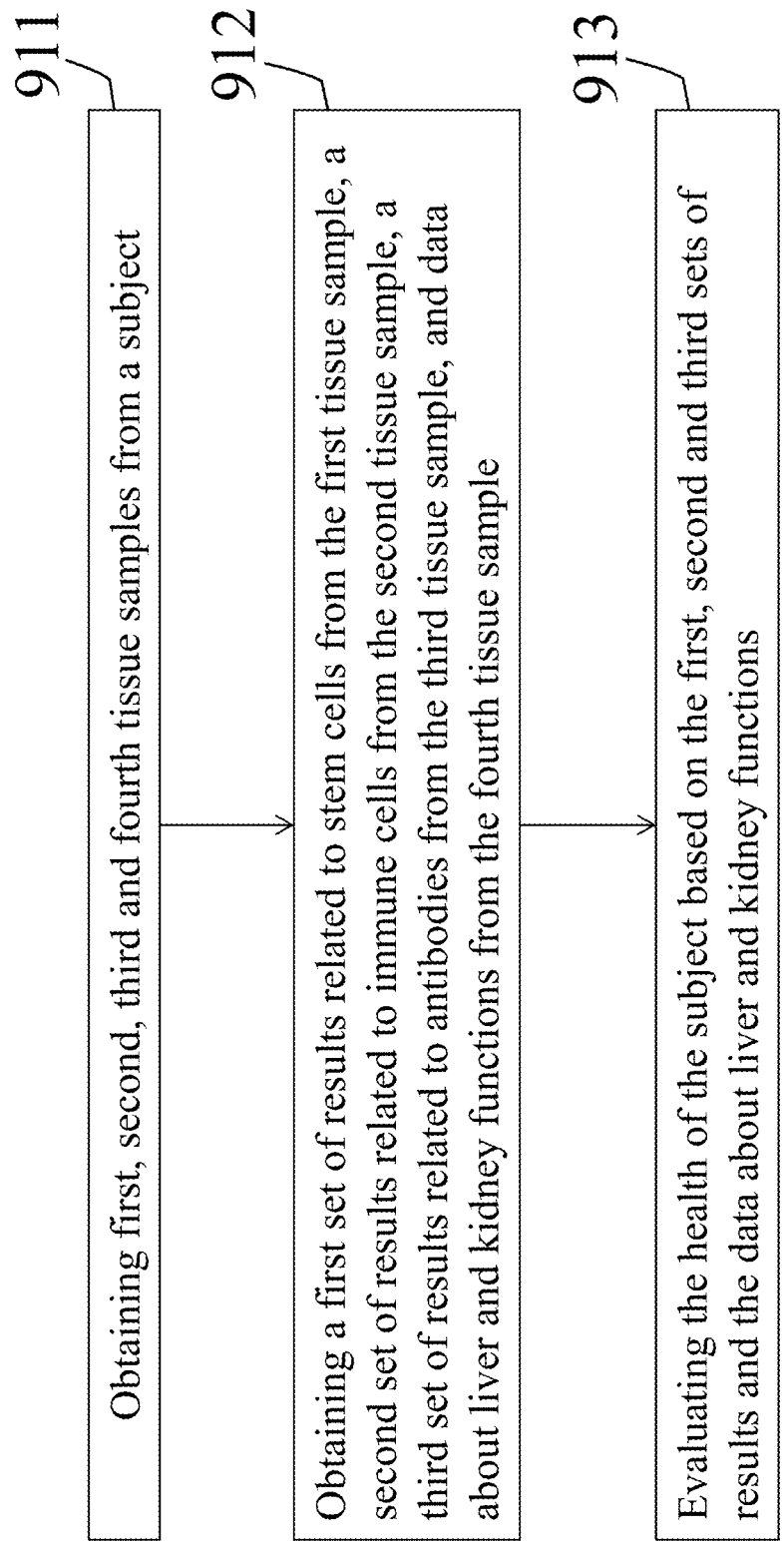
FIG. 22 shows a flow chart for identifying, evaluating or assessing the health of a subject according to a fifteenth embodiment of the present disclosure.

FIG. 22 is a flow chart for identifying, evaluating or assessing the health of a subject that may be referred to the above-mentioned subject (S). Referring to FIG. 22, in step 911, first, second, third and fourth tissue samples, each of which may be referred to the above-mentioned tissue sample (P), are extracted, taken, obtained or derived from the subject.

Next, in step 912, a first test, assessment or measurement including extracting, characterizing, assessing and measuring stem cells, which may be referred to one of the above-mentioned tests, assessments or measurements (M0), (M1) and (M2), is performed on the first tissue sample to obtain a first set of results or data SR11 related to one or more types of stem cells, as listed in the above-mentioned description of stem cells, descriptively, qualitatively or quantitatively. A second test, assessment or measurement including extracting, characterizing, assessing and measuring immune cells is performed on the second tissue sample to obtain a second set of results or data SR12 related to one or more types of immune cells, as described in the step 802 of FIG. 17A, descriptively, qualitatively or quantitatively. A third test, assessment or measurement including extracting, characterizing, assessing and measuring antibodies, which may be referred to the above-mentioned test, assessment or measurement (M3), is performed on the third tissue sample to obtain a third set of results or data SR13 related to one or more classes of antibodies, as described in the step 402 of FIG. 12A, descriptively, qualitatively or quantitatively. One or more fourth tests, assessments or measurements may be performed on the fourth tissue sample(s) to obtain data LKD22 about liver and kidney functions related to the subject. The data LKD22 may include, but not limited to, data about kidney functions (such as BUN, GFR, CCR, ACR, cystatin C, uric acid, microalbumin, urine routine, and/or urine sediment) and data about liver functions (such as AST, ALT, AFP, total bilirubin, direct bilirubin, indirect bilirubin, albumin, globulin, albumin/globulin ratio, γ-GT, ALP, PT, HBsAg, Anti-HBs, and/or Anti-HCV).

The first set of results or data SR11 may include parameters (such as the number, the percentage and/or the sizes) of the one or more types of stem cells. For example, the first set of results or data SR11 may include the same types of information as the first set of results or data illustrated in the step 52 of FIG. 7, that is, the first set of results or data SR11 include multiple results or data $R_{1,1}$-$R_{1,b}$, $R_{2,1}$-$R_{2,b}$, ..., and $R_{a,1}$-$R_{a,b}$, wherein the first and second numbers in the subscript of $R_{1,1}$-$R_{a,b}$ for the first set of results or data SR11 are defined, described or specified as the first set of results or data illustrated in the step 52 of FIG. 7, respectively. For cases required more information for the human body health condition and stem cell dynamics, the selected type or types of stem cells for the test may include more than 3, 5, 10, 15, 20, 25, 50, 100 or 1,000 types of stem cells including one, more, or all of above mentioned types of stem cells.

The second test, assessment or measurement illustrated herein may include using flow cytometry, cytometric bead assay or hematology analysis to obtain the second set of results or data SR12 related to immune cells from the second tissue sample. The second set of results or data SR12 may include parameters (such as the count and/or the percentage) of the one or more types of immune cells. For example, the second set of results or data SR12 may include the same types of information as the second set of results or data illustrated in the step 802 of FIG. 17A, that is, the second set of results or data SR12 include multiple results or data $U_{1,1}$-$U_{1,y}$, $U_{2,1}$-$U_{2,y}$, ..., and $U_{x,1}$-$U_{x,y}$, wherein the first and second numbers in the subscript of $U_{1,1}$-$U_{x,y}$ for the second set of results or data SR12 are defined, described or specified as the second set of results or data illustrated in the step 802 of FIG. 17A, respectively.

The third set of results or data SR13 may include parameters (such as the concentration, e.g., in mg/ml, and/or the number) of the one or more classes of antibodies. For example, the third set of results or data SR13 may include the same types of information as the second set of results or data illustrated in the step 402 of FIG. 12A, that is, the third set of results or data SR13 include multiple results or data $I_{1,1}\text{-}I_{1,f}, I_{2,1}\text{-}I_{2,f}, \ldots$, and $I_{e,1}\text{-}I_{e,f}$, wherein the first and second numbers in the subscript of $I_{1,1}\text{-}I_{e,f}$ for the third set of results or data SR13 are defined, described or specified as the second set of results or data illustrated in the step 402 of FIG. 12A, respectively.

Next, referring to FIG. 22, in step 913, based on the first, second and third sets of results or data SR11, SR12 and SR13 and the data LKD22, the health of the subject may be identified, determined, evaluated or assessed.

Applications:

A research institute, a university, or a research and development (R&D) organization in an institute or in a company may use the criteria or standards (G) established in the third, fourth, fifth, sixth or ninth embodiment, the universal criteria or standards established in the seventh or eighth embodiment, or the steps illustrated in one of the first through ninth embodiments to research and develop a new (brand) drug (e.g., a synthetic drug or a drug including extractions from nature), a new generic drug, a new (brand) nutrient, a new (brand) dietary supplement, a new (brand) healthy food, a new health program, a new recipe or program to cure a disease (such as cancer), an alternative therapy to cure a disease (such as cancer), a (alternative) medicine to cure a disease (such as cancer), and/or a program, therapy, treatment, method, apparatus and/or system for improving body's self-healing or curing a disease (such as cancer). All the above researches and developments include establishing the dosage (for example, the amount of the new drugs, new nutrients, or new dietary supplements each time of use), the frequency (for example, times of use per day), and/or the period of time (for example, use of one week, two weeks or one month). In addition, the items of the above-mentioned actions or stimuli (X1) and (X4) are also included here.

A manufacturer, a pharmaceutical factory, or a pharmaceutical company may use the criteria or standards (G) established in the third, fourth, fifth, sixth or ninth embodiment, the universal criteria or standards established in the seventh or eighth embodiment, or the steps illustrated in one of the first through ninth embodiments to control and monitor the quality of produced drugs, brand nutrients, or dietary supplements in a manufacturing line.

A manufacturer, a farmer, a farm, a food store, a food producer, or a food company may use the criteria or standards (G) established in the third, fourth, fifth, sixth or ninth embodiment, the universal criteria or standards established in the seventh or eighth embodiment, or the steps illustrated in one of the first through ninth embodiments to research and develop safe, healthy foods, to research and develop a new process for food production, and/or to control and monitor the quality of manufacturing or processing of foods.

A government department or authority (such as U.S. FDA) may use the criteria or standards (G) established in the third, fourth, fifth, sixth or ninth embodiment, the universal criteria or standards established in the seventh or eighth embodiment, or the steps illustrated in one of the first through ninth embodiments to approve or disprove a new or generic drug and to suspend a food distribution or a certificate for a certain food producer.

Based on the criteria or standards (G) established in the third, fourth, fifth, sixth or ninth embodiment, the universal criteria or standards established in the seventh or eighth embodiment, or the steps illustrated in one of the first through ninth embodiments, a new standard organization or an existing standard organization (such as International Organization for Standardization (ISO)) may develop and publish new (international) standards for various products and services, including a (brand or generic) drug (e.g., a synthetic drug or a drug including extractions from nature), a herbal or Chinese medicine, a (brand) nutrient, a (brand) dietary supplement, a (brand) healthy food, a health program, a recipe or program to cure a disease (such as cancer), an alternative therapy or treatment to cure a disease (such as cancer), a (alternative) medicine to cure a disease (such as cancer), and/or a program, therapy, treatment, method, apparatus and/or system for improving body's self-healing or curing a disease (such as cancer). Here, in addition, the items of the above-mentioned actions or stimuli (X1) and (X4) are also included. Therefore, the above organizations may qualify or issue a certificate with various levels of quality based on the new (international) standards. The new (international) standards may ensure that the above products and services are safe, reliable and of good quality.

Based on all embodiments disclosed in the present invention, methods to evaluate the health condition of an individual are provided based on the test, assessment or measurement of stem cells and/or the studies of the stem cell dynamics. If necessary, more information of an individual health condition may be obtained by combining the test, assessment or measurement of stem cells and studies of stem cell dynamics with: (1) the test, assessment or measurement of immune cells and studies of immune cell dynamics; and/or (2) the test, assessment or measurement of antibodies and studies of the antibody dynamics; and/or (3) the test, assessment or measurement of kidney and/or liver functions and the dynamics of kidney and/or liver functions. The present invention may be applied in a hospital or in an annual or routine physical examination. For cases required more information for the human or non-human body health condition and stem cell dynamics, the selected type or types of stem cells for the test may include more than 3, 5, 10, 15, 20, 25, 50, 100 or 1,000 types of stem cells including one, more, or all types of stem cells mentioned above in the present invention.

Based on all embodiments disclosed in the present invention, methods to evaluate the effects of actions mentioned above in this invention on an individual are provided based on the test, assessment or measurement of stem cells and/or the studies of the stem cell dynamics. If necessary, more information may be obtained by combining the test, assessment or measurement of stem cells and studies of stem cell dynamics with: (1) the test, assessment or measurement of immune cells and studies of immune cell dynamics; and/or (2) the test, assessment or measurement of antibodies and studies of the antibody dynamics; and/or (3) the test, assessment or measurement of kidney and/or liver functions and the dynamics of kidney and/or liver functions. For cases required more information for consideration, the selected type or types of stem cells for the test may include more than 3, 5, 10, 15, 20, 25, 50, 100 or 1,000 types of stem cells including one, more, or all types of stem cells mentioned above in the present invention.

The components, steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, benefits and advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. Furthermore, unless stated otherwise, the numerical ranges provided are intended to be inclusive of the stated lower and upper values. Moreover, unless stated otherwise, all material selections and numerical values are representative of preferred embodiments and other ranges and/or materials may be used.

The scope of protection is limited solely by the claims, and such scope is intended and should be interpreted to be as broad as is consistent with the ordinary meaning of the language that is used in the claims when interpreted in light of this specification and the prosecution history that follows, and to encompass all structural and functional equivalents thereof.

What is claimed is:

1. A method of determining an effect of one or more actions, comprising:
    obtaining a first peripheral blood sample from a subject before the subject takes a first action;
    performing a first purification process on said first blood sample, wherein said first purification process includes incubating said first blood sample with ethylenediaminetetraacetic acid (EDTA) and isolating from the thus incubated first blood sample a first population of small cells that are between 1.0 and 6.0 micrometers in size;
    obtaining the number or percentage of CD349(+) somatic stem cells in the first population of small cells with flow cytometry;
    obtaining a second peripheral blood sample from said subject after the subject takes the first action;
    performing a second purification process on said second blood sample, wherein said second purification process includes incubating said second blood sample with EDTA and isolating from the thus incubated second blood sample a second population of small cells that are between 1.0 and 6.0 micrometers in size;
    obtaining the number or percentage of CD349(+) somatic stem cells in the second population of small cells with flow cytometry; and
    determining a change in the number or percentage of CD349(+) somatic stem cells in the second population as compared to the first population, whereby an effect of one or more actions is determined.

2. The method of claim 1, wherein said first action comprises taking a drug.

3. The method of claim 1, wherein said first action comprises taking herbal or Chinese medicine.

4. The method of claim 1, wherein said first action comprises taking a fucoidan-containing pill.

5. The method of claim 1, further comprising obtaining the number or percentage of CD9(+) somatic stem cells in the first population of small cells and the second population of small cells with flow cytometry.

6. The method of claim 1, further comprising obtaining the number or percentage of CD66e(+) somatic stem cells in the first population of small cells and the second population of small cells with flow cytometry.

7. The method of claim 1, wherein the incubated first blood sample and the incubated second blood sample are each filtered or centrifuged, whereby the first small population of small cells and the second population of small cells are isolated.

8. The method of claim 1, wherein said first purification process further includes placing the first population of small cells in a medium containing phosphate-buffered saline (PBS).

9. The method of claim 1, wherein said first purification process further includes placing the first population of small cells in a medium containing bovine serum albumin (BSA).

10. The method of claim 1, wherein said first purification process further includes washing the first population of small cells.

11. The method of claim 1, further comprising:
    obtaining a third peripheral blood sample from said subject after the subject takes a second action, the second action occurring after the step of obtaining said second blood sample;
    performing a third purification process on said third blood sample, wherein said third purification process includes incubating said third blood sample with EDTA and isolating from the thus incubated third blood sample a third population of small cells that are between 1.0 and 6.0 micrometers in size; and
    obtaining the number or percentage of CD349(+) somatic stem cells in the third population of small cells with flow cytometry.

12. The method of claim 11, wherein said first action is different from said second action.

13. The method of claim 11, wherein said first action is the same as said second action.

14. The method of claim 1, further comprising obtaining the number or percentage of somatic stem cells that are both CD349(+) and CD9(+) in the first population of small cells and in the second population of small cells with flow cytometry.

* * * * *